US00RE48468E

(19) United States
(12) Reissued Patent
De Kimpe et al.

(10) Patent Number: US RE48,468 E
(45) Date of Reissued Patent: Mar. 16, 2021

(54) MEANS AND METHODS FOR COUNTERACTING MUSCLE DISORDERS

(71) Applicants: BioMarin Technologies B.V., Leiden (NL); Academisch Ziekenhuis Leiden, Leiden (NL)

(72) Inventors: Josephus Johannes De Kimpe, Utrecht (NL); Gerard Johannes Platenburg, Voorschoten (NL); Judith Christina Theodora Van Deutekom, Dordrecht (NL); Annemieke Aartsma-Rus, Hoofddorp (NL); Garrit-Jan Boudewijn Van Ommen, Amsterdam (NL)

(73) Assignees: BioMarin Technologies B.V., Leiden (NL); Academisch Ziekenhuis Leiden, Leiden (NL)

(21) Appl. No.: 15/881,574

(22) Filed: Jan. 26, 2018

Related U.S. Patent Documents

Reissue of:
(64) Patent No.: 9,243,245
Issued: Jan. 26, 2016
Appl. No.: 12/767,702
Filed: Apr. 26, 2010

U.S. Applications:
(63) Continuation of application No. PCT/NL2008/050673, filed on Oct. 27, 2008.

(60) Provisional application No. 61/006,670, filed on Oct. 26, 2007.

(30) Foreign Application Priority Data

Oct. 26, 2007 (EP) ..... 07119351

(51) Int. Cl.

| | |
|---|---|
| ***C12N 15/113*** | (2010.01) |
| ***A61K 31/56*** | (2006.01) |
| ***A61K 31/57*** | (2006.01) |
| ***A61K 31/573*** | (2006.01) |
| ***A61K 31/58*** | (2006.01) |
| ***A61K 31/7088*** | (2006.01) |
| ***A61K 38/17*** | (2006.01) |
| ***A61K 45/06*** | (2006.01) |
| ***A61K 48/00*** | (2006.01) |

(52) U.S. Cl.
CPC ..... *C12N 15/113* (2013.01); *A61K 31/56* (2013.01); *A61K 31/57* (2013.01); *A61K 31/573* (2013.01); *A61K 31/58* (2013.01); *A61K 31/7088* (2013.01); *A61K 38/1719* (2013.01); *A61K 45/06* (2013.01); *A61K 48/00* (2013.01); *C12N 2310/11* (2013.01); *C12N 2310/111* (2013.01); *C12N 2310/31* (2013.01); *C12N 2310/313* (2013.01); *C12N 2310/314* (2013.01); *C12N 2310/315* (2013.01); *C12N 2310/3181* (2013.01); *C12N 2310/321* (2013.01); *C12N 2310/3231* (2013.01); *C12N 2310/3233* (2013.01); *C12N 2310/346* (2013.01); *C12N 2320/31* (2013.01); *C12N 2320/33* (2013.01)

(58) Field of Classification Search
CPC ..... A61K 31/7088; A61K 31/88; A61K 38/1719; A61K 45/06; A61K 2300/00; C12N 15/113
See application file for complete search history.

(56) References Cited

U.S. PATENT DOCUMENTS

| | | | |
|---|---|---|---|
| 5,034,506 | A | 7/1991 | Summerton et al. |
| 5,418,139 | A | 5/1995 | Campbell |
| 5,541,308 | A | 7/1996 | Hogan et al. |
| 5,593,974 | A | 1/1997 | Rosenberg et al. |
| 5,608,046 | A | 3/1997 | Cook et al. |
| 5,624,803 | A | 4/1997 | Noonberg et al. |
| 5,627,263 | A | 5/1997 | Ruoslahti et al. |
| 5,658,764 | A | 8/1997 | Pergolizzi et al. |
| 5,741,645 | A | 4/1998 | Orr et al. |
| 5,766,847 | A | 6/1998 | Jackle et al. |
| 5,853,995 | A | 12/1998 | Lee |
| 5,869,252 | A | 2/1999 | Bouma et al. |
| 5,916,808 | A | 6/1999 | Kole et al. |
| 5,962,332 | A | 10/1999 | Singer et al. |
| 5,968,909 | A | 10/1999 | Agrawal et al. |
| 5,976,879 | A | 11/1999 | Kole et al. |
| 6,124,100 | A | 9/2000 | Jin |
| 6,130,207 | A | 10/2000 | Dean et al. |

(Continued)

FOREIGN PATENT DOCUMENTS

| | | |
|---|---|---|
| CA | 2319149 | 10/2001 |
| CA | 2319149 A1 | 10/2001 |

(Continued)

OTHER PUBLICATIONS

Wilton. Acta Myologica. 2005, XXIV. p. 222-229.*

(Continued)

*Primary Examiner* — Padmashri Ponnaluri

(74) *Attorney, Agent, or Firm* — Rimon, P.C.; Dale L. Rieger

(57) ABSTRACT

The invention provides means and methods for alleviating one or more symptom(s) of Duchenne Muscular Dystrophy and/or Becker Muscular Dystrophy. Therapies using compounds for providing patients with functional muscle proteins are combined with at least one adjunct compound for reducing inflammation, preferably for reducing muscle tissue inflammation, and/or at least one adjunct compound for improving muscle fiber function, integrity and/or survival.

20 Claims, 28 Drawing Sheets

Specification includes a Sequence Listing.

(56) References Cited

U.S. PATENT DOCUMENTS

| | | | | |
|---|---|---|---|---|
| 6,133,031 | A | 10/2000 | Monia et al. | |
| 6,165,786 | A | 12/2000 | Bennett et al. | |
| 6,172,208 | B1 | 1/2001 | Cook | 536/23.1 |
| 6,172,216 | B1 | 1/2001 | Bennett et al. | |
| 6,210,892 | B1 | 4/2001 | Bennett et al. | 435/6 |
| 6,251,589 | B1 | 6/2001 | Tsuji et al. | |
| 6,280,938 | B1 | 8/2001 | Ranum et al. | |
| 6,300,060 | B1 | 10/2001 | Kantoff et al. | |
| 6,322,978 | B1 | 11/2001 | Kahn et al. | |
| 6,329,501 | B1 | 12/2001 | Smith et al. | |
| 6,355,481 | B1 | 3/2002 | Li et al. | |
| 6,355,690 | B1 | 3/2002 | Tsuji | |
| 6,369,038 | B1 | 4/2002 | Blumenfeld et al. | |
| 6,379,698 | B1 | 4/2002 | Leamon | |
| 6,399,575 | B1 | 6/2002 | Smith et al. | |
| 6,514,755 | B1 | 2/2003 | Ranum et al. | |
| 6,623,927 | B1 | 9/2003 | Brahmachari et al. | |
| 6,653,466 | B2 | 11/2003 | Matsuo | |
| 6,653,467 | B1 | 11/2003 | Matsuo et al. | |
| 6,670,461 | B1 | 12/2003 | Wengel et al. | |
| 6,727,355 | B2 | 4/2004 | Matsuo et al. | 536/24.5 |
| 6,794,192 | B2 | 9/2004 | Parums et al. | |
| 6,875,736 | B2 | 4/2005 | Rana | |
| 6,902,896 | B2 | 6/2005 | Ranum et al. | |
| 6,982,150 | B2 | 1/2006 | Sheetz et al. | |
| 7,001,994 | B2 | 2/2006 | Zhu | 536/4.1 |
| 7,034,009 | B2 | 4/2006 | Pavco et al. | |
| 7,118,893 | B2 | 10/2006 | Ranum et al. | |
| 7,189,530 | B2 | 3/2007 | Botstein et al. | |
| 7,202,210 | B2 | 4/2007 | Wolfman et al. | |
| 7,250,404 | B2 | 7/2007 | Felgner et al. | |
| 7,355,018 | B2 | 4/2008 | Glass | 530/399 |
| 7,405,193 | B2 | 7/2008 | Lodish et al. | 514/2 |
| 7,442,782 | B2 | 10/2008 | Ranum et al. | 536/23.1 |
| 7,514,551 | B2 | 4/2009 | Rabbani et al. | 536/26.6 |
| 7,534,879 | B2 | 5/2009 | van Deutekom | 536/24.5 |
| 7,589,189 | B2 | 9/2009 | Ichiro et al. | 536/24.5 |
| 7,655,785 | B1 | 2/2010 | Bentwich | 536/24.1 |
| 7,771,727 | B2 | 8/2010 | Fuselier et al. | 424/185.1 |
| 7,807,816 | B2 | 10/2010 | Wilton et al. | 536/24.5 |
| 7,902,160 | B2 | 3/2011 | Matsuo et al. | 514/44 |
| 7,960,541 | B2 | 6/2011 | Wilton et al. | 536/24.5 |
| 8,232,384 | B2 | 7/2012 | Wilton et al. | 536/24.5 |
| 8,324,371 | B2 | 12/2012 | Popplewell et al. | 536/24.5 |
| 8,450,474 | B2 | 5/2013 | Wilton et al. | 536/24.5 |
| 8,455,634 | B2 | 6/2013 | Wilton et al. | 536/24.5 |
| 8,455,635 | B2 | 6/2013 | Wilton et al. | 536/24.5 |
| 8,455,636 | B2 | 6/2013 | Wilton et al. | 536/24.5 |
| 8,476,423 | B2 | 7/2013 | Wilton et al. | 536/24.5 |
| 8,486,907 | B2 | 7/2013 | Wilton et al. | 514/44 |
| 8,524,880 | B2 | 9/2013 | Wilton et al. | 536/24.5 |
| 8,637,483 | B2 | 1/2014 | Wilton et al. | 514/44 A |
| 2001/0056077 | A1 | 12/2001 | Matsuo | |
| 2002/0049173 | A1 | 4/2002 | Bennett et al. | |
| 2002/0055481 | A1 | 5/2002 | Matsuo et al. | |
| 2002/0109476 | A1 | 8/2002 | Kim | |
| 2002/0115824 | A1 | 8/2002 | Engler et al. | |
| 2002/0165150 | A1 | 11/2002 | Ben-Sasson | |
| 2003/0045488 | A1 | 3/2003 | Brown et al. | |
| 2003/0073215 | A1 | 4/2003 | Baker et al. | |
| 2003/0082763 | A1 | 5/2003 | Baker et al. | |
| 2003/0082766 | A1 | 5/2003 | Baker et al. | |
| 2003/0109476 | A1 | 6/2003 | Kmiec et al. | |
| 2003/0124523 | A1 | 7/2003 | Asselbergs et al. | |
| 2003/0130224 | A1 | 7/2003 | Monahan et al. | |
| 2003/0134790 | A1 | 7/2003 | Langenfeld | |
| 2003/0175389 | A1 | 9/2003 | Shaposhnikov | |
| 2003/0235845 | A1 | 12/2003 | van Ommen et al. | |
| 2003/0236214 | A1 | 12/2003 | Wolff et al. | |
| 2004/0101852 | A1 | 5/2004 | Bennett et al. | |
| 2004/0132684 | A1 | 7/2004 | Sampath et al. | |
| 2004/0219565 | A1 | 11/2004 | Kauppinen et al. | |
| 2004/0226056 | A1 | 11/2004 | Roch et al. | |
| 2005/0048495 | A1 | 3/2005 | Baker et al. | |
| 2005/0096284 | A1 | 5/2005 | McSwiggen | |
| 2005/0222009 | A1 | 10/2005 | Lamensdorf et al. | |
| 2005/0246794 | A1 | 11/2005 | Khvorova et al. | |
| 2005/0277133 | A1 | 12/2005 | McSwiggen | |
| 2005/0288246 | A1 | 12/2005 | Iversen et al. | |
| 2006/0003322 | A1 | 1/2006 | Bentwich | |
| 2006/0024715 | A1 | 2/2006 | Liu et al. | |
| 2006/0074034 | A1 | 4/2006 | Collins et al. | |
| 2006/0099612 | A1 | 5/2006 | Nakao et al. | |
| 2006/0099616 | A1 | 5/2006 | van Ommen et al. | |
| 2006/0147952 | A1 | 7/2006 | van Ommen et al. | |
| 2006/0148740 | A1 | 7/2006 | Platenburg | |
| 2006/0160121 | A1 | 7/2006 | Mounts et al. | |
| 2007/0021360 | A1 | 1/2007 | Nyce et al. | |
| 2007/0082861 | A1 | 4/2007 | Matsuo et al. | |
| 2007/0134655 | A1 | 6/2007 | Bentwich | |
| 2007/0141628 | A1 | 6/2007 | Cunningham et al. | 435/7.1 |
| 2007/0275914 | A1 | 11/2007 | Manoharan et al. | |
| 2007/0292408 | A1 | 12/2007 | Singh et al. | 424/130.1 |
| 2007/0299027 | A1 | 12/2007 | Hung et al. | |
| 2008/0015158 | A1 | 1/2008 | Ichiro et al. | 514/44 |
| 2008/0039418 | A1 | 2/2008 | Freir | 514/44 |
| 2008/0113351 | A1 | 5/2008 | Naito et al. | 435/6 |
| 2008/0207538 | A1 | 8/2008 | Lawrence et al. | 514/41 |
| 2008/0249294 | A1 | 10/2008 | Haeberli et al. | 536/24.5 |
| 2010/0081627 | A1 | 4/2010 | Sampath et al. | 514/47 |
| 2010/0099750 | A1 | 4/2010 | McSwiggen et al. | 514/44 R |
| 2010/0286235 | A1 | 11/2010 | Renzi et al. | |
| 2011/0015253 | A1 | 1/2011 | Wilton et al. | 514/44 A |
| 2011/0015258 | A1 | 1/2011 | Wilton et al. | 514/44 R |
| 2011/0046203 | A1 | 2/2011 | Wilton et al. | 514/44 A |
| 2011/0263686 | A1 | 10/2011 | Wilton et al. | 514/44 A |
| 2012/0022144 | A1 | 1/2012 | Wilton et al. | 514/44 A |
| 2012/0022145 | A1 | 1/2012 | Wilton et al. | 514/44 A |
| 2012/0029057 | A1 | 2/2012 | Wilton et al. | 514/44 A |
| 2012/0029058 | A1 | 2/2012 | Wilton et al. | 514/44 A |
| 2012/0029059 | A1 | 2/2012 | Wilton et al. | 514/44 A |
| 2012/0029060 | A1 | 2/2012 | Wilton et al. | 514/44 A |
| 2012/0041050 | A1 | 2/2012 | Wilton et al. | 514/44 A |
| 2013/0116310 | A1 | 5/2013 | Wilton et al. | 514/44 A |
| 2013/0217755 | A1 | 8/2013 | Wilton et al. | 514/44 A |
| 2013/0253033 | A1 | 9/2013 | Wilton et al. | 514/44 A |
| 2013/0253180 | A1 | 9/2013 | Wilton et al. | 536/24.5 |
| 2013/0274313 | A1 | 10/2013 | Wilton et al. | 514/44 A |

FOREIGN PATENT DOCUMENTS

| | | | |
|---|---|---|---|
| CA | 2526893 | | 11/2004 |
| CA | 2526893 | A1 | 11/2004 |
| EP | 0438512 | A1 | 7/1991 |
| EP | 558697 | | 9/1993 |
| EP | 0558697 | A1 | 9/1993 |
| EP | 0614977 | A2 | 9/1994 |
| EP | 850300 | | 7/1998 |
| EP | 0850300 | A1 | 7/1998 |
| EP | 1054058 | | 5/2000 |
| EP | 1054058 | A1 | 5/2000 |
| EP | 1015628 | A1 | 7/2000 |
| EP | 1133993 | | 9/2001 |
| EP | 1133993 | A1 | 9/2001 |
| EP | 1160318 | | 12/2001 |
| EP | 1160318 | A2 | 12/2001 |
| EP | 1191097 | | 3/2002 |
| EP | 1191097 | A1 | 3/2002 |
| EP | 1191098 | | 3/2002 |
| EP | 1191098 | A2 | 3/2002 |
| EP | 1380644 | | 1/2004 |
| EP | 1380644 | A1 | 1/2004 |
| EP | 1487493 | A2 | 12/2004 |
| EP | 1495769 | | 1/2005 |
| EP | 1495769 | A1 | 1/2005 |
| EP | 1501931 | | 2/2005 |
| EP | 1501931 | A2 | 2/2005 |
| EP | 1544297 | | 6/2005 |
| EP | 1544297 | A2 | 6/2005 |
| EP | 1567667 | A1 | 8/2005 |
| EP | 1568769 | | 8/2005 |
| EP | 1568769 | A1 | 8/2005 |
| EP | 1619249 | | 1/2006 |
| EP | 1619249 | A1 | 1/2006 |

(56) References Cited

FOREIGN PATENT DOCUMENTS

| | | | | |
|---|---|---|---|---|
| EP | 1 191 098 | B9 | 6/2006 | |
| EP | 1857548 | | 11/2007 | ..... C12N 15/11 |
| EP | 1857548 | A1 | 11/2007 | |
| JP | 2002-010790 | | 1/2002 | |
| JP | 2002-325582 | | 11/2002 | |
| KR | 20030035047 | | 5/2003 | |
| KR | 20030035047 | A | 5/2003 | |
| WO | WO 1993/01286 | A2 | 1/1993 | |
| WO | 95/16718 | A1 | 6/1995 | |
| WO | WO 1995/016718 | A1 | 6/1995 | |
| WO | 95/21184 | A1 | 8/1995 | |
| WO | WO 1995/030774 | A1 | 11/1995 | |
| WO | WO-9530774 | | 11/1995 | |
| WO | WO 1997/012899 | A1 | 4/1997 | |
| WO | WO-9712899 | | 4/1997 | |
| WO | WO 1997/030067 | A1 | 8/1997 | |
| WO | WO-9730067 | | 8/1997 | |
| WO | WO 1998/018920 | A1 | 5/1998 | |
| WO | WO-9818920 | A1 | 5/1998 | |
| WO | 98/43993 | A2 | 10/1998 | |
| WO | WO 1998/049345 | A1 | 11/1998 | |
| WO | WO-9849345 | A1 | 11/1998 | |
| WO | WO 98/53804 | | 12/1998 | ..... A61K 31/00 |
| WO | WO 1998/053804 | A1 | 12/1998 | |
| WO | 99/16871 | A2 | 4/1999 | |
| WO | 99/55857 | A2 | 11/1999 | |
| WO | 99/63975 | A2 | 12/1999 | |
| WO | WO 00/24885 | | 5/2000 | ..... C12N 15/11 |
| WO | WO 2000/024885 | A2 | 5/2000 | |
| WO | 00/76554 | A1 | 12/2000 | |
| WO | 01/16312 | A1 | 3/2001 | |
| WO | 01/32832 | A2 | 5/2001 | |
| WO | 01/59102 | A2 | 8/2001 | |
| WO | WO 2001/079283 | A1 | 10/2001 | |
| WO | WO-0179283 | A1 | 10/2001 | |
| WO | WO 01/83503 | | 11/2001 | ..... C07H 21/00 |
| WO | WO 2001/083503 | A2 | 11/2001 | |
| WO | WO 2001/083695 | A2 | 11/2001 | |
| WO | WO-0183695 | | 11/2001 | |
| WO | WO 2002/002406 | A1 | 1/2002 | |
| WO | WO-0202406 | | 1/2002 | |
| WO | WO 2002/024906 | A1 | 3/2002 | |
| WO | WO-0224906 | | 3/2002 | |
| WO | 02/029006 | A2 | 4/2002 | |
| WO | WO 2002/026812 | A1 | 4/2002 | |
| WO | WO 2002/029056 | A2 | 4/2002 | |
| WO | WO-0226812 | A1 | 4/2002 | |
| WO | WO-0229056 | | 4/2002 | |
| WO | WO 2003/002739 | A1 | 1/2003 | |
| WO | WO-03002739 | | 1/2003 | |
| WO | WO 2003/013437 | A2 | 2/2003 | |
| WO | WO 2003/014145 | A2 | 2/2003 | |
| WO | WO-03013437 | | 2/2003 | |
| WO | WO 2003/037172 | A2 | 5/2003 | |
| WO | WO-03037172 | | 5/2003 | |
| WO | 03/062258 | A1 | 7/2003 | |
| WO | WO 2003/095647 | A2 | 11/2003 | |
| WO | WO-03095647 | | 11/2003 | |
| WO | WO 2004/011060 | A2 | 2/2004 | |
| WO | WO 2004/015106 | A1 | 2/2004 | |
| WO | WO 2004/016787 | A1 | 2/2004 | |
| WO | WO-2004015106 | | 2/2004 | |
| WO | WO-2004016787 | | 2/2004 | |
| WO | WO 2004/037854 | | 5/2004 | ..... C07K 1/04 |
| WO | WO 2004/037854 | A1 | 5/2004 | |
| WO | 2004/047741 | A2 | 6/2004 | |
| WO | WO 2004/048570 | A1 | 6/2004 | |
| WO | WO-2004048570 | | 6/2004 | |
| WO | WO 2004/083432 | A1 | 9/2004 | |
| WO | WO 2004/083446 | A2 | 9/2004 | |
| WO | WO-2004083432 | | 9/2004 | |
| WO | WO-2004083446 | | 9/2004 | |
| WO | WO 2004/101787 | A1 | 11/2004 | |
| WO | WO-2004101787 | | 11/2004 | |
| WO | WO 2004/108157 | A2 | 12/2004 | |
| WO | WO-2004108157 | | 12/2004 | |
| WO | 2005/021727 | A2 | 3/2005 | |
| WO | WO 2005/019453 | A2 | 3/2005 | |
| WO | WO 2005/023836 | | 3/2005 | |
| WO | WO 2005/023836 | A2 | 3/2005 | |
| WO | 2005/035550 | A1 | 4/2005 | |
| WO | WO 2005/035550 | A2 | 4/2005 | |
| WO | WO-2005035550 | | 4/2005 | |
| WO | WO 2005/085476 | A1 | 9/2005 | |
| WO | WO 2005/086768 | A2 | 9/2005 | |
| WO | WO-2005086768 | | 9/2005 | |
| WO | WO 2005/105995 | A2 | 11/2005 | |
| WO | 2005/115479 | A2 | 12/2005 | |
| WO | WO 2005/115439 | | 12/2005 | ..... C12N 15/85 |
| WO | WO 2005/115439 | A2 | 12/2005 | |
| WO | WO 2005/115479 | | 12/2005 | ..... A61K 48/00 |
| WO | WO 2005/116204 | A1 | 12/2005 | |
| WO | WO-2005116204 | A1 | 12/2005 | |
| WO | WO 2006/000057 | A1 | 1/2006 | |
| WO | WO 2006/007910 | A1 | 1/2006 | |
| WO | WO-2006000057 | | 1/2006 | |
| WO | W0-2006017522 | | 2/2006 | |
| WO | WO 2006/017522 | A2 | 2/2006 | |
| WO | WO 2006/031267 | A2 | 3/2006 | |
| WO | WO-2006031267 | | 3/2006 | |
| WO | WO 2006/054262 | A2 | 5/2006 | |
| WO | WO 2006/083800 | A2 | 8/2006 | |
| WO | WO-2006083800 | | 8/2006 | |
| WO | WO 2006/108052 | A2 | 10/2006 | |
| WO | WO 2006/112705 | A2 | 10/2006 | |
| WO | WO-2006108052 | | 10/2006 | |
| WO | WO-2006112705 | | 10/2006 | |
| WO | 2006121277 | A1 | 11/2006 | |
| WO | WO 2006/121960 | A2 | 11/2006 | |
| WO | WO 2007/002904 | A2 | 1/2007 | |
| WO | WO 2007/004979 | | 1/2007 | ..... A61K 38/00 |
| WO | WO 2007/004979 | A1 | 1/2007 | |
| WO | 2007/018563 | A2 | 2/2007 | |
| WO | WO 2007/044362 | A2 | 4/2007 | |
| WO | WO-2007044362 | | 4/2007 | |
| WO | WO 2007/089584 | A2 | 8/2007 | |
| WO | WO 2007/089611 | A2 | 8/2007 | |
| WO | WO-2007089584 | | 8/2007 | |
| WO | 2007/117438 | A2 | 10/2007 | |
| WO | WO 2007/123402 | A2 | 11/2007 | |
| WO | WO 2007/135105 | | 11/2007 | ..... C12N 15/11 |
| WO | WO 2007/135105 | A1 | 11/2007 | |
| WO | WO-2007123402 | | 11/2007 | |
| WO | WO 2008/011170 | | 1/2008 | ..... C12Q 1/68 |
| WO | WO 2008/011170 | A2 | 1/2008 | |
| WO | WO 2008/043561 | | 4/2008 | ..... A61K 48/00 |
| WO | WO 2008/043561 | A2 | 4/2008 | |

OTHER PUBLICATIONS

Wilton.*

Reitter. Brain & Development. 1995, 17 (suppl): 39-43.*

Takeshima. Pediatric Research. vol. 59, Bo. 5, 2006. pp. 690-694.* van Deutekon et al. Human Molecular Genetics, 2001, vol. 10, No. 15. a547-1554.*

Aartsma-Rus et al. Am. J. Hu. Genet. 74: 83-92, 2004.*

Aartsma-Rus et al. Molecular Therapy. vol. 17, No. 3. pp. 548-551.*

Aarstsma-Rus et al., "Theoretic applicability of antisense-mediated exon skipping for Duchenne muscular dystrophy mutations," Hum. Mutat. 30(3):293-299 (2009).

Aartsma-Rus et al., "Antisense-induced exon skipping for duplications in Duchenne muscular dystrophy," BMC Med. Genet. 8:43 (2007).

Aartsma-Rus et al., "Antisense-induced multiexon skipping for Duchenne muscular dystrophy makes more sense," Am. J. Hum. Genet. 74(1):83-92 (2004) (Epub Dec. 16, 2003).

Aartsma-Rus et al., "Antisense-mediated exon skipping: a versatile tool with therapeutic and research applications ," RNA 13(10):1609-1624 (2007).

Aartsma-Rus et al., "Comparative analysis of antisense oligonucleotide analogs for targeted DMD exon 46 skipping in muscle cells," Gene Ther. 11(18):1391-1398 (2004).

(56) References Cited

OTHER PUBLICATIONS

Aartsma-Rus et al., "Exploring the frontiers of therapeutic exon skipping for Duchenne muscular dystrophy by double targeting within one or multiple exons," Mol. Ther. 14(3):401-407 (2006) (Epub Jun. 6, 2006).
Aartsma-Rus et al., "Functional analysis of 114 exon-internal AONs for targeted DMD exon skipping: indication for steric hindrance of SR protein binding sites," Oligonucleotides 15(4):284-297 (2005).
Aartsma-Rus et al., "Guidelines for antisense oligonucleotide design and insight into splice-modulating mechanisms," Mol. Ther. 17(3):548-553 (2009) (Epub Sep. 23, 2008).
Aartsma-Rus et al., "Targeted exon skipping as a potential gene correction therapy for Duchenne muscular dystrophy," Neuromuscul. Disord. 12 Suppl:S71-S77 (2002).
Aartsma-Rus et al., "Therapeutic antisense-induced exon skipping in cultured muscle cells from six different DMD patients," Hum. Mol. Genet. 12(8):907-914 (2003).
Aartsma-Rus et at, "Therapeutic modulation of DMD splicing by blocking exonic splicing enhancer sites with antisense oligonucleotides," Ann. NY Acad. Sci. 1082:74-76 (2006).
Abbs et al., "A convenient multiplex PCR system for the detection of dystrophin gene deletions: a comparative analysis with cDNA hybridisation shows mistypings by both methods," J. Med. Genet. 28(5):304-311 (1991).
Abdel-Salam et al., "The anti-inflammatory effects of the phosphodiesterase inhibitor pentoxifylline in the rat," Pharmacol. Res. 47(4):331-340 (2003).
Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Academisch Ziekenhuis Leiden Responsive Motion 4 (to Add Two New Claims), 57 pages, filed Dec. 23, 2014 [Patent Interference No. 106,008 (RES)].
Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Second Declaration of Erik Sontheimer, Ph.D., 44 pages, filed Dec. 23, 2014 [Patent Interference No. 106,008 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Opposition 3 (Standing Order ¶ 203.1 and 37 C.F.R. § 41.202(a) and (e)), 20 pages, filed Feb. 17, 2015 [Patent Interference No. 106,007 (RES)].
Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Academisch Ziekenhuis Leiden List of Exhibits (as of Feb. 17, 2015) 18 pages, filed Feb. 17, 2015 [Patent Interference No. 106,008 (RES)].
Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Academisch Ziekenhuis Leiden Opposition 1 (35 U.S.C. § 112(a)), 83 pages, filed Feb. 17, 2015 [Patent Interference No. 106,008 (RES)].
Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Academisch Ziekenhuis Leiden Opposition 2 (Indefiniteness), 32 pages, filed Feb. 17, 2015 [Patent Interference No. 106,008 (RES)].
Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Academisch Ziekenhuis Leiden Opposition 3 (U.S.C. § 135(b )), 44 pages, filed Feb. 17, 2015 [Patent Interference No. 106,008 (RES)].
Academisch Ziekenhuis Leiden, *University of Western Australia* (U.S. Pat. No. 8,486,907) v. *Academisch Ziekenhuis Leiden* (U.S. Appl. No. 14/198,992), Academisch Ziekenhuis Leiden Opposition 1 (Standing Order ¶ 203.1 and 37 C.F.R. § 41.202 (a) and (e)) 20 pages, filed Feb. 17, 2015 [Patent Interference No. 106,013 (RES)].
Academisch Ziekenhuis Leiden, *University of Western Australia* (U.S. Pat. No. 8,455,636) v. *Academisch Ziekenhuis Leiden* (U.S. Appl. No. 11/233,495)[Patent Interference No. 106,007 (RES)] and *University of Western Australia* (U.S. Pat. Nos. 7,960,541 and 7,807,816) v. *Academisch Ziekenhuis Leiden* (U.S. Appl. No. 13/550,210) [Patent Interference No. 106,008 (RES)], 3rd Declaration of Erik J. Sontheimer, Ph.D. 123 pages, filed Feb. 17, 2015 [Patent Interference Nos. 106,007 and 106,008 (RES)].
Academisch Ziekenhuis Leiden, *University of Western Australia* (U.S. Pat. No. 8,455,636) v. *Academisch Ziekenhuis Leiden* (U.S. Appl. No. 11/233,495)[Patent Interference No. 106,007 (RES)] and *University of Western Australia* (U.S. Pat. Nos. 7,960,541 and 7,807,816) v. *Academisch Ziekenhuis Leiden* (U.S. Appl. No. 13/550,210)[Patent Interference No. 106,008 (RES)], Declaration of Judith Van Deutekom, 45 pages, filed Feb. 17, 2015 [Patent Interference Nos. 106,007 and 106,008 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Reply 1 (For Judgment that UWA's Claims are Unpatentable Under U.S.C. §§ 102 and 103) 17 pages, filed Apr. 3, 2015 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Reply 4 (In Support of Responsive Motion 4 to Add Two New Claims) 17 pages, filed Apr. 3, 2015, [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden List of Exhibits (as of Apr. 3, 2015) 18 pages, filed Apr. 3, 2015 [Patent Interference No. 106,007 (RES)].
Academisch Ziekenhuis Leiden, *University of Western Australia* (U.S. Pat. Nos. 7,960,541 and 7,807,816J v. *Academisch Ziekenhuis Leiden* (U.S. Appl. No. 13/550,210), Academisch Ziekenhuis Leiden Reply 1 (For Judgment that UWA's Claims are Unpatentable Under 35 U.S.C. §§ 102 and 103) 17 pages, filed Apr. 3, 2015 [Patent Interference No. 106,008 (RES)].
Academisch Ziekenhuis Leiden, *University of Western Australia* (U.S. Pat. Nos. 7,960,541 and 7,807,816J v. *Academisch Ziekenhuis Leiden* (U.S. Appl. No. 13/550,210), Academisch Ziekenhuis Leiden Reply 2 (To Deny the Benefit of AU 2004903474) 12 pages, filed Apr. 3, 2015 [Patent Interference No. 106,008 (RES)].
Academisch Ziekenhuis Leiden, *University of Western Australia* (U.S. Pat. Nos. 7,960,541 and 7,807,816J v. *Academisch Ziekenhuis Leiden* (U.S. Appl. No. 13/550,210), Academisch Ziekenhuis Leiden Reply 3 (For Judgment of Unpatentability based on Myriad) 13 pages, filed Apr. 3, 2015 [Patent Interference No. 106,008 (RES)].
Academisch Ziekenhuis Leiden, *University of Western Australia* (U.S. Pat. Nos. 7,960,541 and 7,807,816J v. *Academisch Ziekenhuis Leiden* (U.S. Appl. No. 13/550,210), Academisch Ziekenhuis Leiden Reply 4 (In Support of Responsive Motion 4 to Add Two New Claims) 17 pages, filed Apr. 3, 2015 [Patent Interference No. 106,008 (RES)].
Academisch Ziekenhuis Leiden, *University of Western Australia* (U.S. Pat. Nos. 7,960,541 and 7,807,816J v. *Academisch Ziekenhuis Leiden* (U.S. Appl. No. 13/550,210), Academisch Ziekenhuis Leiden List of Exhibits (as of Apr. 3, 2015) 18 pages, filed Apr. 3, 2015 [Patent Interference No. 106,008 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Request for Oral Argument, 3 pages, filed Apr. 10, 2015 [Patent Interference No. 106,007 (RES)].
Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Academisch Ziekenhuis Leiden Request for Oral Argument, 3 pages, filed Apr. 10, 2015 [Patent Interference No. 106,008 (RES)].
Agrawal and Kandimalla, "Antisense therapeutics: is it as simple as complementary base recognition?" Mol. Med. Today 6(2):72-81 (2000).
Alter et al., "Systemic delivery of morpholino oligonucleotide restores dystrophin expression bodywide and improves dystrophic pathology," Nat. Med. 12(2):175-177 (2006) (Epub Jan. 29, 2006).

(56) References Cited

OTHER PUBLICATIONS

Alter et al., "Systemic delivery of morpholino oligonucleotide restores dystrophin expression bodywide and improves dystrophic pathology," Nat. Med. 12(2):175-177 (2006).
Anderson et al., "Correlated NOS-Imu and myf5 expression by satellite cells in mdx mouse muscle regeneration during NOS manipulation and deflazacort treatment," Neuromuscul. Disord. 13(5):388-396 (2003).
Arap et al., "Steps toward mapping the human vasculature by phage display," Nat. Med. 8(2):121-127 (2002).
Arechavala-Gomeza et al., "Comparative analysis of antisense oligonucleotide sequences for targeted skipping of exon 51 during dystrophin pre-mRNA splicing in human muscle," Hum. Gene Ther. 18(9):798-810 (2007).
Arruda, "The role of immunosuppression in gene- and cell-based treatments for duchenne muscular dystrophy," Mol. Ther. 15(6):1040-1041 (2007).
Arzumanov et al., "Inhibition of HIV-1 Tat-dependent trans activation by steric block chimeric 2'-O-methyl/LNA oligoribonucleotides," Biochemistry 40(48):14645-14654 (2001).
Austin et al., "Cloning and characterization of alternatively spliced isoforms of Dp71," Hum. Mol. Genet. 4(9):1475-1483 (1995).
Austin et al., "Expression and synthesis of alternatively spliced variants of Dp71 in adult human brain," Neuromuscul. Disord. 10(3):187-193 (2000).
Barabino et al., "Antisense probes targeted to an internal domain in U2 snRNP specifically inhibit the second step of pre-mRNA splicing," Nucleic Acids Res. 20(17):4457-4464 (1992).
Barany, "The ligase chain reaction in a PCR world," PCR Methods Appl. 1(1):5-16 (1991).
Beggs et al., "Detection of 98% of DMD/BMD gene deletions by polymerase chain reaction," Hum. Genet. 86(1):45-48 (1990).
Bijvoet et al., "Recombinant human acid alpha-glucosidase: high level production in mouse milk, biochemical characteristics, correction of enzyme deficiency in GSDII KO mice," Hum. Mol. Genet. 7(11):1815-1824 (1998).
Bremmer-Bout et al., "Targeted exon skipping in transgenic hDMD mice: A model for direct preclinical screening of human-specific antisense oligonucleotides," Mol. Ther. 10(2):232-240 (2004).
Brett et al., "EST comparison indicates 38% of human mRNAs contain possible alternative splice forms," FEBS Lett. 474(1):83-86 (2000).
Brown et al., "Gene delivery with synthetic (non viral) carriers," Int. J. Pharm. 229(1-2):1-21 (2001). (Abstract).
Brown et al., "Structure and mutation of the dystrophin gene" in Dystrophin: Gene, protein and cell biology, (Brown and Lucy, eds). Cambridge University Press, Cambridge, 1997, pp. 1-16.
Buck et al., "Design strategies and performance of custom DNA sequencing primers," Biotechniques 27(3):528-536 (1999).
Burnett et al., "DNA sequence-specific polyamides alleviate transcription inhibition associated with long GAA.TTC repeats in Friedreich's ataxia," Proc. Natl. Acad. Sci. U.S.A. 103(31):11497-11502 (2006) (Epub Jul. 20, 2006).
Caplen et al., "Rescue of polyglutamine-mediated cytotoxicity by double-stranded RNA-mediated RNA interference," Hum. Mol. Genet. 11(2):175-184 (2002).
Cartegni et al., "Listening to silence and understanding nonsense: exonic mutations that affect splicing," Nat. Rev. Genet. 3(4):285-298 (2002). (Abstract).
Chamberlain, "Dystrophin Levels Required for Genetic Correction of Duchenne Muscular Dystrophy," Basic Appl Myol. 7(3&4):251-255 (1997).
Chaubourt et al., "Muscular nitric oxide synthase (muNOS) and utrophin," J. Physiol. Paris 96(1-2):43-52 (2002).
Coulter et al., "Identification of a new class of exonic splicing enhancers by in vivo selection," Mol. Cell. Biol. 17(4):2143-2150 (1997).
Dahlqvist et al., "Functional Notch signaling is required for BMP4-induced inhibition of myogenic differentiation," Development 130(24):6089-6099 (2003).
De Angelis et al., "Chimeric snRNA molecules carrying antisense sequences against the splice junctions of exon 51 of the dystrophin pre-mRNA induce exon skipping and restoration of a dystrophin synthesis in Delta 48-50 DMD cells," Proc. Natl. Acad. Sci. U.S.A. 99(14):9456-9461 (2002) (Epub Jun. 20, 2002).
De Luca et al., "Beneficial Effects of Pentoxifylline on Dystrophie Progression of MDX Mice," Acta Pharmacologica Sinica, P090015, Supp. 1, vol. 27, p. 138, 2006.
Declaration of Dr. Adrian Kramer (submitted in Third Party's Stmt for JP Appl. No. 2002-529499, dated Oct. 29, 2010.
Denny et al., "Oligo-riboprobes. Tools for in situ hybridisation," Histochemistry 89(5):481-493 (1988).
Dickson, et al., "Screening for antisense modulation of dystrophin pre-mRNA splicing," Neuromuscul. Disord. Suppl 1:S67-S70 (2002).
Dirkson et al., "Mapping the SF2/ASF binding sites in the bovine growth hormone exonic splicing enhancer," J. Biol. Chem. 275(37):29170-29177 (2000).
Dorchies et al., "Green tea extract and its major polyphenol (−)-epigallocatechin gallate improve muscle function in a mouse model for Duchenne muscular dystrophy," Am. J. Physiol. Cell Physiol. 290(2): C616-C625 (2006).
Duboc et al., "Effect of perindopril on the onset and progression of left ventricular dysfunction in Duchenne muscular dystrophy," J. Am. Coll. Cardiol. 45(6):855-857 (2005).
Dunckley et al., "Modification of splicing in the dystrophin gene in cultured Mdx muscle cells by antisense oligoribonucleotides," Hum. Mol. Genet. 5(1):1083-1090 (1995).
Dunckley et at, "Modulation of Splicing in the DMD Gene by Antisense Oligoribonucleotides," Nucleosides & Nucleotides 16(7-9):1665-1668 (1997).
El-Andaloussi et al., "Induction of splice correction by cell-penetrating peptide nucleic acids," J. Gene Med. 8(10):1262-1273 (2006). (Abstract).
Erba et al., "Structure, chromosome location, and expression of the human gamma-actin gene: differential evolution, location, and expression of the cytoskeletal beta- and gamma-actin genes," Mol. Cell. Biol. 8(4):1775-1789 (1988).
Errington et al., "Target selection for antisense oligonucleotide induced exon skipping in the dystrophin gene," J. Gene Med. 5(6):518-527 (2003).
European Patent Office Action regarding European Patent Application No. EP 05 076 770.6 dated Jan. 29, 2007, 5 pages.
Fernandes et al., "Pentoxifylline reduces pro-inflammatory and increases anti-inflammatory activity in patients with coronary artery disease—a randomized placebo-controlled study," Atherosclerosis 196(1):434-442 (2008) (Epub Dec. 28, 2006).
Fluiter et al., "In vivo tumor growth inhibition and biodistribution studies of locked nucleic acid (LNA) antisense oligonucleotides," Nucleic Acids Res. 31(3):953-962 (2003).
Fu et al., "An unstable triplet repeat in a gene related to myotonic muscular dystrophy," Science 255(5049):1256-1258 (1992).
Furling et al., "Viral vector producing antisense RNA restores myotonic dystrophy myoblast functions," Gene Ther. 10(9):795-802 (2003).
Galderisi et al., "Myotonic dystrophy: antisense oligonucleotide inhibition of DMPK gene expression in vitro," Biochem. Biophys. Res. Commun. 221(3):750-754 (1996).
Garcia-Blanco et al., "Alternative splicing in disease and therapy," Nat. Biotechnol. 22(5):535-546 (2004).
Gen Bank accession No. AZ993191.1, 2M0278E12F mouse 10kb plasmid UUGC2M library Mus muscu genomic clone UUGC2M0278E12F, genomic survey sequence, entry created and last updated on Apr. 27, 2001.
Ghosh et al., "Mannose 6-phosphate receptors: new twists in the tale," Nat. Rev. Mol. Cell Biol. 4(3):202-212 (2003).
Ginjaar et al., "Dystrophin nonsense mutation induces different levels of exon 29 skipping and leads to variable phenotypes within one BMD family," Eur. J. Hum. Genet. 8(10):793-796 (2000).
Gollins et al., "High-efficiency plasmid gene transfer into dystrophic muscle," Gene Ther. 10(6):504-512 (2003).
Granchelli et al., "Pre-clinical screening of drugs using the mdx mouse," Neuromuscul. Disord. 10(4-5):235-239 (2000).

(56) References Cited

OTHER PUBLICATIONS

Gryaznov, "Oligonucleotide N3'-→P5' phosphoramidates as potential therapeutic agents," Biochem. Biophys. Acta 1489(1):131-140 (1999).
Hagiwara et al., "A novel point mutation (G-1 to T) in a 5' splice donor site of intron 13 of the dystrophin gene results in exon skipping and is responsible for Becker muscular dystrophy," Am. J. Hum Genet. 54(1):53-61 (1994).
Handa et al., "The AUUCU repeats responsible for spinocerebellar ataxia type 10 form unusual RNA hairpins," J. Biol. Chem. 280(32):29340-29345 (2005) (Epub Jun. 20, 2005).
Hasholt et al., "Antisense downregulation of mutant huntingtin in a cell model," J. Gene Med. 5(6):528-538 (2003).
Hassan, "Keys to the Hidden Treasures of the Mannose 6-Phosphate/Insulin-Like Growth Factor 2 Receptor," Am. J. Pathol. 162(1):3-6 (2003).
Hoffman et al., "Somatic reversion/suppression of the mouse mdx phenotype in vivo," J. Neurol. Sci. 99(1):9-25 (1990).
Hoffman, "Skipping toward personalized molecular medicine," N. Engl. J. Med. 357(26):2719-2722 (2007).
Hope for muscular dystrophy drug, The Daily Telegraph, Dec. 28, 2007.
Hussey et al., "Analysis of five Duchenne muscular dystrophy exons and gender determination using conventional duplex polymerase chain reaction on single cells," Mol. Hum. Reprod. 5(11):1089-1094 (1999).
Iezzi et al., "Deacetylase inhibitors increase muscle cell size by promoting myoblast recruitment and fusion through induction of follistatin," Dev. Cell 6(5):673-684 (2004).
Ikezawa et al., "Dystrophin gene analysis on 130 patients with Duchenne muscular dystrophy with a special reference to muscle mRNA analysis," Brain Dev. 20(3):165-168 (1998).
International Preliminary Report on Patentability and Written Opinion for PCT/EP2007/054842, dated Nov. 21, 2008, 8 pages.
International Search Report for PCT/EP2007/054842, dated Aug. 21, 2007, 3 pages.
Ito et al., "Purine-rich exon sequences are not necessarily splicing enhancer sequence in the dystrophin gene," Kobe J. Med. Sci. 47(5):193-202 (2001).
Karras et al., "Deletion of individual exons and induction of soluble murine interleukin-5 receptor-alpha chain expression through antisense oligonucleotide-mediated redirection of pre-mRNA splicing," Mol. Pharmacol. 58(2):380-387 (2000).
Kendall et al., "Dantrolene Enhances Antisense-Mediated Exon Skipping in Human and Mouse Models of Duchenne Muscular Dystrophy," Sci. Transl. Med. 4:164ra160 (2012).
Kerr et al., "BMP regulates skeletal myogenesis at two steps," Molecular and Cellular Proteomics, American Society for Biochemistry and Molecular Biology 2(9):976 (2003).
Kinali et al., "Local restoration of dystrophin expression with the morpholino oligomer AVI-4658 in Duchenne muscular dystrophy: a single-blind, placebo-controlled, dose-escalation, proof-of-concept study," Lancet Neurol. 8(10):918-928 (2009) (Epub Aug. 25, 2009).
Kuhihara et al., "Muscular Disorders," Review/Advances in Neurological Therapeutics, 5 pages, 2000.
Kuhihara et al., "Muscular Disorders," Review/Advances in Neurological Therapeutics, 4 pages, 2000 (English Translation).
Kurrek et al., "Design of antisense oligonucleotides stabilized by locked nucleic acids," Nucleic Acids Res. 30(9):1911-1918 (2002).
Langlois et al., "Hammerhead ribozyme-mediated destruction of nuclear foci in myotonic dystrophy myoblasts," Mol. Ther. 7(5 Pt 1):670-680 (2003).
Laptev et al., "Specific inhibition of expression of a human collagen gene (COL1A1) with modified antisense oligonucleotides. The most effective target sites are clustered in double-stranded regions of the predicted secondary structure for the mRNA," Biochemistry 33(36):11033-11039 (1994).
Lee et al., "Receptor mediated uptake of peptides that bind the human transferrin receptor," Eur. J. Biochem. 268(7):2004-2012 (2001).
Letter from Katholieke Universiteit Leuven to Dr. N. Goemans, Child Neurology, UZ dated Jan. 22, 2008, regarding a Phase 1/11, open label, escalating dose, pilot study to assess the effect, safety, tolerability and pharmacokinetics of multiple subcutaneous doses of PR0051 in patients with Duchenne muscular dystrophy. PR0051-02 (translation provided).
Letter from Prosensa Therapeutics B.V. to Federal Agency for Medicines and Health Products dated Jan. 9, 2008, regarding A Phase 1/11, open label, escalating dose, pilot study to assess the effect, safety, tolerability and pharmacokinetics of multiple subcutaneous doses of PRO051 in patients with Duchenne muscular dystrophy.
Liu et al., "A mechanism for exon skipping caused by nonsense or missense mutations in BRCA1 and other genes," Nat. Genet. 27(1):55-58 (2001).
Liu et al., "Identification of functional exonic splicing enhancer motifs recognized by individual SR proteins," Genes Dev. 12(13):1998-2012 (1998).
Liu et al., "Specific inhibition of Huntington's disease gene expression by siRNAs in cultured cells," Proc. Japan Acad. 79(Ser. B):293-298 (2003).
Lu et al., "Functional amounts of dystrophin produced by skipping the mutated exon in the mdx dystrophic mouse," Nat. Med. 9(8):1009-1014 (2003) (Epub Jul. 6, 2003).
Lu et al., "Massive idiosyncratic exon skipping corrects the nonsense mutation in dystrophic mouse muscle and produces functional revertant fibers by clonal expansion," J. Cell Biol. 148(5):985-996 (2000).
Lu et al., "Non-viral gene delivery in skeletal muscle: a protein factory," Gene Ther. 10(2):131-142 (2003).
Lu et al., "Systemic delivery of antisense oligoribonucleotide restores dystrophin expression in body-wide skeletal muscles," Proc. Natl. Acad. Sci. U.S.A. 102(1):198-203 (2005) (Epub Dec. 17, 2004).
LUMC and Prosensa report positive results of DMD study, Pharmaceutical Business Review Online, dated Dec. 28, 2007, <http://www.pharmaceutical-business-review.com/article_news_ rint.as?uid=8462FD44-F35D-4EOB-BC>.
Mann et al., "Antisense-induced exon skipping and synthesis of dystrophin in the mdx mouse," Proc. Natl. Acad. Sci. U.S.A. 98(1):42-47 (2001).
Mann et al., "Improved antisense oligonucleotide induced exon skipping in the mdx mouse model of muscular dystrophy," J. Gene Med. 4(6):644-654 (2002).
Martiniuk et al., "Correction of glycogen storage disease type II by enzyme replacement with a recombinant human acid maltase produced by over-expression in a CHO-DHFR(neg) cell line," Biochem. Biophys. Res. Commun. 276(3):917-923 (2000). (Abstract).
Matsuo et al., "Exon skipping during splicing of dystrophin mRNA precursor due to an intraexon deletion in the dystrophin gene of Duchenne muscular dystrophy kobe," J. Clin. Invest. 87(6):2127-2131 (1991).
Matsuo et al., "Partial deletion of a dystrophin gene leads to exon skipping and to loss of an intra-exon hairpin structure from the predicted mRNA precursor," Biochem. Biophys. Res. Commun. 182(2):495-500 (1992).
Matsuo, et al., "Duchenne/Becker muscular dystrophy: from molecular diagnosis to gene therapy," Brain Dev. 18(3):167-172 (1996).
McClorey et al., "Induced dystrophin exon skipping in human muscle explants," Neuromuscul. Disord. 16(9-10):583-590 (2006) (Epub Aug. 21, 2006).
Monaco et al., "An explanation for the phenotypic differences between patients bearing partial deletions of the DMD locus," Genomics 2(1):90-95 (1988).
Moon et. al., "Target site search and effective inhibition of leukaemic cell growth by a covalently closed multiple anti-sense oligonucleotide to c-myb," Biochem. J. 346 Pt 2:295-303 (2000).
Munroe, "Antisense RNA inhibits splicing of pre-mRNA in vitro," EMBO J. 7(8):2523-2532 (1988).
Muntoni et al., "A mutation in the dystrophin gene selectively affecting dystrophin expression in the heart," J. Clin Invest. 96(2):693-699 (1995).

(56) References Cited

OTHER PUBLICATIONS

New Clinical Trial Results Show How Personalized Medicine Will Alter Treatment of Genetic Disorders, Medical News Today, Dec. 29, 2007 <http://www.medicalnewstoday.com/article/92777.PhP>.
Nishio et al., "Identification of a novel first exon in the human dystrophin gene and of a new promoter located more than 500 kb upstream of the nearest known promoter," J. Clin. Invest. 94(3):1037-1042 (1994).
Opalinska and Gewirtz, "Nucleic-acid therapeutics: basic principles and recent applications," Nat. Rev. Drug. Discov. 1(7):503-514 (2002).
O'Shaughnessy et al., "Superior survival with capecitabine plus docetaxel combination therapy in anthracycline-pretreated patients with advanced breast cancer: phase III trial results," J. Clin. Oncol. 20(12):2812-2823 (2002).
Patel et al., "The function of Myostatin and strategies of Myostatin blockade-new hope for therapies aimed at promoting growth of skeletal muscle," Neuromuscul. Disord. 15(2):117-126 (2005) (Epub Jan. 11, 2005).
Patentee's response during prosecution of opposed patent, dated Jan. 27, 2010.
Politano et al., "Gentamicin administration in Duchenne patients with premature stop codon. Preliminary results," Acta Myol. 22(1):15-21 (2003) (Epub Jan. 29, 2006).
Pramono et al., "Induction of exon skipping of the dystrophin transcript in lymphoblastoid cells by transfecting an antisense oligodeoxynucleotide complementary to an exon recognition sequence," Biochem. Biophys. Res. Commun. 226(2):445-449 (1996). (Abstract).
Radley et al., "Duchenne muscular dystrophy: focus on pharmaceutical and nutritional interventions," Int. J. Biochem. Cell Biol. 39(3):469-477 (2007) (Epub Oct. 10, 2006).
Rando, "Oligonucleotide-mediated gene therapy for muscular dystrophies," Neuromuscul. Disord. 12 Suppl 1:S55-S60 (2002).
Reitter, "Deflazacort vs. prednisone in Duchenne muscular dystrophy: trends of an ongoing study," Brain Dev. 17(suppl):39-43 (1995).
Reuser et al., "Uptake and stability of human and bovine acid alpha-glucosidase in cultured fibroblasts and skeletal muscle cells from glycogenosis type II patients," Exp. Cell Res. 155(1):178-189 (1984).
Roberts et al., "Exon structure of the human dystrophin gene," Genomics 16(2):536-538 (1993).
Roberts et al., "Exon structure of the human dystrophin gene," Lancet 336(8730):1523-1526 (1990).
Roberts et al., "Searching for the 1 in 2,400,000: a review of dystrophin gene point mutations," Hum. Mutat. 4(1):1-11 (1994).
Rolland et at, "Overactivity of exercise-sensitive cation channels and their impaired modulation by IGF-1 in mdx native muscle fibers: beneficial effect of pentoxifylline," Neurobiol. Dis. 24(3):466-474 (2006) (Epub Sep. 28, 2006).
Rosen et al., "Combination chemotherapy and radiation therapy in the treatment of metastatic osteogenic sarcoma," Cancer 35(3):622-630 (1975).
Rosen et al., "Effect of perindopril on the onset and progression of left ventricular dysfunction in Duchenne muscular dystrophy," Cancer 35(3):622-630 (1975).
Samoylova et al., "Elucidation of muscle-binding peptides by phage display screening," Muscle Nerve 22(4):460-466 (1999).
Scanlon, "Anti-genes: siRNA, ribozymes and antisense," Curr. Pharm. Biotechnol. 5(5):415-420 (2004).
Ségalat et al., "CAPON expression in skeletal muscle is regulated by position, repair, NOS activity, and dystrophy," Exp. Cell Res. 302(2):170-179 (2005).
Sertić et al., "Deletion screening of the Duchenne/Becker muscular dystrophy gene in Croatian population," Coll. Antropol. 21(1):151-156 (1997).
Shapiro and Senapathy, "RNA splice junctions of different classes of eukaryotes: sequence statistics and functional implications in gene expression," Nucleic Acids Res. 15(17):7155-7174 (1987).
Sherratt et al., "Exon skipping and translation in patients with frameshift deletions in the dystrophin gene," Am. J. Hum. Genet. 53(5):1007-1015 (1993).
Shiga et al., "Disruption of the splicing enhancer sequence within exon 27 of the dystrophin gene by a nonsense mutation induces partial skipping of the exon and is responsible for Becker muscular dystrophy," J. Clin. Invest. 100(9):2204-2210 (1997).
Simões-Wüst et al., "Bcl-xl antisense treatment induces apoptosis in breast carcinoma cells," Int. J. Cancer 87(4):582-590 (2000).
Smith et al., "Muscle-specific peptide #5", Mar. 23, 1999. From http://www.ebi.ac.uk/cgi-bin/epo/epofetch?AAW89659, downloaded Jul. 16, 2007.
Squires, "An Introduction to Nucleoside and Nucleotide Analogues," Antivir. Ther. 6 (Suppl 3):1-14 (2001).
Sterrenburg et al., "Gene expression profiling highlights defective myogenesis in DMD patients and a possible role for bone morphogenetic protein 4," Neurobiol. Dis. 23(1):228-236 (2006) (Epub May 6, 2006).
Summerton et al., "Morpholino Antisense Oligomers: Design, Preparation, and Properties," Antisense Nucleic Acid Drug Dev. 7(3):187-195 (1997).
Surono et al., "Chimeric RNA/ethylene-bridged nucleic acids promote dystrophin expression in myocytes of duchenne muscular dystrophy by inducing skipping of the nonsense mutation-encoding exon," Hum. Gene Ther. 15(8):749-757 (2004).
Surono et al., "Six novel transcripts that remove a huge intron ranging from 250 to 800 kb are produced by alternative splicing of the 5' region of the dystrophin gene in human skeletal muscle," Biochem. Biophys. Res. Commun. 239(3):895-899 (1997).
Suter et al., "Double-target antisense U7 snRNAs promote efficient skipping of an aberrant exon in three human beta-thalassemic mutations," Hum. Mol. Genet. 8(13):2415-2423 (1999).
Suwanmanee et al., "Restoration of human beta-globin gene expression in murine and human IVS2-654 thalassemic erythroid cells by free uptake of antisense oligonucleotides," Mol. Pharmacol. 62(3):545-553 (2002).
Takashima et al., "Oligonucleotides against a splicing enhancer sequence led to dystrophin production in muscle cells from a Duchenne muscular dystrophy patient," Brain Dev. 23(8):788-790 (2001).
Takeshima et al., "Basic research for treatment of Duchene muscular dystrophy using induction of exon skipping by means of antisense oligo DNA: effect of in vivo administration in mice," Park IP Translations, vol. 15, No. 2, 6 pages, Nov. 2009.
Takeshima et al., "Intravenous infusion of an antisense oligonucleotide results in exon skipping in muscle dystrophin mRNA of Duchenne muscular dystrophy," Pediatr. Res. 59(5):690-694 (2006).
Takeshima et al., "Modulation of in vitro splicing of the upstream intron by modifying an intra-exon sequence which is deleted from the dystrophin gene in dystrophin Kobe.," J. Clin. Invest. 95(2):515-520 (1995).
Tanaka et al., "Polypurine sequences within a downstream exon function as a splicing enhancer," Mol. Cell. Biol. 14(2):1347-1354 (1994).
Thanh et al., "Characterization of revertant muscle fibers in Duchenne muscular dystrophy, using exon-specific monoclonal antibodies against dystrophin," Am. J. Hum. Genet. 56(3):725-731 (1995).
Tian and Kole, "Selection of novel exon recognition elements from a pool of random sequences," Mol. Cell. Biol. 15(11):6291-6298 (1995).
TREAT-NMD Neuromuscular Network, Jan. 11, 2008.
Tsuchida, "The role of myostatin and bone morphogenetic proteins in muscular disorders," Expert Opin. Biol. Ther. 6(2):147-153 (2006).
University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Motion 3 (for judgment that Claims 11-12, 14-15, and 17-29 of U.S. Appl. No. 13/550,210 are barred under 35 U.S.C. §135(b)); 25 pages, filed Nov. 18, 2014 [Patent Interference No. 106,008].
University of Western Australia, *University of Western Australia* (U.S. Pat. Nos. 7,960,541 and 7,807,816) v. *Academisch Ziekenhuis Leiden* (U.S. Appl. No. 13/550,210), University of Western Austra-

(56) References Cited

OTHER PUBLICATIONS lia Motion 2 (for Judgment Under 35 U.S.C. §112(b)), 32 pages, filed Nov. 18, 2014 [Patent Interference No. 106,008 (RES)].
University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Motion 1 (for Judgment Under 35 U.S.C. §112(a)), 38 pages, filed Nov. 18, 2014 [Patent Interference No. 106,008 (RES)].
University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Exhibit List as of Feb. 17, 2015, 8 pages, filed Feb. 17, 2015 [Patent Interference No. 106,008 (RES)].
University of Western Australia, *University of Western Australia* (U.S. Pat. Nos. 7,960,541 and 7,807,816) v.*Academisch Ziekenhuis Leiden* (U.S. Appl. No. 13/550,210), University of Western Australia Opposition 1 (Regarding Patentability Under 35 U.S.C. § 102/103), 39 pages, filed Feb. 17, 2015 [Patent Interference No. 106,008 (RES)].
University of Western Australia, *University of Western Australia* (U.S. Pat. Nos. 7,960,541 and 7,807,816) v. *Academisch Ziekenhuis Leiden* (U.S. Appl. No. 13/550,210) University of Western Australia Opposition 2 (To Retain UWA's Benefit of AU 2004903474), 31 pages, filed Feb. 17, 2015 [Patent Interference No. 106,008 (RES)].
University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Opposition 3 (Regarding Patentability Under 35 U.S.C. § 101), 22 pages, filed Feb. 17, 2015 [Patent Interference No. 106,008 (RES)].
University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Opposition 4 (To deny entry of AZL's Proposed New Claims 30 and 31), 36 pages, filed Feb. 17, 2015 [Patent Interference No. 106,008 (RES)].
University of Western Australia, *University of Western Australia* (U.S. Pat. No. 8,455,636) v. *Academisch Ziekenhuis Leiden* (U.S. Appl. No. 11/233,495)[Patent Interference No. 106,007 (RES)] and *University of Western Australia* (U.S. Pat. Nos. 7,960,541 and 7,807,816) v. *Academisch Ziekenhuis Leiden* (U.S. Appl. No. 13/550,210) [Patent Interference No. 106,008 (RES)], Second Declaration of Matthew J.A. Wood, M.D., D. Phil., 78 pages, filed Feb. 17, 2015.
University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Objections (to Opposition Evidence) 15 pages, filed Feb. 24, 2015 [Patent Interference No. 106,008 (RES)].
University of Western Australia, *University of Western Australia* (U.S. Pat. No. 8,455,636) v. *Academisch Ziekenhuis Leiden* (U.S. Appl. No. 11/233,495), University of Western Australia Reply 1 (to AZL Opposition 1) 28 pages, filed Apr. 3, 2015 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Reply 2 (to AZL Opposition 2) 22 pages, filed Apr. 3, 2015 [Patent Interference No. 106,007 (RES)].
University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Reply 1 (to AZL Opposition 1) 28 pages, filed Apr. 3, 2015 [Patent Interference No. 106,008 (RES)].
University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Reply 2 (to AZL Opposition 2) 22 pages, filed Apr. 3, 2015 [Patent Interference No. 106,008 (RES)].
University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Reply 3 (for judgment under 35 U.S.C. §135(b)) 19 pages, filed Apr. 3, 2015 [Patent Interference No. 106,008 (RES)].
University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Exhibit List, 10 pages, filed Apr. 3, 2015 [Patent Interference No. 106,008 (RES)].
University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Request for Oral Argument, 4 pages, filed Apr. 10, 2015 [Patent Interference No. 106,008 (RES)].
University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Miscellaneous Motion 4 (to exclude evidence), 21 pages, filed Apr. 10, 2015 [Patent Interference No. 106,008 (RES)].
University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Exhibit List, 10 pages, filed Apr. 10, 2015 [Patent Interference No. 106,008 (RES)].
Van Deutekom et al., "Advances in Duchenne muscular dystrophy gene therapy," Nat. Rev. Genet. 4(10):774-783 (2003).
Van Deutekom et al., "Antisense-induced exon skipping restores dystrophin expression in DMD patient derived muscle cells," Hum. Mol. Genet. 10(15):1547-54. (2001).
Van Deutekom et al., "Local dystrophin restoration with antisense oligonucleotide PRO051," N. Engl. J. Med. 357(26):2677-2686 (2007).
Van Ommen, "The Therapeutic Potential of Antisense-Mediated Exon-Skipping," Curr. Opin. Mol. Ther. 10(2):140-149 (2008).
Van Vliet et al., "Assessment of the feasibility of exon 45-55 multiexon skipping for Duchenne muscular dystrophy," BMC Med. Genet. 9:105 (2008).
Varani et al. "The G.U. wobble base pair: A fundamental building block of RNA structure crucial to RNA function in diverse biological systems." EMBO Reports 1:18-23 (2000).
Verhaart et al., "Prednisolone treatment does not interfere with 2'-0-methyl phosphorothioate antisense-mediated exon skipping in Duchenne muscular dystrophy," Hum. Gene Ther. 23(3):262-273 (2012) (Epub Jan. 26, 2012).
Verreault et al., "Gene silencing in the development of personalized cancer treatment: the targets, the agents and the delivery systems.," Curr. Gene Ther. 6(4):505-533 (2006).
Vickers et al., "Efficient reduction of target RNAs by small interfering RNA and RNase H-dependent antisense agents. A comparative analysis," J. Biol. Chem. 278(9):7108-7118 (2003) (Epub Dec. 23, 2002).
Wang et al., "Adeno-associated virus vector carrying human minidystrophin genes effectively ameliorates muscular dystrophy in mdx mouse model," Proc. Natl. Acad. Sci. U.S.A. 97(25):13714-13719 (2000).
Watakabe et al., "The role of exon sequences in splice site selection," Genes Dev. 7(3):407-418 (1993).
Weisbart et al., "Cell type specific targeted intracellular delivery into muscle of a monoclonal antibody that binds myosin IIb," Mol. Immunol. 39(13):783-789 (2003). (Abstract).
Wells et al., "Enhanced in vivo delivery of antisense oligonucleotides to restore dystrophin expression in adult mdx mouse muscle," FEBS Lett. 552(2-3):145-149 (2003).
Wenk et al., "Quantitation of Mr 46000 and Mr 300000 mannose 6-phosphate receptors in human cells and tissues," Biochem. Int. 23(4):723-731 (1991) (Abstract).
Wheway and Roberts, "The dystrophin lymphocyte promoter revisited: 4.5-megabase intron, or artifact?" Neuromuscul. Disord. 13(1):17-20 (2003).
Wilton and Fletcher, "Antisense oligonucleotides, exon skipping and the dystrophin gene transcript," Acta Myol. 24(3):222-229 (2005).

(56) References Cited

OTHER PUBLICATIONS

Wilton et al., "Antisense oligonucleotide-induced exon skipping across the human dystrophin gene transcript," Mol. Ther. 15(7):1288-1296 (2007) (Epub Feb. 6, 2007).
Wilton et al., "Specific removal of the nonsense mutation from the mdx dystrophin mRNA using antisense oligonucleotides," Neuromuscul. Disord. 9(5):330-338 (1999).
Xu et al., "Potential for pharmacology of ryanodine receptor/calcium release channels," Ann. NY Acad. Sci. 853:130-148 (1998).
Yen et al., "Sequence-specific cleavage of Huntingtin mRNA by catalytic DNA," Ann. Neurol. 46(3):366-373 (1999).
Yin et al., "Effective exon skipping and restoration of dystrophin expression by peptide nucleic acid antisense oligonucleotides in mdx mice," Mol. Ther. 16(1):38-45 (2008) (Epub Oct. 30, 2007).
Zhang et al., "Efficient expression of naked dna delivered intraarterially to limb muscles of nonhuman primates," Hum. Gene Ther. 12(4):427-438 (2001). (Abstract).
Zhou et al., "Current understanding of dystrophin-related muscular dystrophy and therapeutic challenges ahead," Chin. Med. J. (Engl.) 119(16):1381-1391 (2006).
United States Patent and Trademark Office Final Office Action for U.S. Appl. No. 14/990,712, dated Jul. 21, 2017 (20 pages).
United States Patent and Trademark Office Non-Final Office Action for U.S. Appl. No. 14/990,712, dated Nov. 14, 2016 (20 pages).
Beenakker et al., "Intermittent prednisone therapy in Duchenne muscular dystrophy: a randomized controlled trial," Arch. Neurol. 62(1):128-132 (2005).
Biggar et al., "Deflazacort in Duchenne muscular dystrophy: a comparison of two different protocols," Neuromuscul. Disord. 14(8-9):476-482 (2004).
Cirak et al., "Exon skipping and dystrophin restoration in patients with Duchenne muscular dystrophy after systemic phosphorodiamidate morpholino oligomer treatment: an open-label, phase 2, dose-escalation study," Lancet 378 (9791)595-605 (2011) (Epub Jul. 23, 2011).
Leiden Muscular Dystrophy pages: DMD (dystrophin), 2004. Retrieved from the Internet on Jun. 26, 2018. URL: http://www.dmd.nl/DMD_home.html.
Anthony et al., "Dystrophin quantification and clinical correlations in Becker muscular dystrophy: implications for clinical trials 2011," Brain 134(12):3547-3559 (2011).
Bernasconi et al., "Cortisol increases transfection efficiency of cells," FEBS Lett. 419(1):103-106 (1997).
BioMarin Press Release, "BioMarin Announces Withdrawal of Market Authorization Application for Kyndrisa™ (drisapersen) in Europe," May 31, 2016.
Braun et al., "In vitro and in vivo effects of glucocorticoids on gene transfer to skeletal muscle," FEBS Lett. 454(3):277-282 (1999).
Bushby et al., "145th ENMC International Workshop: planning for an International Trial of Steroid Dosage Regimes in DMD (for DMD), Oct. 22-24, 2006, Naarden, The Netherlands," Neuromuscul. Disord. 17(5):423-428 (2007) (Epub Apr. 11, 2007).
Bushby et al., "Report on the 124th ENMC International Workshop. Treatment of Duchenne muscular dystrophy; defining the gold standards of management in the use of corticosteroids. Apr. 2-4, 2004, Naarden, The Netherlands," Neuromuscul. Disord. 14(8-9):526-534 (2004).
Chan et al., "Antisense oligonucleotides: from design to therapeutic application," Clin. Exp. Pharmacol. Physiol. 33(5-6):533-540 (2006).
Exondys 51™ prescribing information highlights (eteplirsen label) (dated Sep. 2016).
FDA News Release, "FDA grants accelerated approval to first drug for Duchenne muscular dystrophy," Sep. 19, 2016.
Goemans et al., "Systemic administration of PRO051 in Duchenne's muscular dystrophy," N. Engl. J. Med. 364(16):1513-1522 (2011) (Epub Mar. 23, 2011).
Goemans et al., "Comparison of ambulatory capacity and disease progression of Duchenne muscular dystrophy subjects enrolled in the drisapersen DMD114673 study with a matched natural history cohort of subjects on daily corticosteroids," Neuromuscul. Disord. 27(3):203-213 (2017) (Epub Nov. 25, 2016).
Hardiman et al., "Methylprednisolone selectively affects dystrophin expression in human muscle cultures," Neurology 43(2):342-345 (1993).
Heemskerk et al., "In vivo comparison of 2'-O-methyl phosphorothioate and morpholino antisense oligonucleotides for Duchenne muscular dystrophy exon skipping," J. Gene Med. 11(3):257-266 (2009).
Hussein et al., "The effects of glucocorticoid therapy on the inflammatory and dendritic cells in muscular dystrophies," Int. J. Exp. Pathol. 87(6):451-461 (2006).
Khan, "Corticosteroid therapy in Duchenne muscular dystrophy," J. Neurol. Sci. 120(1):8-14 (1993).
Manning et al., "What has the mdx mouse model of Duchenne muscular dystrophy contributed to our understanding of this disease?" J. Muscle Res. Cell. Motil. 36(2):155-167 (2015) (Epub Feb. 11, 2015).
Manzur et al., "Glucocorticoid corticosteroids for Duchenne muscular dystrophy (Review)," Cochrane Database of Systematic Reviews 1:1-74 (2008).
Merlini & Sabatelli, "Improving clinical trial design for Duchenne," BMC Neurology 15:153 (2015).
Moxley et al., "Practice parameter: corticosteroid treatment of Duchenne dystrophy: report of the Quality Standards Subcommittee of the American Academy of Neurology and the Practice Committee of the Child Neurology Society," Neurology 64(1):13-20 (2005).
Muntoni et al., "Steroids in Duchenne muscular dystrophy: from clinical trials to genomic research," Neuromuscul. Disord. 12 Suppl 1:S162-S165 (2002).
Muntoni et al., "128th ENMC International Workshop on 'Preclinical optimization and Phase I/II Clinical Trials Using Antisense Oligonucleotides in Duchenne Muscular Dystrophy' Oct. 22-24, 2004, Naarden, The Netherlands," Neuromuscul. Disord. 15(6):450-457 (2005).
Priority document EP 07119351.0, filed Oct. 26, 2007.
Priority document U.S. Appl. No. 61/000,670, filed Oct. 26, 2007.
U.S. Food and Drug Administration (FDA) Briefing Document to the Peripheral and Central Nervous System Drugs Advisory Committee Meeting, Nov. 24, 2015, NDA 206031, Drisapersen.
USAN Council Statement for Drisapersen.
Wehling-Henricks et al., "Prednisolone decreases cellular adhesion molecules required for inflammatory cell infiltration in dystrophin-deficient skeletal muscle," Neuromuscul. Disord. 14:483-490 (2004).
Welch et al., "PTC124 targets genetic disorders caused by nonsense mutations," 447(7140):87-91 (2007) (Epub Apr. 22, 2007).
Wuebbles et al., "Levels of α7 integrin and laminin-α2 are increased following prednisone treatment in the mdx mouse and GRMD dog models of Duchenne muscular dystrophy," Dis. Model Mech. 6(5):1175-1184 (2013).
Yagi et al. "Chimeric RNA and 2'-O, 4'-C-Ethylene-Bridged Nucleic Acids Have Stronger Activity than Phosphorothioate Oligodeoxynucleotides in Induction of Exon 19 Skipping in Systrophin mRNA," Oligonucleotides 14 (1):33-40, 2004.
Opalinska et al. "Oxetane Modified, Conformationally Constrained, Antisense Oligodeoxyribonucleotides Function Eddiciently as Gene Silencing Molecules", Nucleic Acids Research, 32(19): 5791-5799, Published Online Oct. 28, 2004.
Cartegni et al. "Correction of Disease-Associated Exon Skipping by Synthetic Exon-Specific Activators", Nature Structural Biology, 10(2): 120-125, Feb. 2003.
Dubowitz "Foreword", Neuromuscular Disorders, 12: S1-S2, 2002.
Dubowitz "Special Centennial Workshop—101st ENMC International Workshop:Therapeutic Possibilities in Duchenne Muscular Dystrophy, Nov. 30-Dec. 2, 2001, Naarden, The Netherlands", Neuromuscular Disorders, 12: 421-431, 2002.
Ginjaar et al. "Dystrophin Nonsense Mutation Induces Different Levels of Exon 29Skipping and Leads to Variable Phenotypes Within One BMD Family", European Journal ofHuman Genetics, 8: 793-796, 2000.
Morita et al. "2'-O,4'-C-Ethylene-Bridged Nucleic Acids (ENA) With Nuclease-Resistance and High Affinity for RNA", Nucleic Acids Research, Suppl.1: 241-242, 2001.

(56) References Cited

OTHER PUBLICATIONS

Harding et al., "The Influence of Antisense Oligonucleotide Length on DystrophinExon Skipping", Molecular Therapy, 15(1): 157-166, Jan. 2007.
Ito et al. "Identification of Splicing Enhancer Sequences Within Exon Sequences ofDystrophin Gene", 42nd convention of Japanese Society for Inherited Metabolic Diseases,Kagoshima, Japan, Nov. 11-13, 1999, Journal of Japanese Society for Inherited MetabolicDiseases, 15(2): # 100, Nov. 1999.
Ittig et al. "Nuclear Antisense Effects in Cyclophilin A Pre-mRNA Splicing byOligonucleotides: A Comparison of Tricyclo-DNA With LNA", Nucleic Acids Research, 32(1):346-353, Published Online Jan. 15, 2004.
McClorey et al., "Antisense Oligonucleotide-Induced Exon Skipping RestoresDystrophin Expression in Vitro in A Canine Model of DMD", Gene Therapy, 13: 1373-1381,Published Online May 25, 2006.
Summerton "Morpholino Antisense Oligomers: The Case for An RNase H-IndependentStructural Type", Biochimica et Biophysica Acta, 1489(1): 141-158, Dec. 10, 1999.
Nang et al. "Sustained AAV-Mediated Dystrophin Expression in A Canine Model ofDuchenne Muscular Dystrophy With A Brief Course of Immunosuppression", Molecular Therapy, 15(6): 1160-1166, Jun. 2007.
Heemskerk et al., "Development of Antisense-Mediated Exon Skipping as a Treatment forDuchenne Muscular Dystrophy", Ann NY Acad Sci vol. 1175 pp. 71-79 (2009).
Goto et al. "Targeted Skipping of A Single Exon Harboring a Premature Termination Codon Mutation: ImGOplications and Potential for Gene Correction Therapy for Selective Dystrophic Epidermolysis Bullosa Patients", Journal of Investigative Dermatology, 126(12): 2614-2620, Published Online Jun. 15, 2006.
Galderisi et al., "Antisense Oligonucleotides as Therapeutic Agents", Journal of Cellular Physiology, 181: 251-257, 1999.
Matsuo, "Duchenne and Becker Muscular Dystrophy: From Gene Diagnosis to Molecular Therapy", IUBMB Life, 53: 147-152, 2002.
Bolli et al. "Bicyclo-DNA: A Hoogsteen-Selective Pairing System", Chemistry & Biology, 3(3): 197-206, Mar. 1996.
Thomsen, et al., "Dramatically improved RNA in situ hybridization signals using LNA-Dmodified probes," RNA, vol. 11, pp. 1745-1748, 2005.
Sironi, et al., "The Dystrophin Gene is Alternatively Spliced Throughout its Coding DSequence," FEBS Letters, 2002, vol. 517 (1-3), pp. 163-166.
Yokota et al., "Optimizing exon skipping therapies for DMD," Acta Myol. 26(3): 179-184 (2007).
Sironi et al., "Silencer elements as possible inhibitors of pseudoexon splicing", Nucleic Acids Research, 2004, vol. 32, No. 4, pp. 1783-1791.
Goyenvalle et al. Rescue of dystrophic muscle through U7 snRNA-mediated exon skipping. Science 2004; 306 (5702): 1796-9.
Gorman et al. Stable alteration of pre-mRNA splicing patterns by modified U7 small nuclear RNAs. Proc Natl Acad Sci USA 1998; 95(9):4929-34.
Denti et al. Chimeric adenoassociated virus/antisense UI small nuclear RNA effectively rescues dystrophin synthesis and muscle function by local treatment of mdx mice. Hum Gene Ther 2006; 17(5): 565-74.
Graham et al. Towards a therapeutic inhibition of dystrophin exon 23 splicing in mdx mouse muscle induced by antisense oligoribonucleotides ( splicomers ): target sequence optimisation using oligonucleotide arrays. J Gene Med 2004; 6(10):1149-58.
Mathews et al. Expanded sequence dependence of thermodynamic parameters improves prediction of RNA secondary structure. J Mol Biol 1999; 288(5):911-40.
Cartegni et al. ESEfinder: A web resource to identify exonic splicing enhancers. Nucleic Acids Res 2003; 31 (13):3568-71.
Braasch et al. Novel antisense and peptide nucleic acid strategies for controlling gene expression, Biochemistry 2002; 41(14):4503-10.
Larsen et al. Anti sense properties of peptide nucleic acid. Biochim Biophys Acta 1999; 1489 (1):159-66.
Wahlestedt et al. Potent and nontoxic antisense oligonucleotides containing locked nucleic acids. Proc Natl Acad Sci USA 2000; 97(10):5633-8.
Politano et al (Acta Myologica 22: 15-21, 2003).*
Alter et al (Nature Med. 12(2): 175-177, 2006).*
Duboc et al (J. Am. Coll. Cardiol. 45(6): 2005).*
Rosen et al (Cancer 35: 622-630, 1975).*
O'Shaughnessy et al (Journal of Clinical Oncology, vol. 20, No. 12 Jun. 15, 2002).*
Abdel-Salam et al (Pharmacological Research 47 (2003) 331-340).*
Fernandez et al (Atherosclerosis 196 (2008) 434-442).*
Dorchies et al (Am J Physiol Cell Physiol 290: C616-C625, 2006).*
Chamberlain (Basic Appl Myol. 7 (3&4): 257-255, 7997).*
Kendall et al (Sci Transl Med 4, 164ra160 (2012)).*
Xu et al (Ann N Y Acad Sci. Sep. 16, 1998;853:130-48).*
Ryanodine receptor. Retrieved from http://en.wikipedia.org/wiki/Ryanodine_receptor on Jun. 6, 2014.*
Rolland et al (Neurobiology of Disease 24 (2006) 466-474.*
Aartsma-Rus, et al., Exploring the Frontiers of Therapeutic Exon Skipping for Duchenne Muscular Dystrophy by Double Targeting Within One or Multiple Exons, Molecular Therapy, 2006, pp. 1-7.
Australian Office Action for AU 2009240879, dated Jun. 22, 2011.
Bionity.Com NEWS-Center, Leiden University Medical Center and Prosensa B.V. Announce First Successful Clinical Study with RNA-based Therapeutic PR0051, dated Jan. 3, 2008, <http://www.bionity.com/news/e/76185>.
Biopharmaceutiques, Merging Pharma & Biotech, Edition 48, Jan. 10, 2008. <http://www.biopharmaceutiques.com/en/num>, visited Jan. 11, 2008.
Cambridge University Press, Cambridge, 1997, pp. 1-16.
Canadian Office Action for CA 2,524,255, dated Jul. 6, 2011.
Crooke. In Basic Principles of Antisense Therapeutics, Springer-Verlag, Eds, NewYork, 1998, pp. 1-50.
European Patent Office Action dated Jan. 29, 2007.
Feener et al., Alternative splicing of human dystrophin mRNA generates isoforms at the carboxy terminus. Nature, 338 (6215): 509-511 (1989).
Genes VII, Jan. 2000, Benjamin Lewin, Chapter 22, Nuclear Splicing, pp. 704-705.
Grady, Promising Dystrophy Drug Clears Early Test, The New York Times, Dec. 27, 2007.
Bionity.Com NEWS-Center, Leiden University Medical Center and Prosensa B.V. Announce First Successful Clinical Study with RNA-based Therapeutic PRO051, dated Jan. 3, 2008, <http://www.bionity.com/news/e/76185>.
International Preliminary Examination Report, International Application No. PCT/NL01/00697, dated Aug. 1, 2002.
International Search Report, International Application No. PCT/NL 2008/050470, dated Jul. 2, 2009.
International Search Report, International Application No. PCT/NL 2008/050475, dated Jun. 25, 2009.
International Search Report, International Application No. PCT/NL01/00697, dated Dec. 21, 2002.
International Search Report, International Application No. PCT/NL2004/000196, dated Oct. 28, 2004.
International Search Report, International Application No. PCT/NL2006/000209, dated Oct. 5, 2006.
Leiden University Medical Center and Prosensa B.V. Announce New England Journal of Medicine Publication of First Successful Clinical Study with RNA-based Therapeutic PRO051 in Duchenne Muscular Dystrophy, Dec. 27, 2007.
Lu, et al., Massive Idiosyncratic Exon Skipping Corrects the Nonsense Mutation in Dystrophic Mouse Muscle and Produces Functional Revertant Fibers by Clonal Expansion, The Journal Cell Biology, Mar. 6, 2000, pp. 985-995, vol. 148, No. 5.
Notice of Opposition filed against EP 1 619 249 B, dated Jun. 23, 2009.
Office Action for U.S. Appl. No. 10/395,031, dated Apr. 2, 2009.
Office Action for U.S. Appl. No. 10/395,031, dated Aug. 23, 2007.
Office Action for U.S. Appl. No. 10/395,031, dated Feb. 6, 2006.
Office Action for U.S. Appl. No. 10/395,031, dated Jul. 8, 2005.

(56) References Cited

OTHER PUBLICATIONS

Office Action for U.S. Appl. No. 10/395,031, dated May 30, 2008.
Office Action for U.S. Appl. No. 10/395,031, dated Nov. 30, 2006.
Office Action for U.S. Appl. No. 10/395,031, dated Oct. 16, 2009.
Office Action for U.S. Appl. No. 11/233,495, dated Dec. 1, 2008.
Office Action for U.S. Appl. No. 11/233,495, dated Jun. 25, 2009.
Office Action for U.S. Appl. No. 11/233,507, dated Jun. 15, 2007.
Office Action for U.S. Appl. No. 11/233,507, dated Mar. 19, 2008.
Office Action for U.S. Appl. No. 11/233,507, dated May 29, 2009.
Office Action for U.S. Appl. No. 11/233,507, dated Nov. 12, 2008.
Office Action for U.S. Appl. No. 11/982,285, dated May 4, 2009.
Office Action for U.S. Appl. No. 11/982,285, dated Sep. 18, 2009.
Opalinska and Gewirtz. "Nucleic-acid therapeutics: basic principles and recent applications." Nature Reviews Drug Discovery, 2002, vol. 1, pp. 503-514.
Oxford Dictionary of English, 2nd Edition, Revised, Oxford University Press, p. 158.
Request for an Opinion under Section 74(A) in relation to Patent No. EP (UK) 1 619 249B in the name of Academisch Ziekenhuis Leiden, opinion issued on Jun. 4, 2009.
Request for UK IPO Opinion (Section 74A & Rule 93)—EP(UK) 1619249 dated Mar. 9, 2009.
Roberts et al., Direct detection of dystrophin gene rearrangements by analysis of dystrophin mRNA in peripheral blood lymphocytes. Am. J. Hum. Genet. 49(2): 298-310 (1991).
Third Party's Statement for Japan Appl. No. 2002-529499, dated Oct. 29, 2010.
International Search Report dated Feb. 9, 2009, corresponding to PCT/NL2008/050673.
European Search Report Annex for EP 03077205 dated Nov. 19, 2003.
European Search Report for EP 03077205 dated Oct. 12, 2003.
Genbank accession No. EW162121.1, rfat0126_k17.y1 fat Sus scrofa cDNA5-, mRNA sequence, entry created on Aug. 13, 2007, last updated on Mar. 3, 2011.
EPO—Munich, Translation of Japanese Patent Application No. 2000-125448 (D64).
EPO—Munich, Translation of Japanese Patent Application No. 2000-256547(D66).
Takeshima et al., "Expression of Dystrophin Protein in Cultured Duchenne Muscular Dystrophy Cells by Exon Skipping Induced by Antisense Oligonucleotide" (Abstract); Abstract of the Japan Society of Human Genetics General Meeting Program, Nov. 17-19, 1999.
Onlo Nederlandsch Octrooibureau, Grounds of Appeal,—EP1619249, 16 pages, Aug. 23, 2013.
Onlo Nederlandsch Octrooibureau, List of all submitted documents—EP1619249, 4 pages, Aug. 23, 2013.
Onlo Nederlandsch Octrooibureau, Alignments of AON exon 53, EP1619249, 1 page, Jan. 8, 2013.
Onlo, "Comparative analysis of AONs for inducing the skipping of exon 45 and 53 from the dystrophin gene in human control muscle cells," EP1619249, 3 pages, Aug. 23, 2013.
Onlo, "Comparative Analysis of AONs for inducing the skipping of exon 53 from the dystrophin gene in human control muscle cells," EP1619249, 3 pages, Jan. 8, 2014.
Sarepta Therapeutics, Inc., "Sarepta Therapeutics and University of Western Australia Announce Exclusive Worldwide Licensing Agreement for Exon-Skipping Program in Duchenne Muscular Dystrophy," *News Release*, EP1619249, 3 pages, Apr. 11, 2013.
University of Western Australia, *University of Western Australia* (U.S. Pat. Nos. 8,455,636, 7,960,541, 7,807,816, 8,486,907) v. *Academisch Ziekenhuis Leiden* (U.S. Appl. Nos. 11/233,495, 13/550,210, 14/198,992), Declaration of Matthew J.A. Wood, M.D.,D. Phil.—UVA Exhibit 2081, 184 pages, filed Sep. 19, 2014 [Patent Interference Nos. 106,007, 106,008, 106,113 (RES)].
University of Western Australia, *University of Western Australia* (U.S. Pat. Nos. 7,960,541, 7,807,816) v. *Academisch Ziekenhuis Leiden* (U.S. Appl. No. 13/550,210), University of Western Australia List of Proposed Motions, 6 pages, filed Sep. 10, 2014 [Patent Interference No. 106,008 (RES)].
Academisch Ziekenhuis Leiden, *University of Western Australia* (U.S. Pat. Nos. 7,960,541, 7,807,816) v. *Academisch Ziekenhuis Leiden* (U.S. Appl. No. 13/550,210), Academisch Ziekenhuis Leiden's List of Proposed Motions, 8 pages, filed Sep. 10, 2014 [Patent Interference No. 106,008 (RES)].
Academisch Ziekenhuis Leiden, *University of Western Australia* (U.S. Pat. Nos. 7,960,541, 7,807,816) v. *Academisch Ziekenhuis Leiden* (U.S. Appl. No. 13/550,210), Academisch Ziekenhuis Leiden's Substantive Motion 1 (for Judgment that UWA's Claims are Unpatentable Under 35 U.S.C. §§ 102 and 103) 69 pages, filed Nov. 18, 2014 [Patent Interference No. 106,008 (RES)].
Academisch Ziekenhuis Leiden, *University of Western Australia* (U.S. Pat. Nos. 7,960,541, 7,807,816) v. *Academisch Ziekenhuis Leiden* (U.S. Appl. No. 13/550,210), Academisch Ziekenhuis Leiden's Substantive Motion 2 (to Deny UWA the Benefit of AU2004903474, 24 pages, filed Nov. 18, 2014 [Patent Interference No. 106,008 (RES)].
Academisch Ziekenhuis Leiden, University of Western Australia (U.S. Pat. Nos. 7,960,541, 7,807,816) v. Academisch Ziekenhuis Leiden (U.S. Appl. No. 13/550,210), Academisch Ziekenhuis Leiden's Substantive Motion 3 (for Judgment of Unpatentability Based on Myriad), 20 pages, filed Nov. 18, 2014 [Patent Interference No. 106,008 (RES)].
Academisch Ziekenhuis Leiden, *University of Western Australia* (U.S. Pat. Nos. 7,960,541, 7,807,816) v. *Academisch Ziekenhuis Leiden* (U.S. Appl. No. 13/550,210), Declaration of Erik Sontheimer, Ph.D., 112 pages, filed Nov. 17, 2014 [Patent Interference No. 106,008 (RES)].
University of Western Australia, *University of Western Australia* (U.S. Pat. No. 8,455,636) v. *Academisch Ziekenhuis Leiden* (U.S. Appl. No. 11/233,495), University of Western Australia List of Proposed Motions, 7 pages, filed Sep. 10, 2014 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Motion 1 (for Judgment Under 35 U.S.C. §112(a)), 40 pages, filed Nov. 18, 2014 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Motion 2 (for Judgment Under 35 U.S.C. §112(b)), 34 pages, filed Nov. 18, 2014 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Motion 3 (Requesting an Additional Interference Between UWA U.S. Pat. No. 8,455,636 and Academisch Ziekenhuis Leiden's U.S. Appl. No. 14/248,279), 36 pages, filed Nov. 18, 2014 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden's Substantive Motion 1 (for Judgment that UWA Claims are Unpatentable Under 35 U.S.C. §§ 102 and 103) 69 pages, filed Nov. 18, 2014 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden's Substantive Motion 3 (for Judgment of Unpatentability based on Myriad), 19 pages, filed Nov. 18, 2014 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), AZL Substantive Motion 2 (To Deny UWA the Benefit of AU 2004903474), 23 pages, filed Nov. 18, 2014 [Patent Interference No. 106,007 (RES)].
Academisch Ziekenhuis Leiden, *University of Western Australia* (U.S. Pat. No. 8,455,636) v. *Academisch Ziekenhuis Leiden* (U.S.

(56) References Cited

OTHER PUBLICATIONS

Appl. No. 11/233,495), Academisch Ziekenhuis Leiden's List of Proposed Motions, 6 pages, filed Sep. 10, 2014 [Patent Interference No. 106,007 (RES)].
University of Western Australia, *University of Western Australia* (U.S. Pat. No. 8,486,907) v. *Academisch Ziekenhuis Leiden* (U.S. Appl. No. 14/198,992),University of Western Australia Motion 1 (to Maintain Interference Between UWA U.S. Pat. No. 8,486,907 and Academisch Ziekenhuis Leiden's U.S. Appl. No. 14/198,992), 45 pages, filed Nov. 18, 2014 [Patent Interference No. 106,013 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Responsive Motion 4 (to Add Two New Claims), 65 pages, filed Dec. 23, 2014 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Exhibit List as of Feb. 17, 2015, 8 pages, filed Feb. 17, 2015 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), University of Western Australia Opposition 1 (Regarding Patentability Under 35 U.S. C. § 102/103), 38 pages, filed Feb. 17, 2015 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Opposition 2 (to Retain UWA's Benefit of AU 2004903474), 37 pages, filed Feb. 17, 2015 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Opposition 3 (Regarding Patentability Under 35 U.S.C. § 101), 22 pages, filed Feb. 17, 2015 [Patent Interference No. 106,007 (Res)].
University of Western Australia, *University of Western Australia* (U.S. Pat. No. 8,455,636) v. *Academisch Ziekenhuis Leiden* (U.S. Appl. No. 11/233,495), University of Western Australia Opposition 4 (to deny entry of AZL's Proposed New Claims 104 and 105), 36 pages, filed Feb. 17, 2015 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden List of Exhibits (as of Feb. 17, 2015), 18 pages, filed Feb. 17, 2015 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Opposition 1 (35 U.S. C. § 112(a)), 93 pages, filed Feb. 17, 2015 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Opposition 2 (Indefiniteness), 31 pages, filed Feb. 17, 2015 [Patent Interference No. 106,007 (RES)].
Academisch Ziekenhuis Leiden, *University of Western Australia* (U.S. Pat. No. 8,486,907) v. *Academisch Ziekenhuis Leiden* (U.S. Appl. No. 14/198,992) Academisch Ziekenhuis Leiden List of Exhibits (as of Feb. 17, 2015) 3 pages, filed Feb. 17, 2015 [Patent Interference No. 106,013 (RES)].
University of Western Australia, *University of Western Australia* (U.S. Pat. No. 8,455,636) v. *Academisch Ziekenhuis Leiden* (U.S. Appl. No. 11/233,495) University of Western Australia Objections (to Opposition Evidence) 15 pages, filed Feb. 24, 2015 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Reply 2 (to Deny the Benefit of AU 2004903474) 11 pages, filed Apr. 3, 2015 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Reply 3 (for Judgment of Unpatentability based on Myriad) 12 pages, filed Apr. 3, 2015 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden List of Exhibits (as of Apr. 3, 2015) 18 pages, filed Apr. 3, 2015 [Patent Inference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Reply 3 (to Institute an Interference) 17 pages, filed Apr. 3, 2015 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Exhibit List, 10 pages, filed Apr. 3, 2015 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495 University of Western Australia Request for Oral Argument, 4 pages, filed Apr. 10, 2015 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495 University of Western Australia Miscellaneous Motion 4 (to exclude evidence), 21 pages, filed Apr. 10, 2015 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495 University of Western Australia Exhibit List, 10 pages, filed Apr. 10, 2015 [Patent Interference No. 106,007 (RES)].
Highfield "Science: Boffin log", The Daily Telegraph, http://www.telegraph.co.uk/science/science-news/3320286/Science-Boffin-log.html, (Hope for Muscular Dystrophy Drug) Jan. 1, 2008.
International Search Report for PCT/NL2009/050006 dated Jul. 31, 2009.
International Search Report for PCT/NL2009/050113 dated Jun. 30, 2010.

* cited by examiner

Figure 7A

SEQ ID NO 1:

MLWWEEVEDCYEREDVQKKTFTKWVNAQFSKFGKQHIENLFSDLQDGRRLLDLLEGLTG
QKLPKEKGSTRVHALNNVNKALRVLQNNNVDLVNIGSTDIVDGNHKLTLGLIWNIILHWQ
VKNVMKNIMAGLQQTNSEKILLSWVRQSTRNYPQVNVINFTTSWSDGLALNALIHSHRPDL
FDWNSVVCQQSATQRLEHAFNIARYQLGIEKLLDPEDVDTTYPDKKSILMYITSLFQVLPQQ
VSIEAIQEVEMLPRPPKVTKEEHFQLHHQMHYSQQITVSLAQGYERTSSPKPRFKSYAYTQ
AAYVTTSDPTRSPFPSQHLEAPEDKSFGSSLMESEVNLDRYQTALEEVLSWLLSAEDTLQA
QGEISNDVEVVKDQFHTHEGYMMDLTAHQGRVGNILQLGSKLIGTGKLSEDEETEVQEQM
NLLNSRWECLRVASMEKQSNLHRVLMDLQNQKLKELNDWLTKTEERTRKMEEEPLGPDL
EDLKRQVQQHKVLQEDLEQEQVRVNSLTHMVVVVDESSGDHATAALEEQLKVLGDRWAN
ICRWTEDRWVLLQDILLKWQRLTEEQCLFSAWLSEKEDAVNKIHTTGFKDQNEMLSSLQK
LAVLKADLEKKKQSMGKLYSLKQDLLSTLKNKSVTQKTEAWLDNFARCWDNLVQKLEKS
TAQISQAVTTTQPSLTQTTVMETVTTVTTREQILVKHAQEELPPPPPQKKRQITVDSEIRKRL
DVDITELHSWITRSEAVLQSPEFAIFRKEGNFSDLKEKVNAIEREKAEKFRKLQDASRSAQA
LVEQMVNEGVNADSIKQASEQLNSRWIEFCQLLSERLNWLEYQNNIIAFYNQLQQLEQMT
TTAENWLKIQPTTPSEPTAIKSQLKICKDEVNRLSGLQPQIERLKIQSIALKEKGQGPMFLDA
DFVAFTNHFKQVFSDVQAREKELQTIFDTLPPMRYQETMSAIRTWVQQSETKLSIPQLSVT
DYEIMEQRLGELQALQSSLQEQQSGLYYLSTTVKEMSKKAPSEISRKYQSEFEEIEGRWKK
LSSQLVEHCQKLEEQMNKLRKIQNHIQTLKKWMAEVDVFLKEEWPALGDSEILKKQLKQC
RLLVSDIQTIQPSLNSVNEGGQKIKNEAEPEFASRLETELKELNTQWDHMCQQVYARKEAL
KGGLEKTVSLQKDLSEMHEWMTQAEEEYLERDFEYKTPDELQKAVEEMKRAKEEAQQKE
AKVKLLTESVNSVIAQAPPVAQEALKKELETLTTNYQWLCTRLNGKCKTLEEVWACWHEL
LSYLEKANKWLNEVEFKLKTTENIPGGAEEISEVLDSLENLMRHSEDNPNQIRILAQTLTD
GGVMDELINEELETFNSRWRELHEEAVRRQKLLEQSIQSAQETEKSLHLIQESLTFIDKQLA
AYIADKVDAAQMPQEAQKIQSDLTSHEISLEEMKKHNQGKEAAQRVLSQIDVAQKKLQDV
SMKFRLFQKPANFEQRLQESKMILDEVKMHLPALETKSVEQEVVQSQLNHCVNLYKSLSE
VKSEVEMVIKTGRQIVQKKQTENPKELDERVTALKLHYNELGAKVTERKQQLEKCLKLSR
KMRKEMNVLTEWLAATDMELTKRSAVEGMPSNLDSEVAWGKATQKEIEKQKVHLKSITE
VGEALKTVLGKKETLVEDKLSLLNSNWIAVTSRAEEWLNLLLEYQKHMETFDQNVDHITK
WIIQADTLLDESEKKKPQQKEDVLKRLKAELNDIRPKVDSTRDQAANLMANRGDHCRKLV
EPQISELNHRFAAISHRIKTGKASIPLKELEQFNSDIQKLLEPLEAEIQQGVNLKEEDFNKD
MNEDNEGTVKELLQRGDNLQQRITDERKREEIKIKQQLLQTKHNALKDLRSQRRKKALEIS
HQWYQYKRQADDLLKCLDDIEKKLASLPEPRDERKIKEIDRELQKKKEELNAVRRQAEGL
SEDGAAMAVEPTQIQLSKRWREIESKFAQFRRLNFAQIHTVREETMMVMTEDMPLEISYVP
STYLTEITHVSQALLEVEQLLNAPDLCAKDFEDLFKQEESLKNIKDSLQQSSGRIDIIHSKKT
AALQSATPVERVKLQEALSQLDFQWEKVNKMYKDRQGRFDRSVEKWRRFHYDIKIFNQW
LTEAEQFLRKTQIPENWEHAKYKWYLKELQDGIGQRQTVVRTLNATGEEIIQQSSKTDASIL
QEKLGSLNLRWQEVCKQLSDRKKRLEEQKNILSEFQRDLNEFVLWLEEADNIASIPLEPGK
EQQLKEKLEQVKLLVEELPLRQGILKQLNETGGPVLVSAPISPEEQDKLENKLKQTNLQWI
KVSRALPEKQGEIEAQIKDLGQLEKKLEDLEEQLNHLLLWLSPIRNQLEIYNQPNQEGPFD
VQETEIAVQAKQPDVEEILSKGQHLYKEKPATQPVKRKLEDLSSEWKAVNRLLQELRAKQP
DLAPGLTTIGASPTQTVTLVTQPVVTKETAISKLEMPSSLMLEVPALADFNRAWTELTDWLS
LLDQVIKSQRVMVGDLEDINEMIIKQKATMQDLEQRRPQLEELITAAQNLKNKTSNQEART
IITDRIERIQNQWDEVQEHLQNRRQQLNEMLKDSTQWLEAKEEAEQVLGQARAKLESWKE
GPYTVDAIQKKITETKQLAKDLRQWQTNVDVANDLALKLLRDYSADDTRKVHMITENINAS
WRSIHKRVSEREAALEETHRLLQQFPLDLEKFLAWLTEAETTANVLQDATRKERLLEDSKG
VKELMKQWQDLQGEIEAHTDVYHNLDENSQKILRSLEGSDDAVLLQRRLDNMNFKWSEL
RKKSLNIRSHLEASSDQWKRLHLSLQELLVWLQLKDDELSRQAPIGGDFPAVQKQNDVHR
AFKRELKTKEPVIMSTLETVRIFLTEQPLEGLEKLYQEPRELPPEERAQNVTRLLRKQAEEV
NTEWEKLNLHSADWQRKIDETLERLQELQEATDELDLKLRQAEVIKGSWQPVGDLLIDSL

Figure 7B

QDHLEKVKALRGEIAPLKENVSHVNDLARQLTTLGIQLSPYNLSTLEDLNTRWKLLQVAVE
DRVRQLHEAHRDFGPASQHFLSTSVQGPWERAISPNKVPYYINHETQTTCWDHPKMTELY
QSLADLNNVRFSAYRTAMKLRRLQKALCLDLLSLSAACDALDQHNLKQNDQPMDILQIINC
LTTIYDRLEQEHNNLVNVPLCVDMCLNWLLNVYDTGRTGRIRVLSFKTGIISLCKAHLEDK
YRYLFKQVASSTGFCDQRRLGLLLHDSIQIPRQLGEVASFGGSNIEPSVRSCFQFANNKPEIE
AALFLDWMRLEPQSMVWLPVLHRVAAAETAKHQAKCNICKECPIIGFRYRSLKHFNYDICQ
SCFFSGRVAKGHKMHYPMVEYCTPTTSGEDVRDFAKVLKNKFRTKRYFAKHPRMGYLPV
QTVLEGDNMETPVTLINFWPVDSAPASSPQLSHDDTHSRIEHYASRLAEMENSNGSYLNDS
ISPNESIDDEHLLIQHYCQSLNQDSPLSQPRSPAQILISLESEERGELERILADLEEENRNLQ
AEYDRLKQQHEHKGLSPLPSPPEMMPTSPQSPRDAELIAEAKLLRQHKGRLEARMQILED
HNKQLESQLHRLRQLLEQPQAEAKVNGTTVSSPSTSLQRSDSSQPMLLRVVGSQTSDSMGE
EDLLSPPQDTSTGLEEVMEQLNNSFPSSRGRNTPGKPMREDTM

Figure 8

Human IGF-1 Isoform 4 amino acid sequence

SEQ ID NO 2:
MGKISSLPTQLFKCCFCDFLKVKMHTMSSSHLFYLALCLLTFTSSATAGPETLCGAELVDAL
QFVCGDRGFYFNKPTGYGSSSRRAPQTGIVDECCFRSCDLRRLEMYCAPLKPAKSARSVRA
QRHTDMPKTQKEVHLKNASRGSAGNKNYRM

Figure 9A

DMD Gene Exon 43

| | |
|---|---|
| SEQ ID NO 3 | CGACC UGAGC UUUGU UGUAG |
| SEQ ID NO 4 | CGACC UGAGC UUUGU UGUAG ACUAU |
| SEQ ID NO 5 | CCUGA GCUUU GUUGU AGACU AUC |
| SEQ ID NO 6 | CGUUG CACUU UGCAA UGCUG CUG |
| SEQ ID NO 7 | CUGUA GCUUC ACCCU UUCC |
| SEQ ID NO 8 | GAGAG AGCUU CCUGU AGCUU CACC |
| SEQ ID NO 9 | GUCCU UGUAC AUUUU GUUAA CUUUU UC |
| SEQ ID NO 263 | GGA GAG AGC UUC CUG UAG CU |
| SEQ ID NO 264 | UCA CCC UUU CCA CAG GCG UUG CA |
| SEQ ID NO 265 | UGCACUUUGCAAUGCUGCUGUCUUCUUG CUAU |

Figure 9B

| | | | |
|---|---|---|---|
| SEQ ID NO 10 | UCAGCUUCUGUUAGCCACUG | SEQ ID NO 35 | AGCUUCUGUUAGCCACUGAUUAAA |
| SEQ ID NO 11 | UUCAGCUUCUGUUAGCCACU | SEQ ID NO 36 | CAGCUUCUGUUAGCCACUGAUUAAA |
| SEQ ID NO 12 | UUCAGCUUCUGUUAGCCACUG | SEQ ID NO 37 | AGCUUCUGUUAGCCACUGAUUAAA |
| SEQ ID NO 13 | UCAGCUUCUGUUAGCCACUGA | SEQ ID NO 38 | AGCUUCUGUUAGCCACUGAU |
| SEQ ID NO 14 | UUCAGCUUCUGUUAGCCACUGA | SEQ ID NO 39 | GCUUCUGUUAGCCACUGAUU |
| SEQ ID NO 15 | UCAGCUUCUGUUAGCCACUGA | SEQ ID NO 40 | AGCUUCUGUUAGCCACUGAUU |
| SEQ ID NO 16 | UUCAGCUUCUGUUAGCCACUGA | SEQ ID NO 41 | GCUUCUGUUAGCCACUGAUUA |
| SEQ ID NO 17 | UCAGCUUCUGUUAGCCACUGAU | SEQ ID NO 42 | AGCUUCUGUUAGCCACUGAUUA |
| SEQ ID NO 18 | UUCAGCUUCUGUUAGCCACUGAU | SEQ ID NO 43 | GCUUCUGUUAGCCACUGAUUAA |
| SEQ ID NO 19 | UCAGCUUCUGUUAGCCACUGAUU | SEQ ID NO 44 | AGCUUCUGUUAGCCACUGAUUAA |
| SEQ ID NO 20 | UUCAGCUUCUGUUAGCCACUGAUU | SEQ ID NO 45 | GCUUCUGUUAGCCACUGAUUAAA |
| SEQ ID NO 21 | UCAGCUUCUGUUAGCCACUGAUUA | SEQ ID NO 46 | AGCUUCUGUUAGCCACUGAUUAAA |
| SEQ ID NO 22 | UUCAGCUUCUGUUAGCCACUGAUA | SEQ ID NO 47 | GCUUCUGUUAGCCACUGAUUAAA |
| SEQ ID NO 23 | UCAGCUUCUGUUAGCCACUGAUUAA | SEQ ID NO 48 | CCAUUUGUAUUUAGCAUGUUCCC |
| SEQ ID NO 24 | UUCAGCUUCUGUUAGCCACUGAUUAA | SEQ ID NO 49 | AGAUACCAUUUGUAUUUAGC |
| SEQ ID NO 25 | UCAGCUUCUGUUAGCCACUGAUUAAA | SEQ ID NO 50 | GCCAUUUCUCAACAGAUCU |
| SEQ ID NO 26 | UUCAGCUUCUGUUAGCCACUGAUUAAA | SEQ ID NO 51 | GCCAUUUCUCAACAGAUCUGUCA |

Figure 9C

| | | | |
|---|---|---|---|
| SEQ ID NO 27 | CAGCUUCUGUUAGCCACUG | SEQ ID NO 52 | AUUCUCAGGAAUUUGUGUCUUUC |
| SEQ ID NO 28 | CAGCUUCUGUUAGCCACUGAU | SEQ ID NO 53 | UCUCAGGAAUUUGUGUCUUUC |
| SEQ ID NO 29 | AGCUUCUGUUAGCCACUGAUU | SEQ ID NO 54 | GUUCAGCUUCUGUUAGCC |
| SEQ ID NO 30 | CAGCUUCUGUUAGCCACUGAUU | SEQ ID NO 55 | CUGAUUAAAUAUCUUUAUAU C |
| SEQ ID NO 31 | AGCUUCUGUUAGCCACUGAUUA | SEQ ID NO 56 | GCCGCCAUUUCUCAACAG |
| SEQ ID NO 32 | CAGCUUCUGUUAGCCACUGAUUA | SEQ ID NO 57 | GUAUUUAGCAUGUUCCCA |
| SEQ ID NO 33 | AGCUUCUGUUAGCCACUGAUUAA | SEQ ID NO 58 | CAGGAAUUUGUGUCUUUC |
| SEQ ID NO 34 | CAGCUUCUGUUAGCCACUGAUUAA | SEQ ID NO 267 | UUU GUG UCU UUC UGA GAA AC |
| SEQ ID NO 266 | UCAUAAUGAAAACGCCGCCAUUUCUCAACAG AUCU | SEQ ID NO 268 | UUUAGCAUGUUCCCAAUUCUCAGGA AUUUG |

Figure 9D

DMD Gene Exon 45

| | | | |
|---|---|---|---|
| SEQ ID NO 59 | UUUGCCGCUGCCCAAUGCCAUCCUG | SEQ ID NO 89 | GUUGCAUUCAAUGUUCUGACAACAG |
| SEQ ID NO 60 | AUUCAAUGUUCUGACAACAGUUUGC | SEQ ID NO 90 | UUGCAUUCAAUGUUCUGACAACAGU |
| SEQ ID NO 61 | CCAGUUGCAUUCAAUGUUCUGACAA | SEQ ID NO 91 | UGCAUUCAAUGUUCUGACAACAGUU |
| SEQ ID NO 62 | CAGUUGCAUUCAAUGUUCUGAC | SEQ ID NO 92 | GCAUUCAAUGUUCUGACAACAGUUU |
| SEQ ID NO 63 | AGUUGCAUUCAAUGUUCUGA | SEQ ID NO 93 | CAUUCAAUGUUCUGACAACAGUUUG |
| SEQ ID NO 64 | GAUUGCUGAAUUAUUUCUUCC | SEQ ID NO 94 | AUUCAAUGUUCUGACAACAGUUUGC |
| SEQ ID NO 65 | GAUUGCUGAAUUAUUUCUUCCCCAG | SEQ ID NO 95 | UCAAUGUUCUGACAACAGUUUGCCG |
| SEQ ID NO 66 | AUUGCUGAAUUAUUUCUUCCCCAGU | SEQ ID NO 96 | CAAUGUUCUGACAACAGUUUGCCGC |
| SEQ ID NO 67 | UUGCUGAAUUAUUUCUUCCCCAGUU | SEQ ID NO 97 | AAUGUUCUGACAACAGUUUGCCGCU |
| SEQ ID NO 68 | UGCUGAAUUAUUUCUUCCCCAGUUG | SEQ ID NO 98 | AUGUUCUGACAACAGUUUGCCGCUG |
| SEQ ID NO 69 | GCUGAAUUAUUUCUUCCCCAGUUGC | SEQ ID NO 99 | UGUUCUGACAACAGUUUGCCGCUGC |
| SEQ ID NO 70 | CUGAAUUAUUUCUUCCCCAGUUGCA | SEQ ID NO 100 | GUUCUGACAACAGUUUGCCGCUGCC |
| SEQ ID NO 71 | UGAAUUAUUUCUUCCCCAGUUGCAU | SEQ ID NO 101 | UUCUGACAACAGUUUGCCGCUGCCC |
| SEQ ID NO 72 | GAAUUAUUUCUUCCCCAGUUGCAUU | SEQ ID NO 102 | UCUGACAACAGUUUGCCGCUGCCCA |
| SEQ ID NO 73 | AAUUAUUUCUUCCCCAGUUGCAUUC | SEQ ID NO 103 | CUGACAACAGUUUGCCGCUGCCCAA |
| SEQ ID NO 74 | AUUAUUUCUUCCCCAGUUGCAUUCA | SEQ ID NO 104 | UGACAACAGUUUGCCGCUGCCCAAU |
| SEQ ID NO 75 | UUAUUUCUUCCCCAGUUGCAUUCAA | SEQ ID NO 105 | GACAACAGUUUGCCGCUGCCCAAUG |
| SEQ ID NO 76 | UAUUUCUUCCCCAGUUGCAUUCAAU | SEQ ID NO 106 | ACAACAGUUUGCCGCUGCCCAAUGC |
| SEQ ID NO 77 | AUUUCUUCCCCAGUUGCAUUCAAUG | SEQ ID NO 107 | CAACAGUUUGCCGCUGCCCAAUGCC |

Figure 9E

| | | | |
|---|---|---|---|
| SEQ ID NO 78 | UUUCUUCCCCAGUUGCAUUCAAUGU | SEQ ID NO 108 | AACAGUUUGCCGCUGCCCAAUGCCA |
| SEQ ID NO 79 | UUCUUCCCCAGUUGCAUUCAAUGUU | SEQ ID NO 109 | ACAGUUUGCCGCUGCCCAAUGCCAU |
| SEQ ID NO 80 | UCUUCCCCAGUUGCAUUCAAUGUUC | SEQ ID NO 110 | CAGUUUGCCGCUGCCCAAUGCCAUC |
| SEQ ID NO 81 | CUUCCCCAGUUGCAUUCAAUGUUCU | SEQ ID NO 111 | AGUUUGCCGCUGCCCAAUGCCAUCC |
| SEQ ID NO 82 | UUCCCCAGUUGCAUUCAAUGUUCUG | SEQ ID NO 112 | GUUUGCCGCUGCCCAAUGCCAUCCU |
| SEQ ID NO 83 | UCCCCAGUUGCAUUCAAUGUUCUGA | SEQ ID NO 113 | UUUGCCGCUGCCCAAUGCCAUCCUG |
| SEQ ID NO84 | CCCCAGUUGCAUUCAAUGUUCUGAC | SEQ ID NO 114 | UUGCCGCUGCCCAAUGCCAUCCUGG |
| SEQ ID NO 85 | CCCAGUUGCAUUCAAUGUUCUGACA | SEQ ID NO 115 | UGCCGCUGCCCAAUGCCAUCCUGGA |
| SEQ ID NO 86 | CCAGUUGCAUUCAAUGUUCUGACAA | SEQ ID NO 116 | GCCGCUGCCCAAUGCCAUCCUGGAG |
| SEQ ID NO 87 | CAGUUGCAUUCAAUGUUCUGACAAC | SEQ ID NO 117 | CCGCUGCCCAAUGCCAUCCUGGAGU |
| SEQ ID NO 88 | AGUUGCAUUCAAUGUUCUGACAACA | SEQ ID NO 118 | CGCUGCCCAAUGCCAUCCUGGAGUU |
| SEQ ID NO 269 | UCC UGU AGA AUA CUG GCA UC | SEQ ID NO 272 | UGU UUU UGA GGA UUG CUG AA |
| SEQ ID NO 270 | UGC AGA CCU CCU GCC ACC GCA GAU UCA | SEQ ID NO 273 | UGUUCUGACAACAGUUUGCCGCUGCCC AAUGCCAUCCUGG |
| SEQ ID NO 271 | UUGCAGACCUCCUGCCACCGCAGAUUCAGGCU UC | | |

Figure 9F

DMD Gene Exon 46

| | | | |
|---|---|---|---|
| SEQ ID NO 119 | GCUUUUCUUUUAGUUGCUGCUCUUU | SEQ ID NO 147 | AGGUUCAAGUGGGAUACUAGCAAUG |
| SEQ ID NO 120 | CUUUUCUUUUAGUUGCUGCUCUUUU | SEQ ID NO 148 | GGUUCAAGUGGGAUACUAGCAAUGU |
| SEQ ID NO 121 | UUUUCUUUUAGUUGCUGCUCUUUUC | SEQ ID NO 149 | GUUCAAGUGGGAUACUAGCAAUGUU |
| SEQ ID NO 122 | UUUCUUUUAGUUGCUGCUCUUUUCC | SEQ ID NO 150 | UUCAAGUGGGAUACUAGCAAUGUUA |
| SEQ ID NO 123 | UUCUUUUAGUUGCUGCUCUUUUCCA | SEQ ID NO 151 | UCAAGUGGGAUACUAGCAAUGUUAU |
| SEQ ID NO 124 | UCUUUUAGUUGCUGCUCUUUUCCAG | SEQ ID NO 152 | CAAGUGGGAUACUAGCAAUGUUAUC |
| SEQ ID NO 125 | CUUUUAGUUGCUGCUCUUUUCCAGG | SEQ ID NO 153 | AAGUGGGAUACUAGCAAUGUUAUCU |
| SEQ ID NO 126 | UUUUAGUUGCUGCUCUUUUCCAGGU | SEQ ID NO 154 | AGUGGGAUACUAGCAAUGUUAUCUG |
| SEQ ID NO 127 | UUUAGUUGCUGCUCUUUUCCAGGUU | SEQ ID NO 155 | GUGGGAUACUAGCAAUGUUAUCUGC |
| SEQ ID NO 128 | UUAGUUGCUGCUCUUUUCCAGGUUC | SEQ ID NO 156 | UGGGAUACUAGCAAUGUUAUCUGCU |
| SEQ ID NO 129 | UAGUUGCUGCUCUUUUCCAGGUUCA | SEQ ID NO 157 | GGGAUACUAGCAAUGUUAUCUGCUU |
| SEQ ID NO 130 | AGUUGCUGCUCUUUUCCAGGUUCAA | SEQ ID NO 158 | GGAUACUAGCAAUGUUAUCUGCUUC |
| SEQ ID NO 131 | GUUGCUGCUCUUUUCCAGGUUCAAG | SEQ ID NO 159 | GAUACUAGCAAUGUUAUCUGCUUCC |
| SEQ ID NO 132 | UUGCUGCUCUUUUCCAGGUUCAAGU | SEQ ID NO 160 | AUACUAGCAAUGUUAUCUGCUUCCU |
| SEQ ID NO 133 | UGCUGCUCUUUUCCAGGUUCAAGUG | SEQ ID NO 161 | UACUAGCAAUGUUAUCUGCUUCCUC |
| SEQ ID NO 134 | GCUGCUCUUUUCCAGGUUCAAGUGG | SEQ ID NO 162 | ACUAGCAAUGUUAUCUGCUUCCUCC |
| SEQ ID NO 135 | CUGCUCUUUUCCAGGUUCAAGUGGG | SEQ ID NO 163 | CUAGCAAUGUUAUCUGCUUCCUCCA |
| SEQ ID NO 136 | UGCUCUUUUCCAGGUUCAAGUGGGA | SEQ ID NO 164 | UAGCAAUGUUAUCUGCUUCCUCCAA |

Figure 9G

| | | | |
|---|---|---|---|
| SEQ ID NO 137 | GCUCUUUUCCAGGUUCAAGUGGGAC | SEQ ID NO 165 | AGCAAUGUUAUCUGCUUCCUCCAAC |
| SEQ ID NO 138 | CUCUUUUCCAGGUUCAAGUGGGAUA | SEQ ID NO 166 | GCAAUGUUAUCUGCUUCCUCCAACC |
| SEQ ID NO 139 | UCUUUUCCAGGUUCAAGUGGGAUAC | SEQ ID NO 167 | CAAUGUUAUCUGCUUCCUCCAACCA |
| SEQ ID NO 140 | CUUUUCCAGGUUCAAGUGGGAUACU | SEQ ID NO 168 | AAUGUUAUCUGCUUCCUCCAACCAU |
| SEQ ID NO 141 | UUUUCCAGGUUCAAGUGGGAUACUA | SEQ ID NO 169 | AUGUUAUCUGCUUCCUCCAACCAUA |
| SEQ ID NO 142 | UUUCCAGGUUCAAGUGGGAUACUAG | SEQ ID NO 170 | UGUUAUCUGCUUCCUCCAACCAUAA |
| SEQ ID NO 143 | UUCCAGGUUCAAGUGGGAUACUAGC | SEQ ID NO 171 | GUUAUCUGCUUCCUCCAACCAUAAA |
| SEQ ID NO 144 | UCCAGGUUCAAGUGGGAUACUAGCA | SEQ ID NO 172 | GCUGCUCUUUUCCAGGUUC |
| SEQ ID NO 145 | CCAGGUUCAAGUGGGAUACUAGCAA | SEQ ID NO 173 | UCUUUUCCAGGUUCAAGUGG |
| SEQ ID NO 146 | CAGGUUCAAGUGGGAUACUAGCAAU | SEQ ID NO 174 | AGGUUCAAGUGGGAUACUA |
| SEQ ID NO 274 | CUCUUUUCCAGGUUCAAGUGGGAUACUAGC | SEQ ID NO 276 | UAUUCUUUUGUUCUUCUAGCCUGGAGAAAG |
| SEQ ID NO 275 | CAAGCUUUUCUUUUAGUUGCUGCUCUUUUCC | SEQ ID NO 277 | CUGCUUCCUCCAACCAUAAAACAAAUUC |

Figure 9H

DMD Gene Exon 50

| | |
|---|---|
| SEQ ID NO 175 | CUCAGCUCUUGAAGUAAACG |
| SEQ ID NO 176 | CCUCAGCUCUUGAAGUAAAC |
| SEQ ID NO 177 | CCUCAGCUCUUGAAGUAAACG |
| SEQ ID NO 178 | AUAGUGGUCAGUCCAGGAGCU |
| SEQ ID NO 179 | CAGUC CAGGA GCUAG GUCAGG |
| SEQ ID NO 180 | UAGUGGUCAGUCCAGGAGCUAGGUC |
| SEQ ID NO 278 | CCACUCAGAGCUCAGAUCUUCUAACUUCC |
| SEQ ID NO 279 | CUUCCACUCAGAGCUCAGAUCUUCUAA |
| SEQ ID NO 280 | CAGUCCAGGAGCUAGGUCAGGCUGCUUUGC |
| SEQ ID NO 281 | UCUUGAAGUAAACGGUUUACCGCCUUCCACU CAGAGC |

Figure 9I

DMD Gene Exon 51

| | | | |
|---|---|---|---|
| SEQ ID NO 181 | AGAGCAGGUACCUCCAACAUCAAGG | SEQ ID NO 203 | UCAAGGAAGAUGGCAUUUCUAGUUU |
| SEQ ID NO 182 | GAGCAGGUACCUCCAACAUCAAGGA | SEQ ID NO 204 | UCAAGGAAGAUGGCAUUUCU |
| SEQ ID NO 183 | AGCAGGUACCUCCAACAUCAAGGAA | SEQ ID NO 205 | CAAGGAAGAUGGCAUUUCUAGUUUG |
| SEQ ID NO 184 | GCAGGUACCUCCAACAUCAAGGAAG | SEQ ID NO 206 | AAGGAAGAUGGCAUUUCUAGUUUGG |
| SEQ ID NO 185 | CAGGUACCUCCAACAUCAAGGAAGA | SEQ ID NO 207 | AGGAAGAUGGCAUUUCUAGUUUGGA |
| SEQ ID NO 186 | AGGUACCUCCAACAUCAAGGAAGAU | SEQ ID NO 208 | GGAAGAUGGCAUUUCUAGUUUGGAG |
| SEQ ID NO 187 | GGUACCUCCAACAUCAAGGAAGAUG | SEQ ID NO 209 | GAAGAUGGCAUUUCUAGUUUGGAGA |
| SEQ ID NO 188 | GUACCUCCAACAUCAAGGAAGAUGG | SEQ ID NO 210 | AAGAUGGCAUUUCUAGUUUGGAGAU |
| SEQ ID NO 189 | UACCUCCAACAUCAAGGAAGAUGGC | SEQ ID NO 211 | AGAUGGCAUUUCUAGUUUGGAGAUG |
| SEQ ID NO 190 | ACCUCCAACAUCAAGGAAGAUGGCA | SEQ ID NO 212 | GAUGGCAUUUCUAGUUUGGAGAUGG |
| SEQ ID NO 191 | CCUCCAACAUCAAGGAAGAUGGCAU | SEQ ID NO 213 | AUGGCAUUUCUAGUUUGGAGAUGGC |
| SEQ ID NO 192 | CUCCAACAUCAAGGAAGAUGGCAUU | SEQ ID NO 214 | UGGCAUUUCUAGUUUGGAGAUGGCA |
| SEQ ID NO 193 | CUCCAACAUCAAGGAAGAUGGCAUU UCUAG | SEQ ID NO 215 | GGCAUUUCUAGUUUGGAGAUGGCAG |
| SEQ ID NO 194 | UCCAACAUCAAGGAAGAUGGCAUUU | SEQ ID NO 216 | GCAUUUCUAGUUUGGAGAUGGCAGU |
| SEQ ID NO 195 | CCAACAUCAAGGAAGAUGGCAUUUC | SEQ ID NO 217 | CAUUUCUAGUUUGGAGAUGGCAGUU |
| SEQ ID NO 196 | CAACAUCAAGGAAGAUGGCAUUUCU | SEQ ID NO 218 | AUUUCUAGUUUGGAGAUGGCAGUUU |
| SEQ ID NO 197 | AACAUCAAGGAAGAUGGCAUUUCUA | SEQ ID NO 219 | UUUCUAGUUUGGAGAUGGCAGUUUC |
| SEQ ID NO 198 | ACAUCAAGGAAGAUGGCAUUUCUAG | SEQ ID NO 220 | UUCUAGUUUGGAGAUGGCAGUUUCC |

Figure 9J

| | | | |
|---|---|---|---|
| SEQ ID NO 199 | ACAUCAAGGAAGAUGGCAUUUCUAG UUUGG | | |
| SEQ ID NO 200 | ACAUCAAGGAAGAUGGCAUUUCUAG | | |
| SEQ ID NO 201 | CAUCAAGGAAGAUGGCAUUUCUAGU | | |
| SEQ ID NO 202 | AUCAAGGAAGAUGGCAUUUCUAGUU | | |

Figure 9K

DMD Gene Exon 52

| | | | |
|---|---|---|---|
| SEQ ID NO 221 | CCUCUUGAUUGCUGGUCUUGUUUUU | SEQ ID NO 250 | UUUUGGGCAGCGGUAAUGAGUUCUU |
| SEQ ID NO 222 | CUCUUGAUUGCUGGUCUUGUUUUUC | SEQ ID NO 251 | UUUGGGCAGCGGUAAUGAGUUCUUC |
| SEQ ID NO 223 | UCUUGAUUGCUGGUCUUGUUUUUCA | SEQ ID NO 252 | UUGGGCAGCGGUAAUGAGUUCUUCC |
| SEQ ID NO 224 | CUUGAUUGCUGGUCUUGUUUUUCAA | SEQ ID NO 253 | UGGGCAGCGGUAAUGAGUUCUUCCA |
| SEQ ID NO 225 | UUGAUUGCUGGUCUUGUUUUUCAAA | SEQ ID NO 254 | GGGCAGCGGUAAUGAGUUCUUCCAA |
| SEQ ID NO 226 | UGAUUGCUGGUCUUGUUUUUCAAAU | SEQ ID NO 255 | GGCAGCGGUAAUGAGUUCUUCCAAC |
| SEQ ID NO 227 | GAUUGCUGGUCUUGUUUUUCAAAUU | SEQ ID NO 256 | GCAGCGGUAAUGAGUUCUUCCAACU |
| SEQ ID NO 228 | AUUGCUGGUCUUGUUUUUCAAAUUU | SEQ ID NO 257 | CAGCGGUAAUGAGUUCUUCCAACUG |
| SEQ ID NO 229 | UUGCUGGUCUUGUUUUUCAAAUUUU | SEQ ID NO 258 | AGCGGUAAUGAGUUCUUCCAACUGG |
| SEQ ID NO 230 | UGCUGGUCUUGUUUUUCAAAUUUUG | SEQ ID NO 259 | GCGGUAAUGAGUUCUUCCAACUGGG |
| SEQ ID NO 231 | GCUGGUCUUGUUUUUCAAAUUUUGG | SEQ ID NO 260 | CGGUAAUGAGUUCUUCCAACUGGGG |
| SEQ ID NO 232 | CUGGUCUUGUUUUUCAAAUUUUGGG | SEQ ID NO 261 | GGUAAUGAGUUCUUCCAACUGGGGA |
| SEQ ID NO 233 | UGGUCUUGUUUUUCAAAUUUUGGGC | SEQ ID NO 262 | GUAAUGAGUUCUUCCAACUGGGGAC |
| SEQ ID NO 234 | GGUCUUGUUUUUCAAAUUUUGGGCA | SEQ ID NO 263 | UAAUGAGUUCUUCCAACUGGGGACG |
| SEQ ID NO 235 | GUCUUGUUUUUCAAAUUUUGGGCAG | SEQ ID NO 264 | AAUGAGUUCUUCCAACUGGGGACGC |
| SEQ ID NO 236 | UCUUGUUUUUCAAAUUUUGGGCAGC | SEQ ID NO 265 | AUGAGUUCUUCCAACUGGGGACGCC |
| SEQ ID NO 237 | CUUGUUUUUCAAAUUUUGGGCAGCG | SEQ ID NO 266 | UGAGUUCUUCCAACUGGGGACGCCU |
| SEQ ID NO 238 | UUGUUUUUCAAAUUUUGGGCAGCGG | SEQ ID NO 267 | GAGUUCUUCCAACUGGGGACGCCUC |

Figure 9L

| | | | |
|---|---|---|---|
| SEQ ID NO 239 | UGUUUUUCAAAUUUUGGGCAGCGGU | SEQ ID NO 268 | AGUUCUUCCAACUGGGGACGCCUCU |
| SEQ ID NO 240 | GUUUUUCAAAUUUUGGGCAGCGGUA | SEQ ID NO 269 | GUUCUUCCAACUGGGGACGCCUCUG |
| SEQ ID NO 241 | UUUUUCAAAUUUUGGGCAGCGGUAA | SEQ ID NO 270 | UUCUUCCAACUGGGGACGCCUCUGU |
| SEQ ID NO 242 | UUUUCAAAUUUUGGGCAGCGGUAAU | SEQ ID NO 271 | UCUUCCAACUGGGGACGCCUCUGUU |
| SEQ ID NO 243 | UUUCAAAUUUUGGGCAGCGGUAAUG | SEQ ID NO 272 | CUUCCAACUGGGGACGCCUCUGUUC |
| SEQ ID NO 244 | UUCAAAUUUUGGGCAGCGGUAAUGA | SEQ ID NO 273 | UUCCAACUGGGGACGCCUCUGUUCC |
| SEQ ID NO 245 | UCAAAUUUUGGGCAGCGGUAAUGAG | SEQ ID NO 274 | GAUUG CUGGU CUUGU UUUUC |
| SEQ ID NO 246 | CAAAUUUUGGGCAGCGGUAAUGAGU | SEQ ID NO 275 | CCUCU UGAUU GCUGG UCUUG |
| SEQ ID NO 247 | AAAUUUUGGGCAGCGGUAAUGAGUU | SEQ ID NO 276 | GGUAA UGAGU UCUUC CAACU GG |
| SEQ ID NO 248 | AAUUUUGGGCAGCGGUAAUGAGUUC | SEQ ID NO 277 | ACUGG GGACG CCUCU GUUCC |
| SEQ ID NO 249 | AUUUUGGGCAGCGGUAAUGAGUUCU | SEQ ID NO 283 | ACUGGGGACGCCUCUGUUCCA |
| SEQ ID NO 282 | UCCAACUGGGGACGCCUCUGUUCC AAAUCC | SEQ ID NO 284 | CCGUAAUGAUUGUUCUAGCC |

Figure 9M

DMD Gene Exon 53

| | |
|---|---|
| SEQ ID NO 250 | CCAUUGUGUUGAAUCCUUUAACAUU |
| SEQ ID NO 251 | CCAUUGUGUUGAAUCCUUUAAC |
| SEQ ID NO 252 | AUUGUGUUGAAUCCUUUAAC |
| SEQ ID NO 253 | CCUGUCCUAAGACCUGCUCA |
| SEQ ID NO 254 | CUUUUGGAUUGCAUCUACUGUAUAG |
| SEQ ID NO 255 | CAUUCAACUGUUGCCUCCGGUUCUG |
| SEQ ID NO 256 | CUGUUGCCUCCGGUUCUGAAGGUG |
| SEQ ID NO 257 | CAUUCAACUGUUGCCUCCGGUUCUGAAGGUG |
| SEQ ID NO 258 | CUGAAGGUGUUCUUGUACUUCAUCC |
| SEQ ID NO 259 | UGUAUAGGGACCCUCCUUCCAUGACUC |
| SEQ ID NO 260 | AUCCCACUGAUUCUGAAUUC |
| SEQ ID NO 261 | UUGGCUCUGGCCUGUCCUAAGA |
| SEQ ID NO 262 | AAGACCUGCUCAGCUUCUUCCUUAGCUUCCAG CCA |

MEANS AND METHODS FOR COUNTERACTING MUSCLE DISORDERS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*Notice: More than one reissue application has been filed for the reissue of U.S. Pat. No. 9,243,245. Besides the instant application, other reissue applications include two reissue applications (U.S. application Ser. No. 15/881,604 and U.S. application Ser. No. 15/881,610), which were both filed on Jan. 26, 2018; two continuation reissue applications (U.S. application Ser. No. 16/249,759 and U.S. application Ser. No. 16/249,777) which were both filed on Jan. 16, 2019; one continuation reissue application (U.S. application Ser. No. 16/353,978) which was filed on Mar. 14, 2019; and two divisional reissue applications (U.S. application Ser. No. 16/373,429 and U.S. application Ser. No. 16/373,459), which were both filed on Apr. 2, 2019.*

This application is a *reissue of U.S. Pat. No. 9,243,245, filed as U.S. application Ser. No. 12/767,702 on Apr. 26, 2010, which is a* continuation [application of and claims priority to] *of* PCT/NL2008/050673, filed *on* Oct. 27, 2008, *which claims priority to* EPO Application No. 07119351.0, filed *on* Oct. 26, 2007, and U.S. Provisional Application No. 61/000,670, filed *on* Oct. 26, 2007[, the]. *The* contents of [which] *each of the above applications* are hereby incorporated *by reference* in their entirety [by this reference].

The invention relates to the fields of molecular biology and medicine. A muscle disorder is a disease that usually has a significant impact on the life of an individual. A muscle disorder can either have a genetic cause or a non-genetic cause. An important group of muscle diseases with a genetic cause are Becker Muscular Dystrophy (BMD) and Duchenne Muscular Dystrophy (DMD). These disorders are caused by defects in a gene for a muscle protein.

Becker Muscular Dystrophy and Duchenne Muscular Dystrophy are genetic muscular dystrophies with a relatively high incidence. In both Duchenne and Becker muscular dystrophy the muscle protein dystrophin is affected. In Duchenne dystrophin is absent, whereas in Becker some dystrophin is present but its production is most often not sufficient and/or the dystrophin present is abnormally formed. Both diseases are associated with recessive X-linked inheritance. DMD results from a frameshift mutation in the DMD gene. The frameshift in the DMD gene results in the production of a truncated non-functional dystrophin protein, resulting in progressive muscle wasting and weakness. BMD occurs as a mutation does not cause a frame-shift in the DMD gene. As in BMD some dystrophin is present in contrast to DMD where dystrophin is absent, BMD has less severe symptoms then DMD. The onset of DMD is earlier than BMD. DMD usually manifests itself in early childhood, BMD in the teens or in early adulthood. The progression of BMD is slower and less predictable than DMD. Patients with BMD can survive into mid to late adulthood. Patients with DMD rarely survive beyond their thirties.

Dystrophin plays an important structural role in the muscle fiber, connecting the extracellular matrix and the cytoskeleton. The N-terminal region binds actin, whereas the C-terminal end is part of the dystrophin glycoprotein complex (DGC), which spans the sarcolemma. In the absence of dystrophin, mechanical stress leads to sarcolemmal ruptures, causing an uncontrolled influx of calcium into the muscle fiber interior, thereby triggering calcium-activated proteases and fiber necrosis.

For most genetic muscular dystrophies no clinically applicable and effective therapies are currently available. Exon skipping techniques are nowadays explored in order to combat genetic muscular dystrophies. Promising results have recently been reported by us and others on a genetic therapy aimed at restoring the reading frame of the dystrophin pre-mRNA in cells from the mdx mouse and DMD patients[1-11]. By the targeted skipping of a specific exon, a DMD phenotype (lacking dystrophin) is converted into a milder BMD phenotype (partly to largely functional dystrophin). The skipping of an exon is preferably induced by the binding of antisense oligoribonucleotides (AONs) targeting either one or both of the splice sites, or exon-internal sequences. Since an exon will only be included in the mRNA when both the splice sites are recognised by the spliceosome complex, splice sites are obvious targets for AONs. Alternatively, or additionally, one or more AONs are used which are specific for at least part of one or more exonic sequences. Using exon-internal AONs specific for an exon 46 sequence, we were previously able to modulate the splicing pattern in cultured myotubes from two different DMD patients with an exon 45 deletion[11]. Following AON treatment, exon 46 was skipped, which resulted in a restored reading frame and the induction of dystrophin synthesis in at least 75% of the cells. We have recently shown that exon skipping can also efficiently be induced in human control and patient muscle cells for 39 different DMD exons using exon-internal AONs[1,2,11-15].

Hence, exon skipping techniques applied on the dystrophin gene result in the generation of at least partially functional—albeit shorter—dystrophin protein in DMD patients. Since DMD is caused by a dysfunctional dystrophin protein, it would be expected that the symptoms of DMD are sufficiently alleviated once a DMD patient has been provided with functional dystrophin protein. However, the present invention provides the insight that, even though exon skipping techniques are capable of inducing dystrophin synthesis, DMD symptom(s) is/are still further alleviated by administering to a DMD patient an adjunct compound for reducing inflammation, preferably for reducing muscle tissue inflammation, and/or an adjunct compound for improving muscle fiber function, integrity and/or survival. According to the present invention, even when a dystrophin protein deficiency has been restored in a DMD patient, the presence of tissue inflammation and damaged muscle cells still continues to contribute to the symptoms of DMD. Hence, even though the cause of DMD—i.e. a dysfunctional dystrophin protein—is alleviated, treatment of DMD is still further improved by additionally using an adjunct therapy according to the present invention. Furthermore, the present invention provides the insight that a reduction of inflammation does not result in significant reduction of AON uptake by muscle cells. This is surprising because, in general, inflammation enhances the trafficking of cells, blood and other compounds. As a result, AON uptake/delivery is also enhanced during inflammation. Hence, before the present invention it would be expected that an adjunct therapy counteracting inflammation involves the risk of negatively influencing AON therapy. This, however, appears not to be the case.

The present invention therefore provides a method for alleviating one or more symptom(s) of Duchenne Muscular Dystrophy or Becker Muscular Dystrophy in an individual, the method comprising:

administering to said individual a compound for providing said individual with a (at least partially) functional dystrophin protein, and administering to said individual an adjunct compound for reducing inflammation, preferably for reducing muscle tissue inflammation, and/or an adjunct compound for improving muscle fiber function, integrity and/or survival.

In another preferred embodiment the method for alleviating one or more symptom(s) of Duchenne Muscular Dystrophy or Becker Muscular Dystrophy in an individual comprises administering to said individual an adjunct compound for reducing inflammation, preferably for reducing muscle tissue inflammation, and/or an adjunct compound for improving muscle fiber function, integrity and/or survival.

It has surprisingly been found that the skipping frequency of a dystrophin exon from a pre-mRNA comprising said exon, when using an oligonucleotide directed toward the exon or to one or both splice sites of said exon, is enhanced if cells expressing said pre-mRNA are also provided with an adjunct compound for reducing inflammation, preferably for reducing muscle tissue inflammation, and/or an adjunct compound for improving muscle fiber function, integrity and/or survival. The enhanced skipping frequency also increases the level of functional dystrophin protein produced in a muscle cell of a DMD or BMD individual.

The present invention further provides a method for enhancing skipping of an exon from a dystrophin pre-mRNA in cells expressing said pre-mRNA, said method comprising contacting said pre-mRNA in said cells with an oligonucleotide for skipping said exon and, contacting said cells with an adjunct compound for reducing inflammation, preferably for reducing muscle tissue inflammation, and/or an adjunct compound for improving muscle fiber function, integrity and/or survival.

As Duchenne and Becker muscular dystrophy have a pronounced phenotype in muscle cells, it is preferred that said cells are muscle cells. Preferably said cells comprise a gene encoding a mutant dystrophin protein. Preferably said cells are cells of an individual suffering from DMD or BMD.

The present invention further provides a method for enhancing skipping of an exon from a dystrophin pre-mRNA in cells expressing said pre-mRNA in an individual suffering from Duchenne Muscular Dystrophy or Becker Muscular Dystrophy, the method comprising:

administering to said individual a compound for providing said individual with a (at least partially) functional dystrophin protein, and administering to said individual an adjunct compound for reducing inflammation, preferably for reducing muscle tissue inflammation, and/or an adjunct compound for improving muscle fiber function, integrity and/or survival An individual is provided with a functional dystrophin protein in various ways. In one embodiment an exon skipping technique is applied. However, alternative methods are available, such as for instance stop codon suppression by gentamycin or PTC124[16,17] (also known as 3-(5-(2-fluorophenyl)-1,2,4-oxadiazol-3-yl)benzoic acid), and/or adeno-associated virus (AAV)-mediated gene delivery of a functional mini- or micro-dystrophin gene[18-20]. PTC124™ is a registered trademark of PTC Therapeutics, Inc. South Plainfield, N.J.

As defined herein, a functional dystrophin is preferably a wild type dystrophin corresponding to a protein having the amino acid sequence as identified in SEQ ID NO: 1. A functional dystrophin is preferably a dystrophin, which has an actin binding domain in its N terminal part (first 240 amino acids at the N terminus), a cystein-rich domain (amino acid 3361 till 3685) and a C terminal domain (last 325 amino acids at the C terminus) each of these domains being present in a wild type dystrophin as known to the skilled person. The amino acids indicated herein correspond to amino acids of the wild type dystrophin being represented by SEQ ID NO:1. In other words, a functional dystrophin is a dystrophin which exhibits at least to some extent an activity of a wild type dystrophin "At least to some extent" preferably means at least 30%, 40%, 50%, 60%, 70%, 80%, 90%, 95% or 100% of a corresponding activity of a wild type functional dystrophin. In this context, an activity of a functional dystrophin is preferably binding to actin and to the dystrophin-associated glycoprotein complex (DGC)[56]. Binding of dystrophin to actin and to the DGC complex may be visualized by either co-immunoprecipitation using total protein extracts or immunofluorescence analysis of cross-sections, from a biopsy of a muscle suspected to be dystrophic, as known to the skilled person.

Individuals suffering from Duchenne muscular dystrophy typically have a mutation in the gene encoding dystrophin that prevent synthesis of the complete protein, i.e of a premature stop prevents the synthesis of the C-terminus. In Becker muscular dystrophy the dystrophin gene also comprises a mutation compared tot the wild type but the mutation does typically not include a premature stop and the C-terminus is typically synthesized. As a result a functional dystrophin protein is synthesized that has at least the same activity in kind as the wild type protein, not although not necessarily the same amount of activity. The genome of a BMD individual typically encodes a dystrophin protein comprising the N terminal part (first 240 amino acids at the N terminus), a cystein-rich domain (amino acid 3361 till 3685) and a C terminal domain (last 325 amino acids at the C terminus) but its central rod shaped domain may be shorter than the one of a wild type dystrophin[56]. Exon—skipping for the treatment of DMD is typically directed to overcome a premature stop in the pre-mRNA by skipping an exon in the rod-domain shaped domain to correct the reading frame and allow synthesis of remainder of the dystrophin protein including the C-terminus, albeit that the protein is somewhat smaller as a result of a smaller rod domain. In a preferred embodiment, an individual having DMD and being treated by a method as defined herein will be provided a dystrophin which exhibits at least to some extent an activity of a wild type dystrophin. More preferably, if said individual is a Duchennes patient or is suspected to be a Duchennes patient, a functional dystrophin is a dystrophin of an individual having BMD: typically said dystrophin is able to interact with both actin and the DGC, but its central rod shaped domain may be shorter than the one of a wild type dystrophin (Aartsma-Rus et al (2006, ref 56). The central rod domain of wild type dystrophin comprises 24 spectrin-like repeats[56]. For example, a central rod shaped domain of a dystrophin as provided herein may comprise 5 to 23, 10 to 22 or 12 to 18 spectrin-like repeats as long as it can bind to actin and to DGC.

Alleviating one or more symptom(s) of Duchenne Muscular Dystrophy or Becker Muscular Dystrophy in an individual in a method of the invention may be assessed by any of the following assays: prolongation of time to loss of walking, improvement of muscle strength, improvement of the ability to lift weight, improvement of the time taken to rise from the floor, improvement in the nine-meter walking time, improvement in the time taken for four-stairs climbing, improvement of the leg function grade, improvement of the pulmonary function, improvement of cardiac function, improvement of the quality of life. Each of these assays is known to the skilled person. As an example, the publication of Manzur at al (2008, ref 58) gives an extensive explanation of each of these assays. For each of these assays, as soon as a detectable improvement or prolongation of a parameter measured in an assay has been found, it will preferably mean that one or more symptoms of Duchenne Muscular Dystrophy or Becker Muscular Dystrophy has been alleviated in an individual using a method of the invention. Detectable improvement or prolongation is preferably a statistically significant improvement or prolongation as described in Hodgetts et al (2006, ref 57). Alternatively, the alleviation of one or more symptom(s) of Duchenne Muscular Dystrophy or Becker Muscular Dystrophy may be assessed by measuring an improvement of a muscle fiber function, integrity and/or survival as later defined herein.

An adjunct compound for reducing inflammation comprises any therapy which is capable of at least in part reducing inflammation, preferably inflammation caused by damaged muscle cells. Said adjunct compound is most preferably capable of reducing muscle tissue inflammation. Inflammation is preferably assessed by detecting an increase in the number of infiltrating immune cells such as neutrophils and/or mast cells and/or dendritic cells and/or lymphocytes in muscle tissue suspected to be dystrophic. This assessment is preferably carried out in cross-sections of a biopsy[57] of muscle tissue suspected to be dystrophic after having specifically stained immune cells as identified above. The quantification is preferably carried out under the microscope. Reducing inflammation is therefore preferably assessed by detecting a decrease in the number of immune cells in a cross-section of muscle tissue suspected to be dystrophic. Detecting a decrease preferably means that the number of at least one sort of immune cells as identified above is decreased of at least 1%, 2%, 3%, 5%, 7%, 10%, 12%, 15%, 17%, 20%, 30%, 40%, 50%, 60%, 70%, 80%, 90% or more compared to the number of a corresponding immune cell in a same individual before treatment. Most preferably, no infiltrating immune cells are detected in cross-sections of said biopsy.

An adjunct compound for improving muscle fiber function, integrity and/or survival comprises any therapy which is capable of measurably enhancing muscle fiber function, integrity and/or survival as compared to an otherwise similar situation wherein said adjunct compound is not present. The improvement of muscle fiber function, integrity and/or survival may be assessed using at least one of the following assays: a detectable decrease of creatine kinase in blood, a detectable decrease of necrosis of muscle fibers in a biopsy cross-section of a muscle suspected to be dystrophic, and/or a detectable increase of the homogeneity of the diameter of muscle fibers in a biopsy cross-section of a muscle suspected to be dystrophic. Each of these assays is known to the skilled person.

Creatine kinase may be detected in blood as described in 57. A detectable decrease in creatine kinase may mean a decrease of 5%, 10%, 20%, 30%, 40%, 50%, 60%, 70%, 80%, 90% or more compared to the concentration of creatine kinase in a same individual before treatment.

A detectable decrease of necrosis of muscle fibers is preferably assessed in a muscle biopsy, more preferably as described in 57 using biopsy cross-sections. A detectable decrease of necrosis may be a decrease of 5%, 10%, 20%, 30%, 40%, 50%, 60%, 70%, 80%, 90% or more of the area wherein necrosis has been identified using biopsy cross-sections. The decrease is measured by comparison to the necrosis as assessed in a same individual before treatment.

A detectable increase of the homogeneity of the diameter of a muscle fiber is preferably assessed in a muscle biopsy cross-section, more preferably as described in 57.

A treatment in a method according to the invention is about at least one week, about at least one month, about at least several months, about at least one year, about at least 2, 3, 4, 5, 6 years or more.

In one embodiment an adjunct compound for increasing turnover of damaged muscle cells is used. An adjunct compound for increasing turnover of damaged muscle cells comprises any therapy which is capable of at least in part inducing and/or increasing turnover of damaged muscle cells. Damaged muscle cells are muscle cells which have significantly less clinically measurable functionality than a healthy, intact muscle cell. In the absence of dystrophin, mechanical stress leads to sarcolemmal ruptures, causing an uncontrolled influx of calcium into the muscle fiber interior, thereby triggering calcium-activated proteases and fiber necrosis, resulting in damaged muscle cells. Increasing turnover of damaged muscle cells means that damaged muscle cells are more quickly broken down and/or removed as compared to a situation wherein turnover of damaged muscle cells is not increased. Turnover of damaged muscle cells is preferably assessed in a muscle biopsy, more preferably as described in 57 using a cross-section of a biopsy. A detectable increase of turnover may be an increase of 5%, 10%, 20%, 30%, 40%, 50%, 60%, 70%, 80%, 90% or more of the area wherein turnover has been identified using a biopsy cross-section. The increase is measured by comparison to the turnover as assessed in a same individual before treatment.

Without wishing to be bound to theory, it is believed that increasing turnover of muscle cells is preferred because this reduces inflammatory responses.

According to the present invention, a combination of a therapy for providing an individual with a functional dystrophin protein, together with an adjunct therapy for reducing inflammation, preferably for reducing muscle tissue inflammation in an individual, is particularly suitable for use as a medicament. Such combination is even better capable of alleviating one or more symptom(s) of Duchenne Muscular Dystrophy or Becker Muscular Dystrophy as compared to a sole therapy for providing an individual with a functional dystrophin protein. This embodiment also enhances the skipping frequency of a dystrophin exon from a pre-mRNA comprising said exon, when using an oligonucleotide directed toward the exon or to one or both splice sites of said exon. The enhanced skipping frequency also increases the level of functional dystrophin protein produced in a muscle cell of a DMD or BMD individual.

Further provided is therefore a combination of a compound for providing an individual with a functional dystrophin protein, and an adjunct compound for reducing inflammation, preferably for reducing muscle tissue inflammation in said individual, for use as a medicament. Since said combination is particularly suitable for counteracting DMD, the invention also provides a use of a compound for providing an individual with a functional dystrophin protein, and an adjunct compound for reducing inflammation, preferably for reducing muscle tissue inflammation in said individual, for the preparation of a medicament for alleviating one or more symptom(s) of Duchenne Muscular Dystrophy. In one embodiment, said combination is used in order to alleviate one or more symptom(s) of a severe form of BMD wherein a very short dystrophin protein is formed which is not sufficiently functional.

Preferred adjunct compound for reducing inflammation include a steroid, a TNF□ inhibitor, a source of mIGF-1 and/or an antioxidant. However, any other compound able to reduce inflammation as defined herein is also encompassed within the present invention. Each of these compounds is later on extensively presented. Each of the compounds extensively presented may be used separately or in combination with each other and/or in combination with one or more of the adjunct compounds used for improving muscle fiber function, integrity and/or survival.

Furthermore, a combination of a therapy for providing an individual with a functional dystrophin protein, together with an adjunct therapy for improving muscle fiber function, integrity and/or survival in an individual is particularly suitable for use as a medicament. Such combination is even better capable of alleviating one or more symptom(s) of Duchenne Muscular Dystrophy as compared to a sole therapy for providing an individual with a functional dystrophin protein.

Further provided is therefore a combination of a compound for providing an individual with a functional dystrophin protein, and an adjunct compound for improving muscle fiber function, integrity and/or survival in said individual, for use as a medicament. This combination is also particularly suitable for counteracting DMD. A use of a compound for providing an individual with a functional dystrophin protein, and an adjunct compound for improving muscle fiber function, integrity and/or survival in said individual, for the preparation of a medicament for alleviating one or more symptom(s) of Duchenne Muscular Dystrophy is therefore also provided. In one embodiment, said combination is used in order to alleviate one or more symptom(s) of a severe form of BMD wherein a very short dystrophin protein is formed which is not sufficiently functional.

Preferred adjunct compounds for improving muscle fiber function, integrity and/or survival include a ion channel inhibitor, a protease inhibitor, L-arginine and/or an angiotensin II type I receptor blocker. However, any other compound able to improving muscle fiber function, integrity and/or survival as defined herein is also encompassed within the present invention. Each of these compounds is later on extensively presented. Each of the compounds extensively presented may be used separately or in combination with each other and/or in combination with one or more of the adjunct compounds used for reducing inflammation.

In one embodiment a pharmaceutical preparation is made which comprises at least one of the above mentioned combinations comprising a compound for providing an individual with a functional dystrophin protein together with an adjunct compound according to the invention. Further provided is therefore a pharmaceutical preparation comprising:

a compound for providing an individual with a functional dystrophin protein, and an adjunct compound for reducing inflammation, preferably for reducing muscle tissue inflammation in said individual, and/or an adjunct compound for improving muscle fiber function, integrity and/or survival in said individual, and a pharmaceutically acceptable carrier, adjuvant, diluent and/or excipient. Examples of suitable carriers and adjuvants are well known in the art and for instance comprise a saline solution. Dose ranges of compounds used in a pharmaceutical preparation according to the invention are designed on the basis of rising dose studies in clinical trials for which rigorous protocol requirements exist.

In a particularly preferred embodiment, a compound for providing an individual with a functional dystrophin protein is combined with a steroid. As shown in the Examples, such combination results in significant alleviation of DMD symptoms. One preferred embodiment of the present invention therefore provides a method for alleviating one or more symptom(s) of Duchenne Muscular Dystrophy in an individual, the method comprising administering to said individual a steroid and a compound for providing said individual with a functional dystrophin protein. A combination of a steroid and a compound for providing an individual with a functional dystrophin protein for use as a medicament is also provided, as well as a use of a steroid and a compound for providing an individual with a functional dystrophin protein for the preparation of a medicament for alleviating one or more symptom(s) of DMD. This embodiment also enhances the skipping frequency of a dystrophin exon from a pre-mRNA comprising said exon, when using an oligonucleotide directed toward the exon or to one or both splice sites of said exon. The enhanced skipping frequency also increases the level of functional dystrophin protein produced in a muscle cell of a DMD or BMD individual.

In one embodiment, said combination is used in order to alleviate one or more symptom(s) of a severe form of BMD wherein a very short dystrophin protein is formed which is not sufficiently functional.

A steroid is a terpenoid lipid characterized by a carbon skeleton with four fused rings, generally arranged in a 6-6-6-5 fashion. Steroids vary by the functional groups attached to these rings and the oxidation state of the rings. Steroids include hormones and drugs which are usually used to relieve swelling and inflammation, such as for instance prednisone, dexamethasone and vitamin D.

According to the present invention, supplemental effects of adjunct steroid therapy in DMD patients include reduction of tissue inflammation, suppression of cytotoxic cells, and improved calcium homeostasis. Most positive results are obtained in younger boys. Preferably the steroid is a corticosteroid (glucocorticosteroid). Preferably, prednisone steroids (such as prednisone, prednizolone or deflazacort) are used in a method according to the invention[21]. Dose ranges of (glucocortico)steroids to be used in the therapeutic applications as described herein are designed on the basis of rising dose studies in clinical trials for which rigorous protocol requirements exist. The usual doses are about 0.5-1.0 mg/kg/day, preferably about 0.75 mg/kg/day for prednisone and prednisolone, and about 0.4-1.4 mg/kg/day, preferably about 0.9 mg/kg/day for deflazacort.

In one embodiment, a steroid is administered to said individual prior to administering a compound for providing an individual with a functional dystrophin protein. In this embodiment, it is preferred that said steroid is administered at least one day, more preferred at least one week, more preferred at least two weeks, more preferred at least three weeks prior to administering a compound for providing said individual with a functional dystrophin protein.

In another preferred embodiment, a compound for providing an individual with a functional dystrophin protein is combined with a tumour necrosis factor-alpha (TNFα) inhibitor. Tumour necrosis factor-alpha (TNFα) is a pro-inflammatory cytokine that stimulates the inflammatory response. Pharmacological blockade of TNFα activity with the neutralising antibody infliximab (Remicade) is highly effective clinically at reducing symptoms of inflammatory diseases. In mdx mice, both infliximab and etanercept delay and reduce the necrosis of dystrophic muscle[24,25], with additional physiological benefits on muscle strength, chloride channel function and reduced CK levels being demonstrated in chronically treated exercised adult mdx mice[26]. Such highly specific anti-inflammatory drugs designed for use in other clinical conditions, are attractive alternatives to the use of steroids for DMD. In one embodiment, the use of a TNFα inhibitor is limited to periods of intensive muscle growth in boys when muscle damage and deterioration are especially pronounced.

One aspect of the present invention thus provides a method for alleviating one or more symptom(s) of Duchenne Muscular Dystrophy in an individual, the method comprising administering to said individual a TNFα inhibitor and a compound for providing said individual with a functional dystrophin protein. A combination of a TNFα inhibitor and a compound for providing an individual with a functional dystrophin protein for use as a medicament is also provided, as well as a use of a TNFα inhibitor and a compound for providing an individual with a functional dystrophin protein for the preparation of a medicament for alleviating one or more symptom(s) of DMD. In one embodiment, said combination is used in order to alleviate one or more symptom(s) of a severe form of BMD wherein a very short dystrophin protein is formed which is not sufficiently functional. A preferred TNFα inhibitor is a dimeric fusion protein consisting of the extracellular ligand-binding domain of the human p75 receptor of TNFα linked to the Fc portion of human IgGl. A more preferred TNFα inhibitor is ethanercept (Amgen, America)[26]. The usual doses of ethanercept is about 0.2 mg/kg, preferably about 0.5 mg/kg twice a week. The administration is preferably subcutaneous.

In another preferred embodiment, a compound for providing an individual with a functional dystrophin protein is combined with a source of mIGF-1. As defined herein, a source of IGF-1 preferably encompasses mIGF-1 itself, a compound able of enhancing mIGF-1 expression and/or activity. Enhancing is herein synonymous with increasing. Expression of mIGF-1 is synonymous with amount of mIGF-1. mIGF-1 promotes regeneration of muscles through increase in satellite cell activity, and reduces inflammation and fibrosis[27]. Local injury of muscle results in increased mIGF-1 expression. In transgenic mice with extra IGF-1 genes, muscle hypertrophy and enlarged muscle fibers are observed[27]. Similarly, transgenic mdx mice show reduced muscle fiber degeneration[28]. Upregulation of the mIGF-1 gene and/or administration of extra amounts of mIGF-1 protein or a functional equivalent thereof (especially the mIGF-1 Ea isoform [as described in 27, human homolog IGF-1 isoform 4: SEQ ID NO: 2]) thus promotes the effect of other, preferably genetic, therapies for DMD, including antisense-induced exon skipping. The additional mIGF-1 levels in the above mentioned transgenic mice do not induce cardiac problems nor promote cancer, and have no pathological side effects. One aspect of the present invention thus provides a method for alleviating one or more symptom(s) of Duchenne Muscular Dystrophy in an individual, the method comprising administering to said individual a compound for providing said individual with a functional dystrophin protein, and providing said individual with a source of mIGF-1, preferably mIGF-1 itself, a compound able of increasing mIGF-1 expression and/or activity. As stated before, the amount of mIGF-1 is for instance increased by enhancing expression of the mIGF-1 gene and/or by administration of mIGF-1 protein and/or a functional equivalent thereof (especially the mIGF-1 Ea isoform [as described in 27, human homolog IGF-1 isoform 4: SEQ ID NO: 2]). A combination of mIGF-1, or a compound capable of enhancing mIGF-1 expression or an mIGF-1 activity, and a compound for providing an individual with a functional dystrophin protein for use as a medicament is also provided, as well as a use of mIGF-1, or a compound capable of enhancing mIGF-1 expression or mIGF-1 activity, and a compound for providing an individual with a functional dystrophin protein for the preparation of a medicament for alleviating one or more symptom(s) of DMD. In one embodiment, such combination is used in order to alleviate one or more symptom(s) of a severe form of BMD wherein a very short dystrophin protein is formed which is not sufficiently functional.

Within the context of the invention, an increased amount or activity of mIGF-1 may be reached by increasing the gene expression level of an IGF-1 gene, by increasing the amount of a corresponding IGF-1 protein and/or by increasing an activity of an IGF1-protein. A preferred mIGF-1 protein has been earlier defined herein. An increase of an activity of said protein is herein understood to mean any detectable change in a biological activity exerted by said protein or in the steady state level of said protein as compared to said activity or steady-state in a individual who has not been treated. Increased amount or activity of mIGF-1 is preferably assessed by detection of increased expression of muscle hypertrophy biomarker GATA-2 (as described in 27).

Gene expression level is preferably assessed using classical molecular biology techniques such as (real time) PCR, arrays or Northern analysis. A steady state level of a protein is determined directly by quantifying the amount of a protein. Quantifying a protein amount may be carried out by any known technique such as Western blotting or immunoassay using an antibody raised against a protein. The skilled person will understand that alternatively or in combination with the quantification of a gene expression level and/or a corresponding protein, the quantification of a substrate of a corresponding protein or of any compound known to be associated with a function or activity of a corresponding protein or the quantification of said function or activity of a corresponding protein using a specific assay may be used to assess the alteration of an activity or steady state level of a protein.

In a method of the invention, an activity or steady-state level of a said protein may be altered at the level of the protein itself, e.g. by providing a protein to a cell from an exogenous source.

Preferably, an increase or an upregulation of the expression level of a said gene means an increase of at least 5% of the expression level of said gene using arrays. More preferably, an increase of the expression level of said gene means an increase of at least 10%, even more preferably at least 20%, at least 30%, at least 40%, at least 50%, at least 70%, at least 90%, at least 150% or more. In another preferred embodiment, an increase of the expression level of said protein means an increase of at least 5% of the expression level of said protein using western blotting and/or using ELISA or a suitable assay. More preferably, an increase of the expression level of a protein means an increase of at least 10%, even more preferably at least 20%, at least 30%, at least 40%, at least 50%, at least 70%, at least 90%, at least 150% or more.

In another preferred embodiment, an increase of a polypeptide activity means an increase of at least 5% of a polypeptide activity using a suitable assay. More preferably, an increase of a polypeptide activity means an increase of at least 10%, even more preferably at least 20%, at least 30%, at least 40%, at least 50%, at least 70%, at least 90%, at least 150% or more. The increase is preferably assessed by comparison to corresponding activity in the individual before treatment.

A preferred way of providing a source of mIGF1 is to introduce a transgene encoding mIGF1, preferably an mIGF-1 Ea isoform (as described in 27, human homolog IGF-1 isoform 4: SEQ ID NO: 2), more preferably in an AAV vector as later defined herein. Such source of mIGF1 is specifically expressed in muscle tissue as described in mice in 27.

In another preferred embodiment, a compound for providing an individual with a functional dystrophin protein is combined with an antioxidant. Oxidative stress is an important factor in the progression of DMD and promotes chronic inflammation and fibrosis[29]. The most prevalent products of oxidative stress, the peroxidized lipids, are increased by an average of 35% in Duchenne boys. Increased levels of the enzymes superoxide dismutase and catalase reduce the excessive amount of free radicals causing these effects. In fact, a dietary supplement Protandim® (LifeVantage) was clinically tested and found to increase levels of superoxide dismutase (up to 30%) and catalase (up to 54%), which indeed significantly inhibited the peroxidation of lipids in 29 healthy persons[30]. Such effective management of oxidative stress thus preserves muscle quality and so promotes the positive effect of DMD therapy. Idebenone is another potent antioxidant with a chemical structure derived from natural coenzyme Q10. It protects mitochondria where adenosine triphosphate, ATP, is generated by oxidative phosphorylation. The absence of dystrophin in DMD negatively affects this process in the heart, and probably also in skeletal muscle. Idebenone was recently applied in clinical trials in the US and Europe demonstrating efficacy on neurological aspects of Friedreich's Ataxia[31]. A phase-IIa double-blind, placebo-controlled randomized clinical trial with Idebenone has recently been started in Belgium, including 21 Duchenne boys at 8 to 16 years of age. The primary objective of this study is to determine the effect of Idebenone on heart muscle function. In addition several different tests will be performed to detect the possible functional benefit on muscle strength in the patients. When effective, Idebenone is a preferred adjunct compound for use in a method according to the present invention in order to enhance the therapeutic effect of DMD therapy, especially in the heart. One aspect of the present invention thus provides a method for alleviating one or more symptom(s) of Duchenne Muscular Dystrophy in an individual, the method comprising administering to said individual an antioxidant and a compound for providing said individual with a functional dystrophin protein. A combination of an antioxidant and a compound for providing an individual with a functional dystrophin protein for use as a medicament is also provided, as well as a use of an antioxidant and a compound for providing an individual with a functional dystrophin protein for the preparation of a medicament for alleviating one or more symptom(s) of DMD. In one embodiment, said combination is used in order to alleviate one or more symptom(s) of a severe form of BMD wherein a very short dystrophin protein is formed which is not sufficiently functional. Depending on the identity of the antioxidant, the skilled person will know which quantities are preferably used. An antioxidant may include bacoside, silymarin, curcumin, a polyphenol, preferably epigallocatechin-3-gallate (EGCG). Preferably, an anti-oxidant is a mixture of antioxidants as the dietary supplement Protandim® (LifeVantage). A daily capsule of 675 mg of Protandim® comprises 150 mg of B. monniera (45% bacosides), 225 mg of S. marianum (70-80% silymarin), 150 mg of W. somnifera powder, 75 mg green tea (98% polyphenols wherein 45% EGCG) and 75 mg turmeric (95% curcumin).

In another preferred embodiment, a compound for providing an individual with a functional dystrophin protein is combined with an ion channel inhibitor. The presence of damaged muscle membranes in DMD disturbs the passage of calcium ions into the myofibers, and the consequently disrupted calcium homeostasis activates many enzymes, e.g. proteases, that cause additional damage and muscle necrosis. Ion channels that directly contribute to the pathological accumulation of calcium in dystrophic muscle are potential targets for adjunct compounds to treat DMD. There is evidence that some drugs, such as pentoxifylline, block exercise-sensitive calcium channels[32] and antibiotics that block stretch activated channels reduce myofibre necrosis in mdx mice and CK levels in DMD boys[33]. One embodiment thus provides a method for alleviating one or more symptom(s) of Duchenne Muscular Dystrophy in an individual, the method comprising administering to said individual an ion channel inhibitor and a compound for providing said individual with a functional dystrophin protein. A combination of an ion channel inhibitor and a compound for providing an individual with a functional dystrophin protein for use as a medicament is also provided, as well as a use of an ion channel inhibitor and a compound for providing an individual with a functional dystrophin protein for the preparation of a medicament for alleviating one or more symptom(s) of DMD. In one embodiment, said combination is used in order to alleviate one or more symptom(s) of a severe form of BMD wherein a very short dystrophin protein is formed which is not sufficiently functional.

Preferably, ion channel inhibitors of the class of xanthines are used. More preferably, said xanthines are derivatives of methylxanthines, and most preferably, said methylxanthine derivates are chosen from the group consisting of pentoxifylline, furafylline, lisofylline, propentofylline, pentifylline, theophylline, torbafylline, albifylline, enprofylline and derivatives thereof. Most preferred is the use of pentoxifylline. Ion channel inhibitors of the class of xanthines enhance the skipping frequency of a dystrophin exon from a pre-mRNA comprising said exon, when using an oligonucleotide directed toward the exon or to one or both splice sites of said exon. The enhanced skipping frequency also increases the level of functional dystrophin protein produced in a muscle cell of a DMD or BMD individual.

Depending on the identity of the ion channel inhibitor, the skilled person will know which quantities are preferably used. Suitable dosages of pentoxifylline are between about 1 mg/kg/day to about 100 mg/kg/day, preferred dosages are between about 10 mg/kg/day to 50 mg/kg/day. Typical dosages used in humans are 20 mg/kg/day.

In one embodiment, an ion channel inhibitor is administered to said individual prior to administering a compound for providing an individual with a functional dystrophin protein. In this embodiment, it is preferred that said ion channel inhibitor is administered at least one day, more preferred at least one week, more preferred at least two weeks, more preferred at least three weeks prior to administering a compound for providing said individual with a functional dystrophin protein.

In another preferred embodiment, a compound for providing an individual with a functional dystrophin protein is combined with a protease inhibitor. Calpains are calcium activated proteases that are increased in dystrophic muscle and account for myofiber degeneration. Calpain inhibitors such as calpastatin, leupeptin[34], calpeptin, calpain inhibitor III, or PD150606 are therefore applied to reduce the degeneration process. A new compound, BN 82270 (Ipsen) that has dual action as both a calpain inhibitor and an antioxidant increased muscle strength, decreased serum CK and reduced fibrosis of the mdx diaphragm, indicating a therapeutic effect with this new compound[35]. Another compound of Leupeptin/Carnitine (Myodur) has recently been proposed for clinical trials in DMD patients.

MG132 is another proteasomal inhibitor that has shown to reduce muscle membrane damage, and to ameliorate the histopathological signs of muscular dystrophy[36]. MG-132 (CBZ-leucyl-leucyl-leucinal) is a cell-permeable, proteasomal inhibitor (Ki=4 nM) which inhibits NFkappaB activation by preventing IkappaB degradation (IC50=3 □M). In addition, it is a peptide aldehyde that inhibits ubiquitin-mediated proteolysis by binding to and inactivating 20S and 26S proteasomes. MG-132 has shown to inhibit the proteasomal degradation of dystrophin-associated proteins in the dystrophic mdx mouse model[36]. This compound is thus also suitable for use as an adjunct pharmacological compound for DMD. Further provided is therefore a method for alleviating one or more symptom(s) of Duchenne Muscular Dystrophy in an individual, the method comprising administering to said individual a protease inhibitor and a compound for providing said individual with a functional dystrophin protein. A combination of a protease inhibitor and a compound for providing an individual with a functional dystrophin protein for use as a medicament is also provided, as well as a use of a protease inhibitor and a compound for providing an individual with a functional dystrophin protein for the preparation of a medicament for alleviating one or more symptom(s) of DMD. In one embodiment, said combination is used in order to alleviate one or more symptom(s) of a severe form of BMD wherein a very short dystrophin protein is formed which is not sufficiently functional. Depending on the identity of the protease inhibitor, the skilled person will know which quantities are preferably used.

In another preferred embodiment, a compound for providing an individual with a functional dystrophin protein is combined with L-arginine. Dystrophin-deficiency is associated with the loss of the DGC-complex at the fiber membranes, including neuronal nitric oxide synthase (nNOS). Expression of a nNOS transgene in mdx mice greatly reduced muscle membrane damage. Similarly, administration of L-arginine (the substrate for nitric oxide synthase) increased NO production and upregulated utrophin expression in mdx mice. Six weeks of L-arginine treatment improved muscle pathology and decreased serum CK in mdx mice[37]. The use of L-arginine as an adjunct therapy in combination with a compound for providing said individual with a functional dystrophin protein has not been disclosed.

Further provided is therefore a method for alleviating one or more symptom(s) of Duchenne Muscular Dystrophy in an individual, the method comprising administering to said individual L-arginine and a compound for providing said individual with a functional dystrophin protein. A combination of L-arginine and a compound for providing an individual with a functional dystrophin protein for use as a medicament is also provided, as well as a use of L-arginine and a compound for providing an individual with a functional dystrophin protein for the preparation of a medicament for alleviating one or more symptom(s) of DMD. In one embodiment, said combination is used in order to alleviate one or more symptom(s) of a severe form of BMD wherein a very short dystrophin protein is formed which is not sufficiently functional.

In another preferred embodiment, a compound for providing an individual with a functional dystrophin protein is combined with angiotensin II type 1 receptor blocker Losartan which normalizes muscle architecture, repair and function, as shown in the dystrophin-deficient mdx mouse model[23]. One aspect of the present invention thus provides a method for alleviating one or more symptom(s) of Duchenne Muscular Dystrophy in an individual, the method comprising administering to said individual angiotensin II type 1 receptor blocker Losartan, and a compound for providing said individual with a functional dystrophin protein. A combination of angiotensin II type 1 receptor blocker Losartan and a compound for providing an individual with a functional dystrophin protein for use as a medicament is also provided, as well as a use of angiotensin II type 1 receptor blocker Losartan and a compound for providing an individual with a functional dystrophin protein for the preparation of a medicament for alleviating one or more symptom(s) of DMD. In one embodiment, said combination is used in order to alleviate one or more symptom(s) of a severe form of BMD wherein a very short dystrophin protein is formed which is not sufficiently functional. Depending on the identity of the angiotensin II type 1 receptor blocker, the skilled person will know which quantities are preferably used.

In another preferred embodiment, a compound for providing an individual with a functional dystrophin protein is combined with an angiotensin-converting enzyme (ACE) inhibitor, preferably perindopril. ACE inhibitors are capable of lowering blood pressure. Early initiation of treatment with perindopril is associated with a lower mortality in DMD patients[22]. One aspect of the present invention thus provides a method for alleviating one or more symptom(s) of Duchenne Muscular Dystrophy in an individual, the method comprising administering to said individual an ACE inhibitor, preferably perindopril, and a compound for providing said individual with a functional dystrophin protein. A combination of an ACE inhibitor, preferably perindopril, and a compound for providing an individual with a functional dystrophin protein for use as a medicament is also provided, as well as a use of an ACE inhibitor, preferably perindopril, and a compound for providing an individual with a functional dystrophin protein for the preparation of a medicament for alleviating one or more symptom(s) of DMD. In one embodiment, said combination is used in order to alleviate one or more symptom(s) of a severe form of BMD wherein a very short dystrophin protein is formed which is not sufficiently functional. The usual doses of an ACE inhibitor, preferably perindopril are about 2 to 4 mg/day[22].

In a more preferred embodiment, an ACE inhibitor is combined with at least one of the previously identified adjunct compounds.

In another preferred embodiment, a compound for providing an individual with a functional dystrophin protein is combined with a compound which is capable of enhancing exon skipping and/or inhibiting spliceosome assembly and/or splicing. Small chemical compounds, such as for instance specific indole derivatives, have been shown to selectively inhibit spliceosome assembly and splicing[38], for instance by interfering with the binding of serine- and arginine-rich (SR) proteins to their cognate splicing enhancers (ISEs or ESEs) and/or by interfering with the binding of splicing repressors to silencer sequences (ESSs or ISSs). These compounds are therefore suitable for applying as adjunct compounds that enhance exon skipping.

Further provided is therefore a method for alleviating one or more symptom(s) of Duchenne Muscular Dystrophy in an individual, the method comprising administering to said individual a compound for enhancing exon skipping and/or inhibiting spliceosome assembly and/or splicing, and a compound for providing said individual with a functional dystrophin protein. A combination of a compound for enhancing exon skipping and/or inhibiting spliceosome assembly and/or splicing and a compound for providing an individual with a functional dystrophin protein for use as a medicament is also provided, as well as a use of a compound for enhancing exon skipping and/or inhibiting spliceosome assembly and/or splicing and a compound for providing an individual with a functional dystrophin protein for the preparation of a medicament for alleviating one or more symptom(s) of DMD. In one embodiment, said combination is used in order to alleviate one or more symptom(s) of a severe form of BMD wherein a very short dystrophin protein is formed which is not sufficiently functional. Depending on the identity of the compound which is capable of enhancing exon skipping and/or inhibiting spliceosome assembly and/or splicing, the skilled person will know which quantities are preferably used. In a more preferred embodiment, a compound for enhancing exon skipping and/or inhibiting spliceosome assembly and/or splicing is combined with a ACE inhibitor and/or with any adjunct compounds as identified earlier herein.

A pharmaceutical preparation comprising a compound for providing an individual with a functional dystrophin protein, any of the above mentioned adjunct compounds, and a pharmaceutically acceptable carrier, filler, preservative, adjuvant, solubilizer, diluent and/or excipient is also provided. Such pharmaceutically acceptable carrier, filler, preservative, adjuvant, solubilizer, diluent and/or excipient may for instance be found in Remington: The Science and Practice of Pharmacy, 20th Edition. Baltimore, Md.: Lippincott Williams & Wilkins, 2000.

The invention thus provides a method, combination, use or pharmaceutical preparation according to the invention, wherein said adjunct compound comprises a steroid, an ACE inhibitor (preferably perindopril), angiotensin II type 1 receptor blocker Losartan, a tumour necrosis factor-alpha (TNF$\alpha$) inhibitor, a source of mIGF-1, preferably mIGF-1, a compound for enhancing mIGF-1 expression, a compound for enhancing mIGF-1 activity, an antioxidant, an ion channel inhibitor, a protease inhibitor, L-arginine and/or a compound for enhancing exon skipping and/or inhibiting spliceosome assembly and/or splicing.

As described herein before, an individual is provided with a functional dystrophin protein in various ways, for instance by stop codon suppression by gentamycin or PTC124[16,17], or by adeno-associated virus (AAV)-mediated gene delivery of a functional mini- or micro-dystrophin gene[18-20].

Preferably, however, said compound for providing said individual with a functional dystrophin protein comprises an oligonucleotide, or a functional equivalent thereof, for at least in part decreasing the production of an aberrant dystrophin protein in said individual. Decreasing the production of an aberrant dystrophin mRNA, or aberrant dystrophin protein, preferably means that 90%, 80%, 70%, 60%, 50%, 40%, 30%, 20%, 10%, 5% or less of the initial amount of aberrant dystrophin mRNA, or aberrant dystrophin protein, is still detectable by RT PCR (mRNA) or immunofluorescence or western blot analysis (protein). An aberrant dystrophin mRNA or protein is also referred to herein as a non-functional dystrophin mRNA or protein. A non functional dystrophin protein is preferably a dystrophin protein which is not able to bind actin and/or members of the DGC protein complex. A non-functional dystrophin protein or dystrophin mRNA does typically not have, or does not encode a dystrophin protein with an intact C-terminus of the protein. Said oligonucleotide preferably comprises an antisense oligoribonucleotide. In a preferred embodiment an exon skipping technique is applied.

Exon skipping interferes with the natural splicing processes occurring within a eukaryotic cell. In higher eukaryotes the genetic information for proteins in the DNA of the cell is encoded in exons which are separated from each other by intronic sequences. These introns are in some cases very long. The transcription machinery of eukaryotes generates a pre-mRNA which contains both exons and introns, while the splicing machinery, often already during the production of the pre-mRNA, generates the actual coding region for the protein by splicing together the exons present in the pre-mRNA.

Exon-skipping results in mature mRNA that lacks at least one skipped exon. Thus, when said exon codes for amino acids, exon skipping leads to the expression of an altered product. Technology for exon-skipping is currently directed towards the use of antisense oligonucleotides (AONs). Much of this work is done in the mdx mouse model for Duchenne muscular dystrophy. The mdx mouse, which carries a non-sense mutation in exon 23 of the dystrophin gene, has been used as an animal model of DMD. Despite the mdx mutation, which should preclude the synthesis of a functional dystrophin protein, rare, naturally occurring dystrophin positive fibers have been observed in mdx muscle tissue. These dystrophin-positive fibers are thought to have arisen from an apparently naturally occurring exon-skipping mechanism, either due to somatic mutations or through alternative splicing. AONs directed to, respectively, the 3' and/or 5' splice sites of introns 22 and 23 in dystrophin pre-mRNA, have been shown to interfere with factors normally involved in removal of intron 23 so that also exon 23 was removed from the mRNA[3,5,6,39,40].

By the targeted skipping of a specific exon, a DMD phenotype is converted into a milder BMD phenotype. The skipping of an exon is preferably induced by the binding of AONs targeting either one or both of the splice sites, or exon-internal sequences. An oligonucleotide directed toward an exon internal sequence typically exhibits no overlap with non-exon sequences. It preferably does not overlap with the splice sites at least not insofar as these are present in the intron. An oligonucleotide directed toward an exon internal sequence preferably does not contain a sequence complementary to an adjacent intron. Further provided is thus a method, combination, use or pharmaceutical preparation according to the invention, wherein said compound for providing said individual with a functional dystrophin protein comprises an oligonucleotide, or a functional equivalent thereof, for inhibiting inclusion of an exon of a dystrophin pre-mRNA into mRNA produced from splicing of said pre-mRNA. An exon skipping technique is preferably applied such that the absence of an exon from mRNA produced from dystrophin pre-mRNA generates a coding region for a functional—albeit shorter—dystrophin protein. In this context, inhibiting inclusion of an exon preferably means that the detection of the original, aberrant dystrophin mRNA is decreased of at least about 10% as assessed by RT-PCR or that a corresponding aberrant dystrophin protein is decreased of at least about 10% as assessed by immunofluorescence or western blot analysis. The decrease is preferably of at least 20%, 30%, 40%, 50%, 60%, 70%, 80%, 90% or 100%.

Once a DMD patient is provided with a functional dystrophin protein, the cause of DMD is taken away. Hence, it would then be expected that the symptoms of DMD are sufficiently alleviated. However, as already described before, the present invention provides the insight that, even though exon skipping techniques are capable of providing a functional dystrophin protein, a symptom of DMD is still further alleviated by administering to a DMD patient an adjunct compound for reducing inflammation, preferably for reducing muscle tissue inflammation, and/or an adjunct compound for improving muscle fiber function, integrity and/or survival. Moreover, the present invention provides the insight that an adjunct therapy counteracting inflammation does not negatively influence AON therapy. The present invention further provides the insight that the skipping frequency of a dystrophin exon from a pre-mRNA comprising said exon is enhanced, when using an oligonucleotide directed toward the exon or to one or both splice sites of said exon. The enhanced skipping frequency also increases the level of functional dystrophin protein produced in a muscle cell of a DMD or BMD individual.

Since an exon of a dystrophin pre-mRNA will only be included into the resulting mRNA when both the splice sites are recognised by the spliceosome complex, splice sites are obvious targets for AONs. One embodiment therefore provides a method, combination, use or pharmaceutical preparation according to the invention, wherein said compound for providing said individual with a functional dystrophin protein comprises an oligonucleotide, or a functional equivalent thereof, comprising a sequence which is complementary to a non-exon region of a dystrophin pre mRNA. In one embodiment an AON is used which is solely complementary to a non-exon region of a dystrophin pre mRNA. This is however not necessary: it is also possible to use an AON which comprises an intron-specific sequence as well as exon-specific sequence. Such AON comprises a sequence which is complementary to a non-exon region of a dystrophin pre mRNA, as well as a sequence which is complementary to an exon region of a dystrophin pre mRNA. Of course, an AON is not necessarily complementary to the entire sequence of a dystrophin exon or intron. AONs which are complementary to a part of such exon or intron are preferred. An AON is preferably complementary to at least part of a dystrohin exon and/or intron, said part having at least 13 nucleotides.

Splicing of a dystrophin pre-mRNA occurs via two sequential transesterification reactions. First, the 2'OH of a specific branch-point nucleotide within the intron that is defined during spliceosome assembly performs a nucleophilic attack on the first nucleotide of the intron at the 5' splice site forming the lariat intermediate. Second, the 3'OH of the released 5' exon then performs a nucleophilic attack at the last nucleotide of the intron at the 3' splice site thus joining the exons and releasing the intron lariat. The branch point and splice sites of an intron are thus involved in a splicing event. Hence, an oligonucleotide comprising a sequence which is complementary to such branch point and/or splice site is preferably used for exon skipping. Further provided is therefore a method, combination, use or pharmaceutical preparation according to the invention, wherein said compound for providing said individual with a functional dystrophin protein comprises an oligonucleotide, or a functional equivalent thereof, comprising a sequence which is complementary to a splice site and/or branch point of a dystrophin pre mRNA.

Since splice sites contain consensus sequences, the use of an oligonucleotide or a functional equivalent thereof (herein also called an AON) comprising a sequence which is complementary of a splice site involves the risk of promiscuous hybridization. Hybridization of AONs to other splice sites than the sites of the exon to be skipped could easily interfere with the accuracy of the splicing process. To overcome these and other potential problems related to the use of AONs which are complementary to an intron sequence, one preferred embodiment provides a method, combination, use or pharmaceutical preparation according to the invention, wherein said compound for providing said individual with a functional dystrophin protein comprises an oligonucleotide, or a functional equivalent thereof, comprising a sequence which is complementary to a dystrophin pre-mRNA exon. Preferably, said AON is capable of specifically inhibiting an exon inclusion signal of at least one exon in said dystrophin pre-mRNA. Interfering with an exon inclusion signal (EIS) has the advantage that such elements are located within the exon. By providing an AON for the interior of the exon to be skipped, it is possible to interfere with the exon inclusion signal thereby effectively masking the exon from the splicing apparatus. The failure of the splicing apparatus to recognize the exon to be skipped thus leads to exclusion of the exon from the final mRNA. This embodiment does not interfere directly with the enzymatic process of the splicing machinery (the joining of the exons). It is thought that this allows the method to be more specific and/or reliable. It is thought that an EIS is a particular structure of an exon that allows splice acceptor and donor to assume a particular spatial conformation. In this concept it is the particular spatial conformation that enables the splicing machinery to recognize the exon. However, the invention is certainly not limited to this model. It has been found that agents capable of binding to an exon are capable of inhibiting an EIS. An AON may specifically contact said exon at any point and still be able to specifically inhibit said EIS.

Using exon-internal AONs specific for an exon 46 sequence, we were previously able to modulate the splicing pattern in cultured myotubes from two different DMD patients with an exon 45 deletion[11]. Following AON treatment, exon 46 was skipped, which resulted in a restored reading frame and the induction of dystrophin synthesis in at least 75% of the cells. We have recently shown that exon skipping can also efficiently be induced in human control and series of patients with different mutations, including deletions, duplications and point mutations, for 39 different DMD exons using exon-internal AONs[1,2,11-15].

Within the context of the invention, a functional equivalent of an oligonucleotide preferably means an oligonucleotide as defined herein wherein one or more nucleotides have been substituted and wherein an activity of said functional equivalent is retained to at least some extent. Preferably, an activity of said functional equivalent is providing a functional dystrophin protein. Said activity of said functional equivalent is therefore preferably assessed by quantifying the amount of a functional dystrophin protein. A functional dystrophin is herein preferably defined as being a dystrophin able to bind actin and members of the DGC protein complex. The assessment of said activity of an oligonucleotide is preferably done by RT-PCR or by immunofluorescence or Western blot analyses. Said activity is preferably retained to at least some extent when it represents at least 50%, or at least 60%, or at least 70% or at least 80% or at least 90% or at least 95% or more of corresponding activity of said oligonucleotide the functional equivalent derives from. Throughout this application, when the word oligonucleotide is used it may be replaced by a functional equivalent thereof as defined herein.

Hence, the use of an oligonucleotide, or a functional equivalent thereof, comprising or consisting of a sequence which is complementary to a dystrophin pre-mRNA exon provides good anti-DMD results. In one preferred embodiment an oligonucleotide, or a functional equivalent thereof, is used which comprises or consists of a sequence which is complementary to at least part of dystrophin pre-mRNA exon 2, 8, 9, 17, 19, 29, 40-46, 48-53, 55 or 59, said part having at least 13 nucleotides. However, said part may also have at least 14, 15, 16, 17, 18, 19, 20, 21, 22, 23, 24, 25, 26, 27, 28, 29, 30 nucleotides.

Most preferably an AON is used which comprises or consists of a sequence which is complementary to at least part of dystrophin pre-mRNA exon 51, 44, 45, 53, 46, 43, 2, 8, 50 and/or 52, said part having at least 13 nucleotides. However, said part may also have at least 14, 15, 16, 17, 18, 19, 20, 21, 22, 23, 24, 25, 26, 27, 28, 29, 30 nucleotides. Most preferred oligonucleotides are identified by each of the following sequences SEQ ID NO: 3 to SEQ ID NO: 284. Accordingly, a most preferred oligonucleotide as used herein is represented by a sequence from SEQ ID NO:3 to SEQ ID NO:284. A most preferred oligonucleotide as used herein is selected from the group consisting of SEQ ID NO:3 to NO:284.

Said exons are listed in decreasing order of patient population applicability. Hence, the use of an AON comprising a sequence which is complementary to at least part of dystrophin pre-mRNA exon 51 is suitable for use in a larger part of the DMD patient population as compared to an AON comprising a sequence which is complementary to dystrophin pre-mRNA exon 44, et cetera.

In a preferred embodiment, an oligonucleotide of the invention which comprises a sequence that is complementary to part of dystrophin pre-mRNA is such that the complementary part is at least 50% of the length of the oligonucleotide of the invention, more preferably at least 60%, even more preferably at least 70%, even more preferably at least 80%, even more preferably at least 90% or even more preferably at least 95%, or even more preferably 98% or more. In a most preferred embodiment, the oligonucleotide of the invention consists of a sequence that is complementary to part of dystrophin pre-mRNA as defined herein. For example, an oligonucleotide may comprise a sequence that is complementary to part of dystrophin pre-mRNA as defined herein and additional flanking sequences. In a more preferred embodiment, the length of said complementary part of said oligonucleotide is of at least 13, 14, 15, 16, 17, 18, 19, 20, 21, 22, 23, 24, 25, 26, 27, 28, 29, 30 nucleotides. Preferably, additional flanking sequences are used to modify the binding of a protein to the oligonucleotide, or to modify a thermodynamic property of the oligonucleotide, more preferably to modify target RNA binding affinity.

One preferred embodiment provides a method, combination, use or pharmaceutical preparation according to the invention, wherein said compound for providing said individual with a functional dystrophin protein comprises an oligonucleotide, or a functional equivalent thereof, which comprises:

a sequence which is complementary to a region of a dystrophin pre-mRNA exon that is hybridized to another part of a dystrophin pre-mRNA exon (closed structure), and a sequence which is complementary to a region of a dystrophin pre-mRNA exon that is not hybridized in said dystrophin pre-mRNA (open structure).

For this embodiment, reference is made to our WO 2004/083432 patent application. RNA molecules exhibit strong secondary structures, mostly due to base pairing of complementary or partly complementary stretches within the same RNA. It has long since been thought that structures in the RNA play a role in the function of the RNA. Without being bound by theory, it is believed that the secondary structure of the RNA of an exon plays a role in structuring the splicing process. Through its structure, an exon is recognized as a part that needs to be included in the mRNA. Herein this signalling function is referred to as an exon inclusion signal. A complementary oligonucleotide of this embodiment is capable of interfering with the structure of the exon and thereby capable of interfering with the exon inclusion signal of the exon. It has been found that many complementary oligonucleotides indeed comprise this capacity, some more efficient than others. Oligonucleotides of this preferred embodiment, i.e. those with the said overlap directed towards open and closed structures in the native exon RNA, are a selection from all possible oligonucleotides. The selection encompasses oligonucleotides that can efficiently interfere with an exon inclusion signal. Without being bound by theory it is thought that the overlap with an open structure improves the invasion efficiency of the oligonucleotide (i.e. increases the efficiency with which the oligonucleotide can enter the structure), whereas the overlap with the closed structure subsequently increases the efficiency of interfering with the secondary structure of the RNA of the exon, and thereby interfere with the exon inclusion signal. It is found that the length of the partial complementarity to both the closed and the open structure is not extremely restricted. We have observed high efficiencies with oligonucleotides with variable lengths of complementarity in either structure. The term complementarity is used herein to refer to a stretch of nucleic acids that can hybridise to another stretch of nucleic acids under physiological conditions. It is thus not absolutely required that all the bases in the region of complementarity are capable of pairing with bases in the opposing strand. For instance, when designing the oligonucleotide one may want to incorporate for instance a residue that does not base pair with the base on the complementary strand. Mismatches may to some extent be allowed, if under the circumstances in the cell, the stretch of nucleotides is capable of hybridising to the complementary part. In a preferred embodiment a complementary part (either to said open or to said closed structure) comprises at least 3, and more preferably at least 4 consecutive nucleotides. The complementary regions are preferably designed such that, when combined, they are specific for the exon in the pre-mRNA. Such specificity may be created with various lengths of complementary regions as this depends on the actual sequences in other (pre-)mRNA in the system. The risk that also one or more other pre-mRNA will be able to hybridise to the oligonucleotide decreases with increasing size of the oligonucleotide. It is clear that oligonucleotides comprising mismatches in the region of complementarity but that retain the capacity to hybridise to the targeted region(s) in the pre-mRNA, can be used in the present invention. However, preferably at least the complementary parts do not comprise such mismatches as these typically have a higher efficiency and a higher specificity, than oligonucleotides having such mismatches in one or more complementary regions. It is thought that higher hybridisation strengths, (i.e. increasing number of interactions with the opposing strand) are favourable in increasing the efficiency of the process of interfering with the splicing machinery of the system. Preferably, the complementarity is between 90 and 100%. In general this allows for approximately 1 or 2 mismatch(es) in an oligonucleotide of around 20 nucleotides The secondary structure is best analysed in the context of the pre-mRNA wherein the exon resides. Such structure may be analysed in the actual RNA. However, it is currently possible to predict the secondary structure of an RNA molecule (at lowest energy costs) quite well using structure-modelling programs. A non-limiting example of a suitable program is RNA mfold version 3.1 server[41]. A person skilled in the art will be able to predict, with suitable reproducibility, a likely structure of the exon, given the nucleotide sequence. Best predictions are obtained when providing such modelling programs with both the exon and flanking intron sequences. It is typically not necessary to model the structure of the entire pre-mRNA.

The open and closed structure to which the oligonucleotide is directed, are preferably adjacent to one another. It is thought that in this way the annealing of the oligonucleotide to the open structure induces opening of the closed structure whereupon annealing progresses into this closed structure. Through this action the previously closed structure assumes a different conformation. The different conformation results in the disruption of the exon inclusion signal. However, when potential (cryptic) splice acceptor and/or donor sequences are present within the targeted exon, occasionally a new exon inclusion signal is generated defining a different (neo) exon, i.e. with a different 5' end, a different 3' end, or both. This type of activity is within the scope of the present invention as the targeted exon is excluded from the mRNA. The presence of a new exon, containing part of the targeted exon, in the mRNA does not alter the fact that the targeted exon, as such, is excluded. The inclusion of a neo-exon can be seen as a side effect which occurs only occasionally. There are two possibilities when exon skipping is used to restore (part of) an open reading frame of dystrophin that is disrupted as a result of a mutation. One is that the neo-exon is functional in the restoration of the reading frame, whereas in the other case the reading frame is not restored. When selecting oligonucleotides for restoring dystrophin reading frames by means of exon-skipping it is of course clear that under these conditions only those oligonucleotides are selected that indeed result in exon-skipping that restores the dystrophin open reading frame, with or without a neo-exon.

Further provided is a method, combination, use or pharmaceutical preparation according to the invention, wherein said compound for providing said individual with a functional dystrophin protein comprises an oligonucleotide, or a functional equivalent thereof, which comprises a sequence that is complementary to a binding site for a serine-arginine (SR) protein in RNA of an exon of a dystrophin pre-mRNA. In our WO 2006/112705 patent application we have disclosed the presence of a correlation between the effectivity of an exon-internal antisense oligonucleotide (AON) in inducing exon skipping and the presence of a (for example by ESEfinder) predicted SR binding site in the target pre-mRNA site of said AON. Therefore, in one embodiment an oligonucleotide is generated comprising determining a (putative) binding site for an SR (Ser-Arg) protein in RNA of a dystrophin exon and producing an oligonucleotide that is complementary to said RNA and that at least partly overlaps said (putative) binding site. The term "at least partly overlaps" is defined herein as to comprise an overlap of only a single nucleotide of an SR binding site as well as multiple nucleotides of said binding site as well as a complete overlap of said binding site. This embodiment preferably further comprises determining from a secondary structure of said RNA, a region that is hybridised to another part of said RNA (closed structure) and a region that is not hybridised in said structure (open structure), and subsequently generating an oligonucleotide that at least partly overlaps said (putative) binding site and that overlaps at least part of said closed structure and overlaps at least part of said open structure. In this way we increase the chance of obtaining an oligonucleotide that is capable of interfering with the exon inclusion from the pre-mRNA into mRNA. It is possible that a first selected SR-binding region does not have the requested open-closed structure in which case another (second) SR protein binding site is selected which is then subsequently tested for the presence of an open-closed structure. This process is continued until a sequence is identified which contains an SR protein binding site as well as a(n) (partly overlapping) open-closed structure. This sequence is then used to design an oligonucleotide which is complementary to said sequence.

Such a method for generating an oligonucleotide is also performed by reversing the described order, i.e. first generating an oligonucleotide comprising determining, from a secondary structure of RNA from a dystrophin exon, a region that assumes a structure that is hybridised to another part of said RNA (closed structure) and a region that is not hybridised in said structure (open structure), and subsequently generating an oligonucleotide, of which at least a part of said oligonucleotide is complementary to said closed structure and of which at least another part of said oligonucleotide is complementary to said open structure. This is then followed by determining whether an SR protein binding site at least overlaps with said open/closed structure. In this way the method of WO 2004/083432 is improved. In yet another embodiment the selections are performed simultaneously.

Without wishing to be bound by any theory it is currently thought that use of an oligonucleotide directed to an SR protein binding site results in (at least partly) impairing the binding of an SR protein to the binding site of an SR protein which results in disrupted or impaired splicing.

Preferably, an open/closed structure and an SR protein binding site partly overlap and even more preferred an open/closed structure completely overlaps an SR protein binding site or an SR protein binding site completely overlaps an open/closed structure. This allows for an improved disruption of exon inclusion.

Besides consensus splice sites sequences, many (if not all) exons contain splicing regulatory sequences such as exonic splicing enhancer (ESE) sequences to facilitate the recognition of genuine splice sites by the spliceosome[42,43]. A subgroup of splicing factors, called the SR proteins, can bind to these ESEs and recruit other splicing factors, such as U1 and U2AF to (weakly defined) splice sites. The binding sites of the four most abundant SR proteins (SF2/ASF, SC35, SRp40 and SRp55) have been analyzed in detail and these results are implemented in ESEfinder, a web source that predicts potential binding sites for these SR proteins[42,43]. There is a correlation between the effectiveness of an AON and the presence/absence of an SF2/ASF, SC35 and SRp40 binding site. In a preferred embodiment, the invention thus provides a method, combination, use or pharmaceutical preparation as described above, wherein said SR protein is SF2/ASF or SC35 or SRp40.

In one embodiment a DMD patient is provided with a functional dystrophin protein by using an oligonucleotide, or a functional equivalent thereof, which is capable of specifically binding a regulatory RNA sequence which is required for the correct splicing of a dystrophin exon in a transcript. Several cis-acting RNA sequences are required for the correct splicing of exons in a transcript. In particular, supplementary elements such as intronic or exonic splicing enhancers (ISEs and ESEs) or silencers (ISSs and ESEs) are identified to regulate specific and efficient splicing of constitutive and alternative exons. Using sequence-specific antisense oligonucleotides (AONs) that bind to the elements, their regulatory function is disturbed so that the exon is skipped, as shown for DMD. Hence, in one preferred embodiment an oligonucleotide or functional equivalent thereof is used which is complementary to an intronic splicing enhancer (ISE), an exonic splicing enhancer (ESE), an intronic splicing silencer (ISS) and/or an exonic splicing silencer (ESS). As already described herein before, a dystrophin exon is in one preferred embodiment skipped by an agent capable of specifically inhibiting an exon inclusion signal of said exon, so that said exon is not recognized by the splicing machinery as a part that needs to be included in the mRNA. As a result, a mRNA without said exon is formed.

An AON used in a method of the invention is preferably complementary to a consecutive part of between 13 and 50 nucleotides of dystrophin exon RNA or dystrophin intron RNA. In one embodiment an AON used in a method of the invention is complementary to a consecutive part of between 16 and 50 nucleotides of a dystrophin exon RNA or dystrophin intron RNA. Preferably, said AON is complementary to a consecutive part of between 15 and 25 nucleotides of said exon RNA. More preferably, an AON is used which comprises a sequence which is complementary to a consecutive part of between 20 and 25 nucleotides of a dystrophin exon RNA or a dystrophin intron RNA.

Different types of nucleic acid may be used to generate the oligonucleotide. Preferably, said oligonucleotide comprises RNA, as RNA/RNA hybrids are very stable. Since one of the aims of the exon skipping technique is to direct splicing in subjects it is preferred that the oligonucleotide RNA comprises a modification providing the RNA with an additional property, for instance resistance to endonucleases and RNaseH, additional hybridisation strength, increased stability (for instance in a bodily fluid), increased or decreased flexibility, reduced toxicity, increased intracellular transport, tissue-specificity, etc. Preferably said modification comprises a 2'-O-methyl-phosphorothioate oligoribonucleotide modification. Preferably said modification comprises a 2'-O-methyl-phosphorothioate oligodeoxyribonucleotide modification. One embodiment thus provides a method, combination, use or pharmaceutical preparation according to the invention, wherein an oligonucleotide is used which comprises RNA which contains a modification, preferably a 2'-O-methyl modified ribose (RNA) or deoxyribose (DNA) modification.

In one embodiment the invention provides a hybrid oligonucleotide comprising an oligonucleotide comprising a 2'-O-methyl-phosphorothioate oligo(deoxy)ribonucleotide modification and locked nucleic acid. This particular combination comprises better sequence specificity compared to an equivalent consisting of locked nucleic acid, and comprises improved effectivity when compared with an oligonucleotide consisting of 2'-O-methyl-phosphorothioate oligo(deoxy)ribonucleotide modification.

With the advent of nucleic acid mimicking technology it has become possible to generate molecules that have a similar, preferably the same hybridisation characteristics in kind not necessarily in amount as nucleic acid itself. Such functional equivalents are of course also suitable for use in a method of the invention. Preferred examples of functional equivalents of an oligonucleotide are peptide nucleic acid and/or locked nucleic acid. Most preferably, a morpholino phosphorodiamidate is used. Suitable but non-limiting examples of equivalents of oligonucleotides of the invention can be found in[44,50]. Hybrids between one or more of the equivalents among each other and/or together with nucleic acid are of course also suitable. In a preferred embodiment locked nucleic acid is used as a functional equivalent of an oligonucleotide, as locked nucleic acid displays a higher target affinity and reduced toxicity and therefore shows a higher efficiency of exon skipping.

In one embodiment an oligonucleotide, or a functional equivalent thereof, which is capable of inhibiting inclusion of a dystrophin exon into dystrophin mRNA is combined with at least one other oligonucleotide, or functional equivalent thereof, that is capable of inhibiting inclusion of another dystrophin exon into dystrophin mRNA. This way, inclusion of two or more exons of a dystrophin pre-mRNA in mRNA produced from this pre-mRNA is prevented. This embodiment is further referred to as double- or multi-exon skipping[2,15]. In most cases double-exon skipping results in the exclusion of only the two targeted exons from the dystrophin pre-mRNA. However, in other cases it was found that the targeted exons and the entire region in between said exons in said pre-mRNA were not present in the produced mRNA even when other exons (intervening exons) were present in such region. This multi-skipping was notably so for the combination of oligonucleotides derived from the DMD gene, wherein one oligonucleotide for exon 45 and one oligonucleotide for exon 51 was added to a cell transcribing the DMD gene. Such a set-up resulted in mRNA being produced that did not contain exons 45 to 51. Apparently, the structure of the pre-mRNA in the presence of the mentioned oligonucleotides was such that the splicing machinery was stimulated to connect exons 44 and 52 to each other.

Further provided is therefore a method, combination, use or pharmaceutical preparation according to the invention, wherein a nucleotide sequence is used which comprises at least 8, preferably between 16 to 80, consecutive nucleotides that are complementary to a first exon of a dystrophin pre-mRNA and wherein a nucleotide sequence is used which comprises at least 8, preferably between 16 to 80, consecutive nucleotides that are complementary to a second exon of said dystrophin pre-mRNA.

In one preferred embodiment said first and said second exon are separated in said dystrophin pre-mRNA by at least one exon to which said oligonucleotide is not complementary.

It is possible to specifically promote the skipping of also the intervening exons by providing a linkage between the two complementary oligonucleotides. Hence, in one embodiment stretches of nucleotides complementary to at least two dystrophin exons are separated by a linking moiety. The at least two stretches of nucleotides are thus linked in this embodiment so as to form a single molecule. Further provided is therefore a method, combination, use or pharmaceutical preparation according to the invention wherein said oligonucleotide, or functional equivalent thereof, for providing said individual with a functional dystrophin protein is complementary to at least two exons in a dystrophin pre-mRNA, said oligonucleotide or functional equivalent comprising at least two parts wherein a first part comprises an oligonucleotide having at least 8, preferably between 16 to 80, consecutive nucleotides that are complementary to a first of said at least two exons and wherein a second part comprises an oligonucleotide having at least 8, preferably between 16 to 80, consecutive nucleotides that are complementary to a second exon in said dystrophin pre-mRNA. The linkage may be through any means but is preferably accomplished through a nucleotide linkage. In the latter case the number of nucleotides that do not contain an overlap between one or the other complementary exon can be zero, but is preferably between 4 to 40 nucleotides. The linking moiety can be any type of moiety capable of linking oligonucleotides. Preferably, said linking moiety comprises at least 4 uracil nucleotides. Currently, many different compounds are available that mimic hybridisation characteristics of oligonucleotides. Such a compound, called herein a functional equivalent of an oligonucleotide, is also suitable for the present invention if such equivalent comprises similar hybridisation characteristics in kind not necessarily in amount. Suitable functional equivalents are mentioned earlier in this description. As mentioned, oligonucleotides of the invention do not have to consist of only oligonucleotides that contribute to hybridisation to the targeted exon. There may be additional material and/or nucleotides added.

The DMD gene is a large gene, with many different exons. Considering that the gene is located on the X-chromosome, it is mostly boys that are affected, although girls can also be affected by the disease, as they may receive a bad copy of the gene from both parents, or are suffering from a particularly biased inactivation of the functional allele due to a particularly biased X chromosome inactivation in their muscle cells. The protein is encoded by a plurality of exons (79) over a range of at least 2.6 Mb. Defects may occur in any part of the DMD gene. Skipping of a particular exon or particular exons can, very often, result in a restructured mRNA that encodes a shorter than normal but at least partially functional dystrophin protein. A practical problem in the development of a medicament based on exon-skipping technology is the plurality of mutations that may result in a deficiency in functional dystrophin protein in the cell. Despite the fact that already multiple different mutations can be corrected for by the skipping of a single exon, this plurality of mutations, requires the generation of a large number of different pharmaceuticals as for different mutations different exons need to be skipped. An advantage of a compound capable of inducing skipping of two or more exons, is that more than one exon can be skipped with a single pharmaceutical. This property is not only practically very useful in that only a limited number of pharmaceuticals need to be generated for treating many different DMD or particular, severe BMD mutations. Another option now open to the person skilled in the art is to select particularly functional restructured dystrophin proteins and produce compounds capable of generating these preferred dystrophin proteins. Such preferred end results are further referred to as mild phenotype dystrophins.

Each compound, an oligonucleotide and/or an adjunct compound as defined herein for use according to the invention may be suitable for direct administration to a cell, tissue and/or an organ in vivo of individuals affected by or at risk of developing DMD or BMD, and may be administered directly in vivo, ex vivo or in vitro.

Alternatively, suitable means for providing cells with an oligonucleotide or equivalent thereof are present in the art. An oligonucleotide or functional equivalent thereof may for example be provided to a cell in the form of an expression vector wherein the expression vector encodes a transcript comprising said oligonucleotide. The expression vector is preferably introduced into the cell via a gene delivery vehicle. A preferred delivery vehicle is a viral vector such as an adeno-associated virus vector (AAV), or a retroviral vector such as a lentivirus vector[4,51,52] and the like. Also plasmids, artificial chromosomes, plasmids suitable for targeted homologous recombination and integration in the human genome of cells may be suitably applied for delivery of an oligonucleotide as defined herein. Preferred for the current invention are those vectors wherein transcription is driven from PolIII promoters, and/or wherein transcripts are in the form fusions with U1 or U7 transcripts, which yield good results for delivering small transcripts. It is within the skill of the artisan to design suitable transcripts. Preferred are PolIII driven transcripts. Preferably in the form of a fusion transcript with an U1 or U7 transcript[4,51,52]. Such fusions may be generated as described[53,54]. The oligonucleotide may be delivered as is. However, the oligonucleotide may also be encoded by the viral vector. Typically this is in the form of an RNA transcript that comprises the sequence of the oligonucleotide in a part of the transcript.

Improvements in means for providing cells with an oligonucleotide or equivalent thereof, are anticipated considering the progress that has already thus far been achieved. Such future improvements may of course be incorporated to achieve the mentioned effect on restructuring of mRNA using a method of the invention. The oligonucleotide or equivalent thereof can be delivered as is to the cells. When administering the oligonucleotide or equivalent thereof to an individual, it is preferred that the oligonucleotide is dissolved in a solution that is compatible with the delivery method. For intravenous, subcutaneous, intramuscular, intrathecal and/or intraventricular administration it is preferred that the solution is a physiological salt solution. Particularly preferred for a method of the invention is the use of an excipient that will aid in delivery of a compound as defined herein, preferably an oligonucleotide and optionally together with an adjunct compound to a cell and into a cell, preferably a muscle cell. Preferred are excipients capable of forming complexes, vesicles and/or liposomes that deliver such a compound as defined herein, preferably an oligonucleotide and optionally together with an adjunct compound complexed or trapped in a vesicle or liposome through a cell membrane. Many of these excipients are known in the art. Suitable excipients comprise polyethylenimine (PEI), or similar cationic polymers, including polypropyleneimine or polyethylenimine copolymers (PECs) and derivatives, ExGen 500, synthetic amphiphils (SAINT-18), Lipofectin™, DOTAP and/or viral capsid proteins that are capable of self assembly into particles that can deliver such compounds, preferably an oligonucleotide and optionally together with an adjunct compound as defined herein to a cell, preferably a muscle cell. Such excipients have been shown to efficiently deliver (oligonucleotide such as antisense) nucleic acids to a wide variety of cultured cells, including muscle cells. Their high transfection potential is combined with an excepted low to moderate toxicity in terms of overall cell survival. The ease of structural modification can be used to allow further modifications and the analysis of their further (in vivo) nucleic acid transfer characteristics and toxicity.

Lipofectin represents an example of a liposomal transfection agent. It consists of two lipid components, a cationic lipid N-[1-(2,3 dioleoyloxy)propyl]-N,N,N-trimethylammonium chloride (DOTMA) (cp. DOTAP which is the methylsulfate salt) and a neutral lipid dioleoylphosphatidylethanolamine (DOPE). The neutral component mediates the intracellular release. Another group of delivery systems are polymeric nanoparticles.

Polycations such like diethylaminoethylaminoethyl (DEAE)-dextran, which are well known as DNA transfection reagent can be combined with butylcyanoacrylate (PBCA) and hexylcyanoacrylate (PHCA) to formulate cationic nanoparticles that can deliver a compound as defined herein, preferably an oligonucleotide and optionally together with an adjunct compound across cell membranes into cells.

In addition to these common nanoparticle materials, the cationic peptide protamine offers an alternative approach to formulate a compound as defined herein, preferably an oligonucleotide and optionally together with an adjunct compound as colloids. This colloidal nanoparticle system can form so called proticles, which can be prepared by a simple self-assembly process to package and mediate intracellular release of a compound as defined herein, preferably an oligonucleotide and optionally together with an adjunct compound. The skilled person may select and adapt any of the above or other commercially available alternative excipients and delivery systems to package and deliver a compound as defined herein, preferably an oligonucleotide and optionally together with an adjunct compound for use in the current invention to deliver said compound for the treatment of Duchenne Muscular Dystrophy or Becker Muscular Dystrophy in humans.

In addition, a compound as defined herein, preferably an oligonucleotide and optionally together with an adjunct compound could be covalently or non-covalently linked to a targeting ligand specifically designed to facilitate the uptake in to the cell, cytoplasm and/or its nucleus. Such ligand could comprise (i) a compound (including but not limited to peptide (-like) structures) recognising cell, tissue or organ specific elements facilitating cellular uptake and/or (ii) a chemical compound able to facilitate the uptake in to cells and/or the intracellular release of an a compound as defined herein, preferably an oligonucleotide and optionally together with an adjunct compound from vesicles, e.g. endosomes or lysosomes.

Therefore, in a preferred embodiment, a compound as defined herein, preferably an oligonucleotide and optionally together with an adjunct compound are formulated in a medicament which is provided with at least an excipient and/or a targeting ligand for delivery and/or a delivery device of said compound to a cell and/or enhancing its intracellular delivery. Accordingly, the invention also encompasses a pharmaceutically acceptable composition comprising a compound as defined herein, preferably an oligonucleotide and optionally together with an adjunct compound and further comprising at least one excipient and/or a targeting ligand for delivery and/or a delivery device of said compound to a cell and/or enhancing its intracellular delivery.

It is to be understood that an oligonucleotide and an adjunct compound may not be formulated in one single composition or preparation. Depending on their identity, the skilled person will know which type of formulation is the most appropriate for each compound.

In a preferred embodiment the invention provides a kit of parts comprising a compound for providing an individual with a functional dystrophin protein and an adjunct compound for reducing inflammation, preferably for reducing muscle tissue inflammation, and/or an adjunct compound for improving muscle fiber function, integrity and/or survival.

In a preferred embodiment, a concentration of an oligonucleotide as defined herein, which is ranged between about 0.1 nM and about 1 μM is used. More preferably, the concentration used is ranged between about 0.3 to about 400 nM, even more preferably between about 1 to about 200 nM. If several oligonucleotides are used, this concentration may refer to the total concentration of oligonucleotides or the concentration of each oligonucleotide added. The ranges of concentration of oligonucleotide(s) as given above are preferred concentrations for in vitro or ex vivo uses. The skilled person will understand that depending on the oligonucleotide(s) used, the target cell to be treated, the gene target and its expression levels, the medium used and the transfection and incubation conditions, the concentration of oligonucleotide(s) used may further vary and may need to be optimised any further.

More preferably, a compound preferably an oligonucleotide and an adjunct compound to be used in the invention to prevent, treat DMD or BMD are synthetically produced and administered directly to a cell, a tissue, an organ and/or patients in formulated form in a pharmaceutically acceptable composition or preparation. The delivery of a pharmaceutical composition to the subject is preferably carried out by one or more parenteral injections, e.g. intravenous and/or subcutaneous and/or intramuscular and/or intrathecal and/or intraventricular administrations, preferably injections, at one or at multiple sites in the human body.

Besides exon skipping, it is also possible to provide a DMD patient with a functional dystrophin protein with a therapy based on read-through of stopcodons. Compounds capable of suppressing stopcodons are particularly suitable for a subgroup of DMD patients which is affected by nonsense mutations (~7%) resulting in the formation of a stop codon within their dystrophin gene. In one embodiment said compound capable of suppressing stopcodons comprises the antibiotic gentamicin. In a recent study in mdx mice, gentamicin treatment induced novel dystrophin expression up to 20% of normal level, albeit with variability among animals. Human trials with gentamicin have however been inconclusive[55]. PTC124 belongs to a new class of small molecules that mimics at lower concentrations the readthrough activity of gentamicin. Administration of PTC124 resulted in the production of full-length and functionally active dystrophin both in vitro and in mdx mice[16]. Phase I/II trials with PTC124 are currently ongoing, not only for application in DMD but also for cystic fibrosis[16,17]. The references 16 and 17 also describe preferred dosages of the PCT124 compound for use in the present invention. Further provided is therefore a method, combination, use or pharmaceutical preparation according to the invention, wherein said compound for providing said individual with a functional dystrophin protein comprises a compound for suppressing stop codons. Said compound for suppressing stop codons preferably comprises gentamicin, PTC124 or a functional equivalent thereof. Most preferably, said compound comprises PTC124.

In one embodiment an individual is provided with a functional dystrophin protein using a vector, preferably a viral vector, comprising a micro-mini-dystrophin gene. Most preferably, a recombinant adeno-associated viral (rAAV) vector is used. AAV is a single-stranded DNA parvovirus that is non-pathogenic and shows a helper-dependent life cycle. In contrast to other viruses (adenovirus, retrovirus, and herpes simplex virus), rAAV vectors have demonstrated to be very efficient in transducing mature skeletal muscle. Application of rAAV in classical DMD "gene addition" studies has been hindered by its restricted packaging limits (<5 kb). Therefore, rAAV is preferably applied for the efficient delivery of a much smaller micro- or mini-dystrophin gene. Administration of such micro- or mini-dystrophin gene results in the presence of a at least partially functional dystrophin protein. Reference is made to[18-20].

A compound for providing an individual with a functional dystrophin protein and at least one adjunct compound according to the invention can be administered to an individual in any order. In one embodiment, said compound for providing an individual with a functional dystrophin protein and said at least one adjunct compound are administered simultaneously (meaning that said compounds are administered within 10 hours, preferably within one hour). This is however not necessary. In one embodiment at least one adjunct compound is administered to an individual in need thereof before administration of a compound for providing an individual with a functional dystrophin protein. Further provided is therefore a method according to the invention, comprising:

administering to an individual in need thereof an adjunct compound for reducing inflammation, preferably for reducing muscle tissue inflammation, and/or administering to said individual an adjunct compound for improving muscle fiber function, integrity and/or survival, and, subsequently, administering to said individual a compound for providing said individual with a functional dystrophin protein.

In yet another embodiment, said compound for providing an individual with a functional dystrophin protein is administered before administration of said at least one adjunct compound.

Further provided is a method for at least in part increasing the production of a functional dystrophin protein in a cell, said cell comprising pre-mRNA of a dystrophin gene encoding aberrant dystrophin protein, the method comprising:

providing said cell with a compound for inhibiting inclusion of an exon into mRNA produced from splicing of said dystrophin pre-mRNA, and providing said cell with an adjunct compound for reducing inflammation, preferably for reducing muscle tissue inflammation, and/or providing said cell with an adjunct compound for improving muscle fiber function, integrity and/or survival, the method further comprising allowing translation of mRNA produced from splicing of said pre-mRNA. In one embodiment said method is performed in vitro, for instance using a cell culture.

In this context, increasing the production of a functional dystrophin protein has been earlier defined herein.

Unless otherwise indicated each embodiment as described herein may be combined with another embodiment as described herein.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a compound or adjunct compound as defined herein may comprise additional component(s) than the ones specifically identified, said additional component(s) not altering the unique characteristic of the invention.

In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "approximately" or "about" when used in association with a numerical value (approximately 10, about 10) preferably means that the value may be the given value of 10 more or less 1% of the value.

All patent and literature references cited in the present specification are hereby incorporated by reference in their entirety.

The invention is further explained in the following examples. These examples do not limit the scope of the invention, but merely serve to clarify the invention.

In a patient with Duchenne's muscular dystrophy who has a deletion of exon 50, an out-of-frame transcript is generated in which exon 49 is spliced to exon 51 (A). As a result, a stop codon is generated in exon 51, which prematurely aborts dystrophin synthesis. The sequence-specific binding of the exon-internal antisense oligonucleotide PRO051 interferes with the correct inclusion of exon 51 during splicing so that the exon is actually skipped (B). This restores the open reading frame of the transcript and allows the synthesis of a dystrophin similar to that in patients with Becker's muscular dystrophy (BMD).

FIGS. 2A-2E. Prescreening Studies of the Four Patients.

Magnetic resonance images of the lower legs of the four patients (the left leg of Patient 3 and right legs of the other three patients) show the adequate condition of the tibialis anterior muscle (less than 50% fat infiltration and fibrosis) (A). The diagnosis of Duchenne's muscular dystrophy in these patients was confirmed by diaminobenzidine tetrahydrochloride staining of cross sections of biopsy specimens obtained previously from the quadriceps muscle (B). No dystrophin expression was observed, with the exception of one dystrophin-positive, or revertant, fiber in Patient 2 (arrow). Reverse-transcriptase-polymerase chain-reaction (RT-PCR) analysis of the transcript region flanking the patients' mutations and exon 51 confirmed both the individual mutations in nontreated myotubes (NT) and the positive response to PRO051 (i.e., exon 51 skipping) in treated myotubes (T) on the RNA level (C). The efficiencies of exon skipping were 49% for Patient 1, 84% for Patient 2, 58% for Patient 3, and 90% for Patient 4. A cryptic splice site within exon 51 is sometimes activated by PRO051 in cell culture, resulting in an extra aberrant splicing product, as seen in the treated sample from Patient 4. Lane M shows a 100-bp size marker, and lane C RNA from healthy control muscle. Sequence analysis of the RT-PCR fragments from treated and untreated myotubes identified the precise skipping of exon 51 for each patient (D). The new in-frame transcripts led to substantial dystrophin synthesis, as detected by immunofluorescence analysis of treated myotubes with the use of monoclonal antibody NCL-DYS2 (E).

No dystrophin was detected before treatment.

Figure 3:
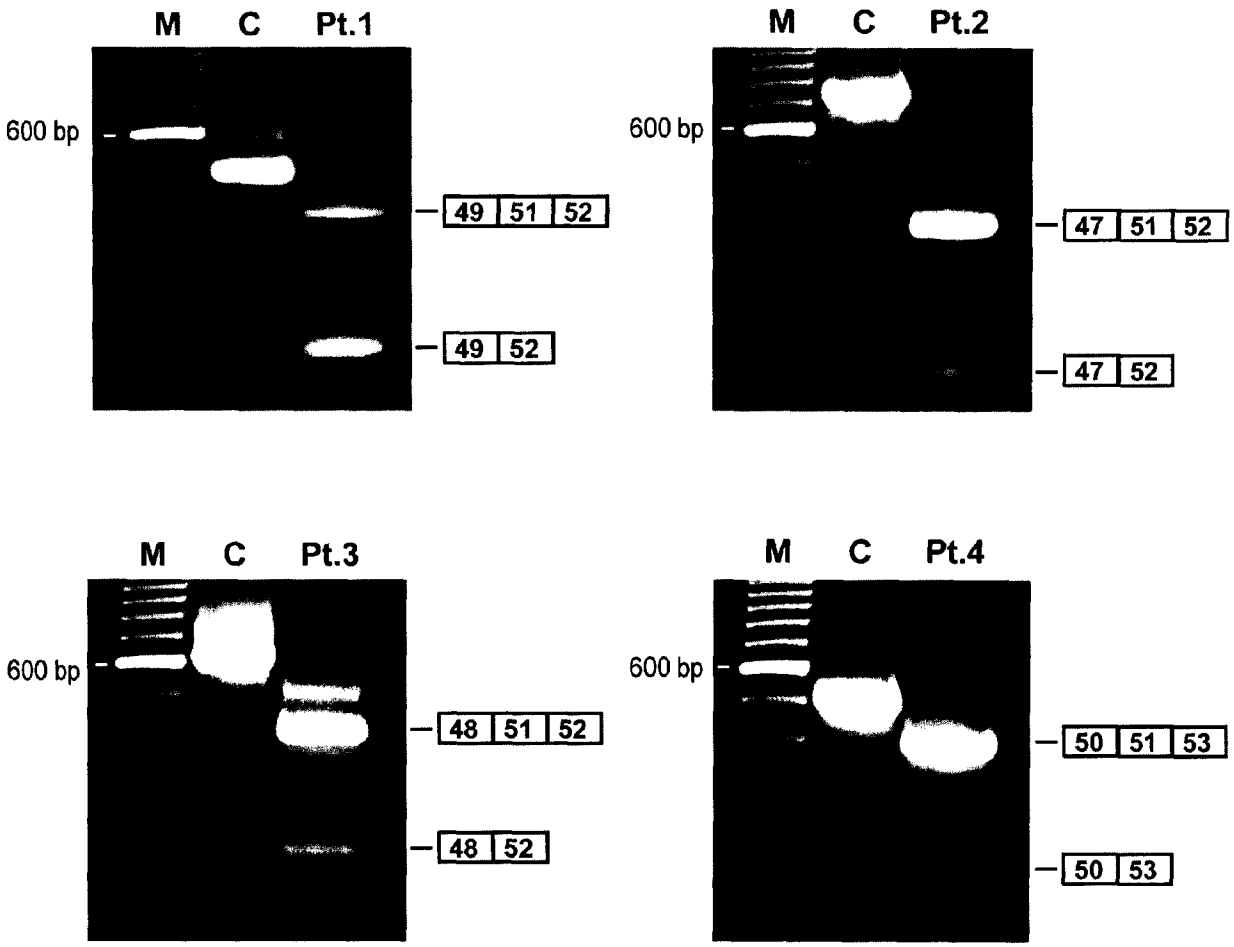

FIG. 3. RT-PCR Analysis of RNA Isolated from Serial Sections of Biopsy Specimens from the Patients.

After treatment with PRO051, reverse-transcriptase-polymerase-chain-reaction (RT-PCR) analysis shows novel, shorter transcript fragments for each patient. Both the size and sequence of these fragments confirm the precise skipping of exon 51. No additional splice variants were observed. At 28 days, still significant in-frame RNA transcripts were detected, suggesting prolonged persistence of PRO051 in muscle. Owing to the small amount of section material, high-sensitivity PCR conditions were used; this process precluded the accurate quantification of skipping efficiencies and the meaningful correlation between levels of RNA and protein. M denotes size marker, and C control.

Figure 4A:
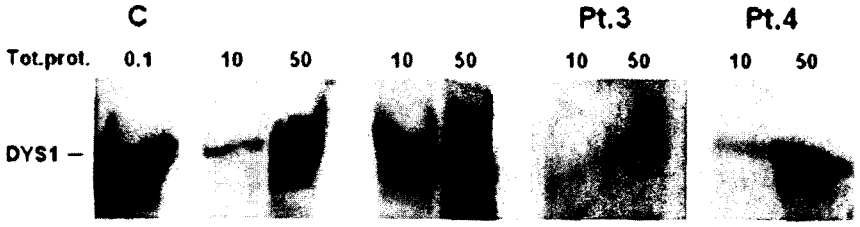
Figure 4B:
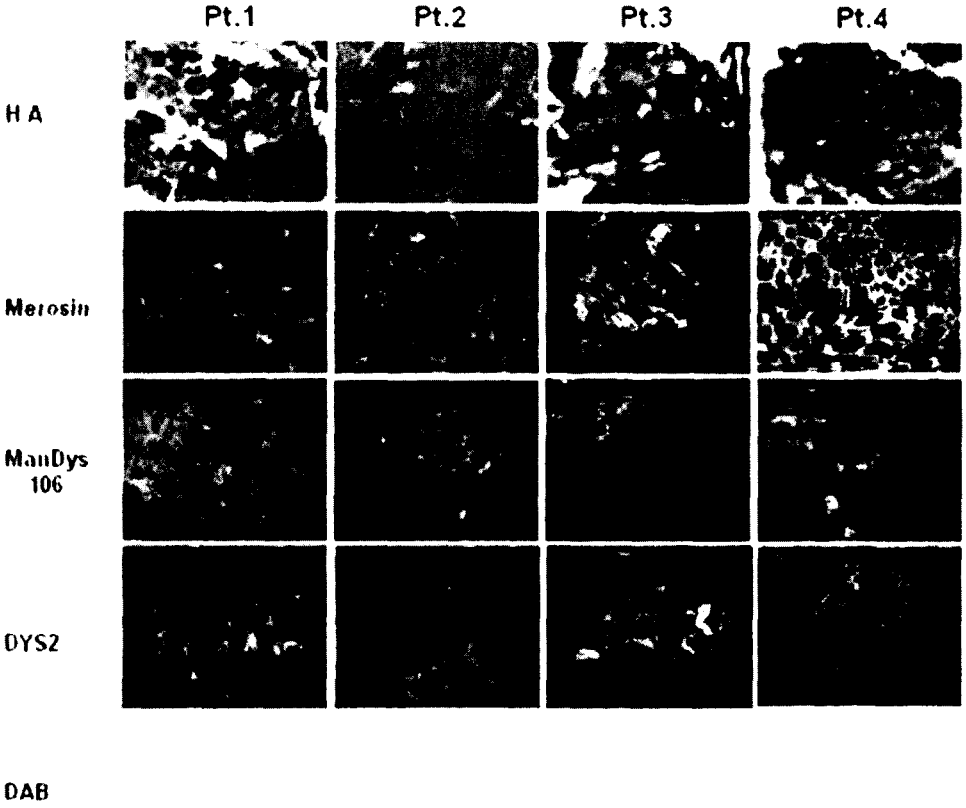

FIGS. 4A-4B. Dystrophin-Restoring Effect of a Single Intramuscular Dose of PRO051. Immuno fluorescence analysis with the use of the dystrophin antibody MAN-DYS106 clearly shows dystrophin expression at the membranes of the majority of fibers throughout the biopsy specimen obtained from each patient (B). Western blot analysis of total protein extracts isolated from the patients' biopsy specimens with the use of NCL-DYS1 antibody show restored dystrophin expression in all patients (A).

Figure 5:
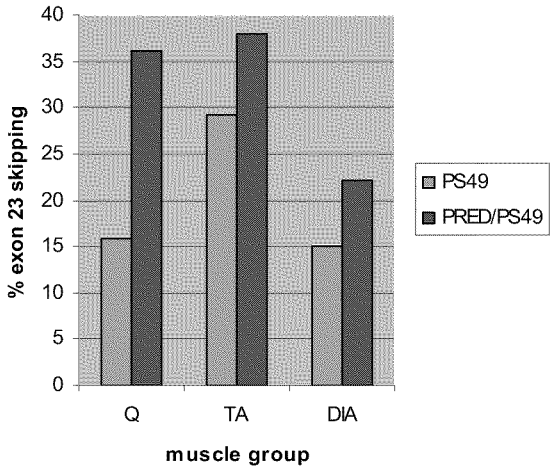

FIG. 5. Exon 23 skipping levels on RNA level in different muscle groups (Q: quadriceps muscle; TA: tibialis anterior muscle; DIA: diaphragm muscle) in mdx mice (two mice per group) treated with PS49 alone (group 3) or with PS49 and prednisolone (group 4).

Figure 6A:
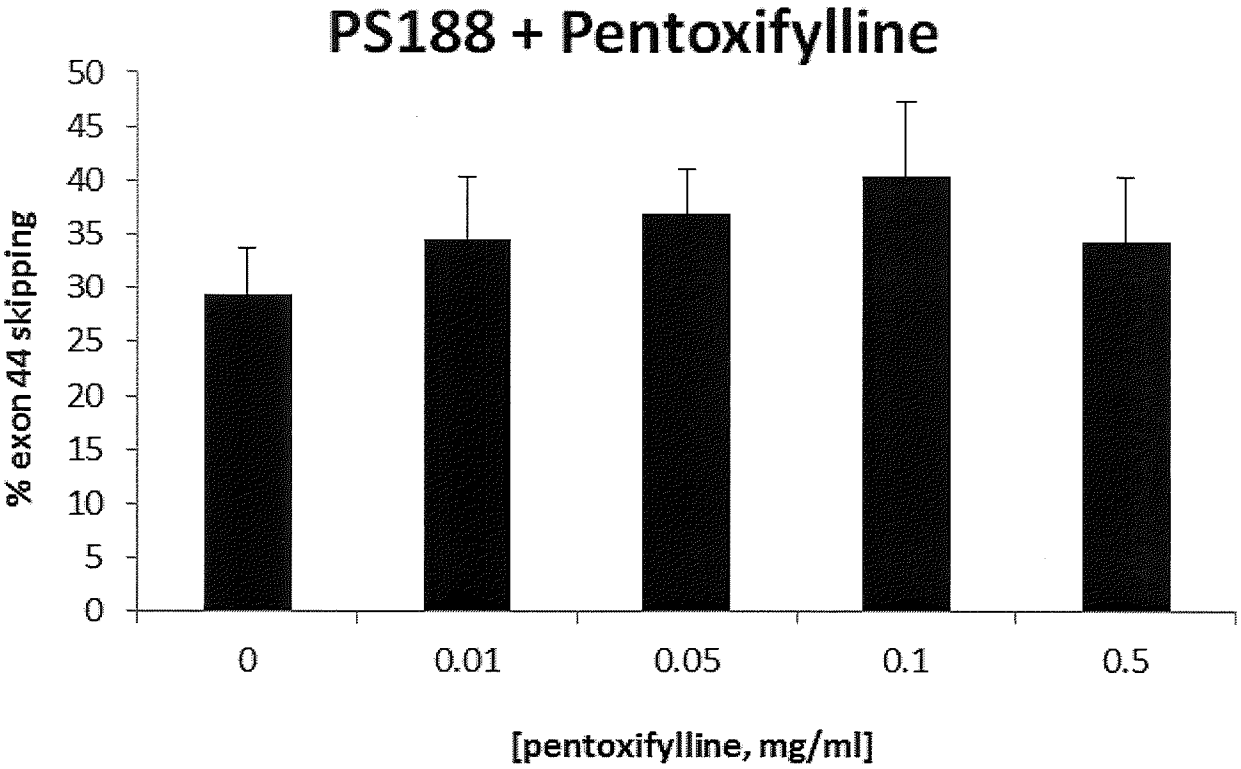
Figure 6B:
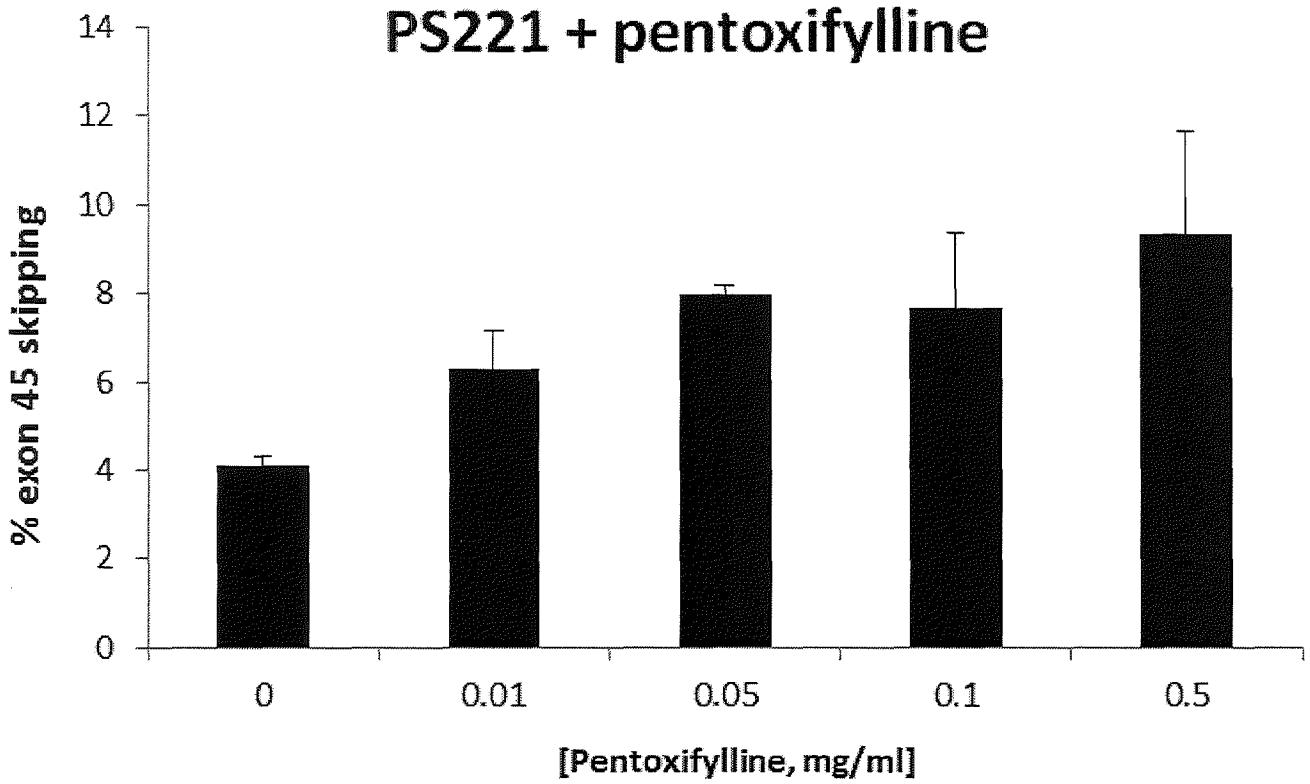
Figure 6C:
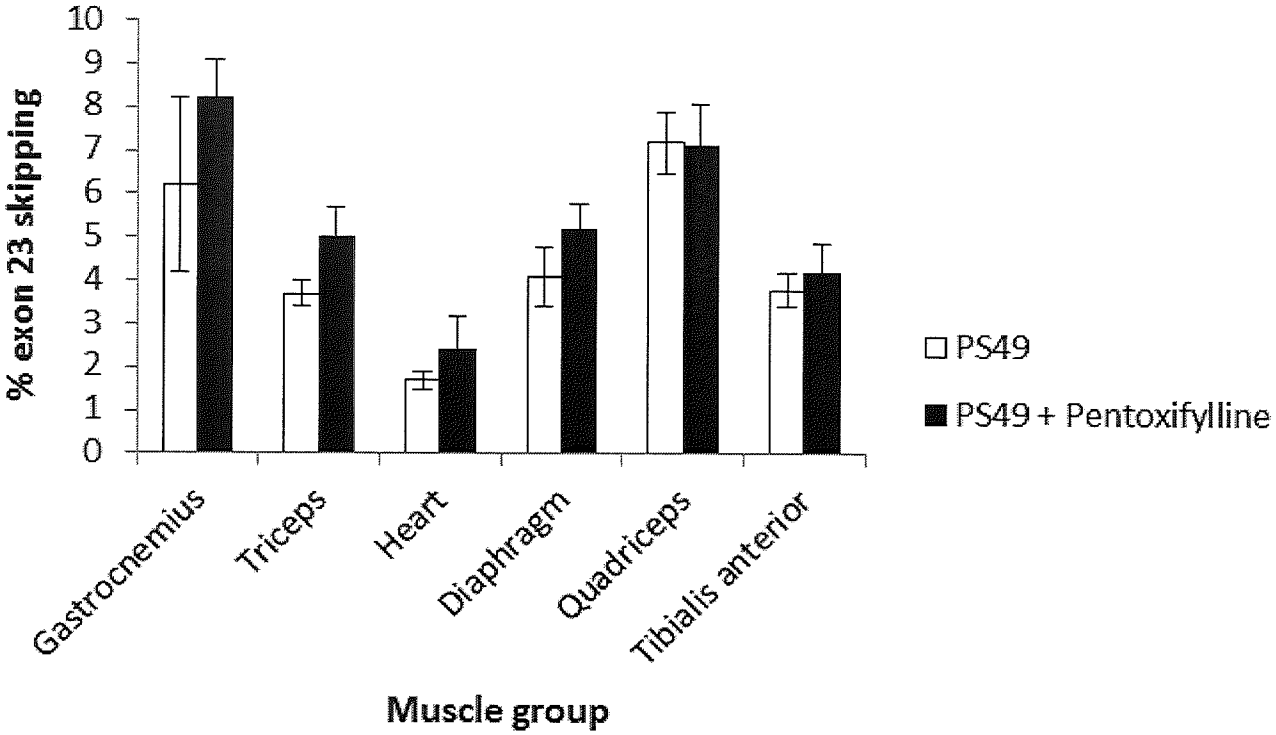

FIGS. 6A-6B. In muscle cells, DMD gene exon 44 (A) or exon 45 (B) skipping levels are enhanced with increasing concentrations of pentoxyfilline (from 0 to 0.5 mg/ml). FIG. 6C Exon 23 skipping levels on RNA level in different muscle groups (Q: quadriceps muscle; TA: tibialis anterior muscle; Tri: triceps muscle; HRT: heart muscle) in mdx mice (two mice per group) treated with PS49 alone (group 3) or with PS49 and pentoxyfilline (group 4).

FIGS. 7A-7B. Dystrophin (DMD) gene amino acid sequence

FIG. 8. Human IGF-1 Isoform 4 amino acid sequence.

FIGS. 9A-9M. Various oligonucleotides directed against the indicated exons of the dystrophin 20 (DMD)

EXAMPLES

Example 1

In a recent clinical study the local safety, tolerability, and dystrophin-restoring effect of antisense compound PRO051 was assessed. The clinical study was recently published. The content of the publication is reproduced herein under example 1A. In brief, PRO051 is a synthetic, modified RNA molecule with sequence 5'-UCA AGG AAG AUG GCA UUU CU-3', and designed to specifically induce exon 51 skipping[59]. It carries full-length 2'-O-methyl substituted ribose moieties and phosphorothioate internucleotide linkages. Four DMD patients with different specific DMD gene deletions correctable by exon 51 skipping were included. At day 0, a series of safety parameters was assessed. The patient's leg (i.e. tibialis anterior muscle) was fixed with a tailor-made plastic mould and its position was carefully recorded. A topical anesthetic (EMLA) was used to numb the skin Four injections of PRO051 were given along a line of 1.5 cm between two small skin tattoos, using a 2.5 cm electromyographic needle (MyoJect Disposable Hypodermic Needle Electrode, TECA Accessories) to ensure intramuscular delivery. Each injection volume was 200 μl, containing 200 μg PRO051, dispersed in equal portions at angles of approximately 30 degrees. At day 28, the same series of safety parameters was assessed again. The leg was positioned using the patient's own mould, and a semi-open muscle biopsy was taken between the tattoos under local anesthesia using a forceps with two sharp-edged jaws (Blakesley Conchotoma, DK Instruments). The biopsy was snap-frozen in liquid nitrogen-cooled 2-methylbutane. Patients were treated sequentially. At the time of study, two patients (nr. 1 and 2) were also on corticosteroids (prednisone or deflazacort), one had just stopped steroid treatment (nr. 4) and one patient never used steroids (nr. 3) (see Table 1). This latter patient was also the one who lost ambulance at the youngest age when compared to the other three patients. The biopsy was analysed, for detection of specific exon skipping on RNA level (RT-PCR analysis, not shown) and novel expression of dystrophin on protein level (immunofluorescence and western blot analyses, summarized in Table 1). Assessment of the series of safety parameters (routine plasma and urine parameters for renal and liver function, electrolyte levels, blood cell counts, hemoglobin, aPTT, AP50 and CH50 values) before and after treatment, indicated that the PRO051 compound was locally safe and well tolerated. For immunofluorescence analysis, acetone-fixed cross-sections of the biopsy were incubated for 90 minutes with monoclonal antibodies against the central rod domain (MANDYS106, Dr. G. Morris, UK, 1:60), the C-terminal domain (NCL-DYS2, Novocastra Laboratories Ltd., 1:30) or, as reference, laminin-α2 (Chemicon International, Inc, 1:150), followed by Alexa Fluor 488 goat anti-mouse IgG (H+L) (Molecular Probes, Inc, 1:250) antibody for one hour. Sections were mounted with Vectashield Mounting Medium (Vector Laboratories Inc.). For quantitative image analysis the ImageJ software (W. Rasband, NIH, USA; http://rsb.info.nih.gov/ij) was used as described[60,61]. Entire cross-sections were subdivided into series of 6-10 adjacent images, depending on section size. To ensure reliable measurements, staining of the sections and recording of all images was performed in one session, using fixed exposure settings, and avoiding pixel saturation. The lower intensity threshold was set at Duchenne muscular dystrophy background, and positive fluorescence was quantified for each section (area percentage), both for dystrophin and laminin-α2. Western blot analysis was performed as described[1], using pooled homogenates from sets of four serial 50 μm sections throughout the biopsy. For the patients 30 and 60 μg total protein was applied and for the control sample 3 μg. The blot was incubated overnight with dystrophin monoclonal antibody NCL-DYS1 (Novocastra Laboratories, 1:125), followed by goat anti-mouse IgG-HRP (Santa Cruz Biotechnology, 1:10.000) for one hour Immunoreactive bands were visualized using the ECL Plus Western Blotting Detection System (GE Healthcare) and Hyperfilm ECL (Amersham, Biosciences). Signal intensities were measured using ImageJ. Novel dystrophin protein expression at the sarcolemma was detected in the majority of muscle fibers in the treated area in all four patients. The fibers in each section were manually counted after staining for laminin-α2, a basal lamina protein unaffected by dystrophin deficiency. The individual numbers varied, consistent with the biopsy size and the quality of the patients' muscles. In the largest sections, patient 2 had 726 fibers, of which 620 were dystrophin-positive, while patient 3 had 120 fibers, of which 117 were dystrophin-positive. The dystrophin intensities were typically lower than those in a healthy muscle biopsy. Western blot analysis confirmed the presence of dystrophin in varying amounts. The dystrophin signals were scanned and correlated to the control (per μg total protein). The amounts varied from 3% in patient 3 with the most dystrophic muscle, to 12% in patient 2 with the best preserved muscle. Since such comparison based on total protein does not correct for the varying amounts of fibrotic and adipose tissue in Duchenne muscular dystrophy patients, we also quantified the dystrophin fluorescence signal relative to that of the similarly-located laminin-α2 in each section, by ImageJ analysis. When this dystrophin/laminin-α2 ratio was set at 100% for the control section, the two patients that were co-treated with corticosteroids showed the highest percentages of dystrophin, 32% in patient 1 and 35% in patient 2 (Table 1). The lowest percentage of dystrophin was detected in patient 3, 17%. In patient 4 an intermediate percentage of 25% was observed. These percentages correlated to the relative quality of the target muscle, which was best in patients nr. 1 and 2, and worst in patient nr. 3.

TABLE 1

| | Patient 1 | Patient 2 | Patient 3 | Patient 4 |
|---|---|---|---|---|
| Age (yrs) | 10 | 13 | 13 | 11 |
| Age at Loss of Ambulation (yrs) | 9 | 11 | 7 | 10 |
| Steroid Treatment | Yes | Yes | Never | Until January 2006 |
| Ratio Dystrophin/ laminin-alpha2 | 32% | 35% | 17% | 25% |

Conclusion: the effect of the PRO051 antisense compound was more prominent in those patients that were also subjected to corticosteroids.

Example 1A

Reproduced from Van Deutekom J C et al, (2007) Antisense Oligonucleotide PRO051 Restores Local Dystrophin in DMD Patients. N Engl J. Med., 357(26): 2677-86.

Methods

Patients and Study Design

Patients with Duchenne's muscular dystrophy who were between the ages of 8 and 16 years were eligible to participate in the study. All patients had deletions that were correctable by exon-51 skipping and had no evidence of dystrophin on previous diagnostic muscle biopsy. Concurrent glucocorticoid treatment was allowed. Written informed consent was obtained from the patients or their parents, as appropriate. During the prescreening period (up to 60 days), each patient's mutational status and positive exon-skipping response to PRO051 in vitro were confirmed, and the condition of the tibialis anterior muscle was determined by $T_1$-weighted magnetic resonance imaging (MRI).[62] For patients to be included in the study, fibrotic and adipose tissue could make up no more than 50% of their target muscle.

During the baseline visit, safety measures were assessed. In each patient, the leg that was to be injected was fixed with a tailor-made plastic mold and its position was recorded. A topical eutectic mixture of local anesthetics (EMLA) was used to numb the skin. Four injections of PRO051 were given along a line measuring 1.5 cm running between two small skin tattoos with the use of a 2.5-cm electromyographic needle (MyoJect Disposable Hypodermic Needle Electrode, TECA Accessories) to ensure intramuscular delivery. The volume of each injection was 200 μl containing 200 μg of PRO051, which was dispersed in equal portions at angles of approximately 30 degrees.

At day 28, safety measures were assessed again. The leg that had been injected was positioned with the use of the patient's own mold, and a semiopen muscle biopsy was performed between the tattoos under local anesthesia with a forceps with two sharp-edged jaws (Blakesley Conchotoma, DK Instruments).[63] The biopsy specimen was snap-frozen in 2-methylbutane cooled in liquid nitrogen.

Patients were treated sequentially from May 2006 through March 2007 and in compliance with Good Clinical Practice guidelines and the provisions of the Declaration of Helsinki. The study was approved by the Dutch Central Committee on Research Involving Human Subjects and by the local institutional review board at Leiden University Medical Center. All authors contributed to the study design, participated in the collection and analysis of the data, had complete and free access to the data, jointly wrote the manuscript, and vouch for the completeness and accuracy of the data and analyses presented.

Description of PRO051

PRO051 is a synthetic, modified RNA molecule with sequence 5'-UCAAGGAAGAUGGCAUUUCU-3'.[12] It carries full-length 2'-O-methyl-substituted ribose molecules and phosphorothioate internucleotide linkages. The drug was provided by Prosensa B.V. in vials of 1 mg of freeze-dried material with no excipient. It was dissolved and administered in sterile, unpreserved saline (0.9% sodium chloride). PRO051 was not found to be mutagenic by bacterial Ames testing. In regulatory Good Laboratory Practice safety studies, rats that received a single administration of up to 8 mg per kilogram of body weight intramuscularly and 50 mg per kilogram intravenously showed no adverse effects; monkeys receiving PRO051 for 1 month appeared to tolerate doses up to 16 mg per kilogram per week when the drug was administered by intravenous 1-hour infusion or by subcutaneous injection, without clinically relevant adverse effects.

In Vitro Prescreening

A preexisting primary myoblast culture[1] was used for the prescreening of Patient 4. For the other three patients, fibroblasts were converted into myogenic cells after infection with an adenoviral vector containing the gene for the myogenic transcription factor (MyoD) as described previously.[1,64,65] Myotube cultures were transfected with PRO051 (100 nM) and polyethylenimine (2 μl per microgram of PRO051), according to the manufacturer's instructions for ExGen500 (MBI Fermentas). RNA was isolated after 48 hours. Reverse transcriptase-polymerase chain reaction (RT-PCR), immunofluorescence, and Western blot analyses were performed as reported previously[1,12] PCR fragments were analyzed with the use of the 2100 Bioanalyzer (Agilent) and isolated for sequencing by the Leiden Genome Technology Center.

Safety Assessment

At baseline and at 2 hours, 1 day, and 28 days after injection, all patients received a full physical examination (including the measurement of vital signs) and underwent electrocardiography. In addition, plasma and urine were obtained to determine renal and liver function, electrolyte levels, complete cell counts, the activated partial-thromboplastin time, and complement activity values in the classical (CH50) and alternative (AP50) routes. The use of concomitant medications was recorded. At baseline and on day 28, the strength of the tibialis anterior muscle was assessed with the use of the Medical Research Council scale[66] to evaluate whether the procedures had affected muscle performance. (On this scale, a score of 0 indicates no movement and a score of 5 indicates normal muscle strength.) Since only a small area of the muscle was treated, clinical benefit in terms of increased muscle strength was not expected. At each visit, adverse events were recorded.

RNA Assessment

Serial sections (50 μm) of the frozen muscle-biopsy specimen were homogenized in RNA-Bee solution (Campro Scientific) and MagNA Lyser Green Beads (Roche Diagnostics). Total RNA was isolated and purified according to the manufacturer's instructions. For complementary DNA, synthesis was accomplished with Transcriptor reverse transcriptase (Roche Diagnostics) with the use of 500 ng of RNA in a 20-μl reaction at 55° C. for 30 minutes with human exon 53 or 54 specific reverse primers. PCR analyses were performed as described previously.[1,12] Products were analyzed on 2% agarose gels and sequenced. In addition, RT-PCR with the use of a primer set for the protein-truncation test[67] was used to rapidly screen for aspecific aberrant splicing events throughout the DMD gene.

Assessment of Protein Level

For immunofluorescence analysis, acetone-fixed sections were incubated for 90 minutes with monoclonal antibodies against the central rod domain (MANDYS106, Dr. G. Morris, United Kingdom) at a dilution of 1:60, the C-terminal domain (NCL-DYS2, Novocastra Laboratories) at a dilution of 1:30, or (as a reference) laminin (Chemicon International), a basal lamina protein that is unaffected by dystrophin deficiency, at a dilution of 1:150, followed by Alexa Fluor 488 goat anti-mouse IgG (H+L) antibody (Molecular Probes) at a dilution of 1:250 for 1 hour. Sections were mounted with Vectashield Mounting Medium (Vector Laboratories). ImageJ software (W. Rasband, National Institutes of Health, http://rsb.info.nih.gov/ij) was used for quantitative image analysis as described previously.[60,61] Entire cross sections were subdivided into series of 6 to 10 adjacent images, depending on the size of the section. To ensure reliable measurements, staining of the sections and recording of all images were performed during one session with the use of fixed exposure settings and the avoidance of pixel saturation. The lower-intensity threshold was set at background for Duchenne's muscular dystrophy, and positive fluorescence was quantified for each section (area percentage), both for dystrophin and laminin α2.

Western blot analysis was performed as described previously[1] with the use of pooled homogenates from sets of four serial 50-μm sections throughout the biopsy specimen. For each patient, two amounts of total protein—30 μg and 60 μg—were applied, and for the control sample, 3 μg. The Western blot was incubated overnight with dystrophin monoclonal antibody NCL-DYS1 (Novocastra Laboratories) at a dilution of 1:125, followed by horseradish-peroxidase-labeled goat antimouse IgG (Santa Cruz Biotechnology) at a dilution of 1:10,000 for 1 hour. Immunoreactive bands were visualized with the use of the ECL Plus Western blotting detection system (GE Healthcare) and Hyperfilm ECL (Amersham Biosciences). Signal intensities were measured with the use of ImageJ software.

Results

Prescreening of Patients

Figure 1:
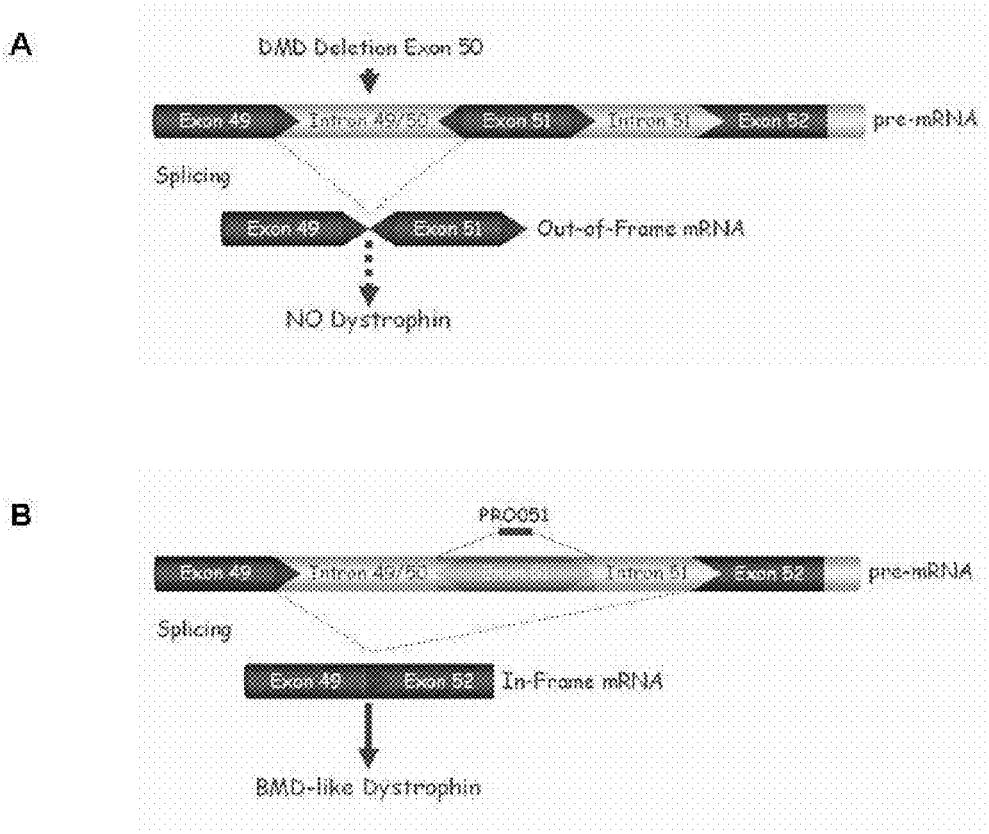
FIGS. 1A-1B. Schematic Representation of Exon Skipping.
Figure 2A:
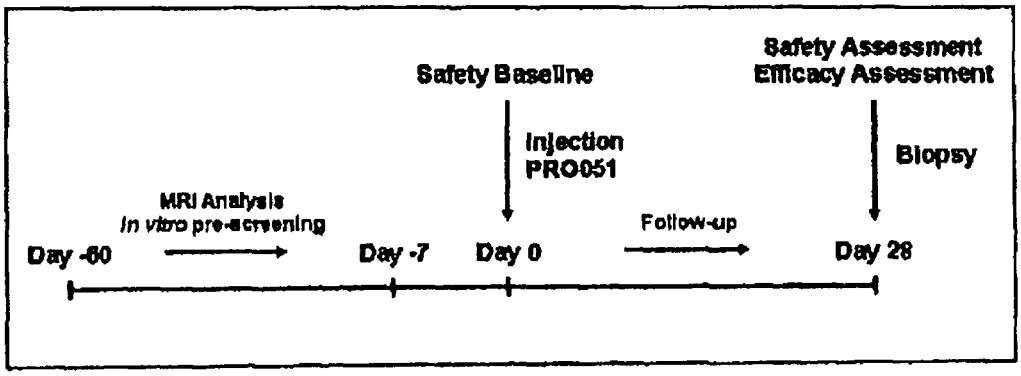
Figure 2B:
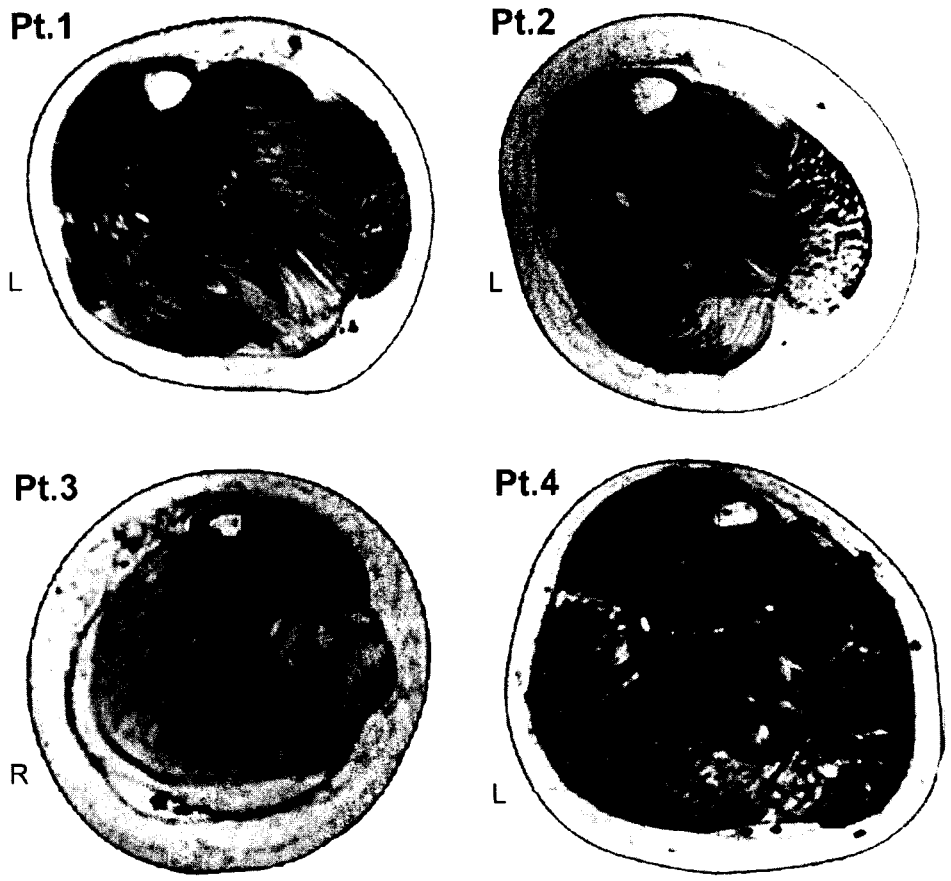
Figure 2C:
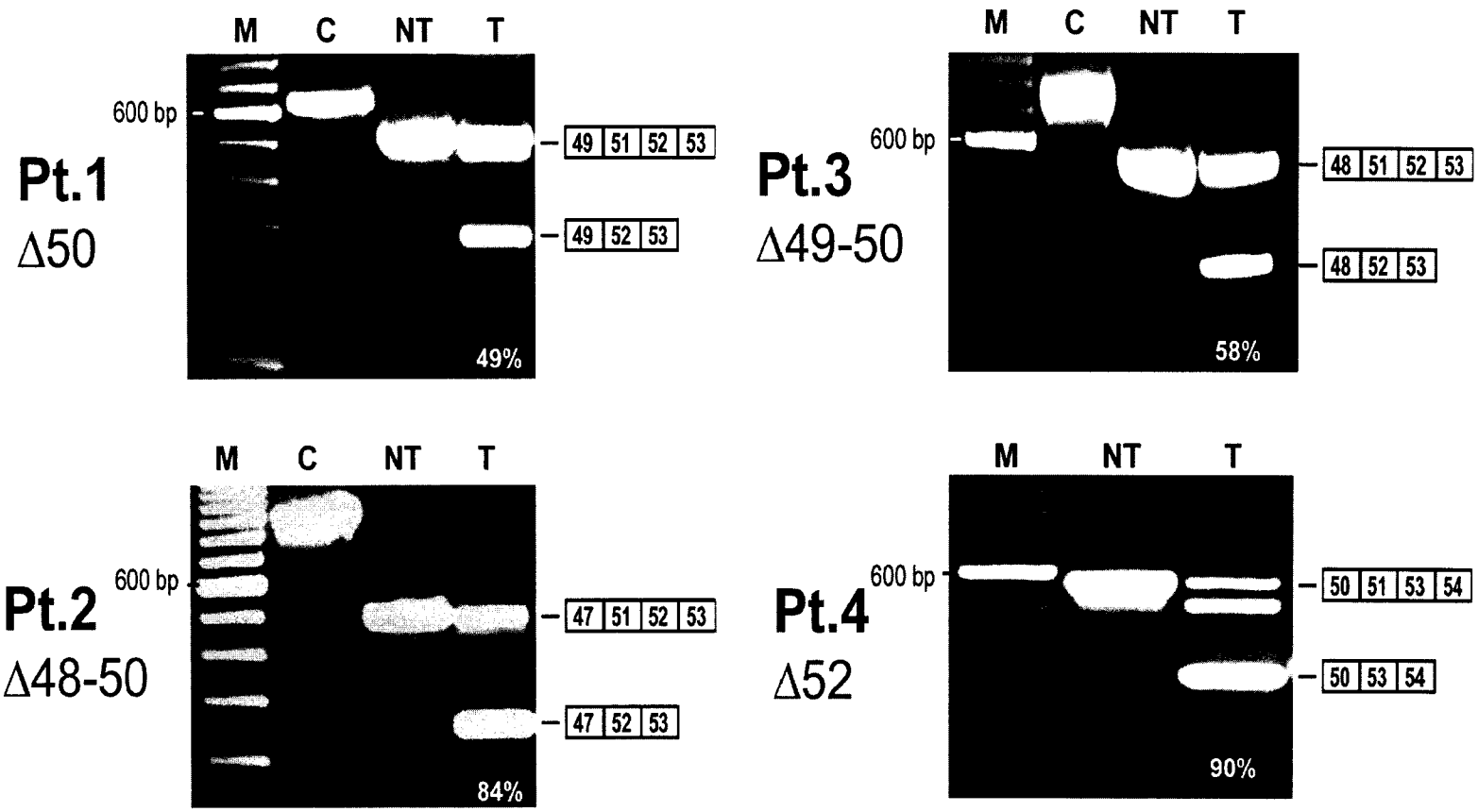
Figure 2D:
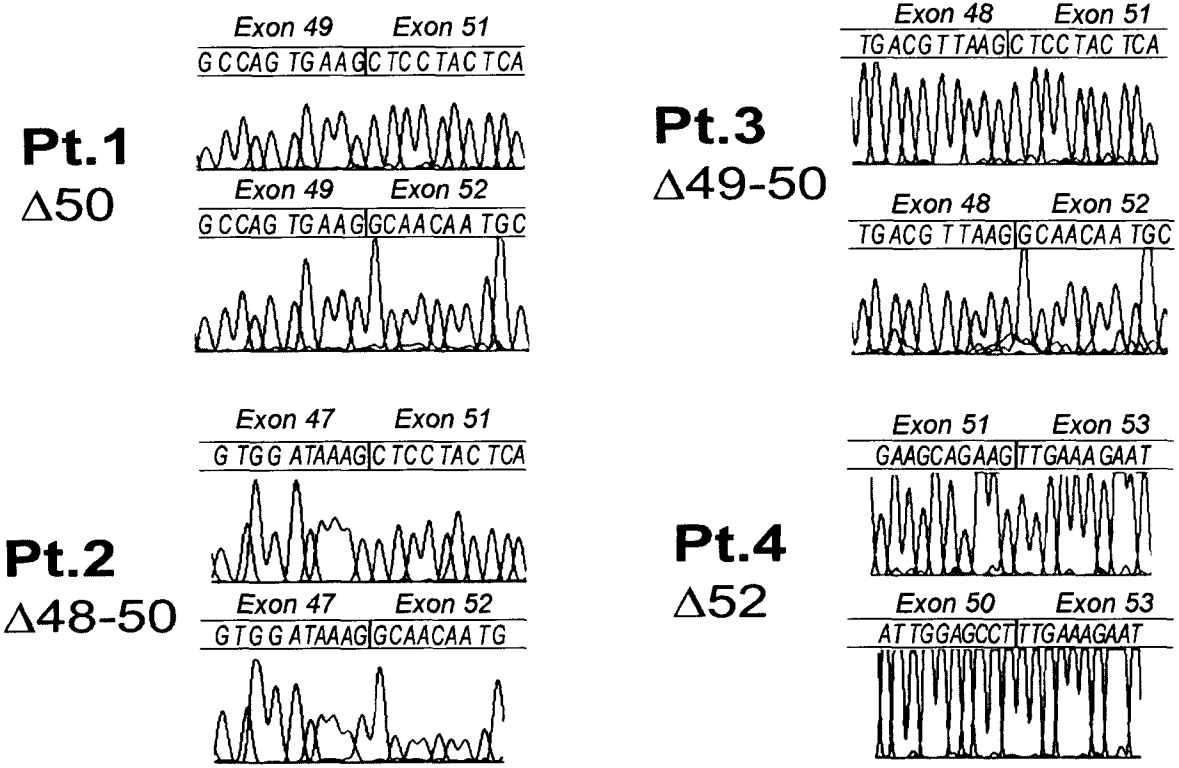
Figure 2E:
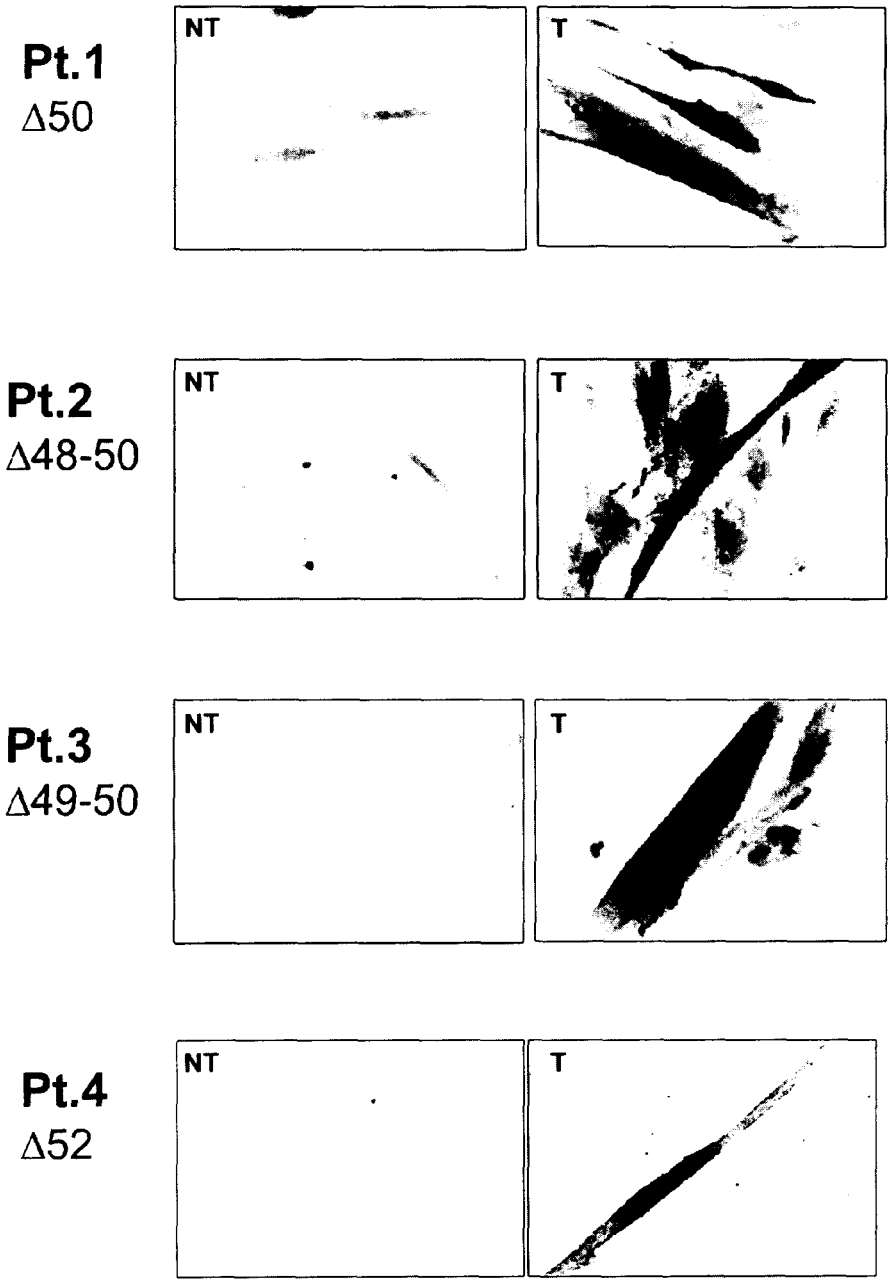

The study was planned to include four to six patients. Six patients were invited to participate, and one declined. The remaining five patients were prescreened. First, the condition of the tibialis anterior muscle was evaluated on MRI. The muscle condition of four patients was deemed to be adequate for the study (FIG. 2B), and the absence of dystrophin was confirmed in the patients' original biopsy specimens (FIG. 2B). Second, the mutational status and positive exon-skipping response to PRO051 of these four patients were confirmed in fibroblast cultures. PRO051 treatment generated a novel, shorter fragment of messenger RNA for each patient, representing 46% (in Patient 4) to 90% (in Patient 1) of the total RT-PCR product (FIG. 2C). Precise exon-51 skipping was confirmed by sequencing (FIG. 2D). No other transcript regions were found to be altered. Immunofluorescence analyses showed a preponderance of dystrophin-positive myotubes (FIG. 2E), a finding that was confirmed by Western blot analysis (not shown). Thus, the four patients were judged to be eligible for PRO051 treatment. Their baseline characteristics are shown in Table 2.

Safety and Adverse Events

All patients had one or more adverse events. However, only one patient reported mild local pain at the injection site, which was considered to be an adverse event related to the study drug. Other events included mild-to-moderate pain after the muscle biopsy. Two patients had blistering under the bandages used for wound closure. In the period between injection and biopsy, two patients reported a few days of flulike symptoms, and one patient had mild diarrhea for 1 day. At baseline, the muscle-strength scores of the treated tibialis anterior muscle in Patients 1, 2, 3, and 4 were 4, 2, 3, and 4, respectively, on the Medical Research Council scale. None of the patients showed changes in the strength of this muscle during the study or significant alterations in standard laboratory measures or increased measures of complement split products or activated partial-thromboplastin time. No local inflammatory or toxic response was detected in the muscle sections of the patients (data not shown). Patient 3 successfully underwent preplanned surgery for scoliosis in the month after the study was completed.

RNA and Protein Level

At day 28, a biopsy of the treated area was performed in each patient. Total muscle RNA was isolated from serial sections throughout the biopsy specimen. In all patients, RT-PCR identified a novel, shorter fragment caused by exon-51 skipping, as confirmed by sequencing (FIG. 3). Further transcript analysis showed no other alterations (data not shown). Immunofluorescence analyses of sections throughout the biopsy specimen of each patient showed clear sarcolemmal dystrophin signals in the majority of muscle fibers (FIGS. 4A and 4B). Dystrophin antibodies proximal and distal to the deletions that were used included MANDYS106 (FIGS. 4A and 4B) and NCL-DYS2 (similar to MANDYS106, not shown). The fibers in each section were manually counted after staining for laminin α2.[68] The individual numbers varied, consistent with the size of the biopsy specimen and the quality of the muscle. In the largest sections, Patient 2 had 726 fibers, of which 620 were dystrophin-positive, whereas Patient 3 had 120 fibers, of which 117 were dystrophin-positive (Data not shown). The dystrophin intensities were typically lower than those in a healthy muscle biopsy specimen (Data not shown). The single fibers with a more intense dystrophin signal in Patients 2 and 3 could well be revertant fibers (Data not shown).

Western blot analysis confirmed the presence of dystrophin in varying amounts (FIG. 4A). The dystrophin signals were scanned and correlated to the control (per microgram of total protein). The amounts varied from 3% in Patient 3, who had the most-dystrophic muscle, to 12% in Patient 2, who had the best-preserved muscle. Since such comparison on the basis of total protein does not correct for the varying amounts of fibrotic and adipose tissue in patients with Duchenne's muscular dystrophy, we also quantified the dystrophin fluorescence signal (Data not shown) relative to that of the similarly located laminin α2 in each section by ImageJ analysis. When the ratio of dystrophin to laminin α2 was set at 100 for the control section, Patients 1, 2, 3, and 4 had ratios of 33, 35, 17, and 25, respectively (Table 1).

Discussion

Our study showed that local intramuscular injection of PRO051, a 2OMePS antisense oligoribonucleotide complementary to a 20-nucleotide sequence within exon 51, induced exon-51 skipping, corrected the reading frame, and thus introduced dystrophin in the muscle in all four patients with Duchenne's muscular dystrophy who received therapy. Dystrophin-positive fibers were found throughout the patients' biopsy specimens, indicating dispersion of the compound in the injected area. Since no delivery-enhancing excipient was used, PRO051 uptake did not seem to be a major potentially limiting factor. We cannot rule out that increased permeability of the dystrophic fiber membrane had a favorable effect. The patients produced levels of dystrophin that were 3 to 12% of the level in healthy control muscle, as shown on Western blot analysis of total protein. Since the presence of fibrosis and fat may lead to some underestimation of dystrophin in total protein extracts, we determined the ratio of dystrophin to laminin α2 in the cross sections, which ranged from 17 to 35, as compared with 100 in control muscle. The dystrophin-restoring effect of PRO051 was limited to the treated area, and no strength improvement of the entire muscle was observed. Future systemic treatment will require repeated administration to increase and maintain dystrophin expression at a higher level and to obtain clinical efficacy.

Because of medical-ethics regulations regarding interventions in minors, we could not obtain a biopsy specimen from the patients' contralateral muscles that had not been injected. However, the patients showed less than 1% of revertant fibers in the original diagnostic biopsy specimens obtained 5 to 9 years before the initiation of the study (Table 2 and FIG. 2B). We consider it very likely that the effects we observed were related to the nature and sequence of the PRO051 reagent rather than to a marked increase in revertant fibers. Indeed, a single, possibly revertant fiber that had an increased dystrophin signal was observed in both Patient 2 and Patient 3 (FIG. 4B).

In summary, our study showed that local administration of PRO051 to muscle in four patients with Duchenne' s muscular dystrophy restored dystrophin to levels ranging from 3 to 12% or 17 to 35%, depending on quantification relative to total protein or myofiber content. Consistent with the distinctly localized nature of the treatment, functional improvement was not observed. The consistently poorer result in Patient 3, who had the most advanced disease, suggests the importance of performing clinical trials in patients at a relatively young age, when relatively little muscle tissue has been replaced by fibrotic and adipose tissue. Our findings provide an indication that antisense-mediated exon skipping may be a potential approach to restoring dystrophin synthesis in the muscles of patients with Duchenne's muscular dystrophy.

Example 2

In a pre-clinical study in mdx mice (animal model for DMD) the effect of adjunct compound prednisone on AON-induced exon skipping was assessed.

Mdx mice (C57Bl/10ScSn-mdx/J) were obtained from Charles River Laboratories (The Netherlands). These mice are dystrophin-deficient due to a nonsense mutation in exon 23. AON-induced exon 23 skipping is therapeutic in mdx mice by removing the nonsense mutation and correction of the open reading frame. Two mdx mice per group were injected subcutaneously with: Group 1) physiologic salt (wk 1-8), Group 2) prednisolone (1 mg/kg, wk 1-8), Group 3) mouse-specific antisense oligonucleotide PS49 designed to specifically induce exon 23 skipping (100 mg/kg, wk 4 (5 times), week 5-8 (2 times), Group 4) prednisolone (1 mg/kg, wk 1-8)+PS49 (100 mg/kg, wk 4 (5 times), week 5-8 (2 times). PS49 (5' GGCCAAACCUCGGCUUACCU 3') has a full-length phosphorothioate backbone and 2'O-methyl modified ribose molecules.

All mice were sacrificed at 1 week post-last-injection. Different muscles groups, including quadriceps, tibialis anterior, and diaphragm muscles were isolated and frozen in liquid nitrogen-cooled 2-methylbutane. For RT-PCR analysis, the muscle samples were homogenized in the RNA-Bee solution (Campro Scientific, The Netherlands). Total RNA was isolated and purified according to the manufacturer's instructions. For cDNA synthesis with reverse transcriptase (Roche Diagnostics, The Netherlands), 300 ng of RNA was used in a 20 μl reaction at 55° C. for 30 min, reverse primed with mouse DMD gene-specific primers. First PCRs were performed with outer primer sets, for 20 cycles of 94° C. (40 sec), 60° C. (40 sec), and 72° C. (60 sec). One μl of this reaction (diluted 1:10) was then re-amplified using nested primer combinations in the exons directly flanking exon 23, with 30 cycles of 94° C. (40 sec), 60° C. (40 sec), and 72° C. (60 sec). PCR products were analysed on 2% agarose gels. Skipping efficiencies were determined by quantification of PCR products using the DNA 1000 LabChip® Kit and the Agilent 2100 bioanalyzer (Agilent Technologies, The Netherlands). No exon 23 skipping was observed in the muscles from mice treated with physiologic salt or prenisolone only (groups 1 and 2). Levels of exon 23 skipping were detected and per muscle group compared between mice treated with PS49 only (group 3) and mice treated with PS49 and adjunct compound prednisolone (group 4). In the quadriceps (Q), tibialis anterior (TA), and diaphragm (DIA) muscles, exon 23 skipping levels were typically higher in group 4 when compared to group 3 (FIG. 5). This indicates that adjunct compound prednisolone indeed enhances exon 23 skipping levels in mdx mice treated with PS49.

Example 3

A., B. Differentiated muscle cell cultures (myotubes) derived from a healthy control individual were transfected with 250 nM PS188 ([5' UCAGCUUCUGUUAGCCACUG 3'; SEQ ID NO:10] an AON optimized to specifically skip exon 44) or 250 nM PS221 ([5' AUUCAAUGUUCUGACAACAGUUUGC 3'; SEQ ID NO: 60] an AON optimized to specifically skip exon 45) in the presence of 0 to 0.5 mg/ml pentoxifylline, using the transfection reagent polymer UNIFectylin (2.0 μl UNIFectylin per μg AON in 0.15M NaCl). UNIFectylin interacts electrostatically with nucleic acids, provided that the nucleic acid is negatively charged (such as 2'-O-methyl phosphorothioate AONs). Pentoxyfillin (Sigma Aldrich) was dissolved in water. Total RNA was isolated 24 hrs after transfection in RNA-Bee solution (Campro Scientific, The Netherlands) according to the manufacturer's instructions. For cDNA synthesis with reverse transcriptase (Roche Diagnostics, The Netherlands), 500 ng of RNA was used in a 20 μl reaction at 55° C. for 30 min, reverse primed with DMD gene-specific primers. First PCRs were performed with outer primer sets, for 20 cycles of 94° C. (40 sec), 60° C. (40 sec), and 72° C. (60 sec). One μl of this reaction (diluted 1:10) was then re-amplified using nested primer combinations in the exons directly flanking exon 44 or 45, with 30 cycles of 94° C. (40 sec), 60° C. (40 sec), and 72° C. (60 sec). PCR products were analysed on 2% agarose gels. Skipping efficiencies were determined by quantification of PCR products using the DNA 1000 LabChip® Kit and the Agilent 2100 bioanalyzer (Agilent Technologies, The Netherlands).

Both with PS188 and PS221, increasing levels of exon 44 or 45 skipping were obtained with increasing concentrations of the adjunct compound pentoxifylline when compared to those obtained in cells that were not co-treated with pentoxyfilline (see FIG. 6). These results indicate that pentoxifylline enhances exon skipping levels in the muscle cells.

C.

In a pre-clinical study in mdx mice (animal model for DMD) the effect of adjunct compound pentoxyfilline on AON-induced exon skipping was assessed. Mdx mice (C57Bl/10ScSn-mdx/J) were obtained from Charles River Laboratories (The Netherlands). These mice are dystrophin-deficient due to a nonsense mutation in exon 23. AON-induced exon 23 skipping is therapeutic in mdx mice by removing the nonsense mutation and correction of the open reading frame. Two mdx mice per group were injected subcutaneously with: Group 1) pentoxyfilline (50 mg/kg, wk 1-2), Group 2) mouse-specific antisense oligonucleotide PS49 designed to specifically induce exon 23 skipping (100 mg/kg, wk 2 (2 times), Group 3) pentoxyfilline (50 mg/kg, wk 1-2)+PS49 (100 mg/kg, wk 2 (2 times). PS49 (5' GGCCAAACCUCGGCUUACCU 3') has a full-length phosphorothioate backbone and 2'O-methyl modified ribose molecules.

All mice were sacrificed at 1 week post-last-injection. Different muscles groups, including quadriceps, tibialis anterior, triceps and heart muscles were isolated and frozen in liquid nitrogen-cooled 2-methylbutane. For RT-PCR analysis, the muscle samples were homogenized in the RNA-Bee solution (Campro Scientific, The Netherlands). Total RNA was isolated and purified according to the manufacturer's instructions. For cDNA synthesis with reverse transcriptase (Roche Diagnostics, The Netherlands), 300 ng of RNA was used in a 20 μl reaction at 55° C. for 30 min, reverse primed with mouse DMD gene-specific primers. First PCRs were performed with outer primer sets, for 20 cycles of 94° C. (40 sec), 60° C. (40 sec), and 72° C. (60 sec). One μl of this reaction (diluted 1:10) was then re-amplified using nested primer combinations in the exons directly flanking exon 23, with 30 cycles of 94° C. (40 sec), 60° C. (40 sec), and 72° C. (60 sec). PCR products were analysed on 2% agarose gels. Skipping efficiencies were determined by quantification of PCR products using the DNA 1000 LabChip® Kit and the Agilent 2100 bioanalyzer (Agilent Technologies, The Netherlands). No exon 23 skipping was observed in the muscles from mice treated with pentoxyfilline only (groups 1). Levels of exon 23 skipping were detected and per muscle group compared between mice treated with PS49 only (group 2) and mice treated with PS49 and adjunct compound pentoxyfilline (group 3). In the quadriceps (Q), tibialis anterior (TA), triceps (Tri) and heart (HRT) muscles, exon 23 skipping levels were typically higher in group 3 when compared to group 2 (FIG. 6c). This indicates that adjunct compound pentoxyfilline indeed enhances exon 23 skipping levels in mdx mice treated with PS49.

TABLE 2

Baseline characteristics of the DMD patients

| | Patient 1 | Patient 2 | Patient 3 | Patient 4 |
|---|---|---|---|---|
| Age (yrs) | 10 | 13 | 13 | 11 |
| Deletion | Exon 50 | Exons 48-50 | Exons 49-50 | Exon 52 |
| Age at Loss of Ambulation (yrs) | 9 | 11 | 7 | 10 |
| Scoliosis | No | No | Yes | Yes |
| Creatine Kinase Levels (U/I)[1] | 5823 | 2531 | 717 | 4711 |
| Steroid treatment | Yes | Yes | Never | Until January 2006 |

TABLE 2-continued

Baseline characteristics of the DMD patients

| | Patient 1 | Patient 2 | Patient 3 | Patient 4 |
|---|---|---|---|---|
| Strength TA muscle (MRC scale) | 4 | 2 | 3 | 4 |
| MRI status TA muscle | Moderate[2] | Moderate[2] | Moderate[2] | Moderate[2] |
| % Revertant fibers | N.D. | <1% | N.D. | |

[1]normal level: <200 U/I

[2]less than 50% fat infiltration and/or fibrosis [Mercuri et al., 2005)

REFERENCES

1. Aartsma-Rus A, Janson A A, Kaman W E, et al. Therapeutic antisense-induced exon skipping in cultured muscle cells from six different DMD patients. Hum Mol Genet. 2003; 12(8):907-14.
2. Aartsma-Rus A, Janson A A, Kaman W E, et al. Antisense-induced multiexon skipping for Duchenne muscular dystrophy makes more sense. Am J Hum Genet. 2004; 74(1):83-92.
3. Alter J, Lou F, Rabinowitz A, et al. Systemic delivery of morpholino oligonucleotide restores dystrophin expression bodywide and improves dystrophic pathology. Nat Med 2006; 12(2):175-7.
4. Goyenvalle A, Vulin A, Fougerousse F, et al. Rescue of dystrophic muscle through U7 snRNA-mediated exon skipping. Science 2004; 306(5702):1796-9.
5. Lu Q L, Mann C J, Lou F, et al. Functional amounts of dystrophin produced by skipping the mutated exon in the mdx dystrophic mouse. Nat Med 2003; 6:6.
6. Lu Q L, Rabinowitz A, Chen Y C, et al. Systemic delivery of antisense oligoribonucleotide restores dystrophin expression in body-wide skeletal muscles. Proc Natl Acad Sci USA 2005; 102(1):198-203.
7. McClorey G, Fall A M, Moulton H M, et al. Induced dystrophin exon skipping in human muscle explants. Neuromuscul Disord 2006; 16(9-10):583-90.
8. McClorey G, Moulton H M, Iversen P L, et al. Antisense oligonucleotide-induced exon skipping restores dystrophin expression in vitro in a canine model of DMD. Gene Ther 2006; 13(19):1373-81.
9. Pramono Z A, Takeshima Y, Alimsardjono H, Ishii A, Takeda S, Matsuo M. Induction of exon skipping of the dystrophin transcript in lymphoblastoid cells by transfecting an antisense oligodeoxynucleotide complementary to an exon recognition sequence. Biochem Biophys Res Commun 1996; 226(2):445-9.
10. Takeshima Y, Yagi M, Wada H, et al. Intravenous infusion of an antisense oligonucleotide results in exon skipping in muscle dystrophin mRNA of Duchenne muscular dystrophy. Pediatr Res 2006; 59(5):690-4.
11. van Deutekom J C, Bremmer-Bout M, Janson A A, et al. Antisense-induced exon skipping restores dystrophin expression in DMD patient derived muscle cells. Hum Mol Genet. 2001; 10(15):1547-54.
12. Aartsma-Rus A, Bremmer-Bout M, Janson A, den Dunnen J, van Ommen G, van Deutekom J. Targeted exon skipping as a potential gene correction therapy for Duchenne muscular dystrophy. Neuromuscul Disord 2002; 12 Suppl:S71-S77.
13. Aartsma-Rus A, De Winter C L, Janson A A, et al. Functional analysis of 114 exon-internal AONs for targeted DMD exon skipping: indication for steric hindrance of SR protein binding sites. Oligonucleotides 2005; 15(4): 284-97.

14. Aartsma-Rus A, Janson A A, Heemskerk J A, CL de Winter, G J Van Ommen, J C Van Deutekom. Therapeutic Modulation of DMD Splicing by Blocking Exonic Splicing Enhancer Sites with Antisense Oligonucleotides. Annals of the New York Academy of Sciences 2006; 1082:74-6.
15. Aartsma-Rus A, Kaman W E, Weij R, den Dunnen J T, van Ommen G J, van Deutekom J C. Exploring the frontiers of therapeutic exon skipping for Duchenne muscular dystrophy by double targeting within one or multiple exons. Mol Ther 2006; 14(3):401-7.
16. Welch E M, Barton E R, Zhuo J, et al. PTC124 targets genetic disorders caused by nonsense mutations. Nature 2007; 447(7140):87-91.
17. Hirawat S, Welch E M, Elfring G L, et al. Safety, tolerability, and pharmacokinetics of PTC124, a nonaminoglycoside nonsense mutation suppressor, following single- and multiple-dose administration to healthy male and female adult volunteers. Journal of clinical pharmacology 2007; 47(4):430-44.
18. Wang B, Li J, Xiao X. Adeno-associated virus vector carrying human minidystrophin genes effectively ameliorates muscular dystrophy in mdx mouse model. Proc Natl Acad Sci USA 2000; 97(25):13714-9.
19. Fabb S A, Wells D J, Serpente P, Dickson G. Adeno-associated virus vector gene transfer and sarcolemmal expression of a 144 kDa micro-dystrophin effectively restores the dystrophin-associated protein complex and inhibits myofibre degeneration in nude/mdx mice. Hum Mol Genet. 2002; 11(7):733-41.
20. Wang Z, Kuhr C S, Allen J M, et al. Sustained AAV-mediated dystrophin expression in a canine model of Duchenne muscular dystrophy with a brief course of immunosuppression. Mol Ther 2007; 15(6):1160-6.
21. Manzur AY, Kuntzer T, Pike M, Swan A. Glucocorticoid corticosteroids for Duchenne muscular dystrophy. Cochrane Database Syst Rev 2004; 2.
22. Duboc D, Meune C, Pierre B, et al. Perindopril preventive treatment on mortality in Duchenne muscular dystrophy: 10 years' follow-up. American heart journal 2007; 154(3):596-602.
23. Cohn R D, van Erp C, Habashi J P, et al. Angiotensin II type 1 receptor blockade attenuates TGF-beta-induced failure of muscle regeneration in multiple myopathic states. Nat Med 2007; 13(2):204-10.
24. Grounds M D, Torrisi J. Anti-TNFalpha (Remicade) therapy protects dystrophic skeletal muscle from necrosis. Faseb J 2004; 18(6):676-82.
25. Hodgetts S, Radley H, Davies M, Grounds M D. Reduced necrosis of dystrophic muscle by depletion of host neutrophils, or blocking TNFalpha function with Etanercept in mdx mice. Neuromuscul Disord 2006; 16(9-10):591-602.
26. Pierno S, Nico B, Burdi R, et al. Role of tumour necrosis factor alpha, but not of cyclo-oxygenase-2-derived eicosanoids, on functional and morphological indices of dystrophic progression in mdx mice: a pharmacological approach. Neuropathology and applied neurobiology 2007; 33(3):344-59.
27. Musaro A, McCullagh K, Paul A, et al. Localized Igf-1 transgene expression sustains hypertrophy and regeneration in senescent skeletal muscle. Nat Genet. 2001; 27(2): 195-200.
28. Barton E R, Morris L, Musaro A, Rosenthal N, Sweeney H L. Muscle-specific expression of insulin-like growth factor I counters muscle decline in mdx mice. J Cell Biol 2002; 157(1):137-48.
29. Disatnik M H, Dhawan J, Yu Y, et al. Evidence of oxidative stress in mdx mouse muscle: studies of the pre-necrotic state. J Neurol Sci 1998; 161(1):77-84.
30. Nelson S K, Bose S K, Grunwald G K, Myhill P, McCord J M. The induction of human superoxide dismutase and catalase in vivo: a fundamentally new approach to antioxidant therapy. Free radical biology & medicine 2006; 40(2):341-7.
31. Hart P E, Lodi R, Rajagopalan B, et al. Antioxidant treatment of patients with Friedreich ataxia: four-year follow-up. Archives of neurology 2005; 62(4):621-6.
32. Rolland J F, De Luca A, Burdi R, Andreetta F, Confalonieri P, Conte Camerino D. Overactivity of exercise-sensitive cation channels and their impaired modulation by IGF-1 in mdx native muscle fibers: beneficial effect of pentoxifylline. Neurobiol Dis 2006; 24(3):466-74.
33. Whitehead N P, Streamer M, Lusambili L I, Sachs F, Allen D G. Streptomycin reduces stretch-induced membrane permeability in muscles from mdx mice. Neuromuscul Disord 2006; 16(12):845-54.
34. Badalamente M A, Stracher A. Delay of muscle degeneration and necrosis in mdx mice by calpain inhibition. Muscle Nerve 2000; 23(1):106-11.
35. Burdi R, Didonna M P, Pignol B, et al. First evaluation of the potential effectiveness in muscular dystrophy of a novel chimeric compound, BN 82270, acting as calpain-inhibitor and anti-oxidant. Neuromuscul Disord 2006; 16(4):237-48.
36. Bonuccelli G, Sotgia F, Schubert W, et al. Proteasome inhibitor (MG-132) treatment of mdx mice rescues the expression and membrane localization of dystrophin and dystrophin-associated proteins. Am J Pathol 2003; 163 (4):1663-75.
37. Voisin V, Sebrie C, Matecki S, et al. L-arginine improves dystrophic phenotype in mdx mice. Neurobiol Dis 2005; 20(1):123-30.
38. Soret J, Bakkour N, Maire S, et al. Selective modification of alternative splicing by indole derivatives that target serine-arginine-rich protein splicing factors. Proc Natl Acad Sci USA 2005; 102(24):8764-9.
39. Mann C J, Honeyman K, McClorey G, Fletcher S, Wilton S D. Improved antisense oligonucleotide induced exon skipping in the mdx mouse model of muscular dystrophy. J Gene Med 2002; 4(6):644-54.
40. Graham I R, Hill V J, Manoharan M, Inamati G B, Dickson G. Towards a therapeutic inhibition of dystrophin exon 23 splicing in mdx mouse muscle induced by antisense oligoribonucleotides (splicomers): target sequence optimisation using oligonucleotide arrays. J Gene Med 2004; 6(10):1149-58.
41. Mathews D H, Sabina J, Zuker M, Turner D H. Expanded sequence dependence of thermodynamic parameters improves prediction of RNA secondary structure. J Mol Biol 1999; 288(5):911-40.
42. Cartegni L, Chew S L, Kramer A R. Listening to silence and understanding nonsense: exonic mutations that affect splicing. Nat Rev Genet. 2002; 3(4):285-98.
43. Cartegni L, Wang J, Zhu Z, Zhang M Q, Krainer A R. ESEfinder: A web resource to identify exonic splicing enhancers. Nucleic Acids Res 2003; 31(13):3568-71.
44. Braasch D A, Corey D R. Locked nucleic acid (LNA): fine-tuning the recognition of DNA and RNA. Chem Biol 2001; 8(1):1-7.

45. Braasch D A, Corey D R. Novel antisense and peptide nucleic acid strategies for controlling gene expression. Biochemistry 2002; 41(14):4503-10.
46. Elayadi A N, Corey D R. Application of PNA and LNA oligomers to chemotherapy. Curr Opin Investig Drugs 2001; 2(4):558-61.
47. Larsen H J, Bentin T, Nielsen P E. Antisense properties of peptide nucleic acid. Biochim Biophys Acta 1999; 1489 (1):159-66.
48. Summerton J. Morpholino antisense oligomers: the case for an RNase H-independent structural type. Biochim Biophys Acta 1999; 1489(1):141-58.
49. Summerton J, Weller D. Morpholino antisense oligomers: design, preparation, and properties. Antisense Nucleic Acid Drug Dev 1997; 7(3):187-95.
50. Wahlestedt C, Salmi P, Good L, et al. Potent and nontoxic antisense oligonucleotides containing locked nucleic acids. Proc Natl Acad Sci USA 2000; 97(10): 5633-8.
51. De Angelis F G, Sthandier O, Berarducci B, et al. Chimeric snRNA molecules carrying antisense sequences against the splice junctions of exon 51 of the dystrophin pre-mRNA induce exon skipping and restoration of a dystrophin synthesis in Delta 48-50 DMD cells. Proc Natl Acad Sci USA 2002; 99(14):9456-61.
52. Denti M A, Rosa A, D'Antona G, et al. Chimeric adeno-associated virus/antisense U1 small nuclear RNA effectively rescues dystrophin synthesis and muscle function by local treatment of mdx mice. Hum Gene Ther 2006; 17(5):565-74.
53. Gorman L, Suter D, Emerick V, Schumperli D, Kole R. Stable alteration of pre-mRNA splicing patterns by modified U7 small nuclear RNAs. Proc Natl Acad Sci USA 1998; 95(9):4929-34.
54. Suter D, Tomasini R, Reber U, Gorman L, Kole R, Schumperli D. Double-target antisense U7 snRNAs promote efficient skipping of an aberrant exon in three human beta-thalassemic mutations. Hum Mol Genet. 1999; 8(13):2415-23.
55. Wagner K R, Hamed S, Hadley D W, et al. Gentamicin treatment of Duchenne and Becker muscular dystrophy due to nonsense mutations. Ann Neurol 2001; 49(6):706-11.
56. Aartsma-Rus A et al, (2006), Entries in the leiden Duchenne Muscular Dystrophy mutation database: an overview of mutation types and paradoxical cases that confirm the reading-frame rule, Muscle Nerve, 34: 135-144.
57. Hodgetts S., et al, (2006), Neuromuscular Disorders, 16:591-602.
58. Manzur A Y et al, (2008), Glucocorticoid corticosteroids for Duchenne muscular dystrophy (review), Wiley publishers, The Cochrane collaboration.
59. Van Deutekom J C et al, (2007) Antisense Oligonucleotide PRO051 Restores Local Dystrophin in DMD Patients. N Engl J. Med., 357(26): 2677-86.
60. Yuan H, Takeuchi E, Taylor G A, McLaughlin M, Brown D, Salant D J. Nephrin dissociates from actin, and its expression is reduced in early experimental membranous nephropathy. J Am Soc Nephrol 2002; 13:946-56.
61. Koop K, Bakker R C, Eikmans M, et al. Differentiation between chronic rejection and chronic cyclosporine toxity by analysis of renal cortical mRNA. Kindney Int 2004; 66:2038-46.
62. Mercuri E, Bushby K, Ricci e., et al. Muscle MRI findings in patients with limb girdle muscular dystrophy with calpain 3 deficiency (LGMD2A) and early contractures. Neuromuscul Disord 2005; 15:164-71.
63. Dorph C, Nennesmo I, Lundberg I E. Percutaneous conchotome muscle biopsy: a useful diagnostic and assessment tool. J Rheumatol 2001; 28:1591-9.
64. Havenga M J, Lemckert A A, Ophorst O J, et al. Exploiting the natural diversity in adenovirus tropism for therapy and prevention of disease. J Virol 2002; 76:4612-20.
65. Roest P A, van der Tuijn A C, Ginjaar H B, et al. Application of in vitro Myo-differentation of non-muscle cells to enhance gene expression and facilitate analysis of muscle proteins. Neuromuscul Disord 1996; 6:195-202.
66. John J. Grading of muscular power: comparison of MRC and analogue scales by physiotherapists. Int J Rehabil Res 1984; 7:173-81.
67. Roest P A, Roberts R G, van der Tuijn A C, Heikoop J C, van Ommen G J, den Dunnen J T. Protein truncation test (PTT) to rapidly screen the DMD gene for translation terminating mutations. Neuromuscul Disord 1993; 3:391-4.
68. Cullen M J, Walsh J, Roberds S L, Campbell K P. Ultra-structural localization of adhalin, alpha-dystroglycan and merosin in normal and dystrophic muscle. Neuropathol Appl Neurobiol 1996; 22:30-7.

SEQUENCE LISTING

```
<160> NUMBER OF SEQ ID NOS: 314

<210> SEQ ID NO 1
<211> LENGTH: 3685
<212> TYPE: PRT
<213> ORGANISM: Homo sapiens

<400> SEQUENCE: 1

Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60
```

```
Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Arg Val
        435                 440                 445

Leu Met Asp Leu Gln Asn Gln Lys Leu Lys Glu Leu Asn Asp Trp Leu
    450                 455                 460

Thr Lys Thr Glu Glu Arg Thr Arg Lys Met Glu Glu Glu Pro Leu Gly
465                 470                 475                 480
```

```
Pro Asp Leu Glu Asp Leu Lys Arg Gln Val Gln Gln His Lys Val Leu
                485                 490                 495

Gln Glu Asp Leu Glu Gln Glu Gln Val Arg Val Asn Ser Leu Thr His
            500                 505                 510

Met Val Val Val Val Asp Glu Ser Ser Gly Asp His Ala Thr Ala Ala
        515                 520                 525

Leu Glu Glu Gln Leu Lys Val Leu Gly Asp Arg Trp Ala Asn Ile Cys
    530                 535                 540

Arg Trp Thr Glu Asp Arg Trp Val Leu Leu Gln Asp Ile Leu Leu Lys
545                 550                 555                 560

Trp Gln Arg Leu Thr Glu Glu Gln Cys Leu Phe Ser Ala Trp Leu Ser
                565                 570                 575

Glu Lys Glu Asp Ala Val Asn Lys Ile His Thr Thr Gly Phe Lys Asp
            580                 585                 590

Gln Asn Glu Met Leu Ser Ser Leu Gln Lys Leu Ala Val Leu Lys Ala
        595                 600                 605

Asp Leu Glu Lys Lys Lys Gln Ser Met Gly Lys Leu Tyr Ser Leu Lys
    610                 615                 620

Gln Asp Leu Leu Ser Thr Leu Lys Asn Lys Ser Val Thr Gln Lys Thr
625                 630                 635                 640

Glu Ala Trp Leu Asp Asn Phe Ala Arg Cys Trp Asp Asn Leu Val Gln
                645                 650                 655

Lys Leu Glu Lys Ser Thr Ala Gln Ile Ser Gln Ala Val Thr Thr Thr
            660                 665                 670

Gln Pro Ser Leu Thr Gln Thr Thr Val Met Glu Thr Val Thr Thr Val
        675                 680                 685

Thr Thr Arg Glu Gln Ile Leu Val Lys His Ala Gln Glu Glu Leu Pro
    690                 695                 700

Pro Pro Pro Pro Gln Lys Lys Arg Gln Ile Thr Val Asp Ser Glu Ile
705                 710                 715                 720

Arg Lys Arg Leu Asp Val Asp Ile Thr Glu Leu His Ser Trp Ile Thr
                725                 730                 735

Arg Ser Glu Ala Val Leu Gln Ser Pro Glu Phe Ala Ile Phe Arg Lys
            740                 745                 750

Glu Gly Asn Phe Ser Asp Leu Lys Glu Lys Val Asn Ala Ile Glu Arg
        755                 760                 765

Glu Lys Ala Glu Lys Phe Arg Lys Leu Gln Asp Ala Ser Arg Ser Ala
    770                 775                 780

Gln Ala Leu Val Glu Gln Met Val Asn Glu Gly Val Asn Ala Asp Ser
785                 790                 795                 800

Ile Lys Gln Ala Ser Glu Gln Leu Asn Ser Arg Trp Ile Glu Phe Cys
                805                 810                 815

Gln Leu Leu Ser Glu Arg Leu Asn Trp Leu Glu Tyr Gln Asn Asn Ile
            820                 825                 830

Ile Ala Phe Tyr Asn Gln Leu Gln Gln Leu Glu Gln Met Thr Thr Thr
        835                 840                 845

Ala Glu Asn Trp Leu Lys Ile Gln Pro Thr Thr Pro Ser Glu Pro Thr
    850                 855                 860

Ala Ile Lys Ser Gln Leu Lys Ile Cys Lys Asp Glu Val Asn Arg Leu
865                 870                 875                 880

Ser Gly Leu Gln Pro Gln Ile Glu Arg Leu Lys Ile Gln Ser Ile Ala
                885                 890                 895

Leu Lys Glu Lys Gly Gln Gly Pro Met Phe Leu Asp Ala Asp Phe Val
```

```
            900                 905                 910

Ala Phe Thr Asn His Phe Lys Gln Val Phe Ser Asp Val Gln Ala Arg
        915                 920                 925

Glu Lys Glu Leu Gln Thr Ile Phe Asp Thr Leu Pro Pro Met Arg Tyr
    930                 935                 940

Gln Glu Thr Met Ser Ala Ile Arg Thr Trp Val Gln Gln Ser Glu Thr
945                 950                 955                 960

Lys Leu Ser Ile Pro Gln Leu Ser Val Thr Asp Tyr Glu Ile Met Glu
                965                 970                 975

Gln Arg Leu Gly Glu Leu Gln Ala Leu Gln Ser Ser Leu Gln Glu Gln
            980                 985                 990

Gln Ser Gly Leu Tyr Tyr Leu Ser  Thr Thr Val Lys Glu  Met Ser Lys
        995                 1000                1005

Lys Ala  Pro Ser Glu Ile Ser  Arg Lys Tyr Gln Ser  Glu Phe Glu
    1010                1015                1020

Glu Ile  Glu Gly Arg Trp Lys  Lys Leu Ser Ser Gln  Leu Val Glu
    1025                1030                1035

His Cys  Gln Lys Leu Glu Glu  Gln Met Asn Lys Leu  Arg Lys Ile
    1040                1045                1050

Gln Asn  His Ile Gln Thr Leu  Lys Lys Trp Met Ala  Glu Val Asp
    1055                1060                1065

Val Phe  Leu Lys Glu Glu Trp  Pro Ala Leu Gly Asp  Ser Glu Ile
    1070                1075                1080

Leu Lys  Lys Gln Leu Lys Gln  Cys Arg Leu Leu Val  Ser Asp Ile
    1085                1090                1095

Gln Thr  Ile Gln Pro Ser Leu  Asn Ser Val Asn Glu  Gly Gly Gln
    1100                1105                1110

Lys Ile  Lys Asn Glu Ala Glu  Pro Glu Phe Ala Ser  Arg Leu Glu
    1115                1120                1125

Thr Glu  Leu Lys Glu Leu Asn  Thr Gln Trp Asp His  Met Cys Gln
    1130                1135                1140

Gln Val  Tyr Ala Arg Lys Glu  Ala Leu Lys Gly Gly  Leu Glu Lys
    1145                1150                1155

Thr Val  Ser Leu Gln Lys Asp  Leu Ser Glu Met His  Glu Trp Met
    1160                1165                1170

Thr Gln  Ala Glu Glu Glu Tyr  Leu Glu Arg Asp Phe  Glu Tyr Lys
    1175                1180                1185

Thr Pro  Asp Glu Leu Gln Lys  Ala Val Glu Glu Met  Lys Arg Ala
    1190                1195                1200

Lys Glu  Glu Ala Gln Gln Lys  Glu Ala Lys Val Lys  Leu Leu Thr
    1205                1210                1215

Glu Ser  Val Asn Ser Val Ile  Ala Gln Ala Pro Pro  Val Ala Gln
    1220                1225                1230

Glu Ala  Leu Lys Lys Glu Leu  Glu Thr Leu Thr Thr  Asn Tyr Gln
    1235                1240                1245

Trp Leu  Cys Thr Arg Leu Asn  Gly Lys Cys Lys Thr  Leu Glu Glu
    1250                1255                1260

Val Trp  Ala Cys Trp His Glu  Leu Leu Ser Tyr Leu  Glu Lys Ala
    1265                1270                1275

Asn Lys  Trp Leu Asn Glu Val  Glu Phe Lys Leu Lys  Thr Thr Glu
    1280                1285                1290

Asn Ile  Pro Gly Gly Ala Glu  Glu Ile Ser Glu Val  Leu Asp Ser
    1295                1300                1305
```

```
Leu Glu  Asn Leu Met Arg His  Ser Glu Asp Asn Pro  Asn Gln Ile
    1310                 1315                 1320

Arg Ile  Leu Ala Gln Thr Leu  Thr Asp Gly Gly Val  Met Asp Glu
    1325                 1330                 1335

Leu Ile  Asn Glu Glu Leu Glu  Thr Phe Asn Ser Arg  Trp Arg Glu
    1340                 1345                 1350

Leu His  Glu Glu Ala Val Arg  Arg Gln Lys Leu Leu  Glu Gln Ser
    1355                 1360                 1365

Ile Gln  Ser Ala Gln Glu Thr  Glu Lys Ser Leu His  Leu Ile Gln
    1370                 1375                 1380

Glu Ser  Leu Thr Phe Ile Asp  Lys Gln Leu Ala Ala  Tyr Ile Ala
    1385                 1390                 1395

Asp Lys  Val Asp Ala Ala Gln  Met Pro Gln Glu Ala  Gln Lys Ile
    1400                 1405                 1410

Gln Ser  Asp Leu Thr Ser His  Glu Ile Ser Leu Glu  Glu Met Lys
    1415                 1420                 1425

Lys His  Asn Gln Gly Lys Glu  Ala Ala Gln Arg Val  Leu Ser Gln
    1430                 1435                 1440

Ile Asp  Val Ala Gln Lys Lys  Leu Gln Asp Val Ser  Met Lys Phe
    1445                 1450                 1455

Arg Leu  Phe Gln Lys Pro Ala  Asn Phe Glu Gln Arg  Leu Gln Glu
    1460                 1465                 1470

Ser Lys  Met Ile Leu Asp Glu  Val Lys Met His Leu  Pro Ala Leu
    1475                 1480                 1485

Glu Thr  Lys Ser Val Glu Gln  Glu Val Val Gln Ser  Gln Leu Asn
    1490                 1495                 1500

His Cys  Val Asn Leu Tyr Lys  Ser Leu Ser Glu Val  Lys Ser Glu
    1505                 1510                 1515

Val Glu  Met Val Ile Lys Thr  Gly Arg Gln Ile Val  Gln Lys Lys
    1520                 1525                 1530

Gln Thr  Glu Asn Pro Lys Glu  Leu Asp Glu Arg Val  Thr Ala Leu
    1535                 1540                 1545

Lys Leu  His Tyr Asn Glu Leu  Gly Ala Lys Val Thr  Glu Arg Lys
    1550                 1555                 1560

Gln Gln  Leu Glu Lys Cys Leu  Lys Leu Ser Arg Lys  Met Arg Lys
    1565                 1570                 1575

Glu Met  Asn Val Leu Thr Glu  Trp Leu Ala Ala Thr  Asp Met Glu
    1580                 1585                 1590

Leu Thr  Lys Arg Ser Ala Val  Glu Gly Met Pro Ser  Asn Leu Asp
    1595                 1600                 1605

Ser Glu  Val Ala Trp Gly Lys  Ala Thr Gln Lys Glu  Ile Glu Lys
    1610                 1615                 1620

Gln Lys  Val His Leu Lys Ser  Ile Thr Glu Val Gly  Glu Ala Leu
    1625                 1630                 1635

Lys Thr  Val Leu Gly Lys Lys  Glu Thr Leu Val Glu  Asp Lys Leu
    1640                 1645                 1650

Ser Leu  Leu Asn Ser Asn Trp  Ile Ala Val Thr Ser  Arg Ala Glu
    1655                 1660                 1665

Glu Trp  Leu Asn Leu Leu Leu  Glu Tyr Gln Lys His  Met Glu Thr
    1670                 1675                 1680

Phe Asp  Gln Asn Val Asp His  Ile Thr Lys Trp Ile  Ile Gln Ala
    1685                 1690                 1695
```

```
Asp Thr  Leu Leu Asp Glu Ser  Glu Lys Lys Lys Pro  Gln Gln Lys
    1700                 1705                 1710

Glu Asp  Val Leu Lys Arg Leu  Lys Ala Glu Leu Asn  Asp Ile Arg
    1715                 1720                 1725

Pro Lys  Val Asp Ser Thr Arg  Asp Gln Ala Ala Asn  Leu Met Ala
    1730                 1735                 1740

Asn Arg  Gly Asp His Cys Arg  Lys Leu Val Glu Pro  Gln Ile Ser
    1745                 1750                 1755

Glu Leu  Asn His Arg Phe Ala  Ala Ile Ser His Arg  Ile Lys Thr
    1760                 1765                 1770

Gly Lys  Ala Ser Ile Pro Leu  Lys Glu Leu Glu Gln  Phe Asn Ser
    1775                 1780                 1785

Asp Ile  Gln Lys Leu Leu Glu  Pro Leu Glu Ala Glu  Ile Gln Gln
    1790                 1795                 1800

Gly Val  Asn Leu Lys Glu Glu  Asp Phe Asn Lys Asp  Met Asn Glu
    1805                 1810                 1815

Asp Asn  Glu Gly Thr Val Lys  Glu Leu Leu Gln Arg  Gly Asp Asn
    1820                 1825                 1830

Leu Gln  Gln Arg Ile Thr Asp  Glu Arg Lys Arg Glu  Glu Ile Lys
    1835                 1840                 1845

Ile Lys  Gln Gln Leu Leu Gln  Thr Lys His Asn Ala  Leu Lys Asp
    1850                 1855                 1860

Leu Arg  Ser Gln Arg Arg Lys  Lys Ala Leu Glu Ile  Ser His Gln
    1865                 1870                 1875

Trp Tyr  Gln Tyr Lys Arg Gln  Ala Asp Asp Leu Leu  Lys Cys Leu
    1880                 1885                 1890

Asp Asp  Ile Glu Lys Lys Leu  Ala Ser Leu Pro Glu  Pro Arg Asp
    1895                 1900                 1905

Glu Arg  Lys Ile Lys Glu Ile  Asp Arg Glu Leu Gln  Lys Lys Lys
    1910                 1915                 1920

Glu Glu  Leu Asn Ala Val Arg  Arg Gln Ala Glu Gly  Leu Ser Glu
    1925                 1930                 1935

Asp Gly  Ala Ala Met Ala Val  Glu Pro Thr Gln Ile  Gln Leu Ser
    1940                 1945                 1950

Lys Arg  Trp Arg Glu Ile Glu  Ser Lys Phe Ala Gln  Phe Arg Arg
    1955                 1960                 1965

Leu Asn  Phe Ala Gln Ile His  Thr Val Arg Glu Glu  Thr Met Met
    1970                 1975                 1980

Val Met  Thr Glu Asp Met Pro  Leu Glu Ile Ser Tyr  Val Pro Ser
    1985                 1990                 1995

Thr Tyr  Leu Thr Glu Ile Thr  His Val Ser Gln Ala  Leu Leu Glu
    2000                 2005                 2010

Val Glu  Gln Leu Leu Asn Ala  Pro Asp Leu Cys Ala  Lys Asp Phe
    2015                 2020                 2025

Glu Asp  Leu Phe Lys Gln Glu  Glu Ser Leu Lys Asn  Ile Lys Asp
    2030                 2035                 2040

Ser Leu  Gln Gln Ser Ser Gly  Arg Ile Asp Ile Ile  His Ser Lys
    2045                 2050                 2055

Lys Thr  Ala Ala Leu Gln Ser  Ala Thr Pro Val Glu  Arg Val Lys
    2060                 2065                 2070

Leu Gln  Glu Ala Leu Ser Gln  Leu Asp Phe Gln Trp  Glu Lys Val
    2075                 2080                 2085

Asn Lys  Met Tyr Lys Asp Arg  Gln Gly Arg Phe Asp  Arg Ser Val
```

```
    2090                2095                2100

Glu Lys  Trp Arg Arg Phe His  Tyr Asp Ile Lys Ile  Phe Asn Gln
    2105                2110                2115

Trp Leu  Thr Glu Ala Glu Gln  Phe Leu Arg Lys Thr  Gln Ile Pro
    2120                2125                2130

Glu Asn  Trp Glu His Ala Lys  Tyr Lys Trp Tyr Leu  Lys Glu Leu
    2135                2140                2145

Gln Asp  Gly Ile Gly Gln Arg  Gln Thr Val Val Arg  Thr Leu Asn
    2150                2155                2160

Ala Thr  Gly Glu Glu Ile Ile  Gln Gln Ser Ser Lys  Thr Asp Ala
    2165                2170                2175

Ser Ile  Leu Gln Glu Lys Leu  Gly Ser Leu Asn Leu  Arg Trp Gln
    2180                2185                2190

Glu Val  Cys Lys Gln Leu Ser  Asp Arg Lys Lys Arg  Leu Glu Glu
    2195                2200                2205

Gln Lys  Asn Ile Leu Ser Glu  Phe Gln Arg Asp Leu  Asn Glu Phe
    2210                2215                2220

Val Leu  Trp Leu Glu Glu Ala  Asp Asn Ile Ala Ser  Ile Pro Leu
    2225                2230                2235

Glu Pro  Gly Lys Glu Gln Gln  Leu Lys Glu Lys Leu  Glu Gln Val
    2240                2245                2250

Lys Leu  Leu Val Glu Glu Leu  Pro Leu Arg Gln Gly  Ile Leu Lys
    2255                2260                2265

Gln Leu  Asn Glu Thr Gly Gly  Pro Val Leu Val Ser  Ala Pro Ile
    2270                2275                2280

Ser Pro  Glu Glu Gln Asp Lys  Leu Glu Asn Lys Leu  Lys Gln Thr
    2285                2290                2295

Asn Leu  Gln Trp Ile Lys Val  Ser Arg Ala Leu Pro  Glu Lys Gln
    2300                2305                2310

Gly Glu  Ile Glu Ala Gln Ile  Lys Asp Leu Gly Gln  Leu Glu Lys
    2315                2320                2325

Lys Leu  Glu Asp Leu Glu Glu  Gln Leu Asn His Leu  Leu Leu Trp
    2330                2335                2340

Leu Ser  Pro Ile Arg Asn Gln  Leu Glu Ile Tyr Asn  Gln Pro Asn
    2345                2350                2355

Gln Glu  Gly Pro Phe Asp Val  Gln Glu Thr Glu Ile  Ala Val Gln
    2360                2365                2370

Ala Lys  Gln Pro Asp Val Glu  Glu Ile Leu Ser Lys  Gly Gln His
    2375                2380                2385

Leu Tyr  Lys Glu Lys Pro Ala  Thr Gln Pro Val Lys  Arg Lys Leu
    2390                2395                2400

Glu Asp  Leu Ser Ser Glu Trp  Lys Ala Val Asn Arg  Leu Leu Gln
    2405                2410                2415

Glu Leu  Arg Ala Lys Gln Pro  Asp Leu Ala Pro Gly  Leu Thr Thr
    2420                2425                2430

Ile Gly  Ala Ser Pro Thr Gln  Thr Val Thr Leu Val  Thr Gln Pro
    2435                2440                2445

Val Val  Thr Lys Glu Thr Ala  Ile Ser Lys Leu Glu  Met Pro Ser
    2450                2455                2460

Ser Leu  Met Leu Glu Val Pro  Ala Leu Ala Asp Phe  Asn Arg Ala
    2465                2470                2475

Trp Thr  Glu Leu Thr Asp Trp  Leu Ser Leu Leu Asp  Gln Val Ile
    2480                2485                2490
```

```
Lys Ser  Gln Arg Val Met Val  Gly Asp Leu Glu Asp  Ile Asn Glu
    2495                 2500                 2505

Met Ile  Ile Lys Gln Lys Ala  Thr Met Gln Asp Leu  Glu Gln Arg
    2510                 2515                 2520

Arg Pro  Gln Leu Glu Glu Leu  Ile Thr Ala Ala Gln  Asn Leu Lys
    2525                 2530                 2535

Asn Lys  Thr Ser Asn Gln Glu  Ala Arg Thr Ile Ile  Thr Asp Arg
    2540                 2545                 2550

Ile Glu  Arg Ile Gln Asn Gln  Trp Asp Glu Val Gln  Glu His Leu
    2555                 2560                 2565

Gln Asn  Arg Arg Gln Gln Leu  Asn Glu Met Leu Lys  Asp Ser Thr
    2570                 2575                 2580

Gln Trp  Leu Glu Ala Lys Glu  Glu Ala Glu Gln Val  Leu Gly Gln
    2585                 2590                 2595

Ala Arg  Ala Lys Leu Glu Ser  Trp Lys Glu Gly Pro  Tyr Thr Val
    2600                 2605                 2610

Asp Ala  Ile Gln Lys Lys Ile  Thr Glu Thr Lys Gln  Leu Ala Lys
    2615                 2620                 2625

Asp Leu  Arg Gln Trp Gln Thr  Asn Val Asp Val Ala  Asn Asp Leu
    2630                 2635                 2640

Ala Leu  Lys Leu Leu Arg Asp  Tyr Ser Ala Asp Asp  Thr Arg Lys
    2645                 2650                 2655

Val His  Met Ile Thr Glu Asn  Ile Asn Ala Ser Trp  Arg Ser Ile
    2660                 2665                 2670

His Lys  Arg Val Ser Glu Arg  Glu Ala Ala Leu Glu  Glu Thr His
    2675                 2680                 2685

Arg Leu  Leu Gln Gln Phe Pro  Leu Asp Leu Glu Lys  Phe Leu Ala
    2690                 2695                 2700

Trp Leu  Thr Glu Ala Glu Thr  Thr Ala Asn Val Leu  Gln Asp Ala
    2705                 2710                 2715

Thr Arg  Lys Glu Arg Leu Leu  Glu Asp Ser Lys Gly  Val Lys Glu
    2720                 2725                 2730

Leu Met  Lys Gln Trp Gln Asp  Leu Gln Gly Glu Ile  Glu Ala His
    2735                 2740                 2745

Thr Asp  Val Tyr His Asn Leu  Asp Glu Asn Ser Gln  Lys Ile Leu
    2750                 2755                 2760

Arg Ser  Leu Glu Gly Ser Asp  Asp Ala Val Leu Leu  Gln Arg Arg
    2765                 2770                 2775

Leu Asp  Asn Met Asn Phe Lys  Trp Ser Glu Leu Arg  Lys Lys Ser
    2780                 2785                 2790

Leu Asn  Ile Arg Ser His Leu  Glu Ala Ser Ser Asp  Gln Trp Lys
    2795                 2800                 2805

Arg Leu  His Leu Ser Leu Gln  Glu Leu Leu Val Trp  Leu Gln Leu
    2810                 2815                 2820

Lys Asp  Asp Glu Leu Ser Arg  Gln Ala Pro Ile Gly  Gly Asp Phe
    2825                 2830                 2835

Pro Ala  Val Gln Lys Gln Asn  Asp Val His Arg Ala  Phe Lys Arg
    2840                 2845                 2850

Glu Leu  Lys Thr Lys Glu Pro  Val Ile Met Ser Thr  Leu Glu Thr
    2855                 2860                 2865

Val Arg  Ile Phe Leu Thr Glu  Gln Pro Leu Glu Gly  Leu Glu Lys
    2870                 2875                 2880
```

```
Leu Tyr  Gln Glu Pro Arg Glu  Leu Pro Pro Glu Glu  Arg Ala Gln
    2885                 2890                 2895

Asn Val  Thr Arg Leu Leu Arg  Lys Gln Ala Glu Glu  Val Asn Thr
    2900                 2905                 2910

Glu Trp  Glu Lys Leu Asn Leu  His Ser Ala Asp Trp  Gln Arg Lys
    2915                 2920                 2925

Ile Asp  Glu Thr Leu Glu Arg  Leu Gln Glu Leu Gln  Glu Ala Thr
    2930                 2935                 2940

Asp Glu  Leu Asp Leu Lys Leu  Arg Gln Ala Glu Val  Ile Lys Gly
    2945                 2950                 2955

Ser Trp  Gln Pro Val Gly Asp  Leu Leu Ile Asp Ser  Leu Gln Asp
    2960                 2965                 2970

His Leu  Glu Lys Val Lys Ala  Leu Arg Gly Glu Ile  Ala Pro Leu
    2975                 2980                 2985

Lys Glu  Asn Val Ser His Val  Asn Asp Leu Ala Arg  Gln Leu Thr
    2990                 2995                 3000

Thr Leu  Gly Ile Gln Leu Ser  Pro Tyr Asn Leu Ser  Thr Leu Glu
    3005                 3010                 3015

Asp Leu  Asn Thr Arg Trp Lys  Leu Leu Gln Val Ala  Val Glu Asp
    3020                 3025                 3030

Arg Val  Arg Gln Leu His Glu  Ala His Arg Asp Phe  Gly Pro Ala
    3035                 3040                 3045

Ser Gln  His Phe Leu Ser Thr  Ser Val Gln Gly Pro  Trp Glu Arg
    3050                 3055                 3060

Ala Ile  Ser Pro Asn Lys Val  Pro Tyr Tyr Ile Asn  His Glu Thr
    3065                 3070                 3075

Gln Thr  Thr Cys Trp Asp His  Pro Lys Met Thr Glu  Leu Tyr Gln
    3080                 3085                 3090

Ser Leu  Ala Asp Leu Asn Asn  Val Arg Phe Ser Ala  Tyr Arg Thr
    3095                 3100                 3105

Ala Met  Lys Leu Arg Arg Leu  Gln Lys Ala Leu Cys  Leu Asp Leu
    3110                 3115                 3120

Leu Ser  Leu Ser Ala Ala Cys  Asp Ala Leu Asp Gln  His Asn Leu
    3125                 3130                 3135

Lys Gln  Asn Asp Gln Pro Met  Asp Ile Leu Gln Ile  Ile Asn Cys
    3140                 3145                 3150

Leu Thr  Thr Ile Tyr Asp Arg  Leu Glu Gln Glu His  Asn Asn Leu
    3155                 3160                 3165

Val Asn  Val Pro Leu Cys Val  Asp Met Cys Leu Asn  Trp Leu Leu
    3170                 3175                 3180

Asn Val  Tyr Asp Thr Gly Arg  Thr Gly Arg Ile Arg  Val Leu Ser
    3185                 3190                 3195

Phe Lys  Thr Gly Ile Ile Ser  Leu Cys Lys Ala His  Leu Glu Asp
    3200                 3205                 3210

Lys Tyr  Arg Tyr Leu Phe Lys  Gln Val Ala Ser Ser  Thr Gly Phe
    3215                 3220                 3225

Cys Asp  Gln Arg Arg Leu Gly  Leu Leu Leu His Asp  Ser Ile Gln
    3230                 3235                 3240

Ile Pro  Arg Gln Leu Gly Glu  Val Ala Ser Phe Gly  Gly Ser Asn
    3245                 3250                 3255

Ile Glu  Pro Ser Val Arg Ser  Cys Phe Gln Phe Ala  Asn Asn Lys
    3260                 3265                 3270

Pro Glu  Ile Glu Ala Ala Leu  Phe Leu Asp Trp Met  Arg Leu Glu
```

```
    3275                3280                3285

Pro Gln  Ser Met Val Trp Leu  Pro Val Leu His Arg  Val Ala Ala
    3290                3295                3300

Ala Glu  Thr Ala Lys His Gln  Ala Lys Cys Asn Ile  Cys Lys Glu
    3305                3310                3315

Cys Pro  Ile Ile Gly Phe Arg  Tyr Arg Ser Leu Lys  His Phe Asn
    3320                3325                3330

Tyr Asp  Ile Cys Gln Ser Cys  Phe Phe Ser Gly Arg  Val Ala Lys
    3335                3340                3345

Gly His  Lys Met His Tyr Pro  Met Val Glu Tyr Cys  Thr Pro Thr
    3350                3355                3360

Thr Ser  Gly Glu Asp Val Arg  Asp Phe Ala Lys Val  Leu Lys Asn
    3365                3370                3375

Lys Phe  Arg Thr Lys Arg Tyr  Phe Ala Lys His Pro  Arg Met Gly
    3380                3385                3390

Tyr Leu  Pro Val Gln Thr Val  Leu Glu Gly Asp Asn  Met Glu Thr
    3395                3400                3405

Pro Val  Thr Leu Ile Asn Phe  Trp Pro Val Asp Ser  Ala Pro Ala
    3410                3415                3420

Ser Ser  Pro Gln Leu Ser His  Asp Asp Thr His Ser  Arg Ile Glu
    3425                3430                3435

His Tyr  Ala Ser Arg Leu Ala  Glu Met Glu Asn Ser  Asn Gly Ser
    3440                3445                3450

Tyr Leu  Asn Asp Ser Ile Ser  Pro Asn Glu Ser Ile  Asp Asp Glu
    3455                3460                3465

His Leu  Leu Ile Gln His Tyr  Cys Gln Ser Leu Asn  Gln Asp Ser
    3470                3475                3480

Pro Leu  Ser Gln Pro Arg Ser  Pro Ala Gln Ile Leu  Ile Ser Leu
    3485                3490                3495

Glu Ser  Glu Glu Arg Gly Glu  Leu Glu Arg Ile Leu  Ala Asp Leu
    3500                3505                3510

Glu Glu  Glu Asn Arg Asn Leu  Gln Ala Glu Tyr Asp  Arg Leu Lys
    3515                3520                3525

Gln Gln  His Glu His Lys Gly  Leu Ser Pro Leu Pro  Ser Pro Pro
    3530                3535                3540

Glu Met  Met Pro Thr Ser Pro  Gln Ser Pro Arg Asp  Ala Glu Leu
    3545                3550                3555

Ile Ala  Glu Ala Lys Leu Leu  Arg Gln His Lys Gly  Arg Leu Glu
    3560                3565                3570

Ala Arg  Met Gln Ile Leu Glu  Asp His Asn Lys Gln  Leu Glu Ser
    3575                3580                3585

Gln Leu  His Arg Leu Arg Gln  Leu Leu Glu Gln Pro  Gln Ala Glu
    3590                3595                3600

Ala Lys  Val Asn Gly Thr Thr  Val Ser Ser Pro Ser  Thr Ser Leu
    3605                3610                3615

Gln Arg  Ser Asp Ser Ser Gln  Pro Met Leu Leu Arg  Val Val Gly
    3620                3625                3630

Ser Gln  Thr Ser Asp Ser Met  Gly Glu Glu Asp Leu  Leu Ser Pro
    3635                3640                3645

Pro Gln  Asp Thr Ser Thr Gly  Leu Glu Glu Val Met  Glu Gln Leu
    3650                3655                3660

Asn Asn  Ser Phe Pro Ser Ser  Arg Gly Arg Asn Thr  Pro Gly Lys
    3665                3670                3675
```

```
Pro Met  Arg Glu Asp Thr Met
    3680                3685


<210> SEQ ID NO 2
<211> LENGTH: 153
<212> TYPE: PRT
<213> ORGANISM: Homo sapiens

<400> SEQUENCE: 2

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45

Gly Pro Glu Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Glu Val His Leu Lys Asn Ala Ser Arg Gly
    130                 135                 140

Ser Ala Gly Asn Lys Asn Tyr Arg Met
145                 150


<210> SEQ ID NO 3
<211> LENGTH: 20
<212> TYPE: DNA
<213> ORGANISM: Artificial
<220> FEATURE:
<223> OTHER INFORMATION: antisense nucleotide

<400> SEQUENCE: 3

cgaccugagc uuuguuguag                                                20


<210> SEQ ID NO 4
<211> LENGTH: 25
<212> TYPE: DNA
<213> ORGANISM: Artificial
<220> FEATURE:
<223> OTHER INFORMATION: antisense nucleotide

<400> SEQUENCE: 4

cgaccugagc uuuguuguag acuau                                          25


<210> SEQ ID NO 5
<211> LENGTH: 23
<212> TYPE: DNA
<213> ORGANISM: Artificial
<220> FEATURE:
<223> OTHER INFORMATION: antisense nucleotide

<400> SEQUENCE: 5

ccugagcuuu guuguagacu auc                                            23
```

<210> SEQ ID NO 6
<211> LENGTH: 23
<212> TYPE: DNA
<213> ORGANISM: Artificial
<220> FEATURE:
<223> OTHER INFORMATION: antisense nucleotide

<400> SEQUENCE: 6 cguugcacuu ugcaaugcug cug 23

<210> SEQ ID NO 7
<211> LENGTH: 19
<212> TYPE: DNA
<213> ORGANISM: Artificial
<220> FEATURE:
<223> OTHER INFORMATION: antisense nucleotide

<400> SEQUENCE: 7 cuguagcuuc acccuuucc 19

<210> SEQ ID NO 8
<211> LENGTH: 24
<212> TYPE: DNA
<213> ORGANISM: Artificial
<220> FEATURE:
<223> OTHER INFORMATION: antisense nucleotide

<400> SEQUENCE: 8 gagagagcuu ccuguagcuu cacc 24

<210> SEQ ID NO 9
<211> LENGTH: 27
<212> TYPE: DNA
<213> ORGANISM: Artificial
<220> FEATURE:
<223> OTHER INFORMATION: antisense nucleotide

<400> SEQUENCE: 9 guccuuguac auuuuguuaa cuuuuuc 27

<210> SEQ ID NO 10
<211> LENGTH: 20
<212> TYPE: DNA
<213> ORGANISM: Artificial
<220> FEATURE:
<223> OTHER INFORMATION: antisense nucleotide

<400> SEQUENCE: 10 ucagcuucug uuagccacug 20

<210> SEQ ID NO 11
<211> LENGTH: 20
<212> TYPE: DNA
<213> ORGANISM: Artificial
<220> FEATURE:
<223> OTHER INFORMATION: antisense nucleotide

<400> SEQUENCE: 11 uucagcuucu guuagccacu 20

<210> SEQ ID NO 12
<211> LENGTH: 21
<212> TYPE: DNA
<213> ORGANISM: Artificial
<220> FEATURE:
<223> OTHER INFORMATION: antisense nucleotide

<400> SEQUENCE: 12 uucagcuucu guuagccacu g 21

<210> SEQ ID NO 13
<211> LENGTH: 21
<212> TYPE: DNA
<213> ORGANISM: Artificial
<220> FEATURE:
<223> OTHER INFORMATION: antisense nucleotide

<400> SEQUENCE: 13 ucagcuucug uuagccacug a 21

<210> SEQ ID NO 14
<211> LENGTH: 22
<212> TYPE: DNA
<213> ORGANISM: Artificial
<220> FEATURE:
<223> OTHER INFORMATION: antisense nucleotide

<400> SEQUENCE: 14 uucagcuucu guuagccacu ga 22

<210> SEQ ID NO 15
<211> LENGTH: 21
<212> TYPE: DNA
<213> ORGANISM: Artificial
<220> FEATURE:
<223> OTHER INFORMATION: antisense nucleotide

<400> SEQUENCE: 15 ucagcuucug uuagccacug a 21

<210> SEQ ID NO 16
<211> LENGTH: 22
<212> TYPE: DNA
<213> ORGANISM: Artificial
<220> FEATURE:
<223> OTHER INFORMATION: antisense nucleotide

<400> SEQUENCE: 16 uucagcuucu guuagccacu ga 22

<210> SEQ ID NO 17
<211> LENGTH: 22
<212> TYPE: DNA
<213> ORGANISM: Artificial
<220> FEATURE:
<223> OTHER INFORMATION: antisense nucleotide

<400> SEQUENCE: 17 ucagcuucug uuagccacug au 22

<210> SEQ ID NO 18
<211> LENGTH: 23
<212> TYPE: DNA
<213> ORGANISM: Artificial
<220> FEATURE:
<223> OTHER INFORMATION: antisense nucleotide

<400> SEQUENCE: 18 uucagcuucu guuagccacu gau 23

<210> SEQ ID NO 19
<211> LENGTH: 23

<212> TYPE: DNA
<213> ORGANISM: Artificial
<220> FEATURE:
<223> OTHER INFORMATION: antisense nucleotide

<400> SEQUENCE: 19 ucagcuucug uuagccacug auu 23

<210> SEQ ID NO 20
<211> LENGTH: 24
<212> TYPE: DNA
<213> ORGANISM: Artificial
<220> FEATURE:
<223> OTHER INFORMATION: antisense nucleotide

<400> SEQUENCE: 20 uucagcuucu guuagccacu gauu 24

<210> SEQ ID NO 21
<211> LENGTH: 24
<212> TYPE: DNA
<213> ORGANISM: Artificial
<220> FEATURE:
<223> OTHER INFORMATION: antisense nucleotide

<400> SEQUENCE: 21 ucagcuucug uuagccacug auua 24

<210> SEQ ID NO 22
<211> LENGTH: 24
<212> TYPE: DNA
<213> ORGANISM: Artificial
<220> FEATURE:
<223> OTHER INFORMATION: antisense nucleotide

<400> SEQUENCE: 22 uucagcuucu guuagccacu gaua 24

<210> SEQ ID NO 23
<211> LENGTH: 25
<212> TYPE: DNA
<213> ORGANISM: Artificial
<220> FEATURE:
<223> OTHER INFORMATION: antisense nucleotide

<400> SEQUENCE: 23 ucagcuucug uuagccacug auuaa 25

<210> SEQ ID NO 24
<211> LENGTH: 26
<212> TYPE: DNA
<213> ORGANISM: Artificial
<220> FEATURE:
<223> OTHER INFORMATION: antisense nucleotide

<400> SEQUENCE: 24 uucagcuucu guuagccacu gauuaa 26

<210> SEQ ID NO 25
<211> LENGTH: 26
<212> TYPE: DNA
<213> ORGANISM: Artificial
<220> FEATURE:
<223> OTHER INFORMATION: antisense nucleotide

<400> SEQUENCE: 25 ucagcuucug uuagccacug auuaaa 26

<210> SEQ ID NO 26
<211> LENGTH: 27
<212> TYPE: DNA
<213> ORGANISM: Artificial
<220> FEATURE:
<223> OTHER INFORMATION: antisense nucleotide

<400> SEQUENCE: 26 uucagcuucu guuagccacu gauuaaa 27

<210> SEQ ID NO 27
<211> LENGTH: 19
<212> TYPE: DNA
<213> ORGANISM: Artificial
<220> FEATURE:
<223> OTHER INFORMATION: antisense nucleotide

<400> SEQUENCE: 27 cagcuucugu uagccacug 19

<210> SEQ ID NO 28
<211> LENGTH: 21
<212> TYPE: DNA
<213> ORGANISM: Artificial
<220> FEATURE:
<223> OTHER INFORMATION: antisense nucleotide

<400> SEQUENCE: 28 cagcuucugu uagccacuga u 21

<210> SEQ ID NO 29
<211> LENGTH: 21
<212> TYPE: DNA
<213> ORGANISM: Artificial
<220> FEATURE:
<223> OTHER INFORMATION: antisense nucleotide

<400> SEQUENCE: 29 agcuucuguu agccacugau u 21

<210> SEQ ID NO 30
<211> LENGTH: 22
<212> TYPE: DNA
<213> ORGANISM: Artificial
<220> FEATURE:
<223> OTHER INFORMATION: antisense nucleotide

<400> SEQUENCE: 30 cagcuucugu uagccacuga uu 22

<210> SEQ ID NO 31
<211> LENGTH: 22
<212> TYPE: DNA
<213> ORGANISM: Artificial
<220> FEATURE:
<223> OTHER INFORMATION: antisense nucleotide

<400> SEQUENCE: 31 agcuucuguu agccacugau ua 22

<210> SEQ ID NO 32
<211> LENGTH: 23
<212> TYPE: DNA
<213> ORGANISM: Artificial

<220> FEATURE:
<223> OTHER INFORMATION: antisense nucleotide

<400> SEQUENCE: 32 cagcuucugu uagccacuga uua 23

<210> SEQ ID NO 33
<211> LENGTH: 23
<212> TYPE: DNA
<213> ORGANISM: Artificial
<220> FEATURE:
<223> OTHER INFORMATION: antisense nucleotide

<400> SEQUENCE: 33 agcuucuguu agccacugau uaa 23

<210> SEQ ID NO 34
<211> LENGTH: 24
<212> TYPE: DNA
<213> ORGANISM: Artificial
<220> FEATURE:
<223> OTHER INFORMATION: antisense nucleotide

<400> SEQUENCE: 34 cagcuucugu uagccacuga uuaa 24

<210> SEQ ID NO 35
<211> LENGTH: 24
<212> TYPE: DNA
<213> ORGANISM: Artificial
<220> FEATURE:
<223> OTHER INFORMATION: antisense nucleotide

<400> SEQUENCE: 35 agcuucuguu agccacugau uaaa 24

<210> SEQ ID NO 36
<211> LENGTH: 25
<212> TYPE: DNA
<213> ORGANISM: Artificial
<220> FEATURE:
<223> OTHER INFORMATION: antisense nucleotide

<400> SEQUENCE: 36 cagcuucugu uagccacuga uuaaa 25

<210> SEQ ID NO 37
<211> LENGTH: 24
<212> TYPE: DNA
<213> ORGANISM: Artificial
<220> FEATURE:
<223> OTHER INFORMATION: antisense nucleotide

<400> SEQUENCE: 37 agcuucuguu agccacugau uaaa 24

<210> SEQ ID NO 38
<211> LENGTH: 20
<212> TYPE: DNA
<213> ORGANISM: Artificial
<220> FEATURE:
<223> OTHER INFORMATION: antisense nucleotide

<400> SEQUENCE: 38 agcuucuguu agccacugau 20

<210> SEQ ID NO 39
<211> LENGTH: 20
<212> TYPE: DNA
<213> ORGANISM: Artificial
<220> FEATURE:
<223> OTHER INFORMATION: antisense nucleotide

<400> SEQUENCE: 39 gcuucuguua gccacugauu 20

<210> SEQ ID NO 40
<211> LENGTH: 21
<212> TYPE: DNA
<213> ORGANISM: Artificial
<220> FEATURE:
<223> OTHER INFORMATION: antisense nucleotide

<400> SEQUENCE: 40 agcuucuguu agccacugau u 21

<210> SEQ ID NO 41
<211> LENGTH: 21
<212> TYPE: DNA
<213> ORGANISM: Artificial
<220> FEATURE:
<223> OTHER INFORMATION: antisense nucleotide

<400> SEQUENCE: 41 gcuucuguua gccacugauu a 21

<210> SEQ ID NO 42
<211> LENGTH: 22
<212> TYPE: DNA
<213> ORGANISM: Artificial
<220> FEATURE:
<223> OTHER INFORMATION: antisense nucleotide

<400> SEQUENCE: 42 agcuucuguu agccacugau ua 22

<210> SEQ ID NO 43
<211> LENGTH: 22
<212> TYPE: DNA
<213> ORGANISM: Artificial
<220> FEATURE:
<223> OTHER INFORMATION: antisense nucleotide

<400> SEQUENCE: 43 gcuucuguua gccacugauu aa 22

<210> SEQ ID NO 44
<211> LENGTH: 23
<212> TYPE: DNA
<213> ORGANISM: Artificial
<220> FEATURE:
<223> OTHER INFORMATION: antisense nucleotide

<400> SEQUENCE: 44 agcuucuguu agccacugau uaa 23

<210> SEQ ID NO 45
<211> LENGTH: 23
<212> TYPE: DNA
<213> ORGANISM: Artificial
<220> FEATURE:
<223> OTHER INFORMATION: antisense nucleotide

<400> SEQUENCE: 45 gcuucuguua gccacugauu aaa 23

<210> SEQ ID NO 46
<211> LENGTH: 24
<212> TYPE: DNA
<213> ORGANISM: Artificial
<220> FEATURE:
<223> OTHER INFORMATION: antisense nucleotide

<400> SEQUENCE: 46 agcuucuguu agccacugau uaaa 24

<210> SEQ ID NO 47
<211> LENGTH: 23
<212> TYPE: DNA
<213> ORGANISM: Artificial
<220> FEATURE:
<223> OTHER INFORMATION: antisense nucleotide

<400> SEQUENCE: 47 gcuucuguua gccacugauu aaa 23

<210> SEQ ID NO 48
<211> LENGTH: 23
<212> TYPE: DNA
<213> ORGANISM: Artificial
<220> FEATURE:
<223> OTHER INFORMATION: antisense nucleotide

<400> SEQUENCE: 48 ccauuuguau uuagcauguu ccc 23

<210> SEQ ID NO 49
<211> LENGTH: 20
<212> TYPE: DNA
<213> ORGANISM: Artificial
<220> FEATURE:
<223> OTHER INFORMATION: antisense nucleotide

<400> SEQUENCE: 49 agauaccauu uguauuuagc 20

<210> SEQ ID NO 50
<211> LENGTH: 19
<212> TYPE: DNA
<213> ORGANISM: Artificial
<220> FEATURE:
<223> OTHER INFORMATION: antisense nucleotide

<400> SEQUENCE: 50 gccauuucuc aacagaucu 19

<210> SEQ ID NO 51
<211> LENGTH: 23
<212> TYPE: DNA
<213> ORGANISM: Artificial
<220> FEATURE:
<223> OTHER INFORMATION: antisense nucleotide

<400> SEQUENCE: 51 gccauuucuc aacagaucug uca 23

<210> SEQ ID NO 52

<211> LENGTH: 23
<212> TYPE: DNA
<213> ORGANISM: Artificial
<220> FEATURE:
<223> OTHER INFORMATION: antisense nucleotide

<400> SEQUENCE: 52 auucucagga auuugugucu uuc 23

<210> SEQ ID NO 53
<211> LENGTH: 21
<212> TYPE: DNA
<213> ORGANISM: Artificial
<220> FEATURE:
<223> OTHER INFORMATION: antisense nucleotide

<400> SEQUENCE: 53 ucucaggaau uugugucuuu c 21

<210> SEQ ID NO 54
<211> LENGTH: 18
<212> TYPE: DNA
<213> ORGANISM: Artificial
<220> FEATURE:
<223> OTHER INFORMATION: antisense nucleotide

<400> SEQUENCE: 54 guucagcuuc uguuagcc 18

<210> SEQ ID NO 55
<211> LENGTH: 21
<212> TYPE: DNA
<213> ORGANISM: Artificial
<220> FEATURE:
<223> OTHER INFORMATION: antisense nucleotide

<400> SEQUENCE: 55 cugauuaaau aucuuuauau c 21

<210> SEQ ID NO 56
<211> LENGTH: 18
<212> TYPE: DNA
<213> ORGANISM: Artificial
<220> FEATURE:
<223> OTHER INFORMATION: antisense nucleotide

<400> SEQUENCE: 56 gccgccauuu cucaacag 18

<210> SEQ ID NO 57
<211> LENGTH: 18
<212> TYPE: DNA
<213> ORGANISM: Artificial
<220> FEATURE:
<223> OTHER INFORMATION: antisense nucleotide

<400> SEQUENCE: 57 guauuuagca uguuccca 18

<210> SEQ ID NO 58
<211> LENGTH: 18
<212> TYPE: DNA
<213> ORGANISM: Artificial
<220> FEATURE:
<223> OTHER INFORMATION: antisense nucleotide

<400> SEQUENCE: 58 caggaauuug ugucuuuc 18

<210> SEQ ID NO 59
<211> LENGTH: 25
<212> TYPE: DNA
<213> ORGANISM: Artificial
<220> FEATURE:
<223> OTHER INFORMATION: antisense nucleotide

<400> SEQUENCE: 59 uuugccgcug cccaaugcca uccug 25

<210> SEQ ID NO 60
<211> LENGTH: 25
<212> TYPE: DNA
<213> ORGANISM: Artificial
<220> FEATURE:
<223> OTHER INFORMATION: antisense nucleotide

<400> SEQUENCE: 60 auucaauguu cugacaacag uuugc 25

<210> SEQ ID NO 61
<211> LENGTH: 25
<212> TYPE: DNA
<213> ORGANISM: Artificial
<220> FEATURE:
<223> OTHER INFORMATION: antisense nucleotide

<400> SEQUENCE: 61 ccaguugcau ucaauguucu gacaa 25

<210> SEQ ID NO 62
<211> LENGTH: 22
<212> TYPE: DNA
<213> ORGANISM: Artificial
<220> FEATURE:
<223> OTHER INFORMATION: antisense nucleotide

<400> SEQUENCE: 62 caguugcauu caauguucug ac 22

<210> SEQ ID NO 63
<211> LENGTH: 20
<212> TYPE: DNA
<213> ORGANISM: Artificial
<220> FEATURE:
<223> OTHER INFORMATION: antisense nucleotide

<400> SEQUENCE: 63 aguugcauuc aauguucuga 20

<210> SEQ ID NO 64
<211> LENGTH: 21
<212> TYPE: DNA
<213> ORGANISM: Artificial
<220> FEATURE:
<223> OTHER INFORMATION: antisense nucleotide

<400> SEQUENCE: 64 gauugcugaa uuauuucuuc c 21

<210> SEQ ID NO 65
<211> LENGTH: 25
<212> TYPE: DNA

<213> ORGANISM: Artificial
<220> FEATURE:
<223> OTHER INFORMATION: antisense nucleotide

<400> SEQUENCE: 65 gauugcugaa uuauuucuuc cccag 25

<210> SEQ ID NO 66
<211> LENGTH: 25
<212> TYPE: DNA
<213> ORGANISM: Artificial
<220> FEATURE:
<223> OTHER INFORMATION: antisense nucleotide

<400> SEQUENCE: 66 auugcugaau uauuucuucc ccagu 25

<210> SEQ ID NO 67
<211> LENGTH: 25
<212> TYPE: DNA
<213> ORGANISM: Artificial
<220> FEATURE:
<223> OTHER INFORMATION: antisense nucleotide

<400> SEQUENCE: 67 uugcugaauu auuucuuccc caguu 25

<210> SEQ ID NO 68
<211> LENGTH: 25
<212> TYPE: DNA
<213> ORGANISM: Artificial
<220> FEATURE:
<223> OTHER INFORMATION: antisense nucleotide

<400> SEQUENCE: 68 ugcugaauua uuucuucccc aguug 25

<210> SEQ ID NO 69
<211> LENGTH: 25
<212> TYPE: DNA
<213> ORGANISM: Artificial
<220> FEATURE:
<223> OTHER INFORMATION: antisense nucleotide

<400> SEQUENCE: 69 gcugaauuau uucuucccca guugc 25

<210> SEQ ID NO 70
<211> LENGTH: 25
<212> TYPE: DNA
<213> ORGANISM: Artificial
<220> FEATURE:
<223> OTHER INFORMATION: antisense nucleotide

<400> SEQUENCE: 70 cugaauuauu ucuuccccag uugca 25

<210> SEQ ID NO 71
<211> LENGTH: 25
<212> TYPE: DNA
<213> ORGANISM: Artificial
<220> FEATURE:
<223> OTHER INFORMATION: antisense nucleotide

<400> SEQUENCE: 71 ugaauuauuu cuuccccagu ugcau 25

<210> SEQ ID NO 72
<211> LENGTH: 25
<212> TYPE: DNA
<213> ORGANISM: Artificial
<220> FEATURE:
<223> OTHER INFORMATION: antisense nucleotide

<400> SEQUENCE: 72 gaauuauuuc uuccccaguu gcauu 25

<210> SEQ ID NO 73
<211> LENGTH: 25
<212> TYPE: DNA
<213> ORGANISM: Artificial
<220> FEATURE:
<223> OTHER INFORMATION: antisense nucleotide

<400> SEQUENCE: 73 aauuauuucu uccccaguug cauuc 25

<210> SEQ ID NO 74
<211> LENGTH: 25
<212> TYPE: DNA
<213> ORGANISM: Artificial
<220> FEATURE:
<223> OTHER INFORMATION: antisense nucleotide

<400> SEQUENCE: 74 auuauuucuu ccccaguugc auuca 25

<210> SEQ ID NO 75
<211> LENGTH: 25
<212> TYPE: DNA
<213> ORGANISM: Artificial
<220> FEATURE:
<223> OTHER INFORMATION: antisense nucleotide

<400> SEQUENCE: 75 uuauuucuuc cccaguugca uucaa 25

<210> SEQ ID NO 76
<211> LENGTH: 25
<212> TYPE: DNA
<213> ORGANISM: Artificial
<220> FEATURE:
<223> OTHER INFORMATION: antisense nucleotide

<400> SEQUENCE: 76 uauuucuucc ccaguugcau ucaau 25

<210> SEQ ID NO 77
<211> LENGTH: 25
<212> TYPE: DNA
<213> ORGANISM: Artificial
<220> FEATURE:
<223> OTHER INFORMATION: antisense nucleotide

<400> SEQUENCE: 77 auuucuuccc caguugcauu caaug 25

<210> SEQ ID NO 78
<211> LENGTH: 25
<212> TYPE: DNA
<213> ORGANISM: Artificial
<220> FEATURE:

<223> OTHER INFORMATION: antisense nucleotide

<400> SEQUENCE: 78 uuucuucccc aguugcauuc aaugu 25

<210> SEQ ID NO 79
<211> LENGTH: 25
<212> TYPE: DNA
<213> ORGANISM: Artificial
<220> FEATURE:
<223> OTHER INFORMATION: antisense nucleotide

<400> SEQUENCE: 79 uucuucccca guugcauuca auguu 25

<210> SEQ ID NO 80
<211> LENGTH: 25
<212> TYPE: DNA
<213> ORGANISM: Artificial
<220> FEATURE:
<223> OTHER INFORMATION: antisense nucleotide

<400> SEQUENCE: 80 ucuuccccag uugcauucaa uguuc 25

<210> SEQ ID NO 81
<211> LENGTH: 25
<212> TYPE: DNA
<213> ORGANISM: Artificial
<220> FEATURE:
<223> OTHER INFORMATION: antisense nucleotide

<400> SEQUENCE: 81 cuuccccagu ugcauucaau guucu 25

<210> SEQ ID NO 82
<211> LENGTH: 25
<212> TYPE: DNA
<213> ORGANISM: Artificial
<220> FEATURE:
<223> OTHER INFORMATION: antisense nucleotide

<400> SEQUENCE: 82 uuccccaguu gcauucaaug uucug 25

<210> SEQ ID NO 83
<211> LENGTH: 25
<212> TYPE: DNA
<213> ORGANISM: Artificial
<220> FEATURE:
<223> OTHER INFORMATION: antisense nucleotide

<400> SEQUENCE: 83 uccccaguug cauucaaugu ucuga 25

<210> SEQ ID NO 84
<211> LENGTH: 25
<212> TYPE: DNA
<213> ORGANISM: Artificial
<220> FEATURE:
<223> OTHER INFORMATION: antisense nucleotide

<400> SEQUENCE: 84 ccccaguugc auucaauguu cugac 25

<210> SEQ ID NO 85
<211> LENGTH: 25
<212> TYPE: DNA
<213> ORGANISM: Artificial
<220> FEATURE:
<223> OTHER INFORMATION: antisense nucleotide

<400> SEQUENCE: 85 cccaguugca uucaauguuc ugaca 25

<210> SEQ ID NO 86
<211> LENGTH: 25
<212> TYPE: DNA
<213> ORGANISM: Artificial
<220> FEATURE:
<223> OTHER INFORMATION: antisense nucleotide

<400> SEQUENCE: 86 ccaguugcau ucaauguucu gacaa 25

<210> SEQ ID NO 87
<211> LENGTH: 25
<212> TYPE: DNA
<213> ORGANISM: Artificial
<220> FEATURE:
<223> OTHER INFORMATION: antisense nucleotide

<400> SEQUENCE: 87 caguugcauu caauguucug acaac 25

<210> SEQ ID NO 88
<211> LENGTH: 25
<212> TYPE: DNA
<213> ORGANISM: Artificial
<220> FEATURE:
<223> OTHER INFORMATION: antisense nucleotide

<400> SEQUENCE: 88 aguugcauuc aauguucuga caaca 25

<210> SEQ ID NO 89
<211> LENGTH: 25
<212> TYPE: DNA
<213> ORGANISM: Artificial
<220> FEATURE:
<223> OTHER INFORMATION: antisense nucleotide

<400> SEQUENCE: 89 guugcauuca auguucugac aacag 25

<210> SEQ ID NO 90
<211> LENGTH: 25
<212> TYPE: DNA
<213> ORGANISM: Artificial
<220> FEATURE:
<223> OTHER INFORMATION: antisense nucleotide

<400> SEQUENCE: 90 uugcauucaa uguucugaca acagu 25

<210> SEQ ID NO 91
<211> LENGTH: 25
<212> TYPE: DNA
<213> ORGANISM: Artificial
<220> FEATURE:
<223> OTHER INFORMATION: antisense nucleotide

<400> SEQUENCE: 91 ugcauucaau guucugacaa caguu 25

<210> SEQ ID NO 92
<211> LENGTH: 25
<212> TYPE: DNA
<213> ORGANISM: Artificial
<220> FEATURE:
<223> OTHER INFORMATION: antisense nucleotide

<400> SEQUENCE: 92 gcauucaaug uucugacaac aguuu 25

<210> SEQ ID NO 93
<211> LENGTH: 25
<212> TYPE: DNA
<213> ORGANISM: Artificial
<220> FEATURE:
<223> OTHER INFORMATION: antisense nucleotide

<400> SEQUENCE: 93 cauucaaugu ucugacaaca guuug 25

<210> SEQ ID NO 94
<211> LENGTH: 25
<212> TYPE: DNA
<213> ORGANISM: Artificial
<220> FEATURE:
<223> OTHER INFORMATION: antisense nucleotide

<400> SEQUENCE: 94 auucaauguu cugacaacag uuugc 25

<210> SEQ ID NO 95
<211> LENGTH: 25
<212> TYPE: DNA
<213> ORGANISM: Artificial
<220> FEATURE:
<223> OTHER INFORMATION: antisense nucleotide

<400> SEQUENCE: 95 ucaauguucu gacaacaguu ugccg 25

<210> SEQ ID NO 96
<211> LENGTH: 25
<212> TYPE: DNA
<213> ORGANISM: Artificial
<220> FEATURE:
<223> OTHER INFORMATION: antisense nucleotide

<400> SEQUENCE: 96 caauguucug acaacaguuu gccgc 25

<210> SEQ ID NO 97
<211> LENGTH: 25
<212> TYPE: DNA
<213> ORGANISM: Artificial
<220> FEATURE:
<223> OTHER INFORMATION: antisense nucleotide

<400> SEQUENCE: 97 aauguucuga caacaguuug ccgcu 25

<210> SEQ ID NO 98
<211> LENGTH: 25

<212> TYPE: DNA
<213> ORGANISM: Artificial
<220> FEATURE:
<223> OTHER INFORMATION: antisense nucleotide

<400> SEQUENCE: 98 auguucugac aacaguuugc cgcug 25

<210> SEQ ID NO 99
<211> LENGTH: 25
<212> TYPE: DNA
<213> ORGANISM: Artificial
<220> FEATURE:
<223> OTHER INFORMATION: antisense nucleotide

<400> SEQUENCE: 99 uguucugaca acaguuugcc gcugc 25

<210> SEQ ID NO 100
<211> LENGTH: 25
<212> TYPE: DNA
<213> ORGANISM: Artificial
<220> FEATURE:
<223> OTHER INFORMATION: antisense nucleotide

<400> SEQUENCE: 100 guucugacaa caguuugccg cugcc 25

<210> SEQ ID NO 101
<211> LENGTH: 25
<212> TYPE: DNA
<213> ORGANISM: Artificial
<220> FEATURE:
<223> OTHER INFORMATION: antisense nucleotide

<400> SEQUENCE: 101 uucugacaac aguuugccgc ugccc 25

<210> SEQ ID NO 102
<211> LENGTH: 25
<212> TYPE: DNA
<213> ORGANISM: Artificial
<220> FEATURE:
<223> OTHER INFORMATION: antisense nucleotide

<400> SEQUENCE: 102 ucugacaaca guuugccgcu gccca 25

<210> SEQ ID NO 103
<211> LENGTH: 25
<212> TYPE: DNA
<213> ORGANISM: Artificial
<220> FEATURE:
<223> OTHER INFORMATION: antisense nucleotide

<400> SEQUENCE: 103 cugacaacag uuugccgcug cccaa 25

<210> SEQ ID NO 104
<211> LENGTH: 25
<212> TYPE: DNA
<213> ORGANISM: Artificial
<220> FEATURE:
<223> OTHER INFORMATION: antisense nucleotide

<400> SEQUENCE: 104 ugacaacagu uugccgcugc ccaau 25

<210> SEQ ID NO 105
<211> LENGTH: 25
<212> TYPE: DNA
<213> ORGANISM: Artificial
<220> FEATURE:
<223> OTHER INFORMATION: antisense nucleotide

<400> SEQUENCE: 105 gacaacaguu ugccgcugcc caaug 25

<210> SEQ ID NO 106
<211> LENGTH: 25
<212> TYPE: DNA
<213> ORGANISM: Artificial
<220> FEATURE:
<223> OTHER INFORMATION: antisense nucleotide

<400> SEQUENCE: 106 acaacaguuu gccgcugccc aaugc 25

<210> SEQ ID NO 107
<211> LENGTH: 25
<212> TYPE: DNA
<213> ORGANISM: Artificial
<220> FEATURE:
<223> OTHER INFORMATION: antisense nucleotide

<400> SEQUENCE: 107 caacaguuug ccgcugccca augcc 25

<210> SEQ ID NO 108
<211> LENGTH: 25
<212> TYPE: DNA
<213> ORGANISM: Artificial
<220> FEATURE:
<223> OTHER INFORMATION: antisense nucleotide

<400> SEQUENCE: 108 aacaguuugc cgcugcccaa ugcca 25

<210> SEQ ID NO 109
<211> LENGTH: 25
<212> TYPE: DNA
<213> ORGANISM: Artificial
<220> FEATURE:
<223> OTHER INFORMATION: antisense nucleotide

<400> SEQUENCE: 109 acaguuugcc gcugcccaau gccau 25

<210> SEQ ID NO 110
<211> LENGTH: 25
<212> TYPE: DNA
<213> ORGANISM: Artificial
<220> FEATURE:
<223> OTHER INFORMATION: antisense nucleotide

<400> SEQUENCE: 110 caguuugccg cugcccaaug ccauc 25

<210> SEQ ID NO 111
<211> LENGTH: 25
<212> TYPE: DNA
<213> ORGANISM: Artificial

<220> FEATURE:
<223> OTHER INFORMATION: antisense nucleotide

<400> SEQUENCE: 111 aguuugccgc ugcccaaugc caucc 25

<210> SEQ ID NO 112
<211> LENGTH: 25
<212> TYPE: DNA
<213> ORGANISM: Artificial
<220> FEATURE:
<223> OTHER INFORMATION: antisense nucleotide

<400> SEQUENCE: 112 guuugccgcu gcccaaugcc auccu 25

<210> SEQ ID NO 113
<211> LENGTH: 25
<212> TYPE: DNA
<213> ORGANISM: Artificial
<220> FEATURE:
<223> OTHER INFORMATION: antisense nucleotide

<400> SEQUENCE: 113 uuugccgcug cccaaugcca uccug 25

<210> SEQ ID NO 114
<211> LENGTH: 25
<212> TYPE: DNA
<213> ORGANISM: Artificial
<220> FEATURE:
<223> OTHER INFORMATION: antisense nucleotide

<400> SEQUENCE: 114 uugccgcugc ccaaugccau ccugg 25

<210> SEQ ID NO 115
<211> LENGTH: 25
<212> TYPE: DNA
<213> ORGANISM: Artificial
<220> FEATURE:
<223> OTHER INFORMATION: antisense nucleotide

<400> SEQUENCE: 115 ugccgcugcc caaugccauc cugga 25

<210> SEQ ID NO 116
<211> LENGTH: 25
<212> TYPE: DNA
<213> ORGANISM: Artificial
<220> FEATURE:
<223> OTHER INFORMATION: antisense nucleotide

<400> SEQUENCE: 116 gccgcugccc aaugccaucc uggag 25

<210> SEQ ID NO 117
<211> LENGTH: 25
<212> TYPE: DNA
<213> ORGANISM: Artificial
<220> FEATURE:
<223> OTHER INFORMATION: antisense nucleotide

<400> SEQUENCE: 117 ccgcugccca augccauccu ggagu 25

<210> SEQ ID NO 118
<211> LENGTH: 25
<212> TYPE: DNA
<213> ORGANISM: Artificial
<220> FEATURE:
<223> OTHER INFORMATION: antisense nucleotide

<400> SEQUENCE: 118 cgcugcccaa ugccauccug gaguu 25

<210> SEQ ID NO 119
<211> LENGTH: 25
<212> TYPE: DNA
<213> ORGANISM: Artificial
<220> FEATURE:
<223> OTHER INFORMATION: antisense nucleotide

<400> SEQUENCE: 119 gcuuuucuuu uaguugcugc ucuuu 25

<210> SEQ ID NO 120
<211> LENGTH: 25
<212> TYPE: DNA
<213> ORGANISM: Artificial
<220> FEATURE:
<223> OTHER INFORMATION: antisense nucleotide

<400> SEQUENCE: 120 cuuuucuuuu aguugcugcu cuuuu 25

<210> SEQ ID NO 121
<211> LENGTH: 25
<212> TYPE: DNA
<213> ORGANISM: Artificial
<220> FEATURE:
<223> OTHER INFORMATION: antisense nucleotide

<400> SEQUENCE: 121 uuuucuuuua guugcugcuc uuuuc 25

<210> SEQ ID NO 122
<211> LENGTH: 25
<212> TYPE: DNA
<213> ORGANISM: Artificial
<220> FEATURE:
<223> OTHER INFORMATION: antisense nucleotide

<400> SEQUENCE: 122 uuucuuuuag uugcugcucu uuucc 25

<210> SEQ ID NO 123
<211> LENGTH: 25
<212> TYPE: DNA
<213> ORGANISM: Artificial
<220> FEATURE:
<223> OTHER INFORMATION: antisense nucleotide

<400> SEQUENCE: 123 uucuuuuagu ugcugcucuu uucca 25

<210> SEQ ID NO 124
<211> LENGTH: 25
<212> TYPE: DNA
<213> ORGANISM: Artificial
<220> FEATURE:
<223> OTHER INFORMATION: antisense nucleotide

<400> SEQUENCE: 124 ucuuuuaguu gcugcucuuu uccag 25

<210> SEQ ID NO 125
<211> LENGTH: 25
<212> TYPE: DNA
<213> ORGANISM: Artificial
<220> FEATURE:
<223> OTHER INFORMATION: antisense nucleotide

<400> SEQUENCE: 125 cuuuuaguug cugcucuuuu ccagg 25

<210> SEQ ID NO 126
<211> LENGTH: 25
<212> TYPE: DNA
<213> ORGANISM: Artificial
<220> FEATURE:
<223> OTHER INFORMATION: antisense nucleotide

<400> SEQUENCE: 126 uuuuaguugc ugcucuuuuc caggu 25

<210> SEQ ID NO 127
<211> LENGTH: 25
<212> TYPE: DNA
<213> ORGANISM: Artificial
<220> FEATURE:
<223> OTHER INFORMATION: antisense nucleotide

<400> SEQUENCE: 127 uuuaguugcu gcucuuuucc agguu 25

<210> SEQ ID NO 128
<211> LENGTH: 25
<212> TYPE: DNA
<213> ORGANISM: Artificial
<220> FEATURE:
<223> OTHER INFORMATION: antisense nucleotide

<400> SEQUENCE: 128 uuaguugcug cucuuuucca gguuc 25

<210> SEQ ID NO 129
<211> LENGTH: 25
<212> TYPE: DNA
<213> ORGANISM: Artificial
<220> FEATURE:
<223> OTHER INFORMATION: antisense nucleotide

<400> SEQUENCE: 129 uaguugcugc ucuuuuccag guuca 25

<210> SEQ ID NO 130
<211> LENGTH: 25
<212> TYPE: DNA
<213> ORGANISM: Artificial
<220> FEATURE:
<223> OTHER INFORMATION: antisense nucleotide

<400> SEQUENCE: 130 aguugcugcu cuuuuccagg uucaa 25

<210> SEQ ID NO 131

<211> LENGTH: 25
<212> TYPE: DNA
<213> ORGANISM: Artificial
<220> FEATURE:
<223> OTHER INFORMATION: antisense nucleotide

<400> SEQUENCE: 131 guugcugcuc uuuuccaggu ucaag 25

<210> SEQ ID NO 132
<211> LENGTH: 25
<212> TYPE: DNA
<213> ORGANISM: Artificial
<220> FEATURE:
<223> OTHER INFORMATION: antisense nucleotide

<400> SEQUENCE: 132 uugcugcucu uuuccagguu caagu 25

<210> SEQ ID NO 133
<211> LENGTH: 25
<212> TYPE: DNA
<213> ORGANISM: Artificial
<220> FEATURE:
<223> OTHER INFORMATION: antisense nucleotide

<400> SEQUENCE: 133 ugcugcucuu uuccagguuc aagug 25

<210> SEQ ID NO 134
<211> LENGTH: 25
<212> TYPE: DNA
<213> ORGANISM: Artificial
<220> FEATURE:
<223> OTHER INFORMATION: antisense nucleotide

<400> SEQUENCE: 134 gcugcucuuu uccagguuca agugg 25

<210> SEQ ID NO 135
<211> LENGTH: 25
<212> TYPE: DNA
<213> ORGANISM: Artificial
<220> FEATURE:
<223> OTHER INFORMATION: antisense nucleotide

<400> SEQUENCE: 135 cugcucuuuu ccagguucaa guggg 25

<210> SEQ ID NO 136
<211> LENGTH: 25
<212> TYPE: DNA
<213> ORGANISM: Artificial
<220> FEATURE:
<223> OTHER INFORMATION: antisense nucleotide

<400> SEQUENCE: 136 ugcucuuuuc cagguucaag uggga 25

<210> SEQ ID NO 137
<211> LENGTH: 25
<212> TYPE: DNA
<213> ORGANISM: Artificial
<220> FEATURE:
<223> OTHER INFORMATION: antisense nucleotide

<400> SEQUENCE: 137 gcucuuuucc agguucaagu gggac 25

<210> SEQ ID NO 138
<211> LENGTH: 25
<212> TYPE: DNA
<213> ORGANISM: Artificial
<220> FEATURE:
<223> OTHER INFORMATION: antisense nucleotide

<400> SEQUENCE: 138 cucuuuucca gguucaagug ggaua 25

<210> SEQ ID NO 139
<211> LENGTH: 25
<212> TYPE: DNA
<213> ORGANISM: Artificial
<220> FEATURE:
<223> OTHER INFORMATION: antisense nucleotide

<400> SEQUENCE: 139 ucuuuuccag guucaagugg gauac 25

<210> SEQ ID NO 140
<211> LENGTH: 25
<212> TYPE: DNA
<213> ORGANISM: Artificial
<220> FEATURE:
<223> OTHER INFORMATION: antisense nucleotide

<400> SEQUENCE: 140 cuuuuccagg uucaaguggg auacu 25

<210> SEQ ID NO 141
<211> LENGTH: 25
<212> TYPE: DNA
<213> ORGANISM: Artificial
<220> FEATURE:
<223> OTHER INFORMATION: antisense nucleotide

<400> SEQUENCE: 141 uuuuccaggu ucaaguggga uacua 25

<210> SEQ ID NO 142
<211> LENGTH: 25
<212> TYPE: DNA
<213> ORGANISM: Artificial
<220> FEATURE:
<223> OTHER INFORMATION: antisense nucleotide

<400> SEQUENCE: 142 uuuccagguu caaguggguau acuag 25

<210> SEQ ID NO 143
<211> LENGTH: 25
<212> TYPE: DNA
<213> ORGANISM: Artificial
<220> FEATURE:
<223> OTHER INFORMATION: antisense nucleotide

<400> SEQUENCE: 143 uuccagguuc aaguggguau cuagc 25

<210> SEQ ID NO 144
<211> LENGTH: 25
<212> TYPE: DNA

<213> ORGANISM: Artificial
<220> FEATURE:
<223> OTHER INFORMATION: antisense nucleotide

<400> SEQUENCE: 144 uccagguuca agugggauac uagca 25

<210> SEQ ID NO 145
<211> LENGTH: 25
<212> TYPE: DNA
<213> ORGANISM: Artificial
<220> FEATURE:
<223> OTHER INFORMATION: antisense nucleotide

<400> SEQUENCE: 145 ccagguucaa gugggauacu agcaa 25

<210> SEQ ID NO 146
<211> LENGTH: 25
<212> TYPE: DNA
<213> ORGANISM: Artificial
<220> FEATURE:
<223> OTHER INFORMATION: antisense nucleotide

<400> SEQUENCE: 146 cagguucaag ugggauacua gcaau 25

<210> SEQ ID NO 147
<211> LENGTH: 25
<212> TYPE: DNA
<213> ORGANISM: Artificial
<220> FEATURE:
<223> OTHER INFORMATION: antisense nucleotide

<400> SEQUENCE: 147 agguucaagu gggauacuag caaug 25

<210> SEQ ID NO 148
<211> LENGTH: 25
<212> TYPE: DNA
<213> ORGANISM: Artificial
<220> FEATURE:
<223> OTHER INFORMATION: antisense nucleotide

<400> SEQUENCE: 148 gguucaagug ggauacuagc aaugu 25

<210> SEQ ID NO 149
<211> LENGTH: 25
<212> TYPE: DNA
<213> ORGANISM: Artificial
<220> FEATURE:
<223> OTHER INFORMATION: antisense nucleotide

<400> SEQUENCE: 149 guucaagugg gauacuagca auguu 25

<210> SEQ ID NO 150
<211> LENGTH: 25
<212> TYPE: DNA
<213> ORGANISM: Artificial
<220> FEATURE:
<223> OTHER INFORMATION: antisense nucleotide

<400> SEQUENCE: 150 uucaaguggg auacuagcaa uguua 25

<210> SEQ ID NO 151
<211> LENGTH: 25
<212> TYPE: DNA
<213> ORGANISM: Artificial
<220> FEATURE:
<223> OTHER INFORMATION: antisense nucleotide

<400> SEQUENCE: 151 ucaaguggga uacuagcaau guuau 25

<210> SEQ ID NO 152
<211> LENGTH: 25
<212> TYPE: DNA
<213> ORGANISM: Artificial
<220> FEATURE:
<223> OTHER INFORMATION: antisense nucleotide

<400> SEQUENCE: 152 caaguggau acuagcaaug uuauc 25

<210> SEQ ID NO 153
<211> LENGTH: 25
<212> TYPE: DNA
<213> ORGANISM: Artificial
<220> FEATURE:
<223> OTHER INFORMATION: antisense nucleotide

<400> SEQUENCE: 153 aaguggaua cuagcaaugu uaucu 25

<210> SEQ ID NO 154
<211> LENGTH: 25
<212> TYPE: DNA
<213> ORGANISM: Artificial
<220> FEATURE:
<223> OTHER INFORMATION: antisense nucleotide

<400> SEQUENCE: 154 agugggauac uagcaauguu aucug 25

<210> SEQ ID NO 155
<211> LENGTH: 25
<212> TYPE: DNA
<213> ORGANISM: Artificial
<220> FEATURE:
<223> OTHER INFORMATION: antisense nucleotide

<400> SEQUENCE: 155 gugggauacu agcaauguua ucugc 25

<210> SEQ ID NO 156
<211> LENGTH: 25
<212> TYPE: DNA
<213> ORGANISM: Artificial
<220> FEATURE:
<223> OTHER INFORMATION: antisense nucleotide

<400> SEQUENCE: 156 ugggauacua gcaauguuau cugcu 25

<210> SEQ ID NO 157
<211> LENGTH: 25
<212> TYPE: DNA
<213> ORGANISM: Artificial
<220> FEATURE:

<223> OTHER INFORMATION: antisense nucleotide

<400> SEQUENCE: 157 gggauacuag caauguuauc ugcuu 25

<210> SEQ ID NO 158
<211> LENGTH: 25
<212> TYPE: DNA
<213> ORGANISM: Artificial
<220> FEATURE:
<223> OTHER INFORMATION: antisense nucleotide

<400> SEQUENCE: 158 ggauacuagc aauguuaucu gcuuc 25

<210> SEQ ID NO 159
<211> LENGTH: 25
<212> TYPE: DNA
<213> ORGANISM: Artificial
<220> FEATURE:
<223> OTHER INFORMATION: antisense nucleotide

<400> SEQUENCE: 159 gauacuagca auguuaucug cuucc 25

<210> SEQ ID NO 160
<211> LENGTH: 25
<212> TYPE: DNA
<213> ORGANISM: Artificial
<220> FEATURE:
<223> OTHER INFORMATION: antisense nucleotide

<400> SEQUENCE: 160 auacuagcaa uguuaucugc uuccu 25

<210> SEQ ID NO 161
<211> LENGTH: 25
<212> TYPE: DNA
<213> ORGANISM: Artificial
<220> FEATURE:
<223> OTHER INFORMATION: antisense nucleotide

<400> SEQUENCE: 161 uacuagcaau guuaucugcu uccuc 25

<210> SEQ ID NO 162
<211> LENGTH: 25
<212> TYPE: DNA
<213> ORGANISM: Artificial
<220> FEATURE:
<223> OTHER INFORMATION: antisense nucleotide

<400> SEQUENCE: 162 acuagcaaug uuaucugcuu ccucc 25

<210> SEQ ID NO 163
<211> LENGTH: 25
<212> TYPE: DNA
<213> ORGANISM: Artificial
<220> FEATURE:
<223> OTHER INFORMATION: antisense nucleotide

<400> SEQUENCE: 163 cuagcaaugu uaucugcuuc cucca 25

<210> SEQ ID NO 164
<211> LENGTH: 25
<212> TYPE: DNA
<213> ORGANISM: Artificial
<220> FEATURE:
<223> OTHER INFORMATION: antisense nucleotide

<400> SEQUENCE: 164 uagcaauguu aucugcuucc uccaa 25

<210> SEQ ID NO 165
<211> LENGTH: 25
<212> TYPE: DNA
<213> ORGANISM: Artificial
<220> FEATURE:
<223> OTHER INFORMATION: antisense nucleotide

<400> SEQUENCE: 165 agcaauguua ucugcuuccu ccaac 25

<210> SEQ ID NO 166
<211> LENGTH: 25
<212> TYPE: DNA
<213> ORGANISM: Artificial
<220> FEATURE:
<223> OTHER INFORMATION: antisense nucleotide

<400> SEQUENCE: 166 gcaauguuau cugcuuccuc caacc 25

<210> SEQ ID NO 167
<211> LENGTH: 25
<212> TYPE: DNA
<213> ORGANISM: Artificial
<220> FEATURE:
<223> OTHER INFORMATION: antisense nucleotide

<400> SEQUENCE: 167 caauguuauc ugcuuccucc aacca 25

<210> SEQ ID NO 168
<211> LENGTH: 25
<212> TYPE: DNA
<213> ORGANISM: Artificial
<220> FEATURE:
<223> OTHER INFORMATION: antisense nucleotide

<400> SEQUENCE: 168 aauguuaucu gcuuccucca accau 25

<210> SEQ ID NO 169
<211> LENGTH: 25
<212> TYPE: DNA
<213> ORGANISM: Artificial
<220> FEATURE:
<223> OTHER INFORMATION: antisense nucleotide

<400> SEQUENCE: 169 auguuaucug cuuccuccaa ccaua 25

<210> SEQ ID NO 170
<211> LENGTH: 25
<212> TYPE: DNA
<213> ORGANISM: Artificial
<220> FEATURE:
<223> OTHER INFORMATION: antisense nucleotide

<400> SEQUENCE: 170 uguuaucugc uuccuccaac cauaa 25

<210> SEQ ID NO 171
<211> LENGTH: 25
<212> TYPE: DNA
<213> ORGANISM: Artificial
<220> FEATURE:
<223> OTHER INFORMATION: antisense nucleotide

<400> SEQUENCE: 171 guuaucugcu uccuccaacc auaaa 25

<210> SEQ ID NO 172
<211> LENGTH: 19
<212> TYPE: DNA
<213> ORGANISM: Artificial
<220> FEATURE:
<223> OTHER INFORMATION: antisense nucleotide

<400> SEQUENCE: 172 gcugcucuuu uccagguuc 19

<210> SEQ ID NO 173
<211> LENGTH: 20
<212> TYPE: DNA
<213> ORGANISM: Artificial
<220> FEATURE:
<223> OTHER INFORMATION: antisense nucleotide

<400> SEQUENCE: 173 ucuuuuccag guucaagugg 20

<210> SEQ ID NO 174
<211> LENGTH: 19
<212> TYPE: DNA
<213> ORGANISM: Artificial
<220> FEATURE:
<223> OTHER INFORMATION: antisense nucleotide

<400> SEQUENCE: 174 agguucaagu gggauacua 19

<210> SEQ ID NO 175
<211> LENGTH: 20
<212> TYPE: DNA
<213> ORGANISM: Artificial
<220> FEATURE:
<223> OTHER INFORMATION: antisense nucleotide

<400> SEQUENCE: 175 cucagcucuu gaaguaaacg 20

<210> SEQ ID NO 176
<211> LENGTH: 20
<212> TYPE: DNA
<213> ORGANISM: Artificial
<220> FEATURE:
<223> OTHER INFORMATION: antisense nucleotide

<400> SEQUENCE: 176 ccucagcucu ugaaguaaac 20

<210> SEQ ID NO 177
<211> LENGTH: 21

<212> TYPE: DNA
<213> ORGANISM: Artificial
<220> FEATURE:
<223> OTHER INFORMATION: antisense nucleotide

<400> SEQUENCE: 177 ccucagcucu ugaaguaaac g 21

<210> SEQ ID NO 178
<211> LENGTH: 21
<212> TYPE: DNA
<213> ORGANISM: Artificial
<220> FEATURE:
<223> OTHER INFORMATION: antisense nucleotide

<400> SEQUENCE: 178 auagugguca guccaggagc u 21

<210> SEQ ID NO 179
<211> LENGTH: 21
<212> TYPE: DNA
<213> ORGANISM: Artificial
<220> FEATURE:
<223> OTHER INFORMATION: antisense nucleotide

<400> SEQUENCE: 179 caguccagga gcuaggucag g 21

<210> SEQ ID NO 180
<211> LENGTH: 25
<212> TYPE: DNA
<213> ORGANISM: Artificial
<220> FEATURE:
<223> OTHER INFORMATION: antisense nucleotide

<400> SEQUENCE: 180 uaguggucag uccaggagcu agguc 25

<210> SEQ ID NO 181
<211> LENGTH: 25
<212> TYPE: DNA
<213> ORGANISM: Artificial
<220> FEATURE:
<223> OTHER INFORMATION: antisense nucleotide

<400> SEQUENCE: 181 agagcaggua ccuccaacau caagg 25

<210> SEQ ID NO 182
<211> LENGTH: 25
<212> TYPE: DNA
<213> ORGANISM: Artificial
<220> FEATURE:
<223> OTHER INFORMATION: antisense nucleotide

<400> SEQUENCE: 182 gagcagguac cuccaacauc aagga 25

<210> SEQ ID NO 183
<211> LENGTH: 25
<212> TYPE: DNA
<213> ORGANISM: Artificial
<220> FEATURE:
<223> OTHER INFORMATION: antisense nucleotide

<400> SEQUENCE: 183 agcagguacc uccaacauca aggaa 25

<210> SEQ ID NO 184
<211> LENGTH: 25
<212> TYPE: DNA
<213> ORGANISM: Artificial
<220> FEATURE:
<223> OTHER INFORMATION: antisense nucleotide

<400> SEQUENCE: 184 gcagguaccu ccaacaucaa ggaag 25

<210> SEQ ID NO 185
<211> LENGTH: 25
<212> TYPE: DNA
<213> ORGANISM: Artificial
<220> FEATURE:
<223> OTHER INFORMATION: antisense nucleotide

<400> SEQUENCE: 185 cagguaccuc caacaucaag gaaga 25

<210> SEQ ID NO 186
<211> LENGTH: 25
<212> TYPE: DNA
<213> ORGANISM: Artificial
<220> FEATURE:
<223> OTHER INFORMATION: antisense nucleotide

<400> SEQUENCE: 186 agguaccucc aacaucaagg aagau 25

<210> SEQ ID NO 187
<211> LENGTH: 25
<212> TYPE: DNA
<213> ORGANISM: Artificial
<220> FEATURE:
<223> OTHER INFORMATION: antisense nucleotide

<400> SEQUENCE: 187 gguaccucca acaucaagga agaug 25

<210> SEQ ID NO 188
<211> LENGTH: 25
<212> TYPE: DNA
<213> ORGANISM: Artificial
<220> FEATURE:
<223> OTHER INFORMATION: antisense nucleotide

<400> SEQUENCE: 188 guaccuccaa caucaaggaa gaugg 25

<210> SEQ ID NO 189
<211> LENGTH: 25
<212> TYPE: DNA
<213> ORGANISM: Artificial
<220> FEATURE:
<223> OTHER INFORMATION: antisense nucleotide

<400> SEQUENCE: 189 uaccuccaac aucaaggaag auggc 25

<210> SEQ ID NO 190
<211> LENGTH: 25
<212> TYPE: DNA
<213> ORGANISM: Artificial

<220> FEATURE:
<223> OTHER INFORMATION: antisense nucleotide

<400> SEQUENCE: 190 accuccaaca ucaaggaaga uggca 25

<210> SEQ ID NO 191
<211> LENGTH: 25
<212> TYPE: DNA
<213> ORGANISM: Artificial
<220> FEATURE:
<223> OTHER INFORMATION: antisense nucleotide

<400> SEQUENCE: 191 ccuccaacau caaggaagau ggcau 25

<210> SEQ ID NO 192
<211> LENGTH: 25
<212> TYPE: DNA
<213> ORGANISM: Artificial
<220> FEATURE:
<223> OTHER INFORMATION: antisense nucleotide

<400> SEQUENCE: 192 cuccaacauc aaggaagaug gcauu 25

<210> SEQ ID NO 193
<211> LENGTH: 30
<212> TYPE: DNA
<213> ORGANISM: Artificial
<220> FEATURE:
<223> OTHER INFORMATION: antisense nucleotide

<400> SEQUENCE: 193 cuccaacauc aaggaagaug gcauuucuag 30

<210> SEQ ID NO 194
<211> LENGTH: 25
<212> TYPE: DNA
<213> ORGANISM: Artificial
<220> FEATURE:
<223> OTHER INFORMATION: antisense nucleotide

<400> SEQUENCE: 194 uccaacauca aggaagaugg cauuu 25

<210> SEQ ID NO 195
<211> LENGTH: 25
<212> TYPE: DNA
<213> ORGANISM: Artificial
<220> FEATURE:
<223> OTHER INFORMATION: antisense nucleotide

<400> SEQUENCE: 195 ccaacaucaa ggaagauggc auuuc 25

<210> SEQ ID NO 196
<211> LENGTH: 25
<212> TYPE: DNA
<213> ORGANISM: Artificial
<220> FEATURE:
<223> OTHER INFORMATION: antisense nucleotide

<400> SEQUENCE: 196 caacaucaag gaagauggca uuucu 25

<210> SEQ ID NO 197
<211> LENGTH: 25
<212> TYPE: DNA
<213> ORGANISM: Artificial
<220> FEATURE:
<223> OTHER INFORMATION: antisense nucleotide

<400> SEQUENCE: 197 aacaucaagg aagauggcau uucua 25

<210> SEQ ID NO 198
<211> LENGTH: 25
<212> TYPE: DNA
<213> ORGANISM: Artificial
<220> FEATURE:
<223> OTHER INFORMATION: antisense nucleotide

<400> SEQUENCE: 198 acaucaagga agauggcauu ucuag 25

<210> SEQ ID NO 199
<211> LENGTH: 30
<212> TYPE: DNA
<213> ORGANISM: Artificial
<220> FEATURE:
<223> OTHER INFORMATION: antisense nucleotide

<400> SEQUENCE: 199 acaucaagga agauggcauu ucuaguuugg 30

<210> SEQ ID NO 200
<211> LENGTH: 25
<212> TYPE: DNA
<213> ORGANISM: Artificial
<220> FEATURE:
<223> OTHER INFORMATION: antisense nucleotide

<400> SEQUENCE: 200 acaucaagga agauggcauu ucuag 25

<210> SEQ ID NO 201
<211> LENGTH: 25
<212> TYPE: DNA
<213> ORGANISM: Artificial
<220> FEATURE:
<223> OTHER INFORMATION: antisense nucleotide

<400> SEQUENCE: 201 caucaaggaa gauggcauuu cuagu 25

<210> SEQ ID NO 202
<211> LENGTH: 25
<212> TYPE: DNA
<213> ORGANISM: Artificial
<220> FEATURE:
<223> OTHER INFORMATION: antisense nucleotide

<400> SEQUENCE: 202 aucaaggaag auggcauuuc uaguu 25

<210> SEQ ID NO 203
<211> LENGTH: 25
<212> TYPE: DNA
<213> ORGANISM: Artificial
<220> FEATURE:
<223> OTHER INFORMATION: antisense nucleotide

<400> SEQUENCE: 203 ucaaggaaga uggcauuucu aguuu 25

<210> SEQ ID NO 204
<211> LENGTH: 20
<212> TYPE: DNA
<213> ORGANISM: Artificial
<220> FEATURE:
<223> OTHER INFORMATION: antisense nucleotide

<400> SEQUENCE: 204 ucaaggaaga uggcauuucu 20

<210> SEQ ID NO 205
<211> LENGTH: 25
<212> TYPE: DNA
<213> ORGANISM: Artificial
<220> FEATURE:
<223> OTHER INFORMATION: antisense nucleotide

<400> SEQUENCE: 205 caaggaagau ggcauuucua guuug 25

<210> SEQ ID NO 206
<211> LENGTH: 25
<212> TYPE: DNA
<213> ORGANISM: Artificial
<220> FEATURE:
<223> OTHER INFORMATION: antisense nucleotide

<400> SEQUENCE: 206 aaggaagaug gcauuucuag uuugg 25

<210> SEQ ID NO 207
<211> LENGTH: 25
<212> TYPE: DNA
<213> ORGANISM: Artificial
<220> FEATURE:
<223> OTHER INFORMATION: antisense nucleotide

<400> SEQUENCE: 207 aggaagaugg cauuucuagu uugga 25

<210> SEQ ID NO 208
<211> LENGTH: 25
<212> TYPE: DNA
<213> ORGANISM: Artificial
<220> FEATURE:
<223> OTHER INFORMATION: antisense nucleotide

<400> SEQUENCE: 208 ggaagauggc auuucuaguu uggag 25

<210> SEQ ID NO 209
<211> LENGTH: 25
<212> TYPE: DNA
<213> ORGANISM: Artificial
<220> FEATURE:
<223> OTHER INFORMATION: antisense nucleotide

<400> SEQUENCE: 209 gaagauggca uuucuaguuu ggaga 25

<210> SEQ ID NO 210

<211> LENGTH: 25
<212> TYPE: DNA
<213> ORGANISM: Artificial
<220> FEATURE:
<223> OTHER INFORMATION: antisense nucleotide

<400> SEQUENCE: 210 aagauggcau uucuaguuug gagau 25

<210> SEQ ID NO 211
<211> LENGTH: 25
<212> TYPE: DNA
<213> ORGANISM: Artificial
<220> FEATURE:
<223> OTHER INFORMATION: antisense nucleotide

<400> SEQUENCE: 211 agauggcauu ucuaguuugg agaug 25

<210> SEQ ID NO 212
<211> LENGTH: 25
<212> TYPE: DNA
<213> ORGANISM: Artificial
<220> FEATURE:
<223> OTHER INFORMATION: antisense nucleotide

<400> SEQUENCE: 212 gauggcauuu cuaguuugga gaugg 25

<210> SEQ ID NO 213
<211> LENGTH: 25
<212> TYPE: DNA
<213> ORGANISM: Artificial
<220> FEATURE:
<223> OTHER INFORMATION: antisense nucleotide

<400> SEQUENCE: 213 auggcauuuc uaguuuggag auggc 25

<210> SEQ ID NO 214
<211> LENGTH: 25
<212> TYPE: DNA
<213> ORGANISM: Artificial
<220> FEATURE:
<223> OTHER INFORMATION: antisense nucleotide

<400> SEQUENCE: 214 uggcauuucu aguuuggaga uggca 25

<210> SEQ ID NO 215
<211> LENGTH: 25
<212> TYPE: DNA
<213> ORGANISM: Artificial
<220> FEATURE:
<223> OTHER INFORMATION: antisense nucleotide

<400> SEQUENCE: 215 ggcauuucua guuuggagau ggcag 25

<210> SEQ ID NO 216
<211> LENGTH: 25
<212> TYPE: DNA
<213> ORGANISM: Artificial
<220> FEATURE:
<223> OTHER INFORMATION: antisense nucleotide

<400> SEQUENCE: 216 gcauuucuag uuuggagaug gcagu 25

<210> SEQ ID NO 217
<211> LENGTH: 25
<212> TYPE: DNA
<213> ORGANISM: Artificial
<220> FEATURE:
<223> OTHER INFORMATION: antisense nucleotide

<400> SEQUENCE: 217 cauuucuagu uuggagaugg caguu 25

<210> SEQ ID NO 218
<211> LENGTH: 25
<212> TYPE: DNA
<213> ORGANISM: Artificial
<220> FEATURE:
<223> OTHER INFORMATION: antisense nucleotide

<400> SEQUENCE: 218 auuucuaguu uggagauggc aguuu 25

<210> SEQ ID NO 219
<211> LENGTH: 25
<212> TYPE: DNA
<213> ORGANISM: Artificial
<220> FEATURE:
<223> OTHER INFORMATION: antisense nucleotide

<400> SEQUENCE: 219 uuucuaguuu ggagauggca guuuc 25

<210> SEQ ID NO 220
<211> LENGTH: 25
<212> TYPE: DNA
<213> ORGANISM: Artificial
<220> FEATURE:
<223> OTHER INFORMATION: antisense nucleotide

<400> SEQUENCE: 220 uucuaguuug gagauggcag uuucc 25

<210> SEQ ID NO 221
<211> LENGTH: 25
<212> TYPE: DNA
<213> ORGANISM: Artificial
<220> FEATURE:
<223> OTHER INFORMATION: antisense nucleotide

<400> SEQUENCE: 221 ccucuugauu gcuggucuug uuuuu 25

<210> SEQ ID NO 222
<211> LENGTH: 25
<212> TYPE: DNA
<213> ORGANISM: Artificial
<220> FEATURE:
<223> OTHER INFORMATION: antisense nucleotide

<400> SEQUENCE: 222 cucuugauug cuggucuugu uuuuc 25

<210> SEQ ID NO 223
<211> LENGTH: 25
<212> TYPE: DNA

<213> ORGANISM: Artificial
<220> FEATURE:
<223> OTHER INFORMATION: antisense nucleotide

<400> SEQUENCE: 223 ucuugauugc uggucuuguu uuuca 25

<210> SEQ ID NO 224
<211> LENGTH: 25
<212> TYPE: DNA
<213> ORGANISM: Artificial
<220> FEATURE:
<223> OTHER INFORMATION: antisense nucleotide

<400> SEQUENCE: 224 cuugauugcu ggucuuguuu uucaa 25

<210> SEQ ID NO 225
<211> LENGTH: 25
<212> TYPE: DNA
<213> ORGANISM: Artificial
<220> FEATURE:
<223> OTHER INFORMATION: antisense nucleotide

<400> SEQUENCE: 225 uugauugcug gucuuguuuu ucaaa 25

<210> SEQ ID NO 226
<211> LENGTH: 25
<212> TYPE: DNA
<213> ORGANISM: Artificial
<220> FEATURE:
<223> OTHER INFORMATION: antisense nucleotide

<400> SEQUENCE: 226 ugauugcugg ucuuguuuuu caaau 25

<210> SEQ ID NO 227
<211> LENGTH: 25
<212> TYPE: DNA
<213> ORGANISM: Artificial
<220> FEATURE:
<223> OTHER INFORMATION: antisense nucleotide

<400> SEQUENCE: 227 gauugcuggu cuuguuuuuc aaauu 25

<210> SEQ ID NO 228
<211> LENGTH: 25
<212> TYPE: DNA
<213> ORGANISM: Artificial
<220> FEATURE:
<223> OTHER INFORMATION: antisense nucleotide

<400> SEQUENCE: 228 auugcugguc uuguuuuuca aauuu 25

<210> SEQ ID NO 229
<211> LENGTH: 25
<212> TYPE: DNA
<213> ORGANISM: Artificial
<220> FEATURE:
<223> OTHER INFORMATION: antisense nucleotide

<400> SEQUENCE: 229 uugcuggucu uguuuuucaa auuuu 25

<210> SEQ ID NO 230
<211> LENGTH: 25
<212> TYPE: DNA
<213> ORGANISM: Artificial
<220> FEATURE:
<223> OTHER INFORMATION: antisense nucleotide

<400> SEQUENCE: 230 ugcuggucuu guuuuucaaa uuuug 25

<210> SEQ ID NO 231
<211> LENGTH: 25
<212> TYPE: DNA
<213> ORGANISM: Artificial
<220> FEATURE:
<223> OTHER INFORMATION: antisense nucleotide

<400> SEQUENCE: 231 gcuggucuug uuuuucaaau uuugg 25

<210> SEQ ID NO 232
<211> LENGTH: 25
<212> TYPE: DNA
<213> ORGANISM: Artificial
<220> FEATURE:
<223> OTHER INFORMATION: antisense nucleotide

<400> SEQUENCE: 232 cuggucuugu uuuucaaauu uuggg 25

<210> SEQ ID NO 233
<211> LENGTH: 25
<212> TYPE: DNA
<213> ORGANISM: Artificial
<220> FEATURE:
<223> OTHER INFORMATION: antisense nucleotide

<400> SEQUENCE: 233 uggucuuguu uuucaaauuu ugggc 25

<210> SEQ ID NO 234
<211> LENGTH: 25
<212> TYPE: DNA
<213> ORGANISM: Artificial
<220> FEATURE:
<223> OTHER INFORMATION: antisense nucleotide

<400> SEQUENCE: 234 ggucuuguuu uucaaauuuu gggca 25

<210> SEQ ID NO 235
<211> LENGTH: 25
<212> TYPE: DNA
<213> ORGANISM: Artificial
<220> FEATURE:
<223> OTHER INFORMATION: antisense nucleotide

<400> SEQUENCE: 235 gucuuguuuu ucaaauuuug ggcag 25

<210> SEQ ID NO 236
<211> LENGTH: 25
<212> TYPE: DNA
<213> ORGANISM: Artificial
<220> FEATURE:

<223> OTHER INFORMATION: antisense nucleotide

<400> SEQUENCE: 236 ucuuguuuuu caaauuuugg gcagc 25

<210> SEQ ID NO 237
<211> LENGTH: 25
<212> TYPE: DNA
<213> ORGANISM: Artificial
<220> FEATURE:
<223> OTHER INFORMATION: antisense nucleotide

<400> SEQUENCE: 237 cuuguuuuuc aaauuuuggg cagcg 25

<210> SEQ ID NO 238
<211> LENGTH: 25
<212> TYPE: DNA
<213> ORGANISM: Artificial
<220> FEATURE:
<223> OTHER INFORMATION: antisense nucleotide

<400> SEQUENCE: 238 uuguuuuuca aauuuugggc agcgg 25

<210> SEQ ID NO 239
<211> LENGTH: 25
<212> TYPE: DNA
<213> ORGANISM: Artificial
<220> FEATURE:
<223> OTHER INFORMATION: antisense nucleotide

<400> SEQUENCE: 239 uguuuuucaa auuuugggca gcggu 25

<210> SEQ ID NO 240
<211> LENGTH: 25
<212> TYPE: DNA
<213> ORGANISM: Artificial
<220> FEATURE:
<223> OTHER INFORMATION: antisense nucleotide

<400> SEQUENCE: 240 guuuuucaaa uuuugggcag cggua 25

<210> SEQ ID NO 241
<211> LENGTH: 25
<212> TYPE: DNA
<213> ORGANISM: Artificial
<220> FEATURE:
<223> OTHER INFORMATION: antisense nucleotide

<400> SEQUENCE: 241 uuuuucaaau uuugggcagc gguaa 25

<210> SEQ ID NO 242
<211> LENGTH: 25
<212> TYPE: DNA
<213> ORGANISM: Artificial
<220> FEATURE:
<223> OTHER INFORMATION: antisense nucleotide

<400> SEQUENCE: 242 uuuucaaauu uugggcagcg guaau 25

<210> SEQ ID NO 243
<211> LENGTH: 25
<212> TYPE: DNA
<213> ORGANISM: Artificial
<220> FEATURE:
<223> OTHER INFORMATION: antisense nucleotide

<400> SEQUENCE: 243 uuucaaauuu ugggcagcgg uaaug 25

<210> SEQ ID NO 244
<211> LENGTH: 25
<212> TYPE: DNA
<213> ORGANISM: Artificial
<220> FEATURE:
<223> OTHER INFORMATION: antisense nucleotide

<400> SEQUENCE: 244 uucaaauuuu gggcagcggu aauga 25

<210> SEQ ID NO 245
<211> LENGTH: 25
<212> TYPE: DNA
<213> ORGANISM: Artificial
<220> FEATURE:
<223> OTHER INFORMATION: antisense nucleotide

<400> SEQUENCE: 245 ucaaauuuug ggcagcggua augag 25

<210> SEQ ID NO 246
<211> LENGTH: 25
<212> TYPE: DNA
<213> ORGANISM: Artificial
<220> FEATURE:
<223> OTHER INFORMATION: antisense nucleotide

<400> SEQUENCE: 246 caaauuuugg gcagcgguaa ugagu 25

<210> SEQ ID NO 247
<211> LENGTH: 25
<212> TYPE: DNA
<213> ORGANISM: Artificial
<220> FEATURE:
<223> OTHER INFORMATION: antisense nucleotide

<400> SEQUENCE: 247 aaauuuuggg cagcgguaau gaguu 25

<210> SEQ ID NO 248
<211> LENGTH: 25
<212> TYPE: DNA
<213> ORGANISM: Artificial
<220> FEATURE:
<223> OTHER INFORMATION: antisense nucleotide

<400> SEQUENCE: 248 aauuuugggc agcgguaaug aguuc 25

<210> SEQ ID NO 249
<211> LENGTH: 25
<212> TYPE: DNA
<213> ORGANISM: Artificial
<220> FEATURE:
<223> OTHER INFORMATION: antisense nucleotide

<400> SEQUENCE: 249 auuuugggca gcgguaauga guucu 25

<210> SEQ ID NO 250
<211> LENGTH: 25
<212> TYPE: DNA
<213> ORGANISM: Artificial
<220> FEATURE:
<223> OTHER INFORMATION: antisense nucleotide

<400> SEQUENCE: 250 ccauuguguu gaauccuuua acauu 25

<210> SEQ ID NO 251
<211> LENGTH: 22
<212> TYPE: DNA
<213> ORGANISM: Artificial
<220> FEATURE:
<223> OTHER INFORMATION: antisense nucleotide

<400> SEQUENCE: 251 ccauuguguu gaauccuuua ac 22

<210> SEQ ID NO 252
<211> LENGTH: 20
<212> TYPE: DNA
<213> ORGANISM: Artificial
<220> FEATURE:
<223> OTHER INFORMATION: antisense nucleotide

<400> SEQUENCE: 252 auuguguuga auccuuuaac 20

<210> SEQ ID NO 253
<211> LENGTH: 20
<212> TYPE: DNA
<213> ORGANISM: Artificial
<220> FEATURE:
<223> OTHER INFORMATION: antisense nucleotide

<400> SEQUENCE: 253 ccuguccuaa gaccugcuca 20

<210> SEQ ID NO 254
<211> LENGTH: 25
<212> TYPE: DNA
<213> ORGANISM: Artificial
<220> FEATURE:
<223> OTHER INFORMATION: antisense nucleotide

<400> SEQUENCE: 254 cuuuuggauu gcaucuacug uauag 25

<210> SEQ ID NO 255
<211> LENGTH: 25
<212> TYPE: DNA
<213> ORGANISM: Artificial
<220> FEATURE:
<223> OTHER INFORMATION: antisense nucleotide

<400> SEQUENCE: 255 cauucaacug uugccuccgg uucug 25

<210> SEQ ID NO 256
<211> LENGTH: 24

<212> TYPE: DNA
<213> ORGANISM: Artificial
<220> FEATURE:
<223> OTHER INFORMATION: antisense nucleotide

<400> SEQUENCE: 256 cuguugccuc cgguucugaa ggug 24

<210> SEQ ID NO 257
<211> LENGTH: 31
<212> TYPE: DNA
<213> ORGANISM: Artificial
<220> FEATURE:
<223> OTHER INFORMATION: antisense nucleotide

<400> SEQUENCE: 257 cauucaacug uugccuccgg uucugaaggu g 31

<210> SEQ ID NO 258
<211> LENGTH: 25
<212> TYPE: DNA
<213> ORGANISM: Artificial
<220> FEATURE:
<223> OTHER INFORMATION: antisense nucleotide

<400> SEQUENCE: 258 cugaaggugu ucuuguacuu caucc 25

<210> SEQ ID NO 259
<211> LENGTH: 27
<212> TYPE: DNA
<213> ORGANISM: Artificial
<220> FEATURE:
<223> OTHER INFORMATION: antisense nucleotide

<400> SEQUENCE: 259 uguauaggga cccuccuucc augacuc 27

<210> SEQ ID NO 260
<211> LENGTH: 20
<212> TYPE: DNA
<213> ORGANISM: Artificial
<220> FEATURE:
<223> OTHER INFORMATION: antisense nucleotide

<400> SEQUENCE: 260 aucccacuga uucugaauuc 20

<210> SEQ ID NO 261
<211> LENGTH: 22
<212> TYPE: DNA
<213> ORGANISM: Artificial
<220> FEATURE:
<223> OTHER INFORMATION: antisense nucleotide

<400> SEQUENCE: 261 uuggcucugg ccuguccuaa ga 22

<210> SEQ ID NO 262
<211> LENGTH: 35
<212> TYPE: DNA
<213> ORGANISM: Artificial
<220> FEATURE:
<223> OTHER INFORMATION: antisense nucleotide

<400> SEQUENCE: 262 aagaccugcu cagcuucuuc cuuagcuucc agcca 35

<210> SEQ ID NO 263
<211> LENGTH: 20
<212> TYPE: DNA
<213> ORGANISM: Artificial
<220> FEATURE:
<223> OTHER INFORMATION: antisense nucleotide

<400> SEQUENCE: 263 ggagagagcu uccuguagcu 20

<210> SEQ ID NO 264
<211> LENGTH: 23
<212> TYPE: DNA
<213> ORGANISM: Artificial
<220> FEATURE:
<223> OTHER INFORMATION: antisense nucleotide

<400> SEQUENCE: 264 ucacccuuuc cacaggcguu gca 23

<210> SEQ ID NO 265
<211> LENGTH: 32
<212> TYPE: DNA
<213> ORGANISM: Artificial
<220> FEATURE:
<223> OTHER INFORMATION: antisense nucleotide

<400> SEQUENCE: 265 ugcacuuugc aaugcugcug ucuucuugcu au 32

<210> SEQ ID NO 266
<211> LENGTH: 35
<212> TYPE: DNA
<213> ORGANISM: Artificial
<220> FEATURE:
<223> OTHER INFORMATION: antisense nucleotide

<400> SEQUENCE: 266 ucauaaugaa aacgccgcca uuucucaaca gaucu 35

<210> SEQ ID NO 267
<211> LENGTH: 20
<212> TYPE: DNA
<213> ORGANISM: Artificial
<220> FEATURE:
<223> OTHER INFORMATION: antisense nucleotide

<400> SEQUENCE: 267 uuugugucuu ucugagaaac 20

<210> SEQ ID NO 268
<211> LENGTH: 30
<212> TYPE: DNA
<213> ORGANISM: Artificial
<220> FEATURE:
<223> OTHER INFORMATION: antisense nucleotide

<400> SEQUENCE: 268 uuuagcaugu ucccaauucu caggaauuug 30

<210> SEQ ID NO 269
<211> LENGTH: 20
<212> TYPE: DNA
<213> ORGANISM: Artificial

<220> FEATURE:
<223> OTHER INFORMATION: antisense nucleotide

<400> SEQUENCE: 269 uccuguagaa uacuggcauc 20

<210> SEQ ID NO 270
<211> LENGTH: 27
<212> TYPE: DNA
<213> ORGANISM: Artificial
<220> FEATURE:
<223> OTHER INFORMATION: antisense nucleotide

<400> SEQUENCE: 270 ugcagaccuc cugccaccgc agauuca 27

<210> SEQ ID NO 271
<211> LENGTH: 34
<212> TYPE: DNA
<213> ORGANISM: Artificial
<220> FEATURE:
<223> OTHER INFORMATION: antisense nucleotide

<400> SEQUENCE: 271 uugcagaccu ccugccaccg cagauucagg cuuc 34

<210> SEQ ID NO 272
<211> LENGTH: 20
<212> TYPE: DNA
<213> ORGANISM: Artificial
<220> FEATURE:
<223> OTHER INFORMATION: antisense nucleotide

<400> SEQUENCE: 272 uguuuuugag gauugcugaa 20

<210> SEQ ID NO 273
<211> LENGTH: 40
<212> TYPE: DNA
<213> ORGANISM: Artificial
<220> FEATURE:
<223> OTHER INFORMATION: antisense nucleotide

<400> SEQUENCE: 273 uguucugaca acaguuugcc gcugcccaau gccauccugg 40

<210> SEQ ID NO 274
<211> LENGTH: 30
<212> TYPE: DNA
<213> ORGANISM: Artificial
<220> FEATURE:
<223> OTHER INFORMATION: antisense nucleotide

<400> SEQUENCE: 274 cucuuuucca gguucaagug ggauacuagc 30

<210> SEQ ID NO 275
<211> LENGTH: 31
<212> TYPE: DNA
<213> ORGANISM: Artificial
<220> FEATURE:
<223> OTHER INFORMATION: antisense nucleotide

<400> SEQUENCE: 275 caagcuuuuc uuuuaguugc ugcucuuuuc c 31

<210> SEQ ID NO 276
<211> LENGTH: 30
<212> TYPE: DNA
<213> ORGANISM: Artificial
<220> FEATURE:
<223> OTHER INFORMATION: antisense nucleotide

<400> SEQUENCE: 276 uauucuuuug uucuucuagc cuggagaaag 30

<210> SEQ ID NO 277
<211> LENGTH: 28
<212> TYPE: DNA
<213> ORGANISM: Artificial
<220> FEATURE:
<223> OTHER INFORMATION: antisense nucleotide

<400> SEQUENCE: 277 cugcuuccuc caaccauaaa acaaauuc 28

<210> SEQ ID NO 278
<211> LENGTH: 29
<212> TYPE: DNA
<213> ORGANISM: Artificial
<220> FEATURE:
<223> OTHER INFORMATION: antisense nucleotide

<400> SEQUENCE: 278 ccacucagag cucagaucuu cuaacuucc 29

<210> SEQ ID NO 279
<211> LENGTH: 27
<212> TYPE: DNA
<213> ORGANISM: Artificial
<220> FEATURE:
<223> OTHER INFORMATION: antisense nucleotide

<400> SEQUENCE: 279 cuuccacuca gagcucagau cuucuaa 27

<210> SEQ ID NO 280
<211> LENGTH: 30
<212> TYPE: DNA
<213> ORGANISM: Artificial
<220> FEATURE:
<223> OTHER INFORMATION: antisense nucleotide

<400> SEQUENCE: 280 caguccagga gcuaggucag gcugcuuugc 30

<210> SEQ ID NO 281
<211> LENGTH: 37
<212> TYPE: DNA
<213> ORGANISM: Artificial
<220> FEATURE:
<223> OTHER INFORMATION: antisense nucleotide

<400> SEQUENCE: 281 ucuugaagua aacgguuuac cgccuuccac ucagagc 37

<210> SEQ ID NO 282
<211> LENGTH: 30
<212> TYPE: DNA
<213> ORGANISM: Artificial
<220> FEATURE:
<223> OTHER INFORMATION: antisense nucleotide

<400> SEQUENCE: 282 uccaacuggg gacgccucug uuccaaaucc 30

<210> SEQ ID NO 283
<211> LENGTH: 21
<212> TYPE: DNA
<213> ORGANISM: Artificial
<220> FEATURE:
<223> OTHER INFORMATION: antisense nucleotide

<400> SEQUENCE: 283 acuggggacg ccucuguucc a 21

<210> SEQ ID NO 284
<211> LENGTH: 20
<212> TYPE: DNA
<213> ORGANISM: Artificial
<220> FEATURE:
<223> OTHER INFORMATION: antisense nucleotide

<400> SEQUENCE: 284 ccguaaugau uguucuagcc 20

<210> SEQ ID NO 285
<211> LENGTH: 25
<212> TYPE: DNA
<213> ORGANISM: Artificial
<220> FEATURE:
<223> OTHER INFORMATION: antisense nucleotide

<400> SEQUENCE: 285 uuuugggcag cgguaaugag uucuu 25

<210> SEQ ID NO 286
<211> LENGTH: 25
<212> TYPE: DNA
<213> ORGANISM: Artificial
<220> FEATURE:
<223> OTHER INFORMATION: antisense nucleotide

<400> SEQUENCE: 286 uuugggcagc gguaaugagu ucuuc 25

<210> SEQ ID NO 287
<211> LENGTH: 25
<212> TYPE: DNA
<213> ORGANISM: Artificial
<220> FEATURE:
<223> OTHER INFORMATION: antisense nucleotide

<400> SEQUENCE: 287 uugggcagcg guaaugaguu cuucc 25

<210> SEQ ID NO 288
<211> LENGTH: 25
<212> TYPE: DNA
<213> ORGANISM: Artificial
<220> FEATURE:
<223> OTHER INFORMATION: antisense nucleotide

<400> SEQUENCE: 288 ugggcagcgg uaaugaguuc uucca 25

<210> SEQ ID NO 289

<211> LENGTH: 25
<212> TYPE: DNA
<213> ORGANISM: Artificial
<220> FEATURE:
<223> OTHER INFORMATION: antisense nucleotide

<400> SEQUENCE: 289 gggcagcggu aaugaguucu uccaa 25

<210> SEQ ID NO 290
<211> LENGTH: 25
<212> TYPE: DNA
<213> ORGANISM: Artificial
<220> FEATURE:
<223> OTHER INFORMATION: antisense nucleotide

<400> SEQUENCE: 290 ggcagcggua augaguucuu ccaac 25

<210> SEQ ID NO 291
<211> LENGTH: 25
<212> TYPE: DNA
<213> ORGANISM: Artificial
<220> FEATURE:
<223> OTHER INFORMATION: antisense nucleotide

<400> SEQUENCE: 291 gcagcgguaa ugaguucuuc caacu 25

<210> SEQ ID NO 292
<211> LENGTH: 25
<212> TYPE: DNA
<213> ORGANISM: Artificial
<220> FEATURE:
<223> OTHER INFORMATION: antisense nucleotide

<400> SEQUENCE: 292 cagcgguaau gaguucuucc aacug 25

<210> SEQ ID NO 293
<211> LENGTH: 25
<212> TYPE: DNA
<213> ORGANISM: Artificial
<220> FEATURE:
<223> OTHER INFORMATION: antisense nucleotide

<400> SEQUENCE: 293 agcgguaaug aguucuucca acugg 25

<210> SEQ ID NO 294
<211> LENGTH: 25
<212> TYPE: DNA
<213> ORGANISM: Artificial
<220> FEATURE:
<223> OTHER INFORMATION: antisense nucleotide

<400> SEQUENCE: 294 gcgguaauga guucuuccaa cuggg 25

<210> SEQ ID NO 295
<211> LENGTH: 25
<212> TYPE: DNA
<213> ORGANISM: Artificial
<220> FEATURE:
<223> OTHER INFORMATION: antisense nucleotide

<400> SEQUENCE: 295 cgguaaugag uucuuccaac ugggg 25

<210> SEQ ID NO 296
<211> LENGTH: 25
<212> TYPE: DNA
<213> ORGANISM: Artificial
<220> FEATURE:
<223> OTHER INFORMATION: antisense nucleotide

<400> SEQUENCE: 296 gguaaugagu ucuuccaacu gggga 25

<210> SEQ ID NO 297
<211> LENGTH: 25
<212> TYPE: DNA
<213> ORGANISM: Artificial
<220> FEATURE:
<223> OTHER INFORMATION: antisense nucleotide

<400> SEQUENCE: 297 guaaugaguu cuuccaacug gggac 25

<210> SEQ ID NO 298
<211> LENGTH: 25
<212> TYPE: DNA
<213> ORGANISM: Artificial
<220> FEATURE:
<223> OTHER INFORMATION: antisense nucleotide

<400> SEQUENCE: 298 uaaugaguuc uuccaacugg ggacg 25

<210> SEQ ID NO 299
<211> LENGTH: 25
<212> TYPE: DNA
<213> ORGANISM: Artificial
<220> FEATURE:
<223> OTHER INFORMATION: antisense nucleotide

<400> SEQUENCE: 299 aaugaguucu uccaacuggg gacgc 25

<210> SEQ ID NO 300
<211> LENGTH: 25
<212> TYPE: DNA
<213> ORGANISM: Artificial
<220> FEATURE:
<223> OTHER INFORMATION: antisense nucleotide

<400> SEQUENCE: 300 augaguucuu ccaacugggg acgcc 25

<210> SEQ ID NO 301
<211> LENGTH: 25
<212> TYPE: DNA
<213> ORGANISM: Artificial
<220> FEATURE:
<223> OTHER INFORMATION: antisense nucleotide

<400> SEQUENCE: 301 ugaguucuuc caacugggga cgccu 25

<210> SEQ ID NO 302
<211> LENGTH: 25
<212> TYPE: DNA

<213> ORGANISM: Artificial
<220> FEATURE:
<223> OTHER INFORMATION: antisense nucleotide

<400> SEQUENCE: 302 gaguucuucc aacuggggac gccuc 25

<210> SEQ ID NO 303
<211> LENGTH: 25
<212> TYPE: DNA
<213> ORGANISM: Artificial
<220> FEATURE:
<223> OTHER INFORMATION: antisense nucleotide

<400> SEQUENCE: 303 aguucuucca acuggggacg ccucu 25

<210> SEQ ID NO 304
<211> LENGTH: 25
<212> TYPE: DNA
<213> ORGANISM: Artificial
<220> FEATURE:
<223> OTHER INFORMATION: antisense nucleotide

<400> SEQUENCE: 304 guucuuccaa cuggggacgc cucug 25

<210> SEQ ID NO 305
<211> LENGTH: 25
<212> TYPE: DNA
<213> ORGANISM: Artificial
<220> FEATURE:
<223> OTHER INFORMATION: antisense nucleotide

<400> SEQUENCE: 305 uucuuccaac uggggacgcc ucugu 25

<210> SEQ ID NO 306
<211> LENGTH: 25
<212> TYPE: DNA
<213> ORGANISM: Artificial
<220> FEATURE:
<223> OTHER INFORMATION: antisense nucleotide

<400> SEQUENCE: 306 ucuuccaacu ggggacgccu cuguu 25

<210> SEQ ID NO 307
<211> LENGTH: 25
<212> TYPE: DNA
<213> ORGANISM: Artificial
<220> FEATURE:
<223> OTHER INFORMATION: antisense nucleotide

<400> SEQUENCE: 307 cuuccaacug gggacgccuc uguuc 25

<210> SEQ ID NO 308
<211> LENGTH: 25
<212> TYPE: DNA
<213> ORGANISM: Artificial
<220> FEATURE:
<223> OTHER INFORMATION: antisense nucleotide

<400> SEQUENCE: 308 uuccaacugg ggacgccucu guucc 25

<210> SEQ ID NO 309
<211> LENGTH: 20
<212> TYPE: DNA
<213> ORGANISM: Artificial
<220> FEATURE:
<223> OTHER INFORMATION: antisense nucleotide

<400> SEQUENCE: 309 gauugcuggu cuuguuuuuc 20

<210> SEQ ID NO 310
<211> LENGTH: 20
<212> TYPE: DNA
<213> ORGANISM: Artificial
<220> FEATURE:
<223> OTHER INFORMATION: antisense nucleotide

<400> SEQUENCE: 310 ccucuugauu gcuggucuug 20

<210> SEQ ID NO 311
<211> LENGTH: 22
<212> TYPE: DNA
<213> ORGANISM: Artificial
<220> FEATURE:
<223> OTHER INFORMATION: antisense nucleotide

<400> SEQUENCE: 311 gguaaugagu ucuuccaacu gg 22

<210> SEQ ID NO 312
<211> LENGTH: 20
<212> TYPE: DNA
<213> ORGANISM: Artificial
<220> FEATURE:
<223> OTHER INFORMATION: antisense nucleotide

<400> SEQUENCE: 312 acuggggacg ccucuguucc 20

<210> SEQ ID NO 313
<211> LENGTH: 20
<212> TYPE: DNA
<213> ORGANISM: Artificial
<220> FEATURE:
<223> OTHER INFORMATION: PRO 51

<400> SEQUENCE: 313 ucaaggaaga uggcauuucu 20

<210> SEQ ID NO 314
<211> LENGTH: 20
<212> TYPE: DNA
<213> ORGANISM: Artificial
<220> FEATURE:
<223> OTHER INFORMATION: PS 49

<400> SEQUENCE: 314 ggccaaaccu cggcuuaccu 20

The invention claimed is:

[1. A composition comprising:

a first compound that increases the level of a functional dystrophin protein produced in a muscle cell of a Duchenne Muscular Dystrophy (DMD) or Becker Muscular Dystrophy (BMD) individual, wherein said first compound is an antisense oligonucleotide that induces skipping of exon 51 of human dystrophin pre-mRNA of said individual;

and a second compound comprising a steroid;

wherein, upon administration to a DMD or BMD patient, the composition increases the ratio of said dystrophin to laminin-α2 in muscle tissue of said patient as compared to the ratio of said dystrophin to laminin-α2 in muscle tissue of a patient administered with said first compound and not said second compound; and wherein said antisense oligonucleotide is 100% complementary to a portion of exon 51 that is 13 to 50 nucleotides in length and wherein said oligonucleotide comprises a non naturally-occurring modification.]

[2. The composition of claim 1, wherein said antisense oligonucleotide is 100% complementary to a portion of exon 51 that is 14 to 25 nucleotides in length.]

[3. The composition of claim 1, wherein said antisense oligonucleotide is 100% complementary to a portion of exon 51 that is 20 to 25 nucleotides in length.]

[4. The composition of claim 1, wherein said oligonucleotide comprises one or more ribonucleotides, and wherein a said ribonucleotide contains a modification.]

[5. The composition of claim 4, wherein said modification is a 2'-O-methyl modified ribose.]

[6. The composition of claim 1, wherein said modification is selected from the group consisting of at least one of a peptide nucleic acid, a locked nucleic acid, and morpholino phosphorodiamidate.]

[7. A method for alleviating one or more symptom(s) of Duchenne Muscular Dystrophy or Becker Muscular Dystrophy in an individual, the method comprising administering to a DMD or BMD patient:

a first compound that increases the level of a functional dystrophin protein produced in a muscle cell of said individual in said individual, wherein said first compound is an antisense oligonucleotide that induces skipping of exon 51 of dystrophin pre-mRNA of said individual, and a second compound, comprising a steroid;

wherein, upon administration to a DMD or BMD patient, the composition increases the ratio of said dystrophin to laminin-α2 in muscle tissue of said patient as compared to the ratio of said dystrophin to laminin-α2 in muscle tissue of a patient administered with said first compound and not said second compound; and wherein said antisense oligonucleotide is 100% complementary to a portion of exon 51 that is 13 to 50 nucleotides in length and wherein said oligonucleotide comprises a non naturally-occurring modification.]

[8. The method of claim 7, wherein said oligonucleotide comprises one or more ribonucleotides, and wherein a said ribonucleotide contains a modification.]

[9. The method of claim 8, wherein said modification is selected from the group consisting of a 2'-O-methyl modified ribose.]

[10. The method of claim 7, wherein said modification is selected from the group consisting of at least one of a peptide nucleic acid, a locked nucleic acid, and morpholino phosphorodiamidate.]

[11. A method for increasing the production of a functional dystrophin protein in a cell, said cell comprising pre-mRNA of a dystrophin gene encoding an aberrant dystrophin protein comprising:

providing said cell with a first compound for inhibiting inclusion of exon 51 into mRNA produced from splicing of said dystrophin pre-mRNA, wherein said first compound is an antisense oligonucleotide that induces the skipping of exon 51 of the human dystrophin pre-mRNA, and providing said cell with a second compound comprising a steroid, said method further comprising allowing translation of mRNA produced from splicing of said pre-mRNA;

wherein, upon administration to a DMD or BMD patient, the composition increases the ratio of said dystrophin to laminin-α2 in muscle tissue of said patient as compared to the ratio of said dystrophin to laminin-α2 in muscle tissue of a patient administered with said first compound and not said second compound; and wherein said antisense oligonucleotide is 100% complementary to a portion of exon 51 that is 13 to 50 nucleotides in length and wherein said oligonucleotide comprises a non naturally-occurring modification.]

[12. A pharmaceutical preparation comprising:

said first compound according to claim 1, said second compound according to claim 1, comprising a steroid, and a pharmaceutically acceptable carrier, adjuvant, diluent and/or excipient.]

[13. A kit comprising:

said first compound according to claim 1, and said second compound according to claim 1.]

[14. The kit of claim 13, further comprising a pharmaceutically acceptable carrier, adjuvant, diluent and/or excipient.]

[15. The kit of claim 13, further comprising packaging means thereof.]

[16. The composition according to claim 1, wherein the oligonucleotide comprises a phosphorothioate internucleotide linkage, a 2'-O-methyl ribose and/or a LNA.]

[17. The kit according to claim 13, wherein the oligonucleotide comprises a phosphorothioate internucleotide linkage, a 2'-O-methyl ribose and/or a LNA.]

[18. A pharmaceutical composition comprising the composition of claim 1 and a pharmaceutically acceptable carrier, adjuvant, diluent, and/or excipient.]

[19. The method of claim 7 wherein said steroid is a glucocorticosteroid.]

[20. The method of claim 19 wherein said glucocorticosteroid is selected from a group consisting of prednisone, dexamethasone, prednizolone and deflazacort.]

[21. The method of claim 20 wherein said prednisone is present at a dosage of 0.5-1.0 mg/kg.]

[22. The method of claim 20 wherein said deflazacort is present at a dosage of 0.4-1.4 mg/kg.]

*23. A method for alleviating one or more symptoms of Duchenne muscular dystrophy in a human patient, comprising administering to the patient an antisense oligonucleotide that is: (a) 100% complementary to a portion of exon 51 of the human dystrophin pre-mRNA and (b) 30 nucleotides in length,*

*wherein the antisense oligonucleotide comprises the sequence 5'-CUC CAA CAU CAA GGA AGA UGG CAU UUC UAG-3' (SEQ ID NO:193),*

*wherein the antisense oligonucleotide is a morpholino phosphorodiamidate,*

*wherein the antisense oligonucleotide is administered intravenously,*

*wherein the antisense oligonucleotide induces skipping of exon 51 of dystrophin pre-mRNA, and*

*wherein the patient is receiving glucocorticosteroid treatment.*

*24. The method of claim 23, wherein the patient was receiving the glucocorticosteroid treatment prior to the administration of the antisense oligonucleotide.*

*25. The method of claim 24, wherein the prior glucocorticosteroid treatment was for a period of at least three weeks.*

*26. The method of claim 23, wherein the glucocorticosteroid is selected from the group consisting of prednisone, dexamethasone, prednisolone, and deflazacort.*

*27. The method of claim 26, wherein the glucocorticosteroid is prednisone.*

*28. The method of claim 27, wherein the patient is receiving the prednisolone at a dose of about 0.5 mg/kg/day to about 1.0 mg/kg/day.*

*29. The method of claim 26, wherein the glucocorticosteroid is deflazacort.*

*30. The method of claim 29, wherein the patient is receiving the deflazacort at a dose of about 0.4 mg/kg/day to about 1.4 mg/kg/day.*

*31. The method of claim 23, wherein the method increases the ratio of dystrophin to laminin-α2 in muscle tissue of the patient as compared to the ratio of dystrophin to laminin-α2 in muscle tissue of a similar patient treated with the antisense oligonucleotide and not the glucocorticosteroid.*

*32. A method for alleviating one or more symptoms of Duchenne muscular dystrophy in a human patient, comprising administering to the patient an antisense oligonucleotide that is: (a) 100% complementary to a portion of exon 51 of the human dystrophin pre-mRNA and (b) 30 nucleotides in length,*

*wherein the antisense oligonucleotide is a functional equivalent of an oligonucleotide comprising the sequence 5'-CUC CAA CAU CAA GGA AGA UGG CAU UUC UAG-3' (SEQ ID NO:193),*

*wherein the antisense oligonucleotide is a morpholino phosphorodiamidate,*

*wherein the antisense oligonucleotide is administered intravenously,*

*wherein the antisense oligonucleotide induces skipping of exon 51 of dystrophin pre-mRNA, and*

*wherein the patient is receiving glucocorticosteroid treatment.*

*33. A method for alleviating one or more symptoms of Duchenne muscular dystrophy in a human patient, comprising administering to the patient an antisense oligonucleotide that is 100% complementary to the portion of exon 51 of the human dystrophin pre-mRNA to which the sequence 5'-CUC CAA CAU CAA GGA AGA UGG CAU UUC UAG-3' (SEQ ID NO:193) is complementary,*

*wherein the antisense oligonucleotide is 30 nucleotides in length,*

*wherein the antisense oligonucleotide is a morpholino phosphorodiamidate,*

*wherein the antisense oligonucleotide is administered intravenously,*

*wherein the antisense oligonucleotide induces skipping of exon 51 of dystrophin pre-mRNA, and*

*wherein the patient is receiving glucocorticosteroid treatment.*

*34. The method of claim 33, wherein the patient has received the glucocorticosteroid treatment prior to the administration of the antisense oligonucleotide.*

*35. The method of claim 34, wherein the prior glucocorticosteroid treatment was for a period of at least three weeks.*

*36. The method of claim 33, wherein the glucocorticosteroid is selected from the group consisting of prednisone, dexamethasone, prednisolone, and deflazacort.*

*37. The method of claim 36, wherein the glucocorticosteroid is prednisone.*

*38. The method of claim 37, wherein the patient is receiving the prednisone at a dose of about 0.5 mg/kg/day to about 1.0 mg/kg/day.*

*39. The method of claim 36, wherein the glucocorticosteroid is deflazacort.*

*40. The method of claim 39, wherein the patient is receiving the deflazacort at a dose of about 04. Mg/kg/day to about 1.4 mg/kg/day.*

*41. The method of claim 33, wherein the method increases the ratio of dystrophin to laminin-α2 in muscle tissue of the patient as compared to the ratio of dystrophin to laminin-α2 in muscle tissue of a similar patient treated with the antisense oligonucleotide and not the glucocorticosteroid.*

*42. A method for alleviating one or more symptoms of Duchenne muscular dystrophy in a human patient, comprising administering to the patient an antisense oligonucleotide that is 100% complementary to the portion of exon 51 of the human dystrophin pre-mRNA to which the sequence 5'-CUC CAA CAU CAA GGA AGA UGG CAU UUC UAG-3' (SEQ ID NO:193) is complementary,*

*wherein the antisense oligonucleotide is 30 nucleotides in length,*

*wherein the antisense oligonucleotide is a morpholino phosphorodiamidate,*

*wherein the antisense oligonucleotide is administered intravenously,*

*wherein the antisense oligonucleotide induces skipping of exon 51 of dystrophin pre-mRNA,*

*wherein the patient is receiving glucocorticosteroid treatment, wherein the glucocorticosteroid is selected from prednisone and deflazacort, and*

*wherein the method increases the ratio of dystrophin to laminin-α2 in muscle tissue of the patient as compared to the ratio of dystrophin to laminin-α2 in muscle tissue of a similar patient treated with the antisense oligonucleotide and not the glucocorticosteroid.*

* * * * *